(12) United States Patent
Ravindranath et al.

(10) Patent No.: US 10,800,847 B2
(45) Date of Patent: Oct. 13, 2020

(54) ANTI-HLA CLASS-IB ANTIBODIES MIMIC IMMUNOREACTIVITY AND IMMUNOMODULATORY FUNCTIONS OF INTRAVENOUS IMMUNOGLOBULIN (IVIG) USEFUL AS THERAPEUTIC IVIG MIMETICS AND METHODS OF THEIR USE

(71) Applicant: THE TERASAKI FAMILY FOUNDATION, Los Angeles, CA (US)

(72) Inventors: Mepur H. Ravindranath, Los Angeles, CA (US); Paul I. Terasaki, Los Angeles, CA (US)

(73) Assignee: Dr. Mepur Ravindranath, Los Angeles, CA (US)

( * ) Notice: Subject to any disclaimer, the term of this patent is extended or adjusted under 35 U.S.C. 154(b) by 0 days.

(21) Appl. No.: 14/371,248

(22) PCT Filed: Jan. 10, 2013

(86) PCT No.: PCT/US2013/021054
§ 371 (c)(1),
(2) Date: Jul. 9, 2014

(87) PCT Pub. No.: WO2013/106586
PCT Pub. Date: Jul. 18, 2013

(65) Prior Publication Data
US 2014/0348846 A1    Nov. 27, 2014

(51) Int. Cl.
*C07K 16/28* (2006.01)
*A61K 39/00* (2006.01)
*C07K 14/74* (2006.01)

(52) U.S. Cl.
CPC .... *C07K 16/2833* (2013.01); *A61K 2039/505* (2013.01); *C07K 2317/33* (2013.01)

(58) Field of Classification Search
None
See application file for complete search history.

(56) References Cited

U.S. PATENT DOCUMENTS

| | | | |
|---|---|---|---|
| 4,816,397 A | 3/1989 | Boss et al. | |
| 4,816,567 A | 3/1989 | Cabilly et al. | |
| 5,225,539 A | 7/1993 | Winter | |
| 5,413,923 A | 5/1995 | Kucherlapati et al. | |
| 5,530,101 A | 6/1996 | Queen et al. | |
| 5,545,806 A | 8/1996 | Lonberg et al. | |
| 5,565,332 A | 10/1996 | Hoogenboom et al. | |
| 5,569,825 A | 10/1996 | Lonberg et al. | |
| 5,585,089 A | 12/1996 | Queen et al. | |
| 5,625,126 A | 4/1997 | Lonberg et al. | |
| 5,633,425 A | 5/1997 | Lonberg et al. | |
| 5,661,016 A | 8/1997 | Lonberg et al. | |
| 5,766,886 A | 6/1998 | Studnicka et al. | |
| 5,807,715 A | 9/1998 | Morrison et al. | |
| 5,814,318 A | 9/1998 | Lonberg et al. | |
| 5,939,598 A | 8/1999 | Kucherlapati et al. | |
| 6,331,415 B1 | 12/2001 | Cabilly et al. | |
| 6,407,213 B1 | 6/2002 | Carter et al. | |
| 6,994,857 B2 | 2/2006 | Rosen et al. | |
| 2003/0125247 A1 | 7/2003 | Rosen et al. | |
| 2003/0171267 A1 | 9/2003 | Rosen et al. | |
| 2003/0219875 A1 | 11/2003 | Rosen et al. | |
| 2004/0010134 A1 | 1/2004 | Rosen et al. | |
| 2004/0171123 A1 | 9/2004 | Rosen et al. | |
| 2005/0042664 A1 | 2/2005 | Wu et al. | |
| 2012/0171195 A1 | 7/2012 | Ravindranath et al. | |
| 2013/0177574 A1 | 7/2013 | Ravindranath et al. | |
| 2014/0010825 A1 | 1/2014 | Ravindranath et al. | |

FOREIGN PATENT DOCUMENTS

| | | |
|---|---|---|
| EP | 0 239 400 A2 | 9/1987 |
| EP | 0 413 622 A1 | 2/1991 |
| EP | 0 519 596 A1 | 12/1992 |
| EP | 0 592 106 A1 | 4/1994 |
| WO | WO 91/09967 A1 | 7/1991 |
| WO | WO 93/15199 A1 | 8/1993 |

(Continued)

OTHER PUBLICATIONS

Zivkovic et al (Medscape 2016).*
Zanelli et al (Rheum. 2000 39: 1060-1066).*
Edwards et al (JMB, 2003, 334: 103-118) (Year: 2003).*
Lloyd et al (Protein Engineering, Eng. Design & Selection, 2009, 22(3): 159-168) (Year: 2009).*
Goel et al (J. Immunol., 2004,173: 7358-7367) (Year: 2004).*
Khan and Salunke (J. Immunol, 2014, 192: 5398-5405) (Year: 2014).*
Poosarla et al (Biotechn. Bioeng., 2017, 114(6): 1331-1342) (Year: 2017).*
Torres and Casadevall (Trend. Immunol., 2008, 29(2): 91-97) (Year: 2008).*
HLA nomenclature (2015) (Year: 2015).*
Merriam Webster online dictionary (2019) (Year: 2019).*
Zips et al (In Vivo, 2005, 19:1-7) (Year: 2005).*

(Continued)

*Primary Examiner* — G. R. Ewoldt
*Assistant Examiner* — Marianne DiBrino
(74) *Attorney, Agent, or Firm* — Squire Patton Boggs (US) LLP

(57) ABSTRACT

Provided herein are compositions comprising anti-HLA-Ib antibodies (monoclonal, mixed monoclonal, recombinant, chimeric, humanized or human antibodies) as IVIg mimetics and methods for using the same for the prevention, treatment, therapy and/or amelioration of inflammation induced diseases and allograft rejection. In certain embodiments, the anti-HLA-Ib antibodies strongly mimic IVIg in immunoreactivity to HLA class Ia (HLA-A, HLA-B and HLA-Cw) and Ib antigens (HLA-E, HLA-F and HLA-G). In certain embodiments, the anti-HLA-Ib antibodies strongly mimic IVIg in immunomodulatory or immunosuppressive activities. Methods are also provided herein to induce production of polyclonal anti-HLA-Ib antibodies in cancer patients for restoring anti-tumor activities of CD8+ T cells and NK cells, by active specific immunotherapy.

6 Claims, 49 Drawing Sheets
Specification includes a Sequence Listing.

(56) References Cited

FOREIGN PATENT DOCUMENTS

| WO | WO 93/15200 A1 | 8/1993 |
|---|---|---|
| WO | WO 93/17105 A1 | 9/1993 |
| WO | WO 96/33735 A1 | 10/1996 |
| WO | WO 96/34096 A1 | 10/1996 |
| WO | WO 98/24893 A2 | 6/1998 |
| WO | WO 2006/063844 A1 | 6/2006 |
| WO | WO 2009/023055 A2 | 2/2009 |

OTHER PUBLICATIONS

De St. Groth et al (Immunology and Cell Biology 2004, 82: 260-268) (Year: 2004).*
Agaugué et al., Human natural killer cells exposed to IL-2, IL-12, IL-18, or IL-4 differently modulate priming of naive T cells by monocyte-derived dendritic calls (2008) *Blood* 112:1776-1783.
Bahri et al., Soluble HLA-G Inhibits Cell Cycle Progression in Human Alloreactive T Lymphocytes (2006) *The Journal of Immunology* 176:1331-1339.
Braud et al., HLA-E binds to natural killer cell receptors CD94/NKG2A, B and C (1998) *Nature* 391:795-799.
Coupel et al., Expression and release of soluble HLA-E is an immunoregulatory feature of endothelial cell activation, *Blood* vol. 109, No. 7, pp. 2806-2814 (2007).
Crow et al., The neonatal Fc receptor (FcRn) is not required for IVIg or anti-CD44 monoclonal antibody-mediated amelioration of murine immune thrombocytopenia (2011) *Blood* 118:6403-6406.
International Search Report and Written Opinion of the International Searching Authority in PCT/US2013/021054, dated Jul. 18, 2013.
Jolliffe L., Humanized Antibodies: Enhancing Therapeutic Utility Through Antibody Engineering (1993) *Int. Rev. Immunol.* 10:241-250.
Kren et al., Production of immune-modulatory nonclassical molecules HLA-G and HLA-E by tumor infiltrating ameboid microglia/macrophages in glioblastomas: a role in innate immunity?, *J. of Neuroimmunology* 220, pp. 131-135 (2010).
Lo Monaco et al., HLA-E and the origin of immunogenic self HLA epitopes, *Molecular Immunology* 47, pp. 1661-1662 (2010).
Lo Monaco et al., HLA-E: Strong Association with $\beta_2$-Microglobulin and Surface Expression in the Absence of HLA Class I Signal Sequence-Derived Peptides (2008) *The Journal of Immunology* 181:5442-5450.
Menier et al., Characterization of Monoclonal Antibodies Recognizing HLA-G or HLA-E: New Tools to Analyze the Expression of Nonclassical HLA Class I Molecules, *Human Immunology* 64, pp. 315-326 (2003).
Mouthon et al., Mechanisms of action of intravenous immune globulin in immune-mediated diseases (1996) *Clin. Exp. Immunol.* 104 Suppl 1:3-9, abstract only.
Pacasova et al., Cell surface detection of HLA-E gene products with a specific monoclonal antibody, *J. of Reproductive Immunology* 43, pp. 195-201 (1999).
Pietra et al., The Emerging Role of HLA-E-Restricted CD8+ T Lymphocytes in the Adaptive Immune Response to Pathogens and Tumors (2010) *Journal of Biomedicine and Biotechnology* 10:1-8.

Ravindranath et al., Antibodies to HLA-E in Nonalloimmunized Males: Pattern of HLA-Ia Reactivity of Anti-HLA-E-Positive Sera, *J. of Immunol.* 185, pp. 1935-1948 (2010).
Ravindranath et al., Anti HLA-E mAb 3D12 mimics MEM-E/02 in binding to HLA-B and HLA-C alleles: Web-tools validate the immunogenic epitopes of HLA-E recognized by the antibodies, *Molecular Immunology* 48, pp. 423-430 (2011).
Ravindranath et al., Anti-HLA-E Monoclonal Antibodies Reacting with HLA-Ia and Ib Alleles Like IVIg as Potential IVIg-Immunomimetics: An Evolving Therapeutic Concept (2013) *Clinical Transplants*, Chapter 35:293-305.
Ravindranath et al., Augmentation of anti-HLA-E antibodies with concomitant HLA-Ia reactivity in IFNγ-treated autologous melanoma cell vaccine recipients (2012) *Journal of Immunotoxicology* 9:282-291.
Ravindranath et al., HLA-E monoclonal antibodies recognize shared peptide sequences on classical HLA class Ia: Relevance to human natural HLA natibodies, *Molecular Immunology* 47, pp. 1121-1131 (2010).
Ravindranath et al., HLA-E monoclonal antibody MEM-E/02 binds to discontinuous but shared peptide sequences on HLA B&C heavy chains not treated by acid, *Molecular Immunology* 47, pp. 1663-1664 (2010).
Ravindranath et al., Suppression of Blastogenesis and Proliferation of activated CD4+ T-cells: IVIg versus novel anti-HLA-E mAbs mimicking HLA-I reactivity of IVIg. *Clin Exp Immunol.* Jun. 2, 2014. doi: 10.1111/cei.12391. [Epub ahead of print].
Rouas-Freiss et al., The immunotolerance role of HLA-G (1999) *Seminars in Cancer Biology* (1999) 9:3-12.
Seitz et al., The monoclonal antibody HCA2 recognises a broadly shared epitope on selected classical as well as several non-classical HLA class I molecules, *Molecular Immunology* 35, pp. 819-827 (1998).
Sibilio et al., Biochemical characterization of monoclonal antibodies to HLA-E and HLA-G, *Tissue Antigens* vol. 62, issue 4, pp. 273-357, Abstract only (2003).
Sullivan et al., The major histocompatibility complex class Ib molecule HLA-E at the interface between innate and adaptive immunity, *Tissue Antigens* 72, pp. 415-424 (2008).
Wischhusen et al., Immune-refractory cancers and their little helpers—An extended role for immunetolerogenic MHC molecules HLA-G and HLA-E?, Seminars in Cancer Biology, *Saunders Scientific Publ.* vol. 17, No. 6, pp. 459-468 (2007).
Zhu et al., Suppression of allo-human leucocyte antigen (HLA) antibodies secreted by B memory cells in vitro: intravenous immunoglobulin (IVIg) versus a monoclonal anti-HLA-E IgG that mimics HLA-I reactivities of IVIg (2014) Clinical and Experimental Immunology, pp. 1-14.
International Search Report and Written Opinion for PCT/US2011/068178, dated Jun. 22, 2012, 11 pgs.
International Search Report and Written Opinion for PCT/US2013/021054, dated Jul. 18, 2013, 12 pgs.
International Search Report and Written Opinion for PCT/US2013/048975, dated Dec. 5, 2013, 9 pgs.
HLA Alleles Numbers, Nomenclature 2 pgs. (2015).
Yu and Lennon, "Mechanism of Intravenous Immune Globulin Therapy in Antibody-Mediated Autoimmune Diseases", Blood 340 (3), pp. 227-228 (1999).

* cited by examiner

FIGURE 1. Evidence for the presence of IgG antibodies in IVIg reacting to HLA-E, HLA-F and HLA-G heavy chains
FIGURE 1A. IVIg Reactivity to all non-classical HLA-Ib molecules inclusive of HLA-E, HLA-F & HLA-G heavy chains (GamaSTAN™ S/D)
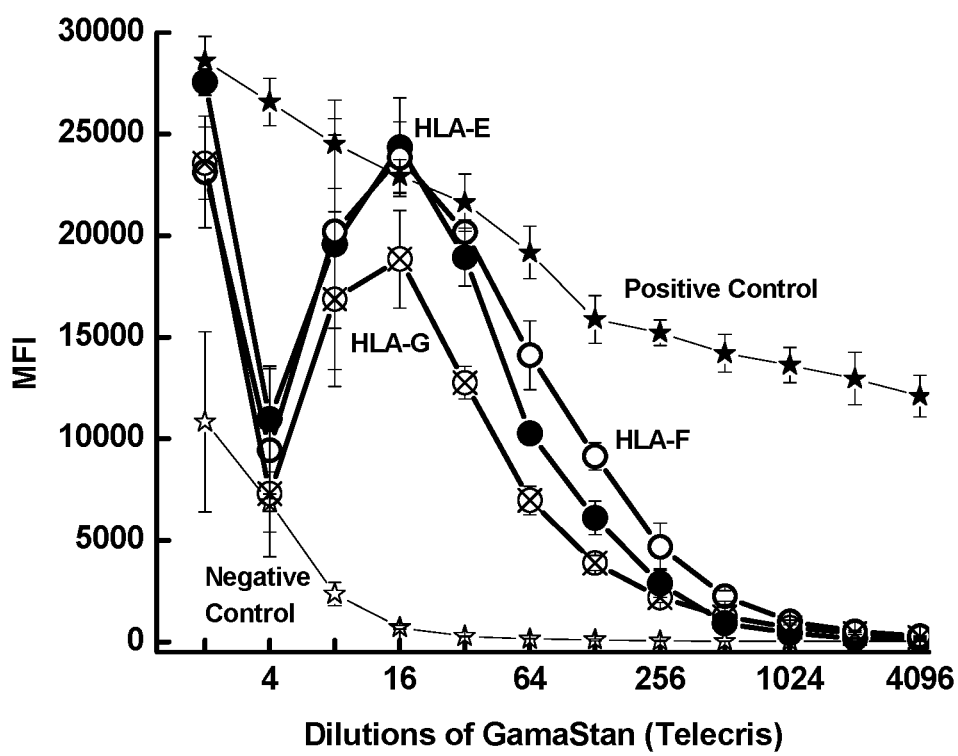

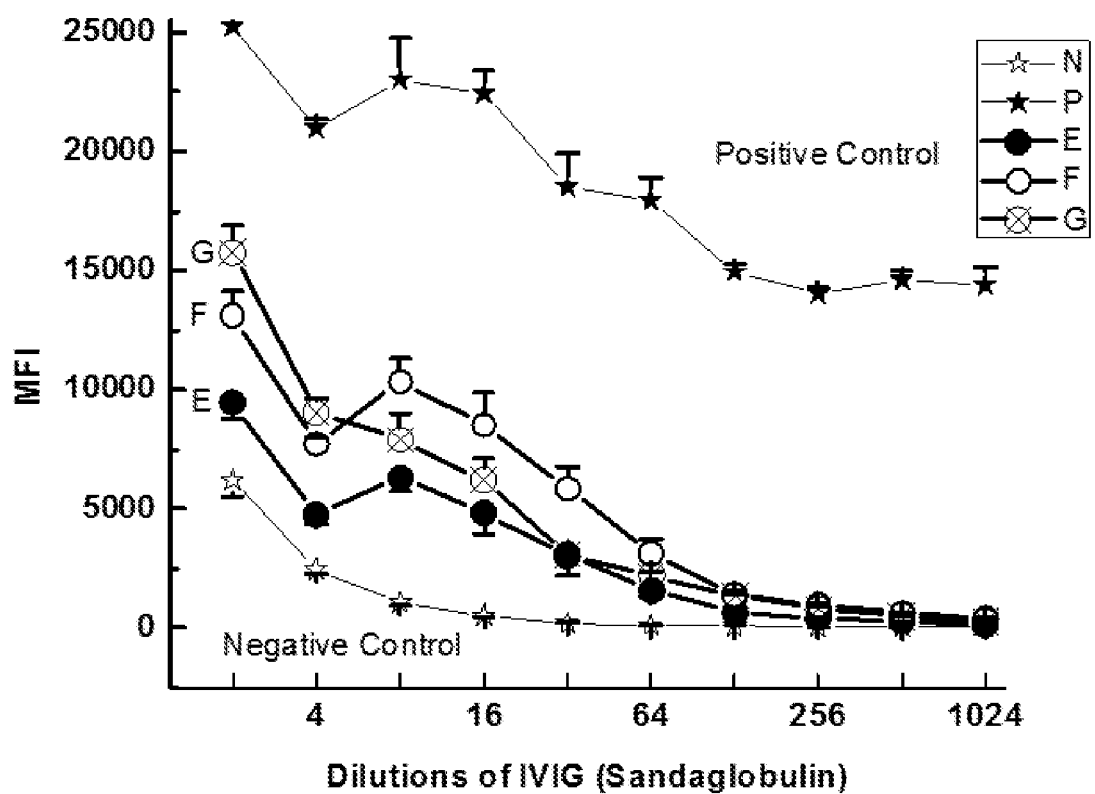
FIGURE 1B. IVIg Reactivity to all non-classical HLA-Ib molecules inclusive of HLA-E, HLA-F & HLA-G heavy chains (Source of IVIg: Sandoglobulin)

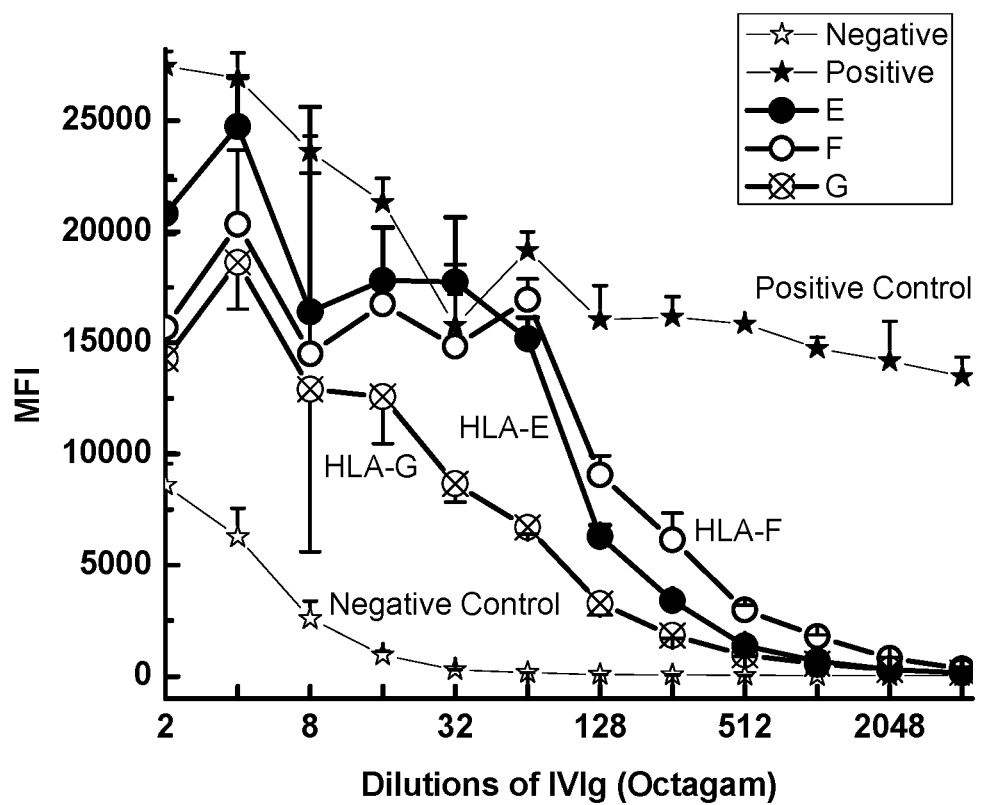
FIGURE 1C. IVIg Reactivity to all non-classical HLA-Ib molecules inclusive of HLA-E, HLA-F & HLA-G heavy chains (Octagam).

FIGURE 1D. IVIg Reactivity to all non-classical HLA-Ib molecules inclusive of HLA-E, HLA-F & HLA-G heavy chains IVIGlob® EX)
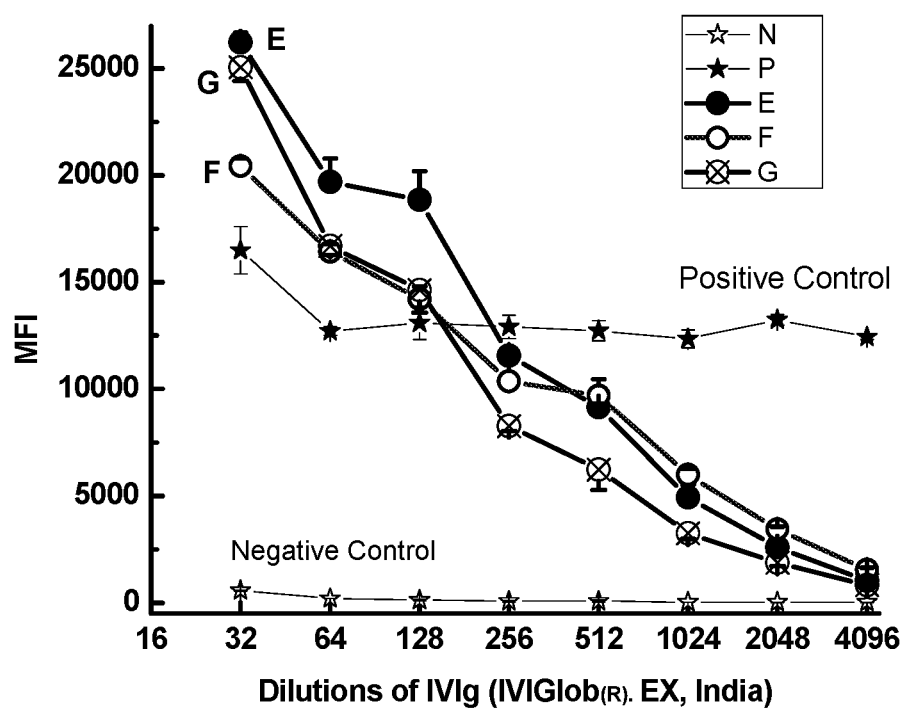

FIGURE 1E. IVIg also contains reactivity against negative control or beads coated with albumin (the beads obtained from One Lambda may be coated either with human and sometimes with bovine albumin).
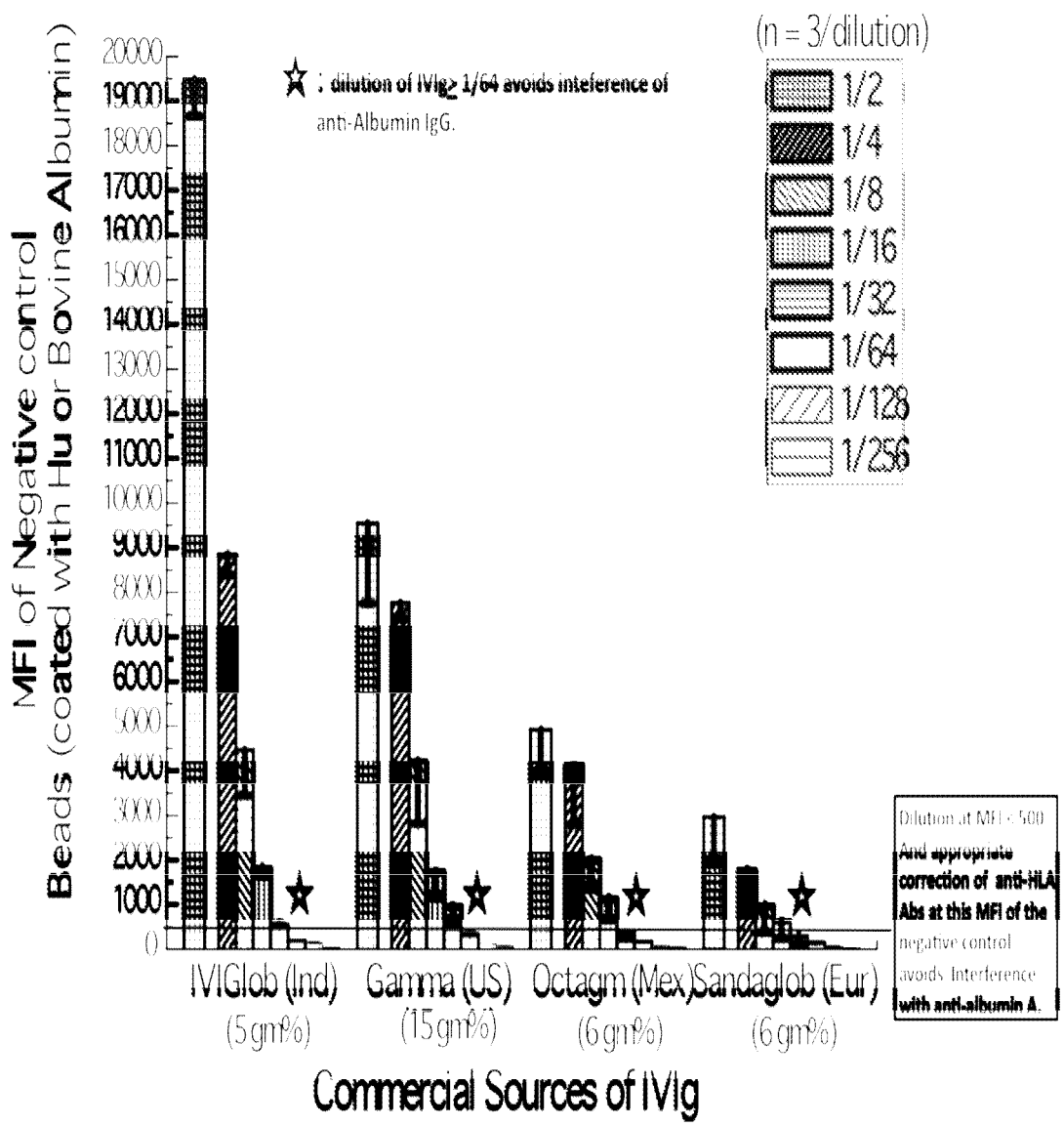

FIGURE 1F. Purified Human IgG commercially available (Source: Southern Biotech [Cat. No: 0150-01] Birmingham, Alabama, 35209) also reveals reactivity to HLA-E, HLA-F and HLA-G at varying degrees.
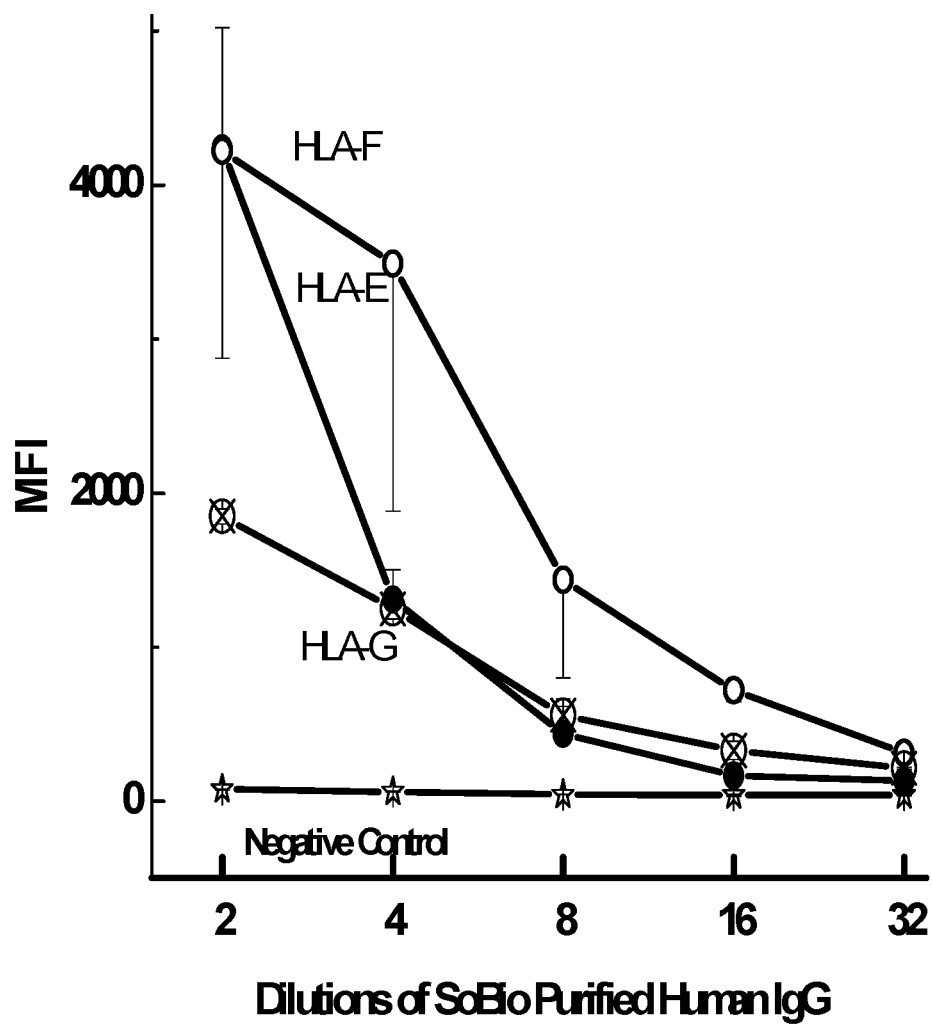

FIGURE 2. Evidence to show that HLA-Ia reactivity of IVIg from two different commercial sources is due to HLA Ia reactivity of anti-HLA-E antibodies
FIGURE 2A. IVIg Reactivity to all classical HLA-Ia molecules HLA-A, HLA-B and HLA-Cw alleles (GamaSTAN™ S/D, experiment done in triplicates)
▓ MFI: >10,000; ▓ MFI: 5000- 9,999; ▓ MFI: 2000- 4999; ▒ MFI: 1000-1999; ░ MFI: 500- 1999; ☐ MFI < 500;
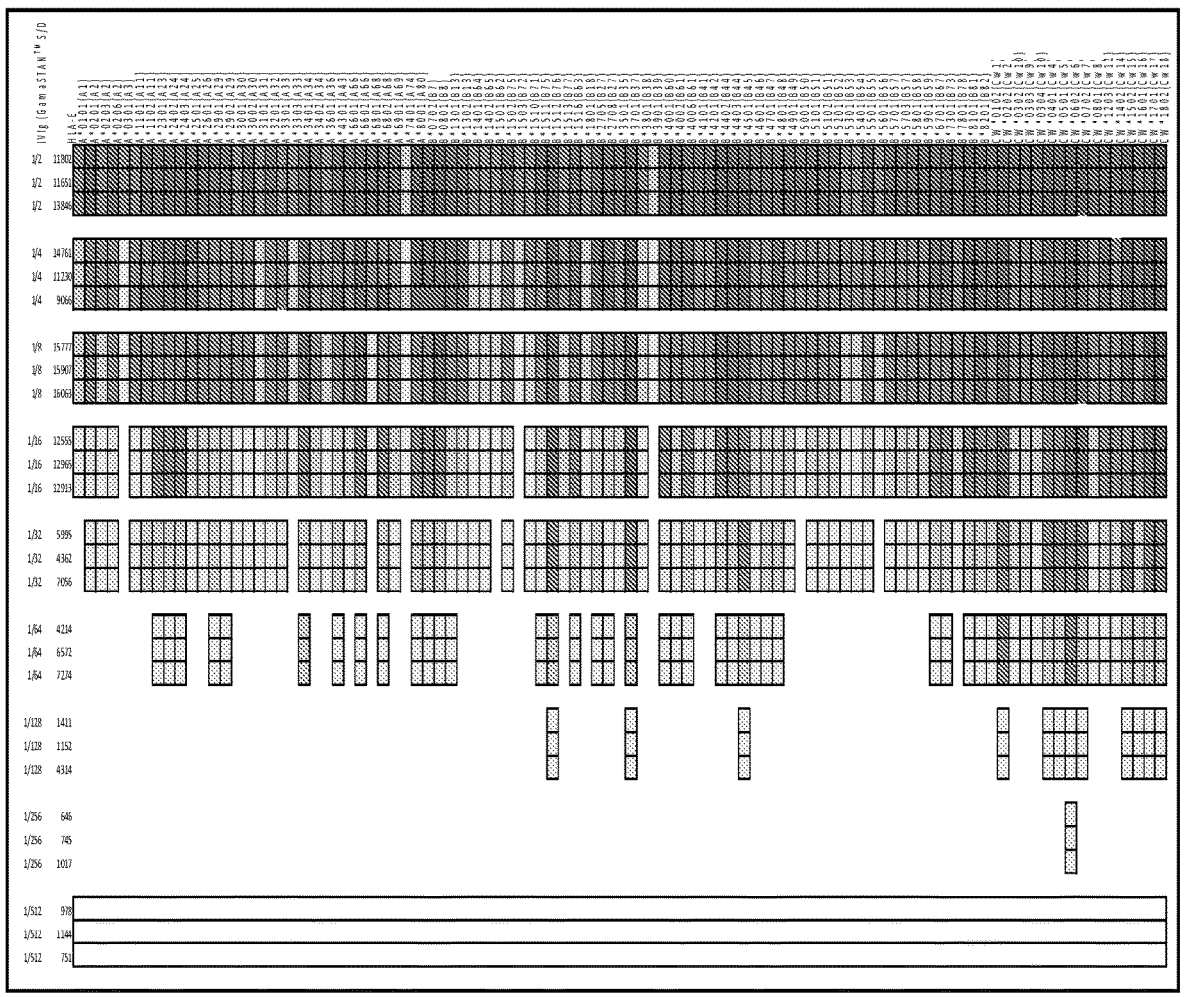

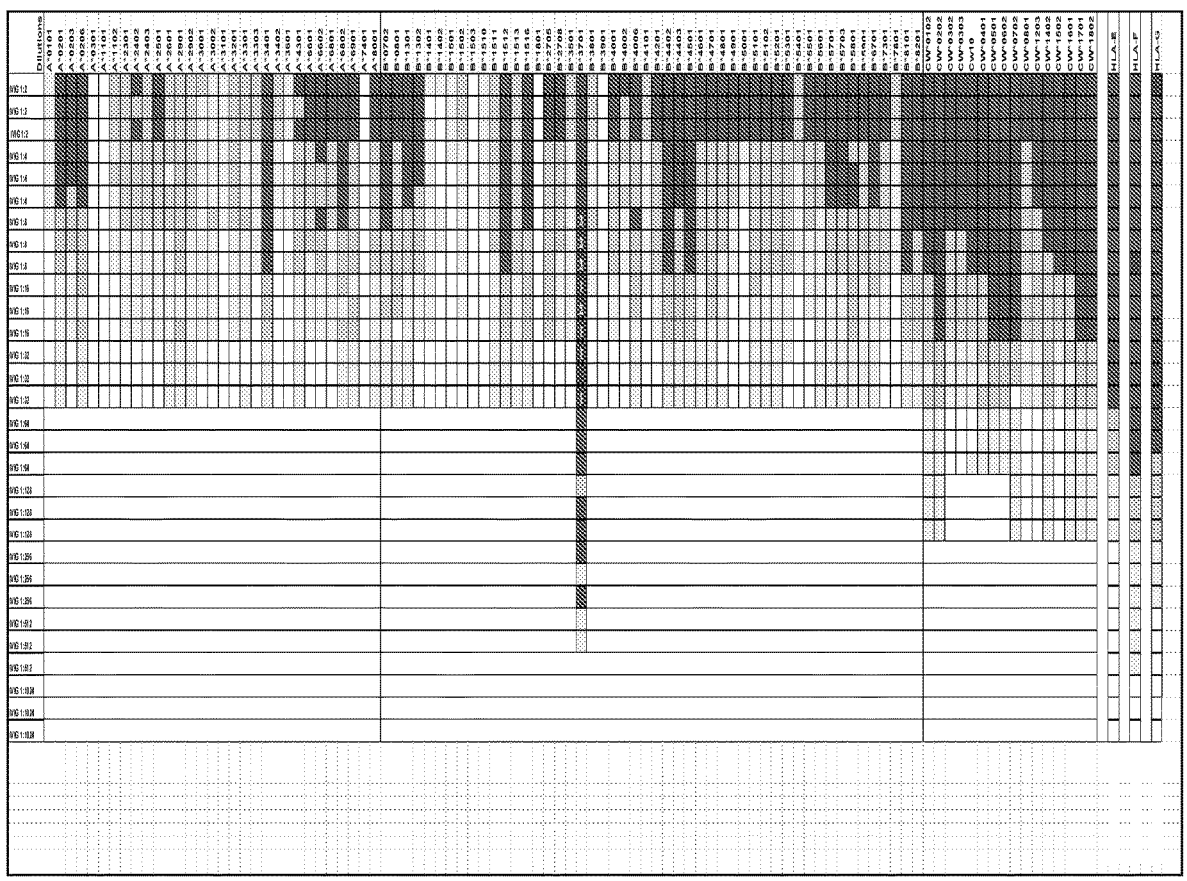
FIGURE 2B. IVIg Reactivity to all non-classical HLA-Ib molecules: HLA-E, HLA-F and HLA-G heavy chains, and all classical HLA-Ia molecules: HLA-A, HLA-B and HLA-Cw alleles (Sandoglobulin)

FIGURE 2C. IVIg Reactivity to all non-classical HLA-Ib molecules: HLA-E, HLA-F and HLA-G heavy chains, and all classical HLA-Ia molecules: HLA-A, HLA-B and HLA-Cw alleles (Octagam)
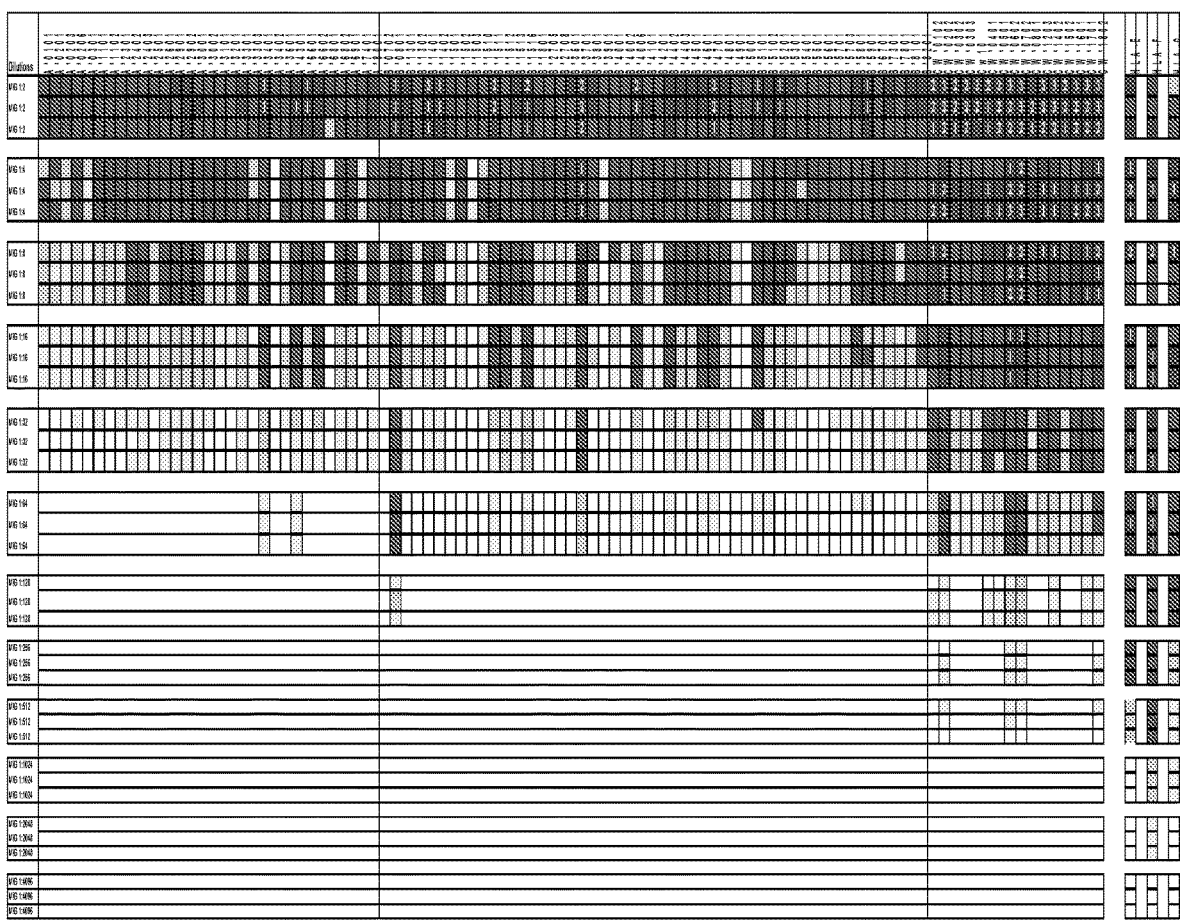

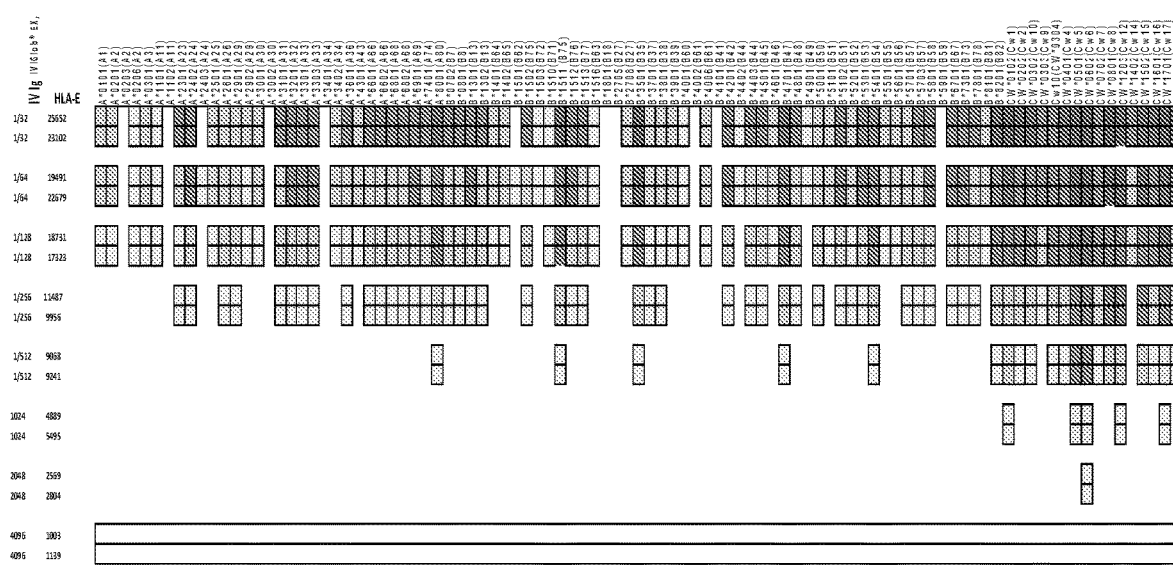
FIGURE 2D. IVIg reactivity to all classical HLA-Ia molecules HLA-A, HLA-B and HLA-Cw alleles (Source: IVIGlob® EX, VHB Life Sciences Ltd. India, experiments done in duplicates)

FIGURE 3. Both HLA-E and HLA-Ia reactivity of IVIg is lost after adsorbing IVIg to Affi-Gel conjugated with HLA-E.
FIGURE 3A. Loss of HLA-E reactivity of IVIG after adsorption with HLA-E-conjugated Affi-Gel 10
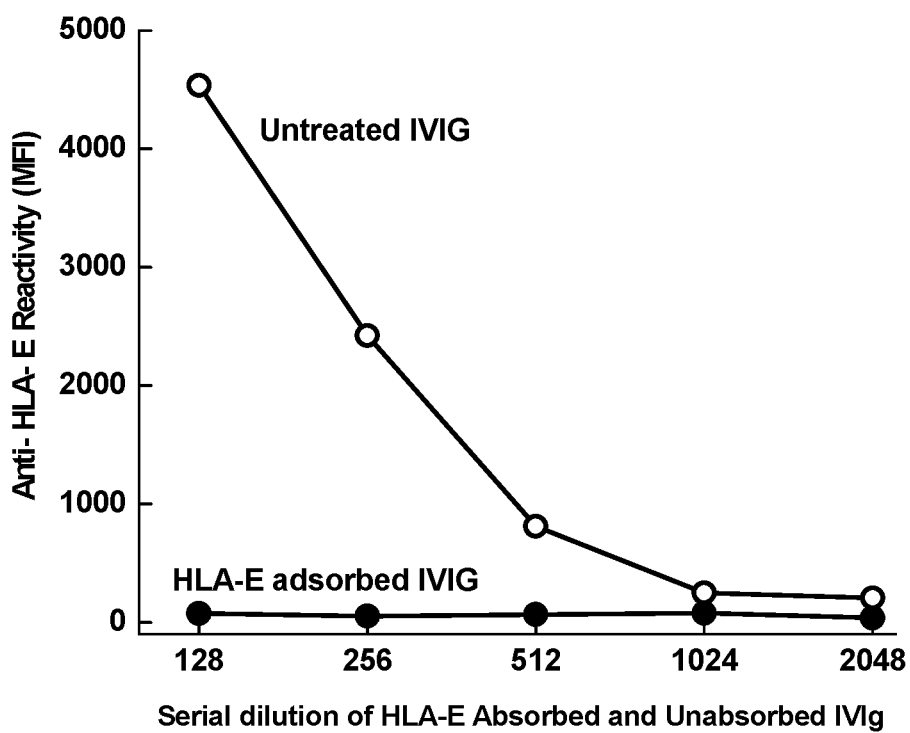

FIGURE 3B. Loss of HLA-Ia reactivity of IVIg after adsorption with HLA-E-conjugated Affi-Gel 10.
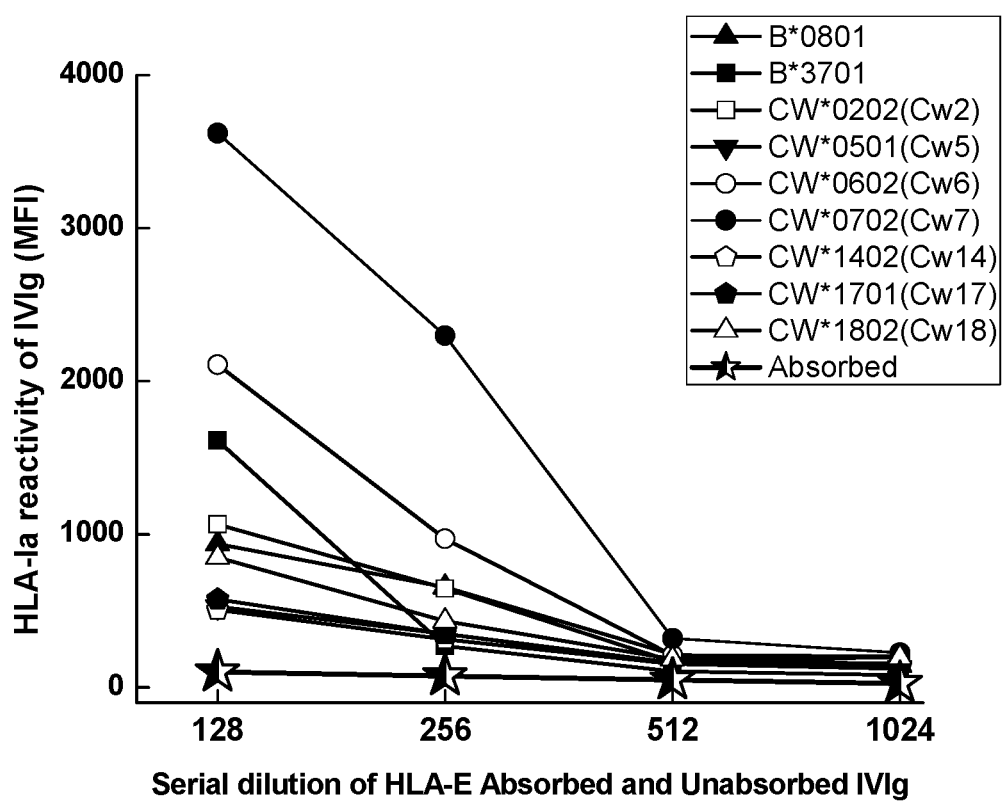

FIGURE 3C. Percentage Loss of HLA-E antibody reactivity of IVIg after adsorption with H

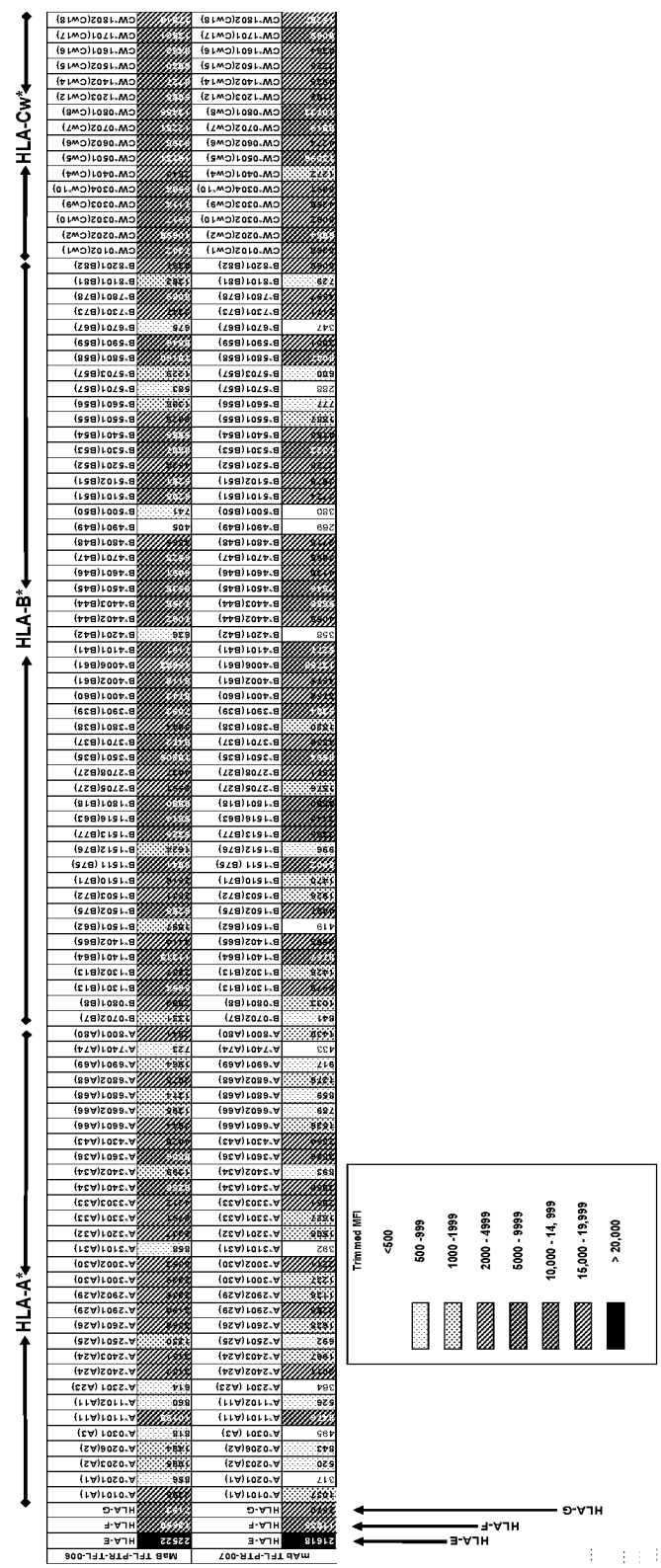
FIGURE 4A. HLA-Ia reactivity comparable to IVIG by anti-HLA-Ib murine monoclonal antibodies (PTER006 in upper row and PTER007 in lower row) reactive to HLA-Ib (HLA-E, HLA-F and HLA-G).

FIGURE 4B. HLA-Ia reactivity comparable to IVIg by anti-HLA-Ib murine monoclonal antibodies: PTER006, PTEG032, PTER007, PTEG016, and PTEG017, which are reactive to HLA-Ib (HLA-E, HLA-F and HLA-G).

| HLA-E^R | | | HLA-E^G | | | HLA-E^R | | | HLA-E^G | | | HLA-E^G | | |
|---|---|---|---|---|---|---|---|---|---|---|---|---|---|---|
| mAb-PTER006 | | | mAb-PTEG032 | | | mAb-PTER007 | | | mAb-PTEG016 | | | mAb-PTEG017 | | |
| IgG2a | | | IgG1 | | | IgG2a | | | IgG1 | | | IgG1 | | |
| E | 22522 | * | E | 15159 | * | E | 21618 | * | E | 13906 | * | E | 14842 | * |
| F | 12650 | * | F | 10193 | * | F | 11035 | * | F | 4985 | | F | 5167 | |
| G | 7193 | | G | 690 | | G | 2670 | | G | 11326 | * | G | 11150 | * |
| A/B/Cw | | | A/B/Cw | | | A/B/Cw | | | A/B/Cw | | | A/B/Cw | | |
| 31/50/16 | | | 29/48/16 | | | 26/44/16 | | | 22/44/16 | | | 21/43/16 | | |
| HLA-Ia | | | HLA-Ia | | | HLA-Ia | | | HLA-Ia | | | HLA-Ia | | |
| A*0101 | 2395 | | A*0203 | 2053 | | A*0101 | 1037 | | A*0101 | 760 | | A*0101 | 655 | |
| A*0201 | 856 | | A*0206 | 2931 | | A*0203 | 520 | | A*0206 | 949 | | A*0206 | 845 | |
| A*0203 | 1095 | | A*0301 | 5751 | | A*0206 | 843 | | A*1101 | 4187 | | A*1101 | 3744 | |
| A*0206 | 1494 | | A*1101 | 10309 | * | A*1101 | 8476 | | A*2402 | 1764 | | A*2402 | 1578 | |
| A*0301 | 818 | | A*1102 | 1171 | | A*1102 | 526 | | A*2403 | 1199 | | A*2403 | 1054 | |
| A*1101 | 10190 | * | A*2301 | 8029 | | A*2402 | 2011 | | A*2601 | 2466 | | A*2601 | 2204 | |
| A*1102 | 860 | | A*2402 | 13185 | * | A*2403 | 1967 | | A*2901 | 1549 | | A*2901 | 1347 | |
| A*2301 | 614 | | A*2403 | 11398 | * | A*2501 | 692 | | A*2902 | 553 | | A*2902 | 504 | |
| A*2402 | 3133 | | A*2501 | 708 | | A*2601 | 1638 | | A*3001 | 1264 | | A*3001 | 1071 | |
| A*2403 | 3151 | | A*2601 | 1172 | | A*2901 | 2256 | | A*3002 | 959 | | A*3002 | 812 | |
| A*2501 | 1230 | | A*2901 | 4837 | | A*2902 | 1136 | | A*3201 | 1003 | | A*3201 | 913 | |
| A*2601 | 3368 | | A*2902 | 5382 | | A*3001 | 1237 | | A*3301 | 1203 | | A*3301 | 1066 | |
| A*2901 | 3194 | | A*3001 | 4129 | | A*3002 | 2211 | | A*3303 | 1663 | | A*3303 | 1459 | |
| A*2902 | 2235 | | A*3002 | 6240 | | A*3201 | 1508 | | A*3401 | 560 | | A*3401 | 517 | |
| A*3001 | 2229 | | A*3101 | 3076 | | A*3301 | 1627 | | A*3402 | 1113 | | A*3402 | 988 | |
| A*3002 | 3353 | | A*3201 | 2909 | | A*3303 | 2961 | | A*3601 | 1417 | | A*3601 | 1266 | |
| A*3101 | 858 | | A*3301 | 5732 | | A*3401 | 3968 | | A*4301 | 893 | | A*4301 | 786 | |
| A*3201 | 2237 | | A*3303 | 6839 | | A*3402 | 893 | | A*6601 | 542 | | A*6801 | 519 | |
| A*3301 | 2791 | | A*3401 | 1494 | | A*3601 | 3826 | | A*6801 | 569 | | A*6802 | 1878 | |
| A*3303 | 4212 | | A*3402 | 4152 | | A*4301 | 2364 | | A*6802 | 2202 | | A*6901 | 729 | |
| A*3401 | 6268 | | A*3601 | 1044 | | A*6601 | 1526 | | A*6901 | 808 | | A*7401 | 1287 | |
| A*3402 | 1399 | | A*4301 | 576 | | A*6602 | 789 | | A*7401 | 1478 | | B*0702 | 584 | |
| A*3601 | 5806 | | A*6601 | 5904 | | A*6801 | 859 | | B*0702 | 680 | | B*0801 | 2129 | |
| A*4301 | 4420 | | A*6602 | 3197 | | A*6802 | 1276 | | B*0801 | 2398 | | B*1301 | 3927 | |
| A*6601 | 3644 | | A*6801 | 4866 | | A*6901 | 917 | | B*1301 | 4444 | | B*1302 | 2534 | |
| A*6602 | 1395 | | A*6802 | 1830 | | A*8001 | 1430 | | B*1302 | 2842 | | B*1401 | 993 | |

Figure 4B Continued

| HLA-E^R | | | HLA-E^G | | | HLA-E^R | | | HLA-E^G | | | HLA-E^G | |
|---|---|---|---|---|---|---|---|---|---|---|---|---|---|
| mAb-PTER006 | | | mAb-PTEG032 | | | mAb-PTER007 | | | mAb-PTEG016 | | | mAb-PTEG017 | |
| IgG2a | | | IgG1 | | | IgG2a | | | IgG1 | | | IgG1 | |
| A*6801 | 1314 | | A*6901 | 5185 | | B*0702 | 841 | | B*1401 | 1179 | | B*1501 | 1870 |
| A*6802 | 2078 | | A*7401 | 2215 | | B*0801 | 1033 | | B*1501 | 2038 | | B*1502 | 1139 |
| A*6901 | 1964 | | A*8001 | 13073 | * | B*1301 | 3979 | | B*1502 | 1306 | | B*1503 | 1065 |
| A*7401 | 723 | | B*0702 | 17930 | | B*1302 | 1426 | | B*1503 | 1186 | | B*1511 | 6385 |
| A*8001 | 2841 | | B*0801 | 2309 | | B*1401 | 8767 | | B*1511 | 7154 | | B*1512 | 2358 |
| B*0702 | 1331 | | B*1301 | 18154 | * | B*1402 | 2558 | | B*1512 | 2655 | | B*1513 | 1207 |
| B*0801 | 2092 | | B*1302 | 12789 | * | B*1502 | 4497 | | B*1513 | 1403 | | B*1516 | 1911 |
| B*1301 | 5654 | | B*1401 | 14603 | * | B*1503 | 1926 | | B*1516 | 2117 | | B*2708 | 2103 |
| B*1302 | 2237 | | B*1402 | 8465 | | B*1510 | 1470 | | B*2705 | 568 | | B*3501 | 2057 |
| B*1401 | 11319 | * | B*1501 | 4802 | | B*1511 | 5902 | | B*2708 | 2338 | | B*3701 | 1053 |
| B*1402 | 4414 | | B*1502 | 18673 | * | B*1512 | 996 | | B*3501 | 2436 | | B*3901 | 2861 |
| B*1501 | 1097 | | B*1503 | 16573 | * | B*1513 | 3365 | | B*3701 | 1176 | | B*4001 | 1304 |
| B*1502 | 6256 | | B*1510 | 7273 | | B*1516 | 3443 | | B*3901 | 3289 | | B*4002 | 2241 |
| B*1503 | 2831 | | B*1511 | 14785 | * | B*1801 | 4890 | | B*4001 | 1493 | | B*4006 | 893 |
| B*1510 | 2616 | | B*1512 | 3176 | | B*2705 | 1576 | | B*4002 | 2580 | | B*4201 | 2957 |
| B*1511 | 9041 | | B*1513 | 1416 | | B*2708 | 2671 | | B*4006 | 1029 | | B*4402 | 2416 |
| B*1512 | 1624 | | B*1516 | 13709 | * | B*3501 | 8594 | | B*4201 | 3388 | | B*4403 | 849 |
| B*1513 | 5326 | | B*1801 | 10440 | * | B*3701 | 4338 | | B*4402 | 2699 | | B*4501 | 2154 |
| B*1516 | 5614 | | B*2705 | 7853 | | B*3801 | 1820 | | B*4403 | 953 | | B*4601 | 1151 |
| B*1801 | 6990 | | B*2708 | 4557 | | B*3901 | 5304 | | B*4501 | 2439 | | B*4701 | 1656 |
| B*2705 | 2591 | | B*3501 | 19181 | * | B*4001 | 3758 | | B*4601 | 1331 | | B*4801 | 727 |
| B*2708 | 4437 | | B*3701 | 15169 | * | B*4002 | 4675 | | B*4701 | 1903 | | B*5001 | 2728 |
| B*3501 | 10205 | * | B*3801 | 12575 | * | B*4006 | 13758 | * | B*4801 | 814 | | B*5101 | 1575 |
| B*3701 | 6472 | | B*3901 | 19172 | * | B*4101 | 5277 | | B*5001 | 2984 | | B*5102 | 1289 |
| B*3801 | 3844 | | B*4001 | 15242 | * | B*4402 | 4059 | | B*5101 | 1763 | | B*5201 | 5890 |
| B*3901 | 7093 | | B*4002 | 3667 | | B*4403 | 5638 | | B*5102 | 1446 | | B*5301 | 1923 |
| B*4001 | 5743 | | B*4006 | 3933 | | B*4501 | 7646 | | B*5201 | 6656 | | B*5401 | 1539 |
| B*4002 | 6118 | | B*4101 | 15326 | * | B*4601 | 4130 | | B*5301 | 2161 | | B*5501 | 760 |
| B*4006 | 15643 | * | B*4201 | 8756 | | B*4701 | 3895 | | B*5401 | 1721 | | B*5601 | 1335 |
| B*4101 | 7191 | | B*4402 | 6030 | | B*4801 | 2716 | | B*5501 | 861 | | B*5701 | 2112 |
| B*4201 | 636 | | B*4403 | 780 | | B*5101 | 3724 | | B*5601 | 1494 | | B*5703 | 5108 |
| B*4402 | 7062 | | B*4501 | 19369 | * | B*5102 | 3579 | | B*5701 | 2377 | | B*5801 | 2721 |
| B*4403 | 7256 | | B*4601 | 17359 | * | B*5201 | 2728 | | B*5703 | 5710 | | B*5901 | 284 |
| B*4501 | 9535 | | B*4701 | 20225 | * | B*5301 | 7323 | | B*5801 | 3197 | | B*6701 | 1378 |
| B*4601 | 6491 | | B*5001 | 3777 | | B*5401 | 4153 | | B*5901 | 319 | | B*7301 | 1661 |
| B*4701 | 6528 | | B*5101 | 1505 | | B*5501 | 1887 | | B*6701 | 1592 | | B*7801 | 777 |

Figure 4B Continued

| HLA-E^R | | | HLA-E^G | | | HLA-E^R | | | HLA-E^G | | | HLA-E^G | | |
|---|---|---|---|---|---|---|---|---|---|---|---|---|---|---|
| mAb-PTER006 | | | mAb-PTEG032 | | | mAb-PTER007 | | | mAb-PTEG016 | | | mAb-PTEG017 | | |
| IgG2a | | | IgG1 | | | IgG2a | | | IgG1 | | | IgG1 | | |
| B*4801 | 4365 | | B*5102 | 1786 | | B*5601 | 777 | | B*7301 | 1883 | | B*8101 | 2049 | |
| B*4901 | 405 | | B*5201 | 9110 | | B*5703 | 600 | | B*7801 | 908 | | B*8201 | 3241 | |
| B*5001 | 741 | | B*5301 | 2506 | | B*5801 | 8047 | | B*8101 | 2336 | | CW*0102 | 2305 | |
| B*5101 | 6205 | | B*5401 | 2544 | | B*5901 | 3001 | | B*8201 | 3514 | | CW*0202 | 2062 | |
| B*5102 | 5251 | | B*5501 | 2375 | | B*7301 | 2171 | | CW*0102 | 2629 | | CW*0302 | 1956 | |
| B*5201 | 4524 | | B*5601 | 3833 | | B*7801 | 4597 | | CW*0202 | 2302 | | CW*0303 | 2757 | |
| B*5301 | 8807 | | B*5701 | 4811 | | B*8101 | 729 | | CW*0302 | 2233 | | CW*0304 | 1848 | |
| B*5401 | 5556 | | B*5703 | 11525 | * | B*8201 | 3069 | | CW*0303 | 3138 | | CW*0401 | 5625 | |
| B*5501 | 2829 | | B*5801 | 2261 | | CW*0102 | 3268 | | CW*0304 | 2130 | | CW*0501 | 2570 | |
| B*5601 | 1386 | | B*5901 | 8155 | | CW*0202 | 6084 | | CW*0401 | 6299 | | CW*0602 | 6370 | |
| B*5701 | 583 | | B*6701 | 4023 | | CW*0302 | 3062 | | CW*0501 | 2937 | | CW*0702 | 5668 | |
| B*5703 | 1229 | | B*7301 | 3542 | | CW*0303 | 4250 | | CW*0602 | 7058 | | CW*0801 | 1470 | |
| B*5801 | 10160 | * | B*7801 | 17954 | * | CW*0304 | 3891 | | CW*0702 | 6194 | | CW*1203 | 2705 | |
| B*5901 | 5646 | | B*8101 | 19959 | * | CW*0401 | 1272 | | CW*0801 | 1670 | | CW*1402 | 2453 | |
| B*6701 | 675 | | B*8201 | 19447 | * | CW*0501 | 13096 | * | CW*1203 | 3059 | | CW*1502 | 2803 | |
| B*7301 | 3347 | | CW*0102 | 19355 | * | CW*0602 | 4274 | | CW*1402 | 2830 | | CW*1601 | 6267 | |
| B*7801 | 6089 | | CW*0202 | 14059 | * | CW*0702 | 6919 | | CW*1502 | 3247 | | CW*1701 | 6017 | |
| B*8101 | 1352 | | CW*0302 | 759 | | CW*0801 | 10733 | * | CW*1601 | 7137 | | CW*1802 | 3660 | |
| B*8201 | 4367 | | CW*0303 | 6821 | | CW*1203 | 2102 | | CW*1701 | 6788 | | | | |
| CW*0102 | 7242 | | CW*0304 | 1989 | | CW*1402 | 4936 | | CW*1802 | 4093 | | | | |
| CW*0202 | 10690 | * | CW*0401 | 18124 | * | CW*1502 | 3225 | | | | | | | |
| CW*0302 | 5917 | | CW*0501 | 6515 | | CW*1601 | 4364 | | | | | | | |
| CW*0303 | 7114 | | CW*0602 | 4640 | | CW*1701 | 9069 | | | | | | | |
| CW*0304 | 6584 | | CW*0702 | 17837 | | CW*1802 | 15207 | * | | | | | | |
| CW*0401 | 2843 | | CW*0801 | 20752 | * | | | | | | | | | |
| CW*0501 | 16131 | * | CW*1203 | 19529 | * | | | | | | | | | |
| CW*0602 | 9396 | | CW*1402 | 9648 | | | | | | | | | | |
| CW*0702 | 12251 | * | CW*1502 | 20503 | * | | | | | | | | | |
| CW*0801 | 13456 | * | CW*1601 | 19745 | * | | | | | | | | | |
| CW*1203 | 5055 | | CW*1701 | 13087 | * | | | | | | | | | |
| CW*1402 | 8727 | | CW*1802 | 8774 | | | | | | | | | | |
| CW*1502 | 6030 | | | | | | | | | | | | | |
| CW*1601 | 8462 | | | | | | | | | | | | | |
| CW*1701 | 13521 | * | | | | | | | | | | | | |
| CW*1802 | 17918 | * | | | | | | | | | | | | |

FIGURE 5. T-lymphocyte modulatory activity of IVIG and TFL anti-HLA-Ib mAbs (PTER007 and PTER006) reactive to both HLA-classes Ia and Ib similar to IVIG.
FIGURE 5A. Events occurring 70 hrs after PHA-L stimulation of T-Lymphocytes (CD3+/CD4+).
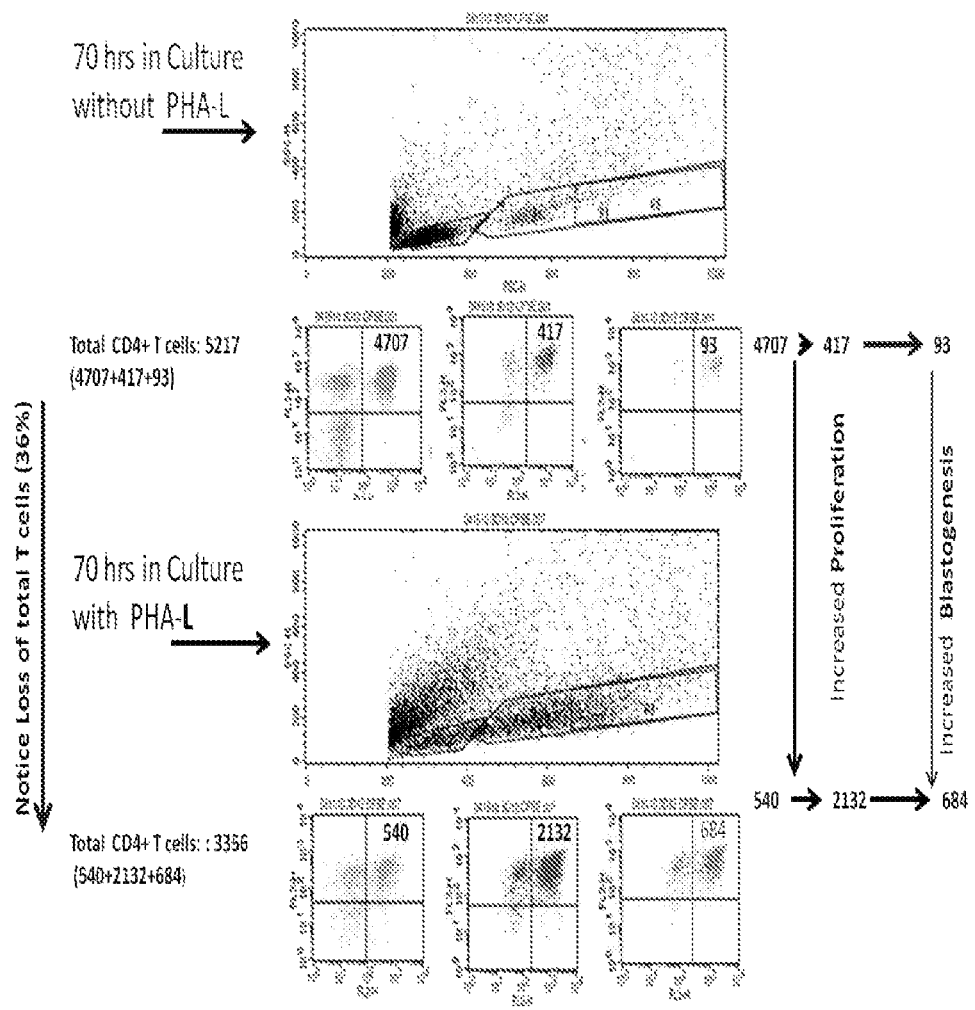

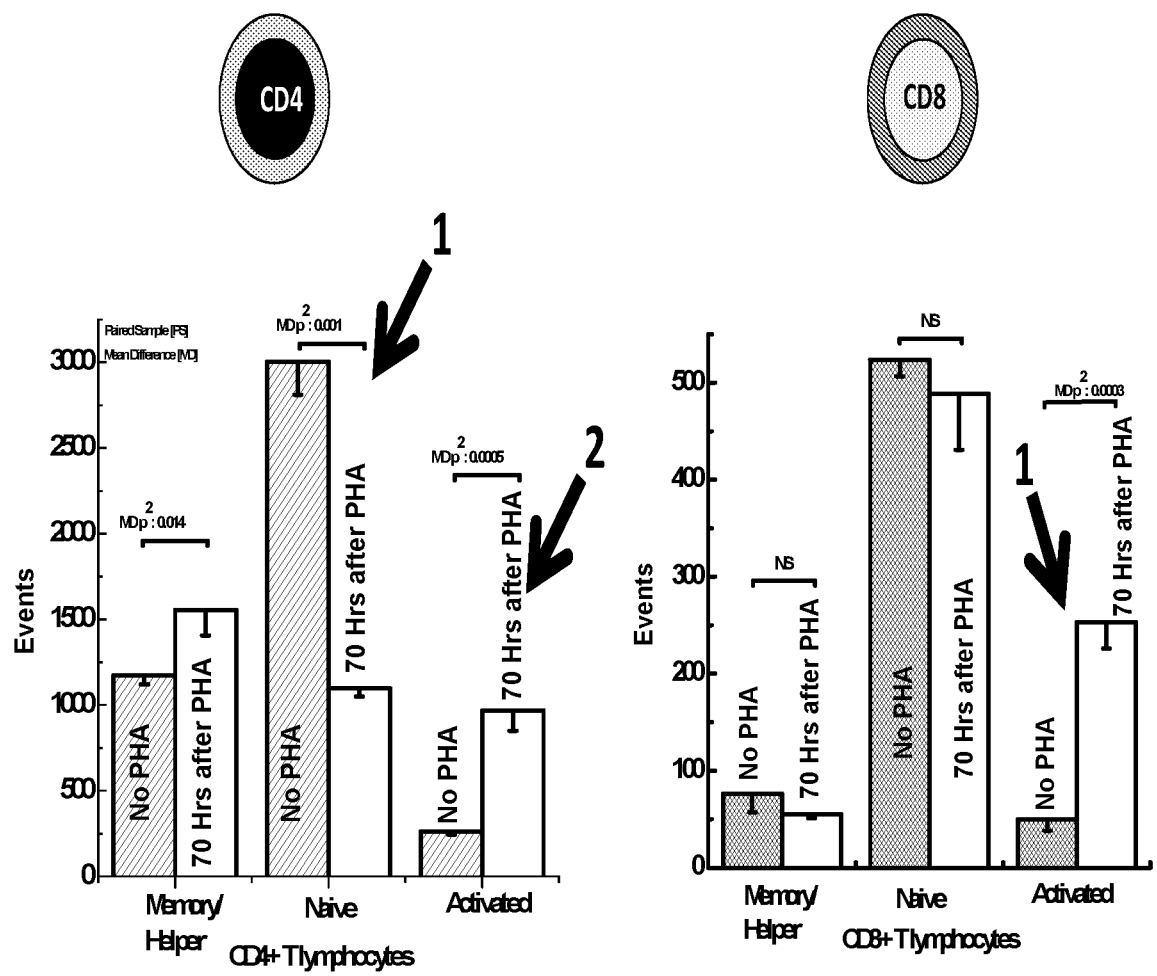
FIGURE 5B. Changes that occur in T-lymphocyte populations 70 hrs after PHA-L stimulation

FIGURE 5C. Human IVIg induces cell death, arrests proliferation and blastogenesis of PHA-L stimulated T-lymphocytes (CD3+/CD4+).
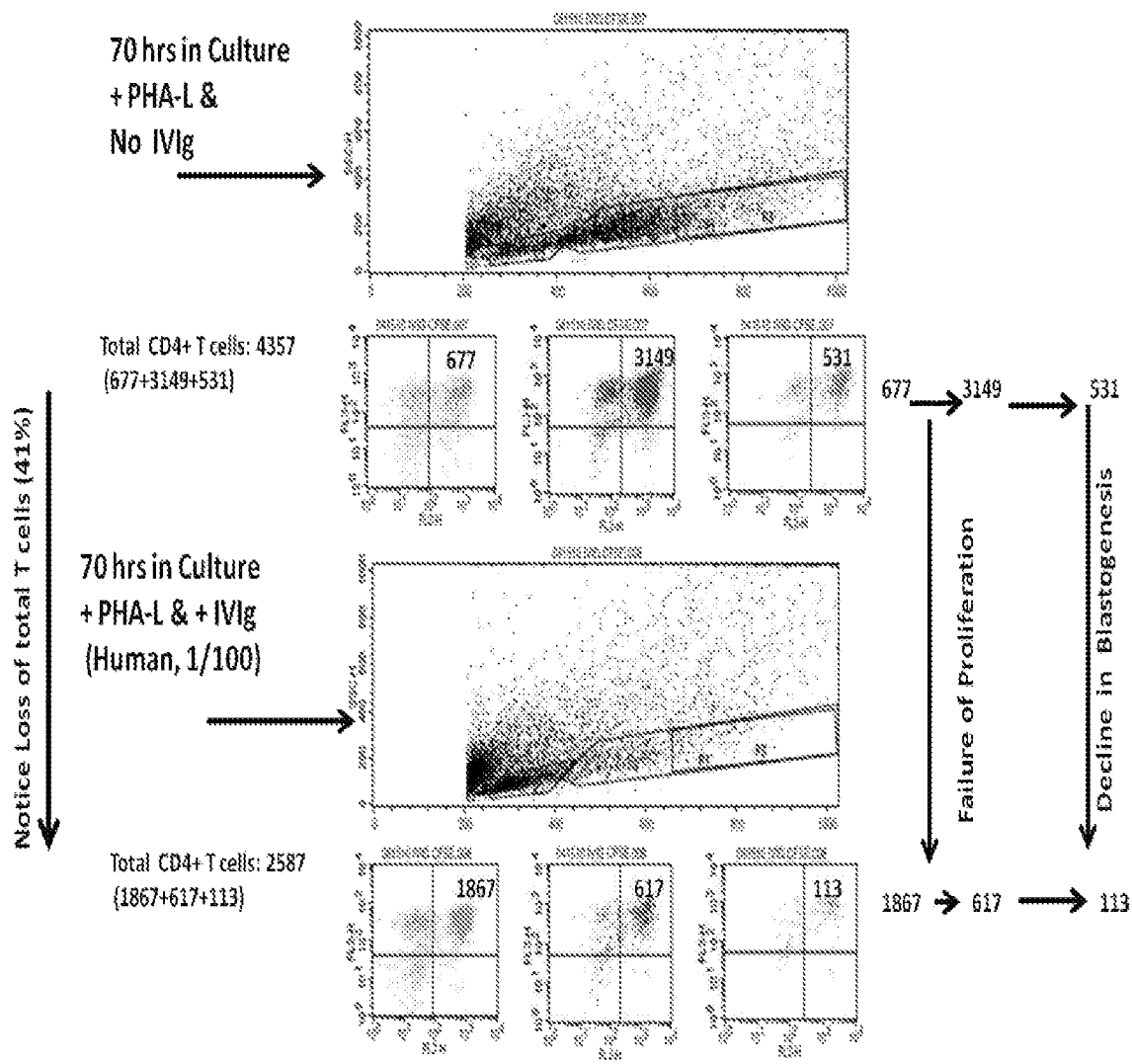

FIGURE 5D. IVIG dosimetrically (at different dilutions) inhibits PHA-stimulated CD4+ T-lymphocytes and T-lymphoblasts
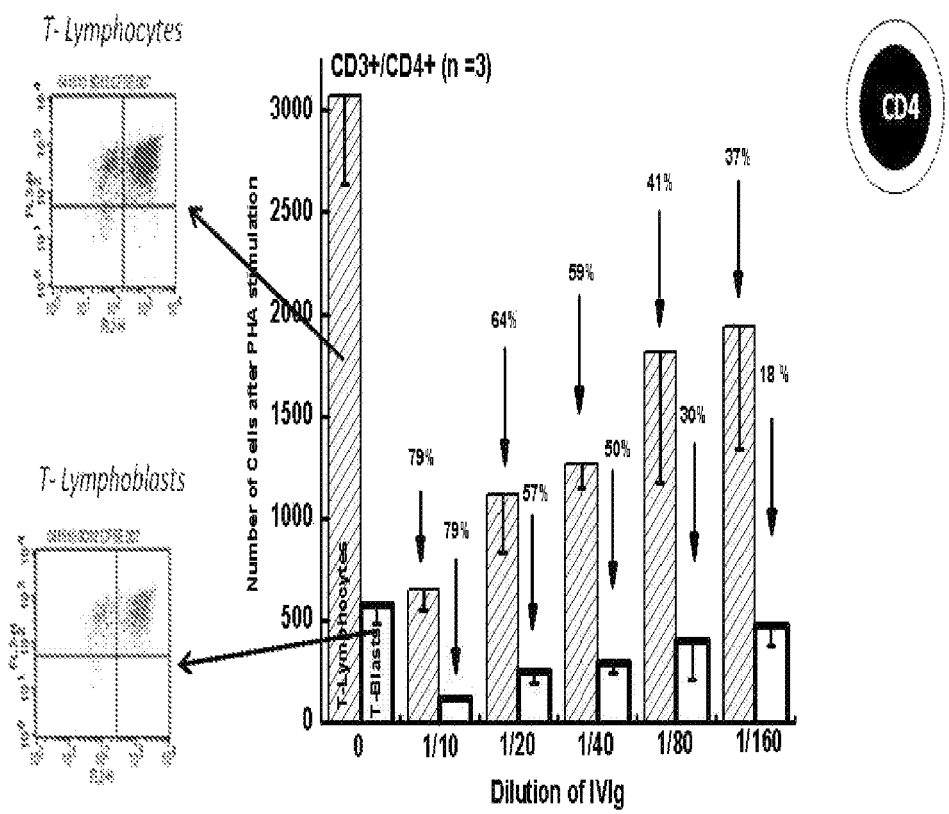
| | | 0 | | 1/8 | | 1/16 | | 1/32 | | 1/64 | | 1/128 | |
|---|---|---|---|---|---|---|---|---|---|---|---|---|---|
| | CD4 | T-cells | T-blasts | T-cells | T-blasts | T-cells | T-blasts | T-cells | T-blasts | T-cells | T-blasts | T-cells | T-blasts |
| IvIg | PHA | 3149 | 531 | 617 | 113 | 1299 | 295 | 1311 | 290 | 1190 | 258 | 2382 | 522 |
| | | 2603 | 511 | 751 | 127 | 1243 | 256 | 1133 | 237 | 1787 | 321 | 2173 | 535 |
| | | 3461 | 675 | 571 | 121 | 791 | 190 | 1346 | 336 | 2470 | 621 | 1259 | 357 |

FIGURE 5E. IVIg dosimetrically (at different dilutions) inhibits PHA-stimulated CD8+ T-lymphocytes and T-lymphoblasts.
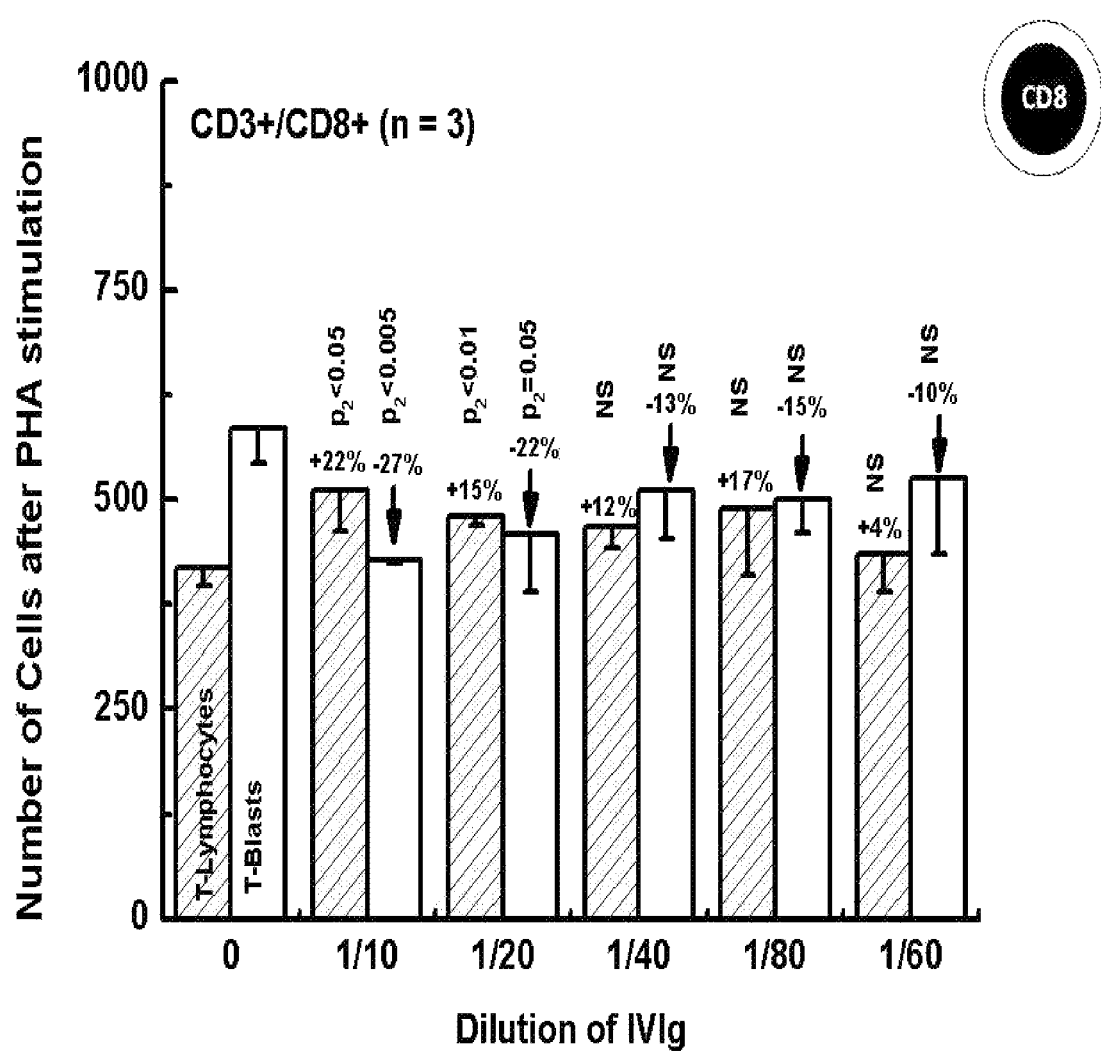

FIGURE 5F. Anti-HLA-Ib monoclonal antibodies (PTER007 at 1/10 dilution) induce arrests of proliferation and blastogenesis of PHA-L stimulated CD4+ T-lymphocytes.
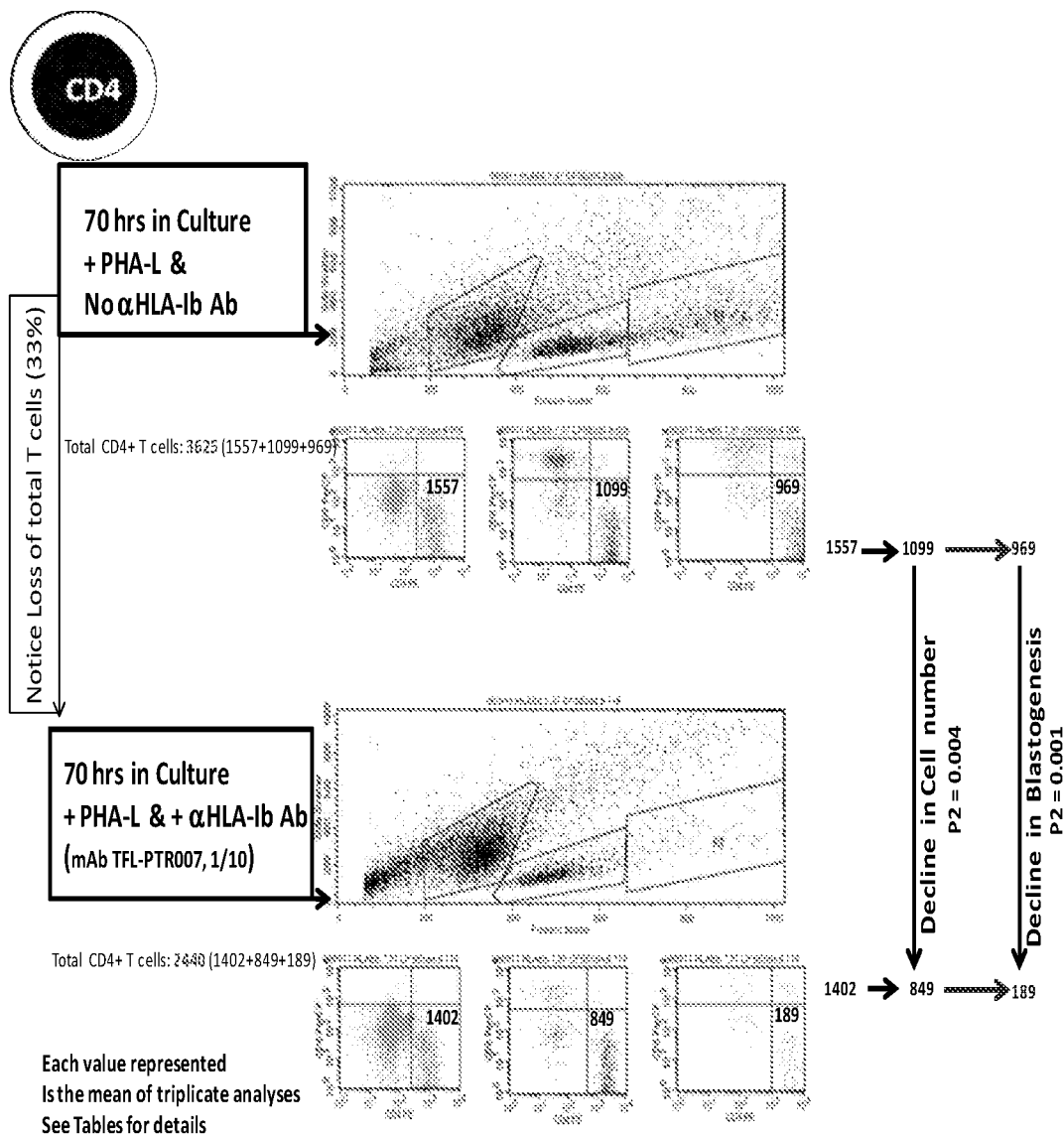

FIGURE 5G. Anti-HLA-Ib monoclonal antibodies (PTER007 at 1/100 dilution) induce arrests of proliferation and blastogenesis of PHA-L stimulated CD4+ T-lymphocytes.
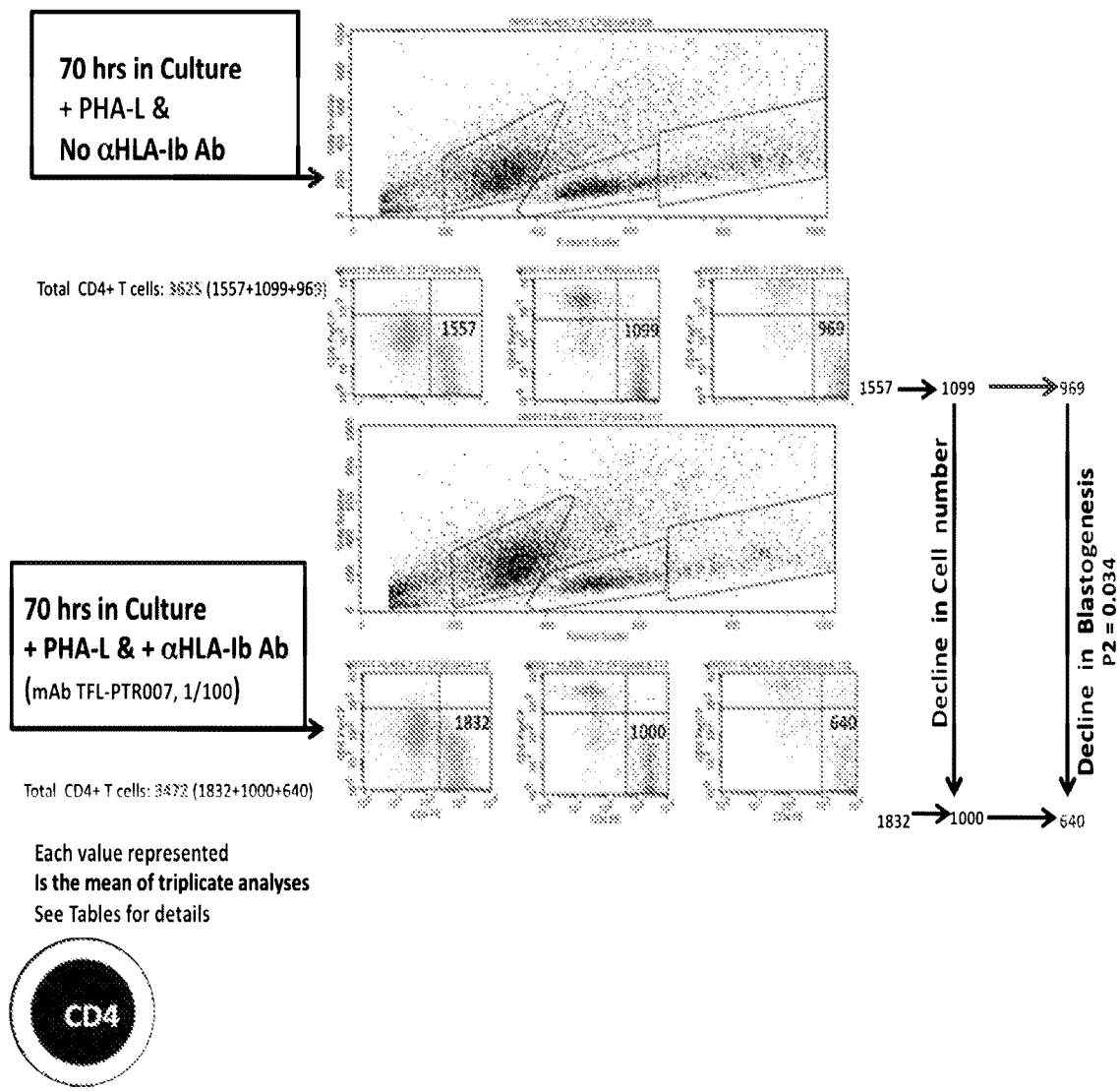
Each value represented
Is the mean of triplicate analyses
See Tables for details

FIGURE 5H. Anti-HLA-Ib monoclonal antibodies (PTER007 at 1/10 & 1/100 dilutions) induce arrests of proliferation and blastogenesis of PHA-L stimulated CD8+ T-lymphocytes.
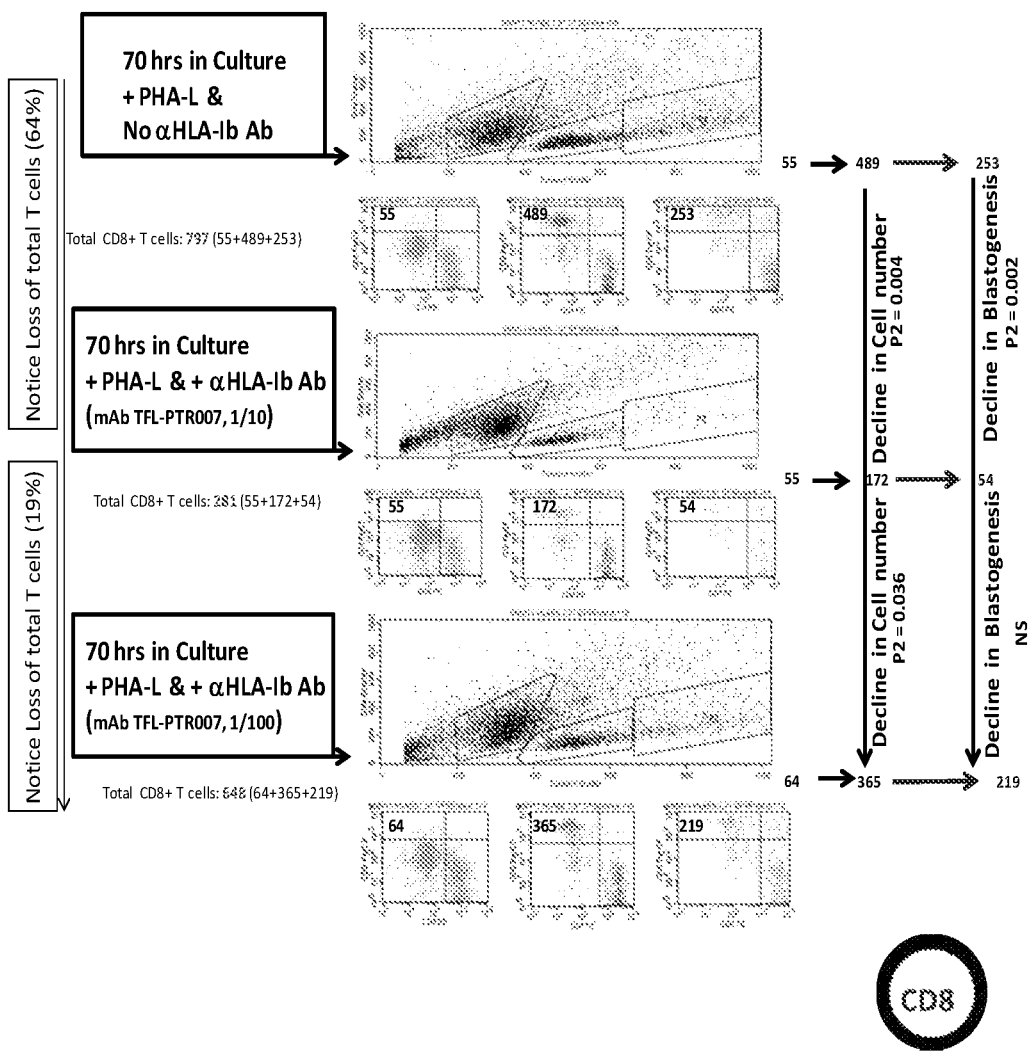

FIGURE 5I. Another anti-HLA-Ib monoclonal antibodies (PTER006) arrest blastogenesis of PHA-L stimulated CD4+ and CD8+ T-lymphocytes at 1/10 dilution. At 1/100 dilution of PTER006, the failure of proliferation of CD4+ T cells were significant at p2 <0.05 decline in Blastogenesis of CD8+ T cells were significant at p2<0.05.
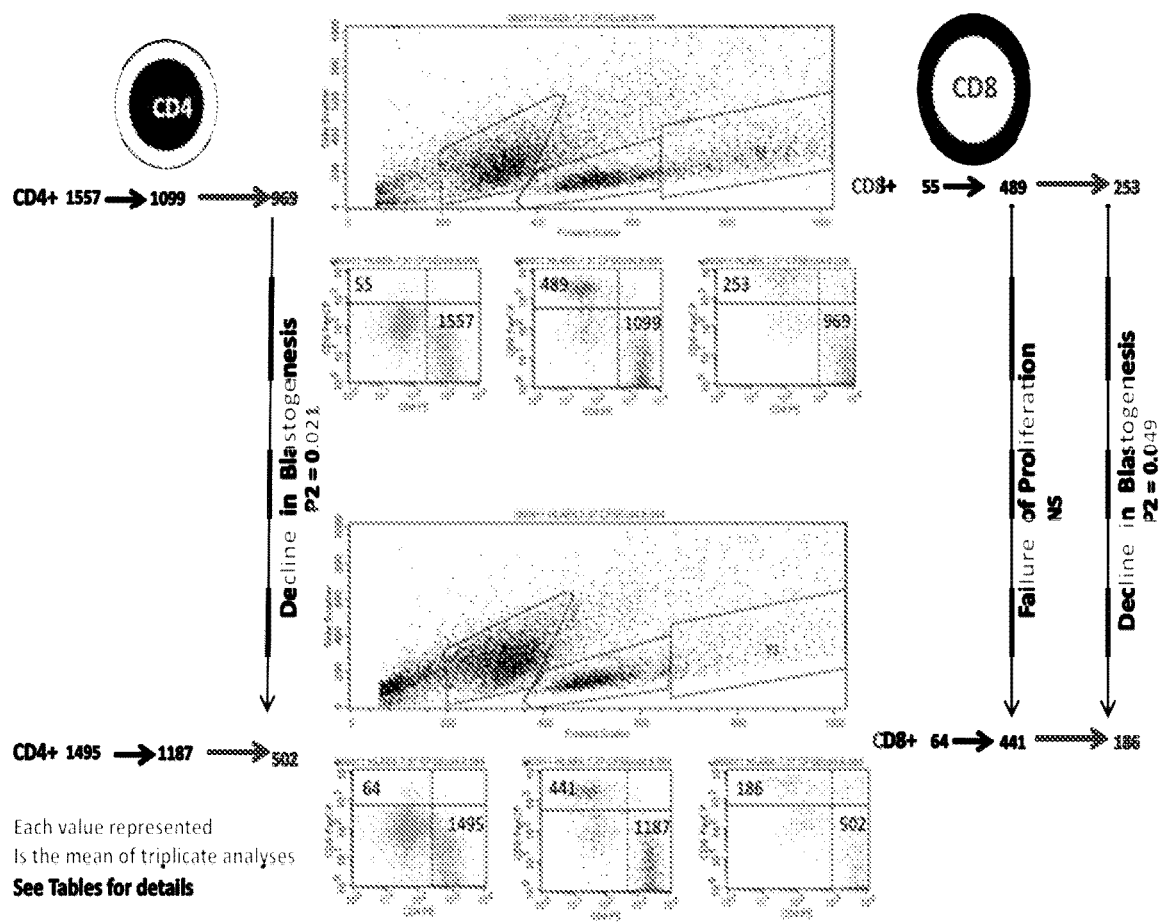

FIGURE 5J. Anti-HLA-Ib monoclonal antibodies (PTER037: non-reactive to HLA-F & -G; PTER006; and PTER007: at two different dilutions) inhibit PHA-stimulated CD4+ T-lymphocytes and T lymphoblasts (Activated).
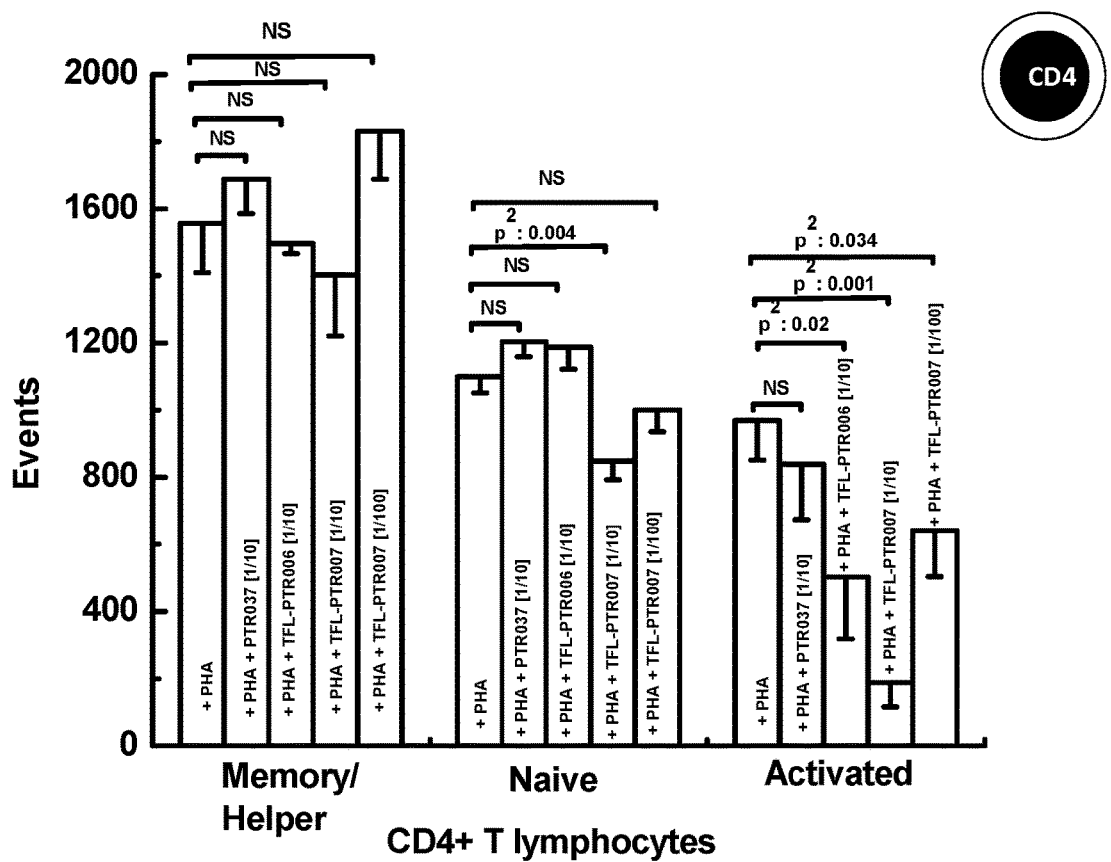

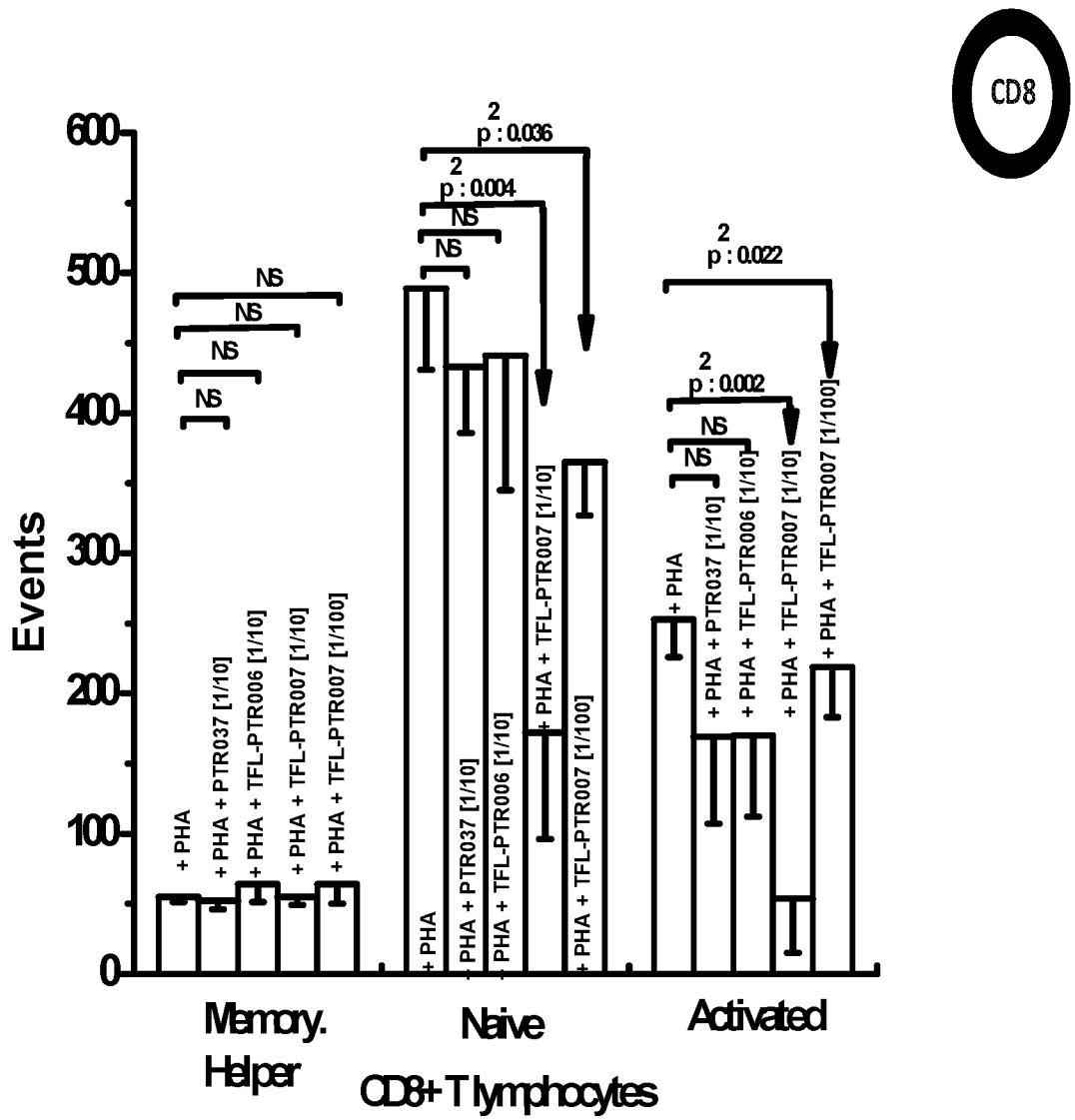
FIGURE 5K. Anti-HLA-Ib monoclonal antibodies (PTER037: non-reactive to HLA-F & -G; PTER006; and PTER007: at two different dilutions) inhibit PHA-stimulated CD8+ T-lymphocytes and T lymphoblasts (Activated).

FIGURE 5L. Illustrated Summary of the influence of anti-HLA-Ib monoclonal antibodies PTER007 at two different dilutions) inhibits PHA-stimulated CD8+ T-lymphocytes and T lymphoblasts (Activated).
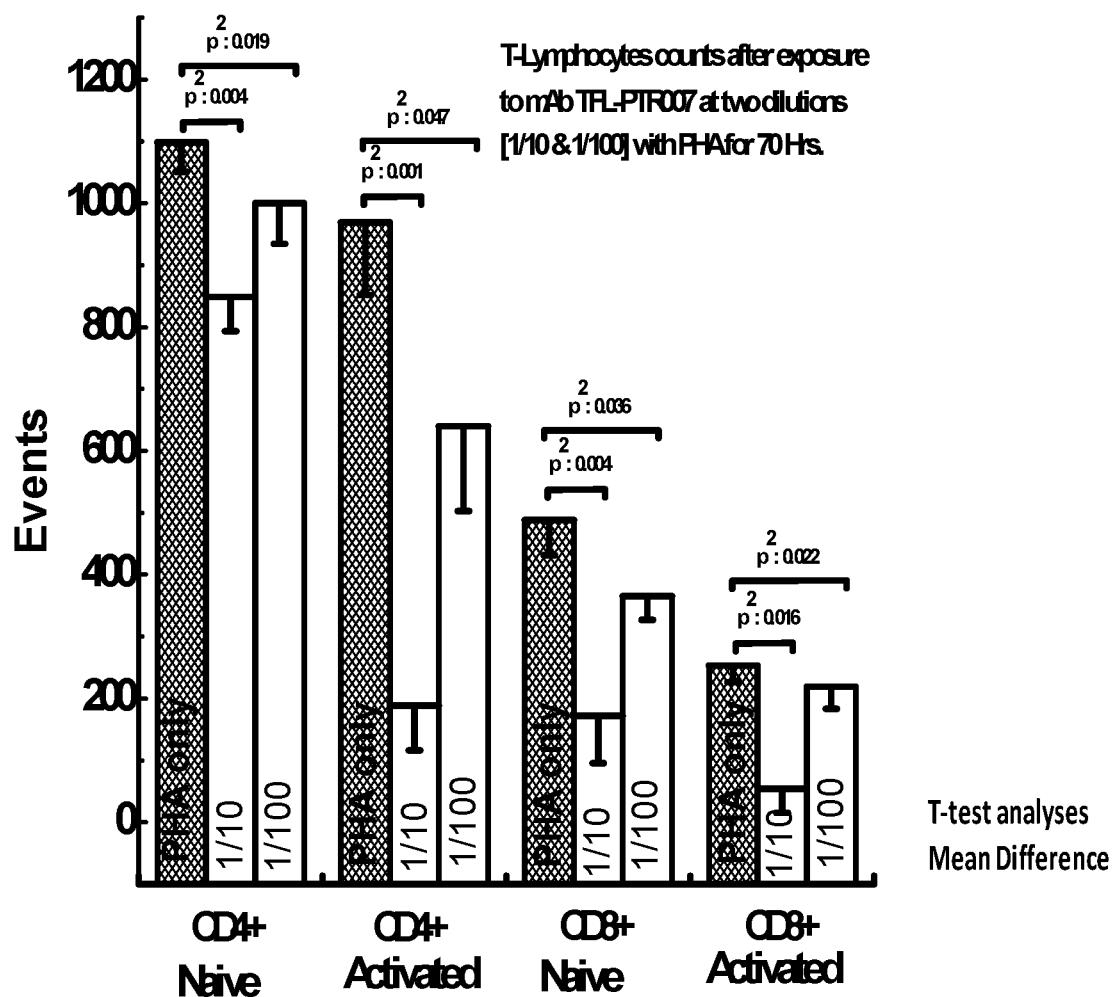

FIGURE 6. IVIg and anti-HLA-E monoclonal antibodies (PTER007 and PTER006) share similarities in activities by T-lymphocyte proliferation Assay.
FIGURE 6A. An Approximated Profile of the CFSE fluorescence intensity of proliferating T cells after 70 hours of exposure to PHA closely follows the predicted sequential halving due to cell division (M1, M2, M3 and M4)
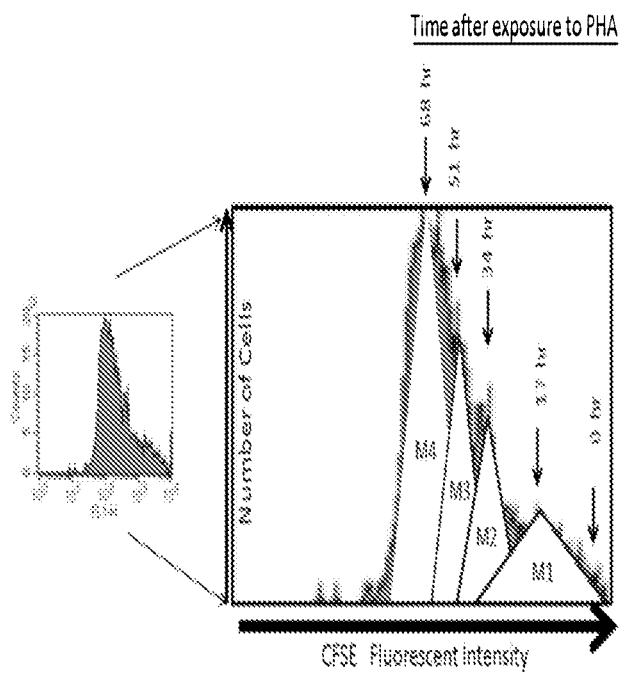

FIGURE 6B. IVIg inhibits PHA-L induced proliferation CD3+ CFSE+ T-Lymphocytes at 72 hrs.
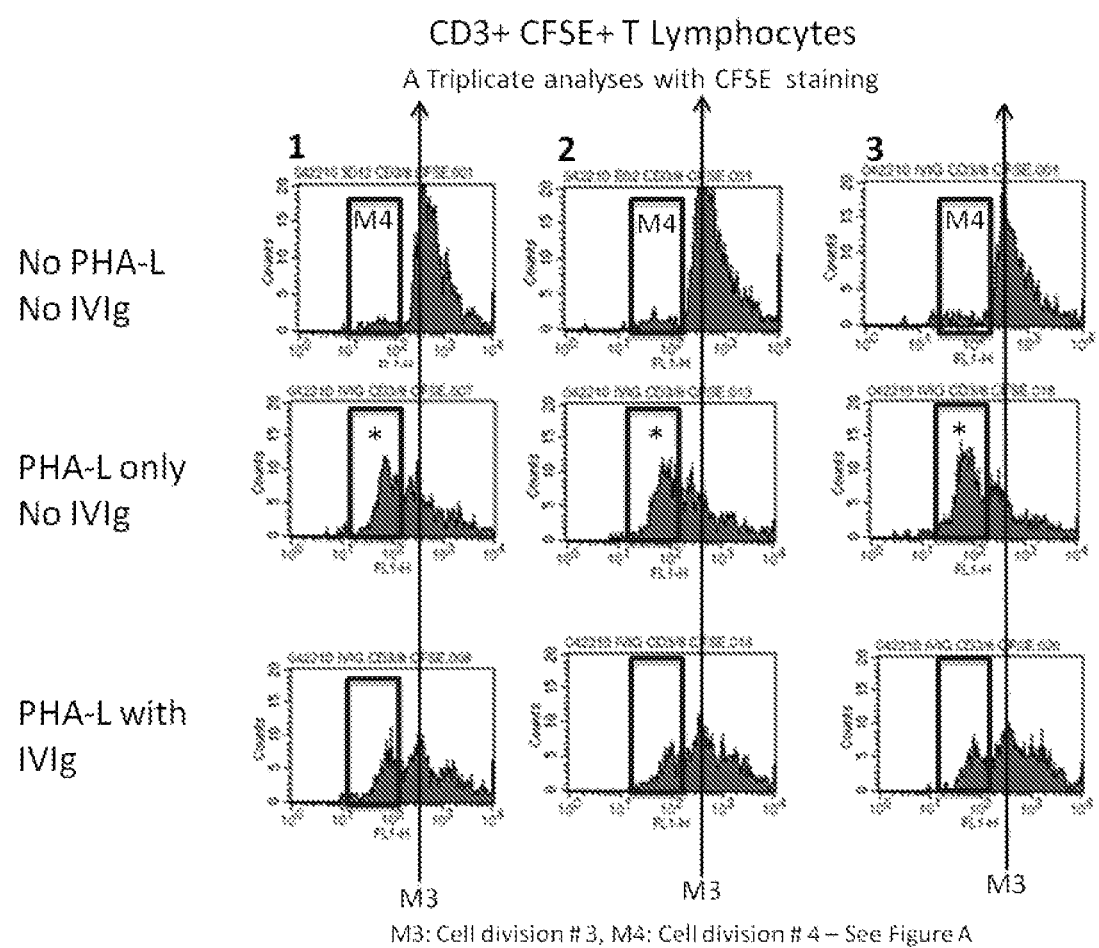

FIGURE 6C. Percentage inhibition of T-cell proliferation by IVIg (at different dilutions) 72 hrs after PHA-stimulation.
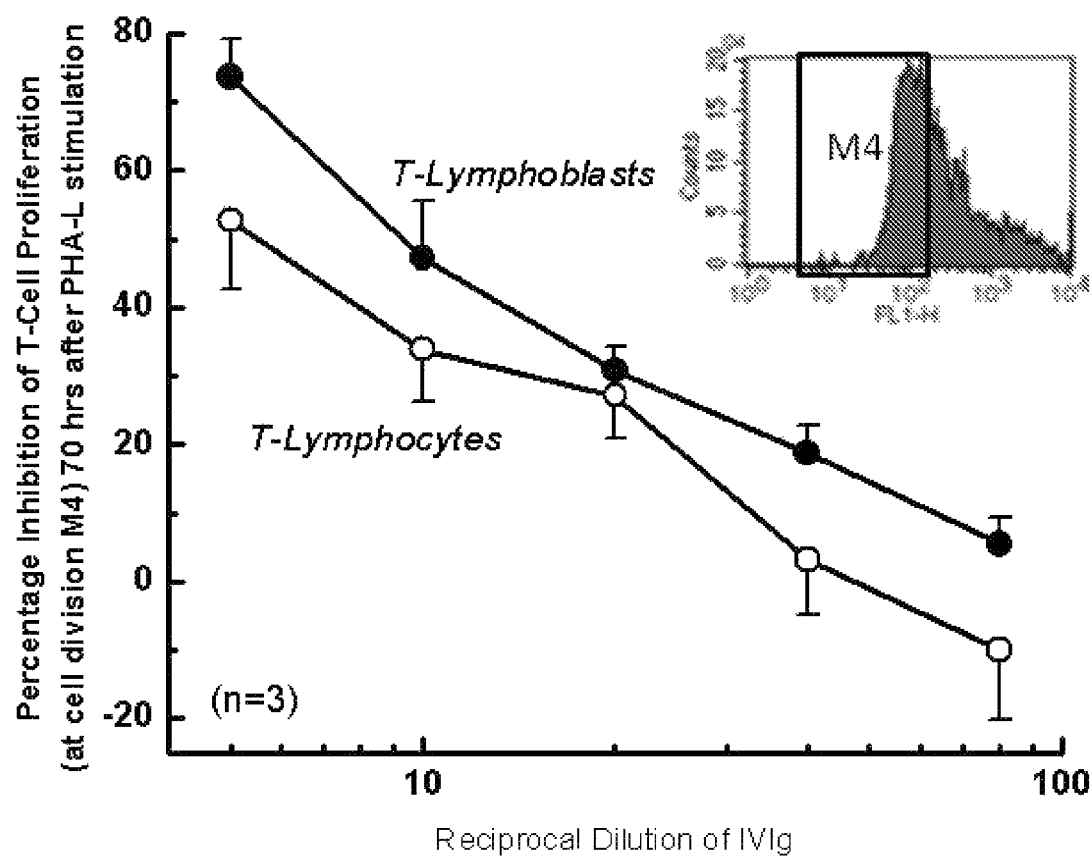

FIGURE 6D. Effects of anti-HLA-Ib monoclonal antibodies (PTER007) on CD4+ T cells.
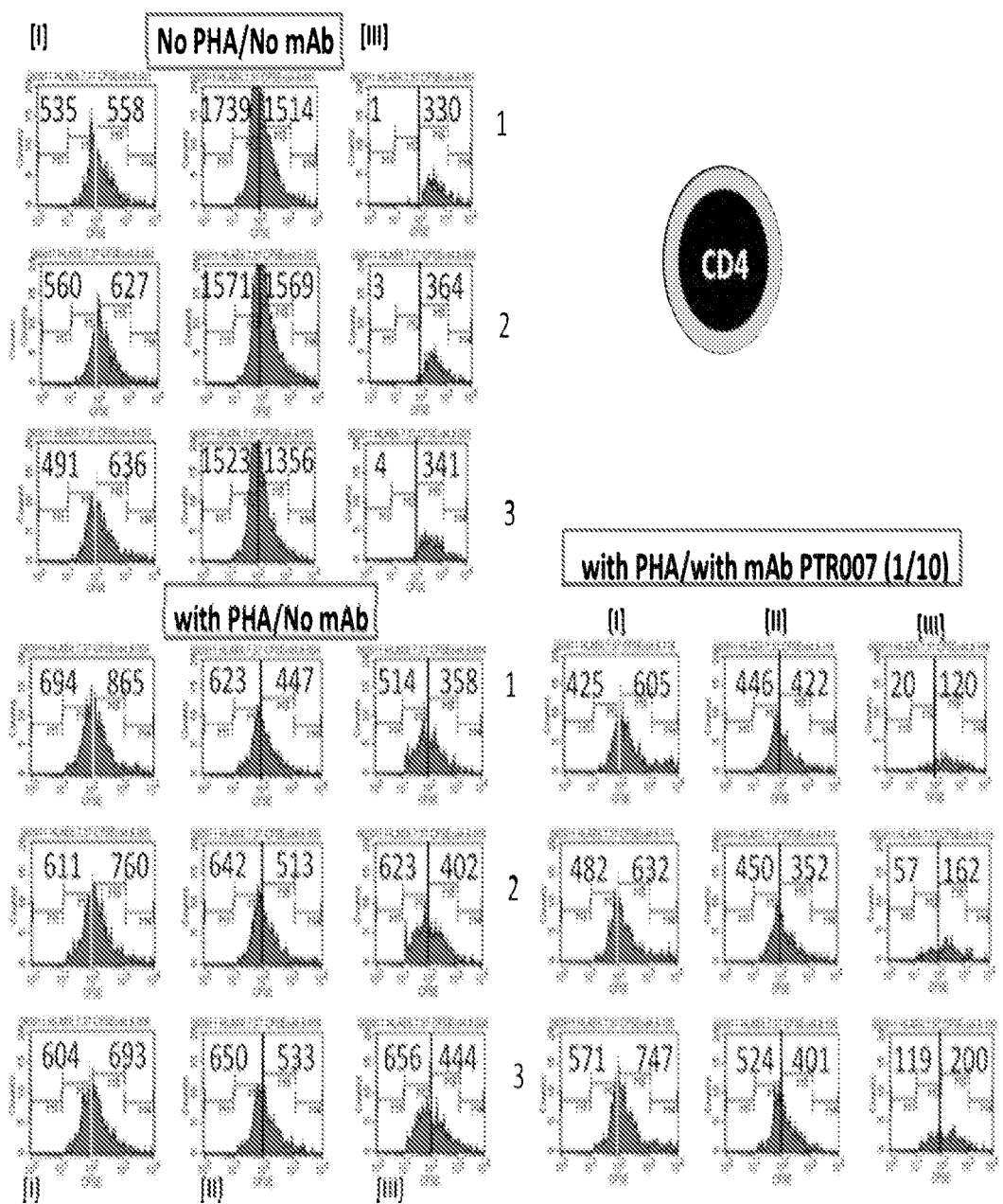

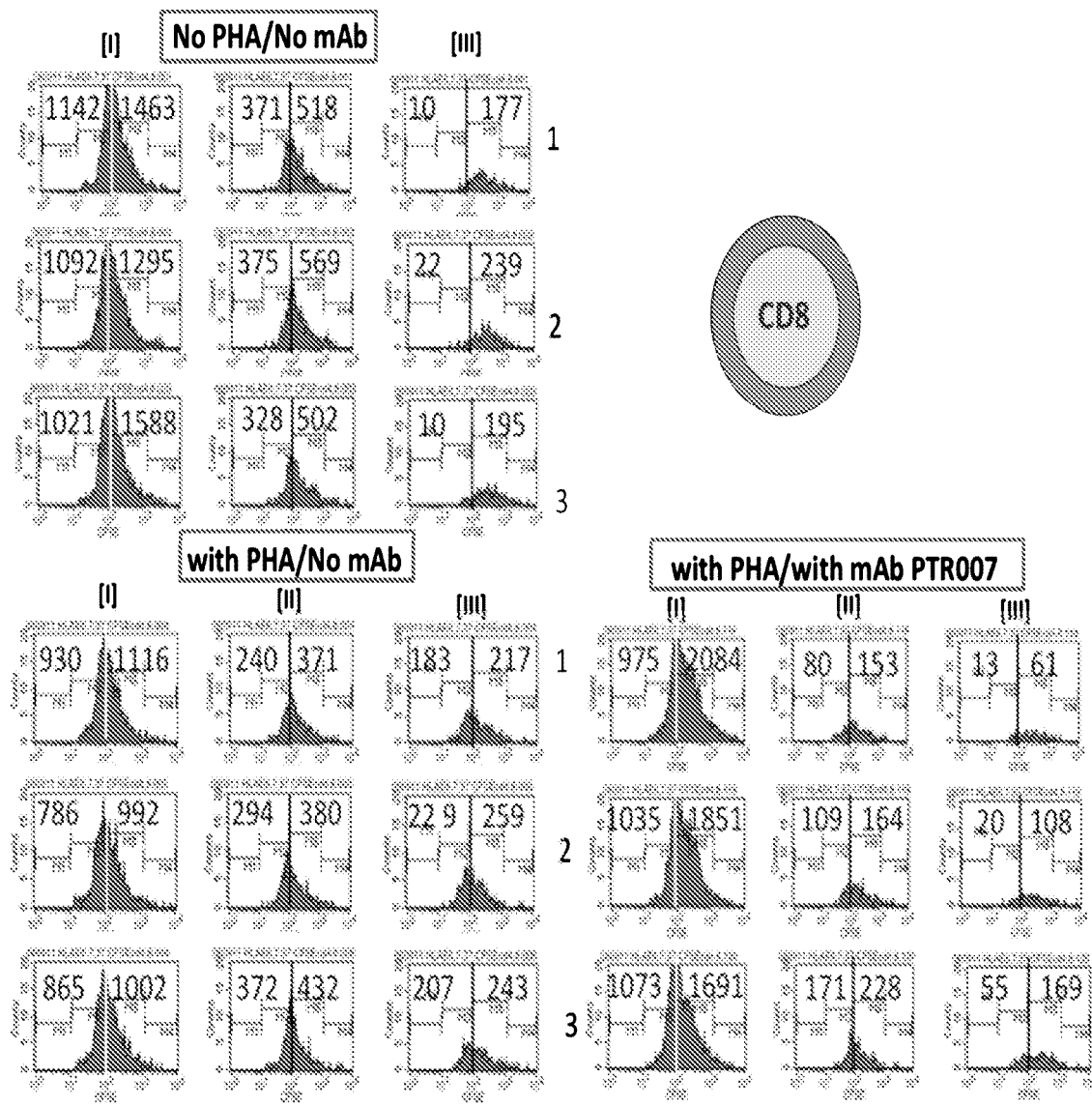
FIGURE 6E. Effects of anti-HLA-Ib monoclonal antibodies (PTER007) on CD8+ T cells:

FIGURE 6F. Effects of anti-HLA-Ib monoclonal antibodies (PTER006) on CD4+ T cells.
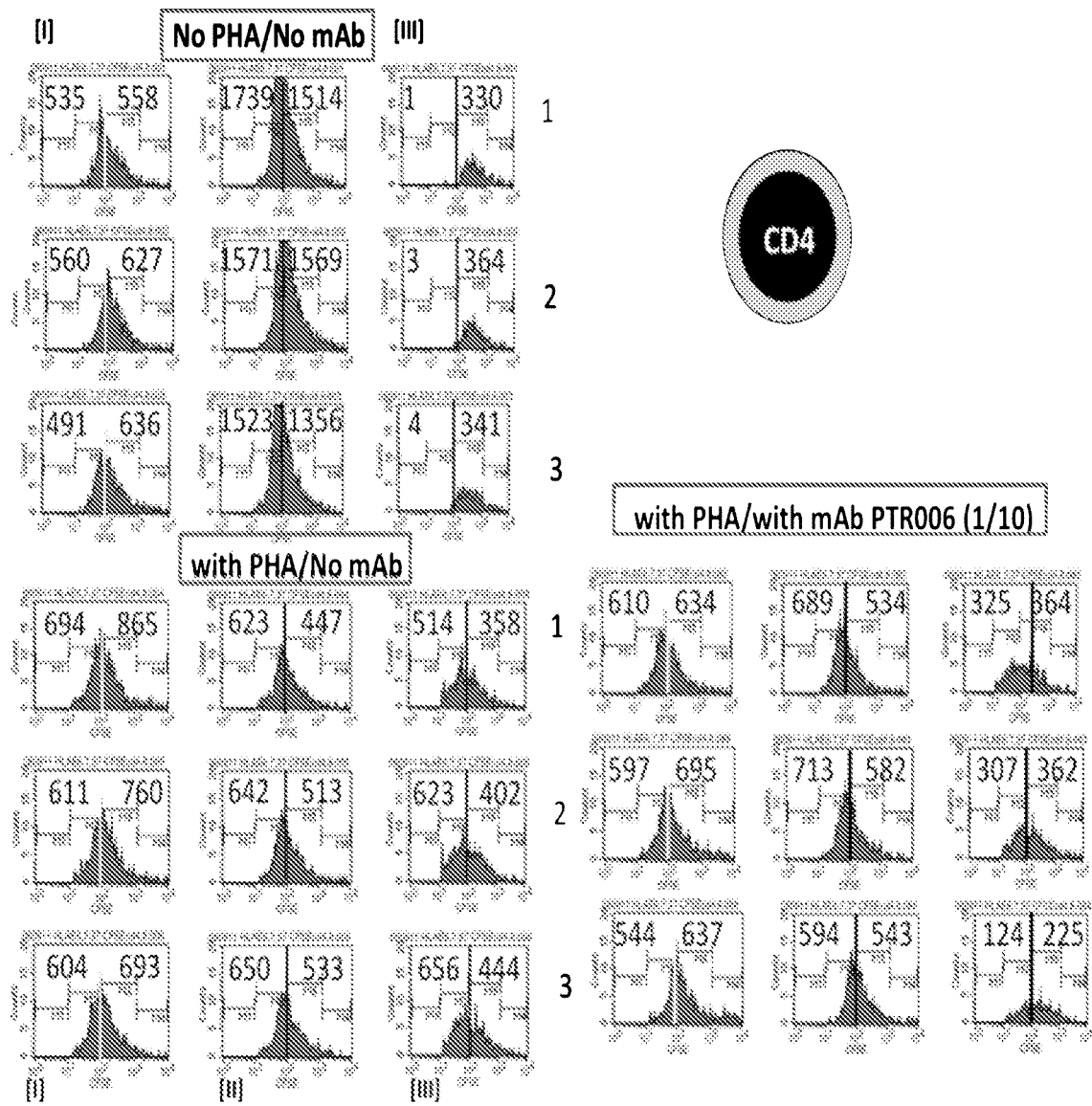

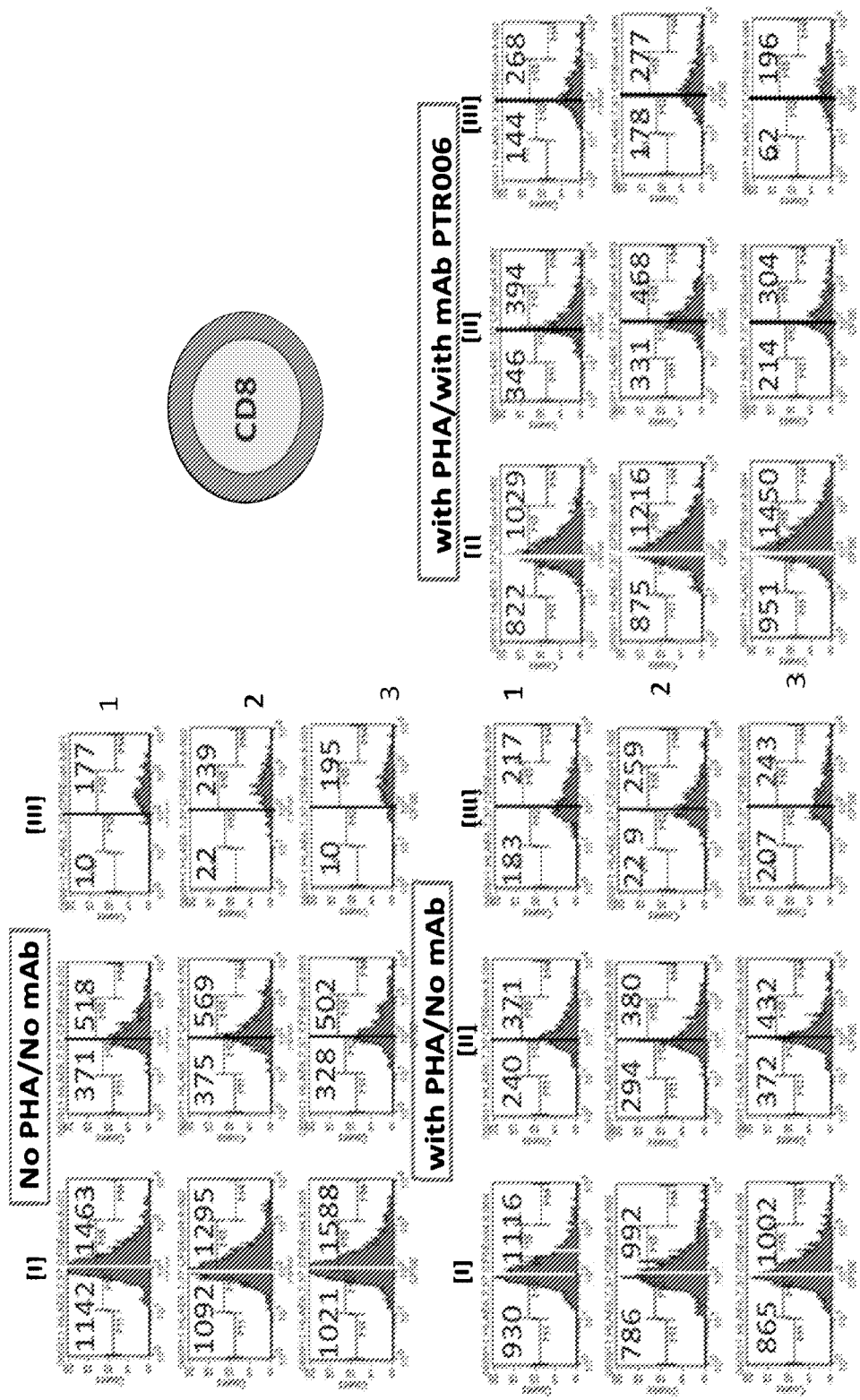
FIGURE 6G. Effects of anti-HLA-Ib monoclonal antibodies (PTER006) on CD8+ T cells.

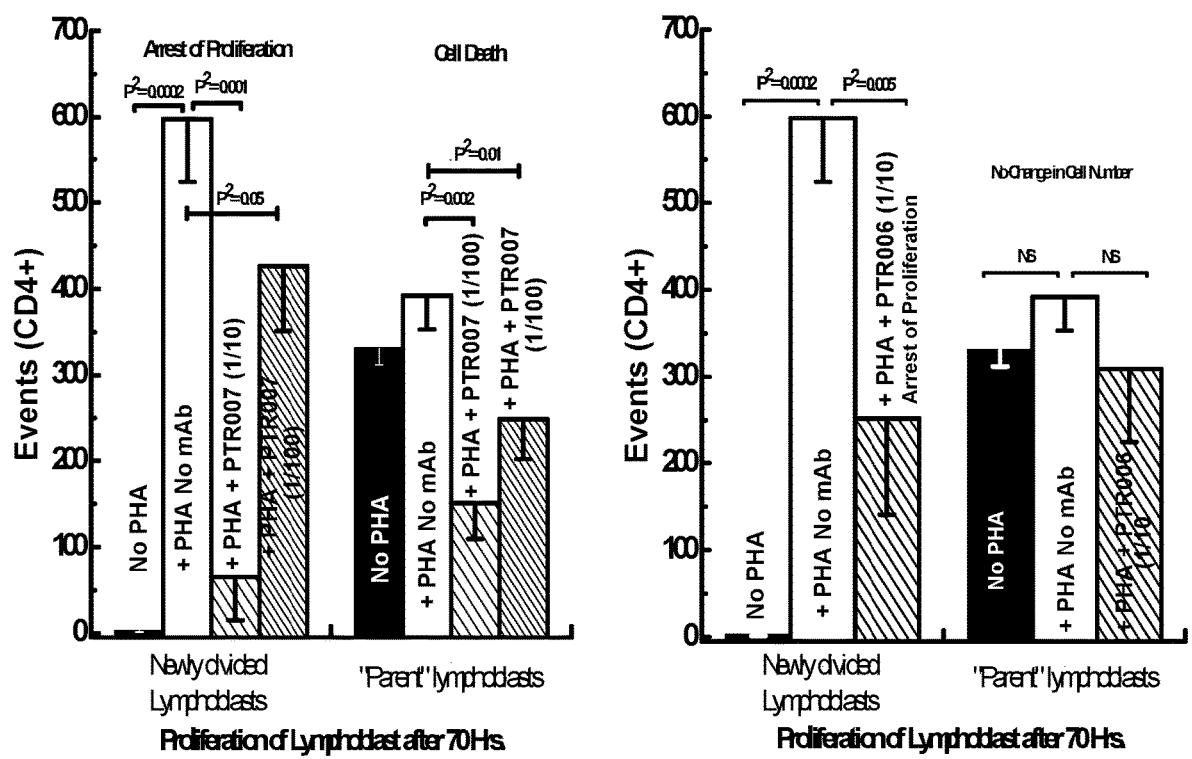
FIGURE 6H. Arrest of PHA-induced Proliferation newly divided CD4+ lymphoblasts and cell death of parent CD4+ lymphoblasts by anti-HLA-Ib monoclonal antibodies (PTER007, Left; and PTER006, right) at different dilutions.

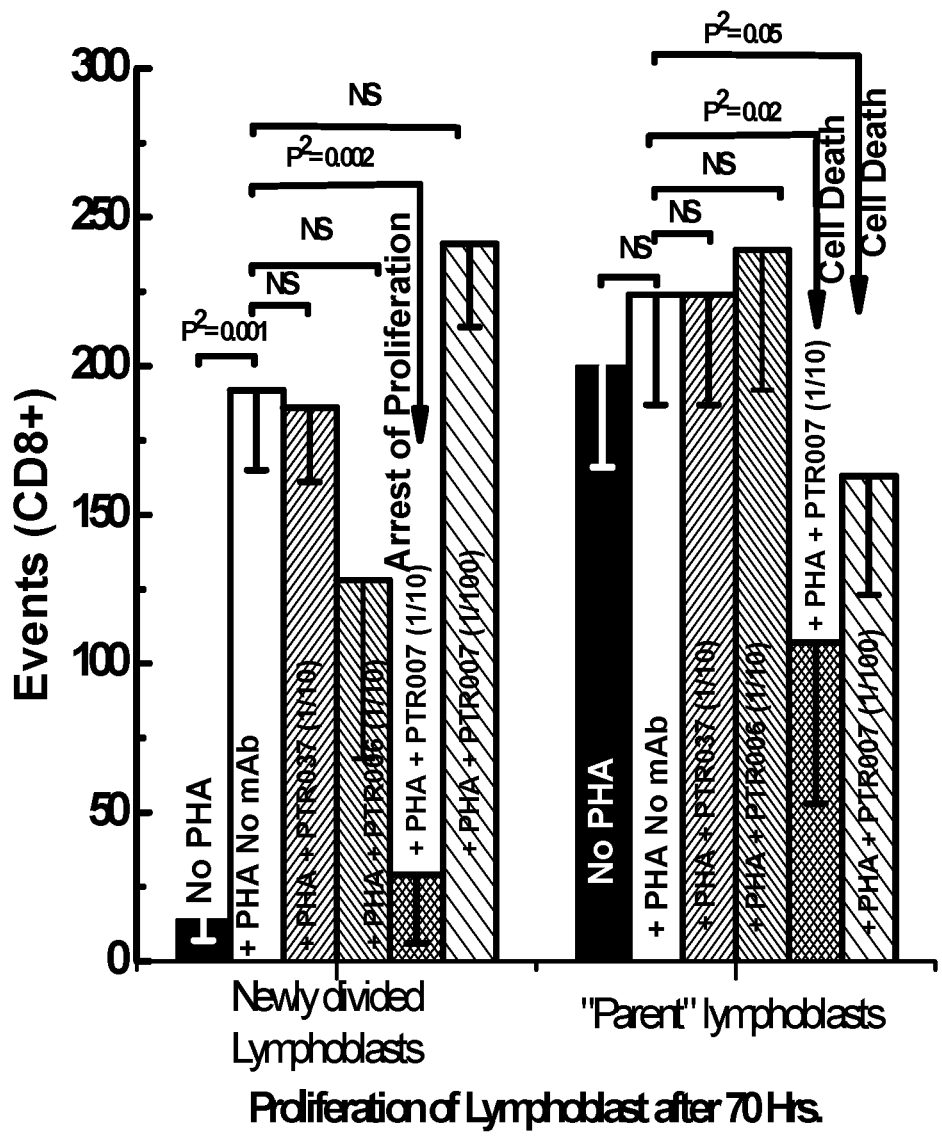
FIGURE 6I. Arrest of PHA-induced Proliferation newly divided CD8+ lymphoblasts and cell death of parent CD8+ lymphoblasts by anti-HLA-Ib monoclonal antibodies (PTER007, Left and PTER006, right) at different dilutions.

FIGURE 7. Immunodulatory role of IVIg.
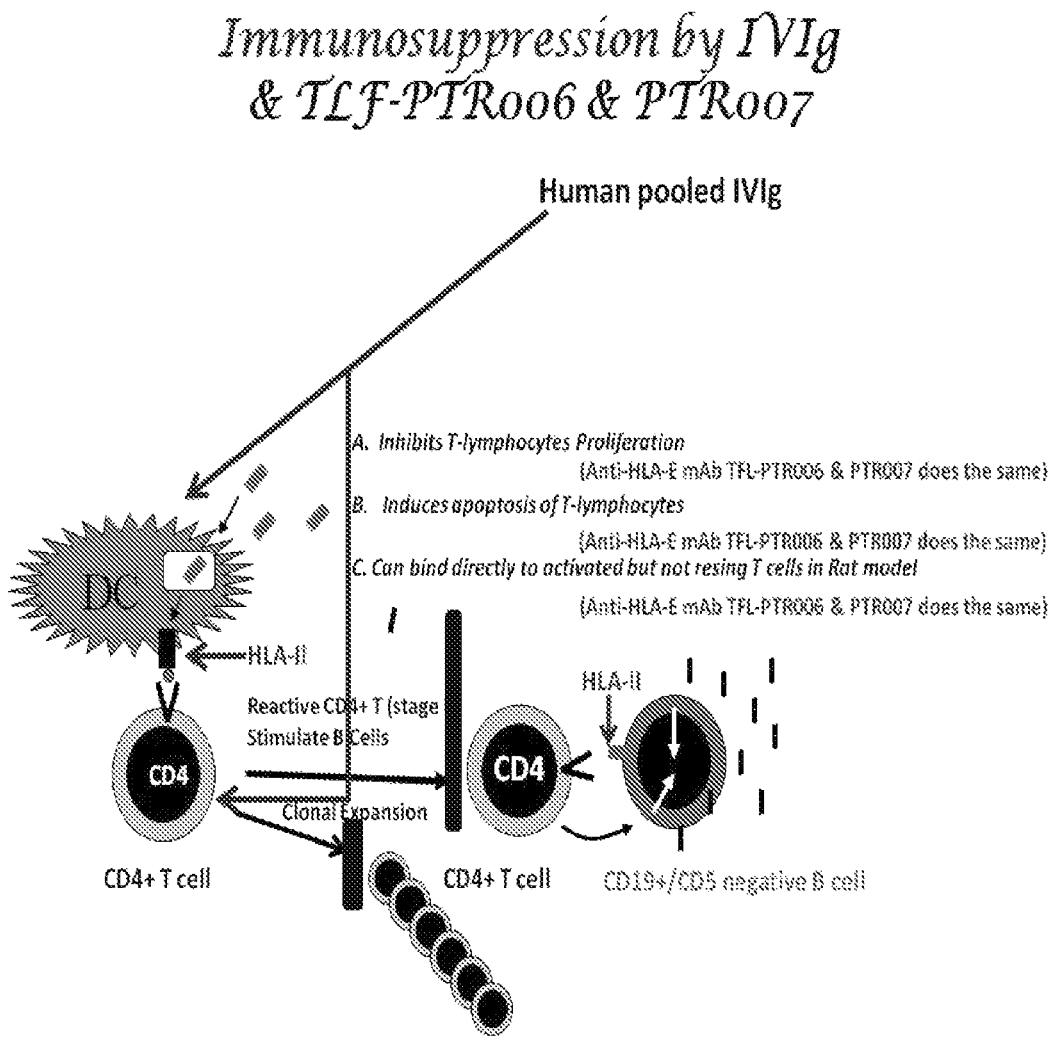

Flow chart showing the purification of B lymphocytes and treatment given prior to monitoring the antibody production by the B cells HLA type of a female allo-immunized during pregnancy:
Note the HLA type of husband and wife.

| Haplotype | HLA-A | HLA-B | HLA-C | HLA-DRB1 | HLA-DRB345 | HLA-DQA1 | HLA-DQB1 | HLA-DPB1 |
|---|---|---|---|---|---|---|---|---|
| a | *3002 | *2703 | *0327 | *1501 | B5*0101 | *0102 | *0602 | *0501 |
| b | *1101 | *3501 | *0410 | 0101 | B5*0101 | 0101 | 0501 | *0402 |
| c | *2402 | *4801 | *0302 | *1302 | B5*0101 | *0505 | *0609 | *0501 |
| d | *3301 | *5801 | *0803 | *1501 | B3*0301 | *0102 | *0301 | *0301 |

Figure 9A. IVIg tends to reduce the secretion of anti-DRB1*01:01 and anti-DRB1*01:02 antibodies by the B cells of JH.
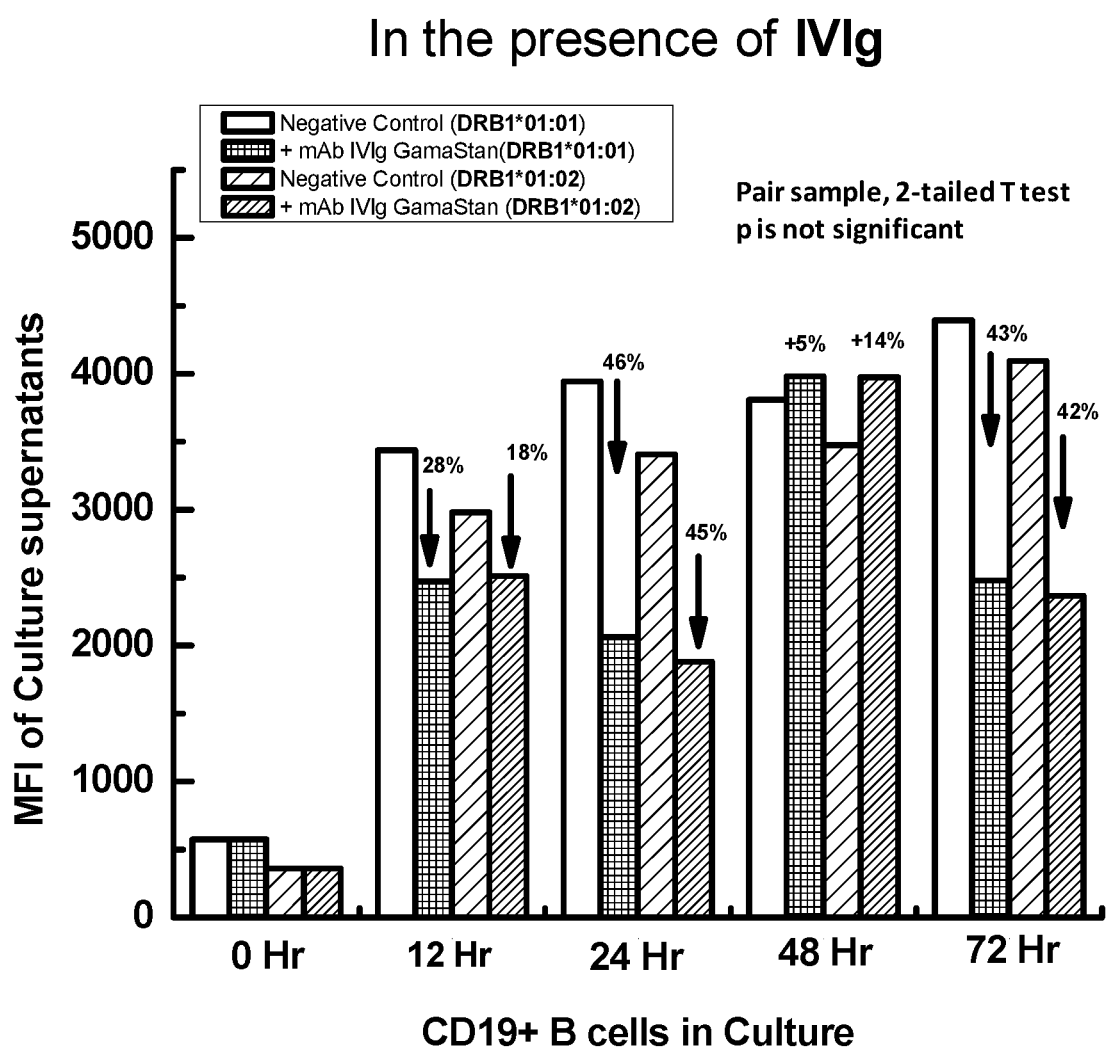

Figure 9B. TFL-mAb PTER007 (the IVIg mimetic) suppresses significantly the secretion of anti-DRB1*01:01 (p<0.007) and anti-DRB1*01:02 (p<0.003) antibodies by the B cells of JH.
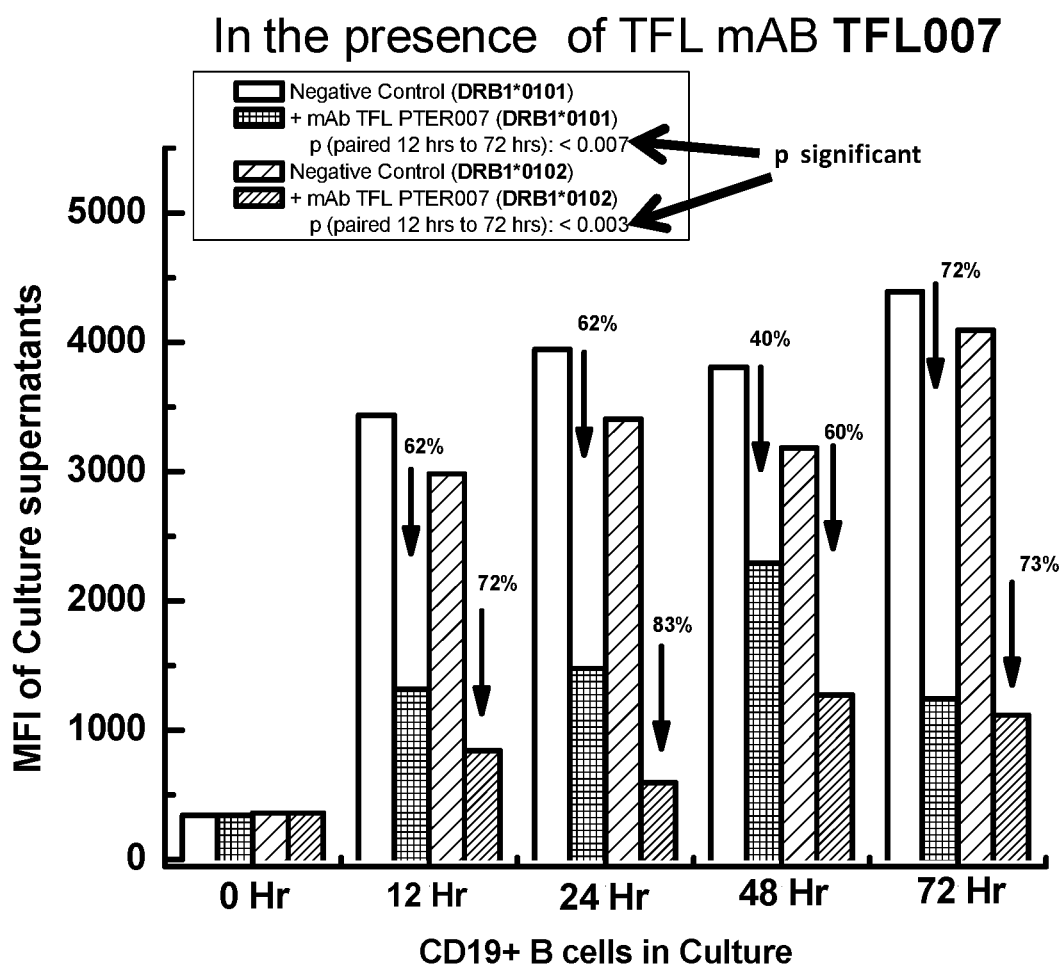

Figure 9C. IVIg increases the secretion of anti-DRB1*04:04 and anti-DRB1*04:02 antibodies by the B cells of JH.
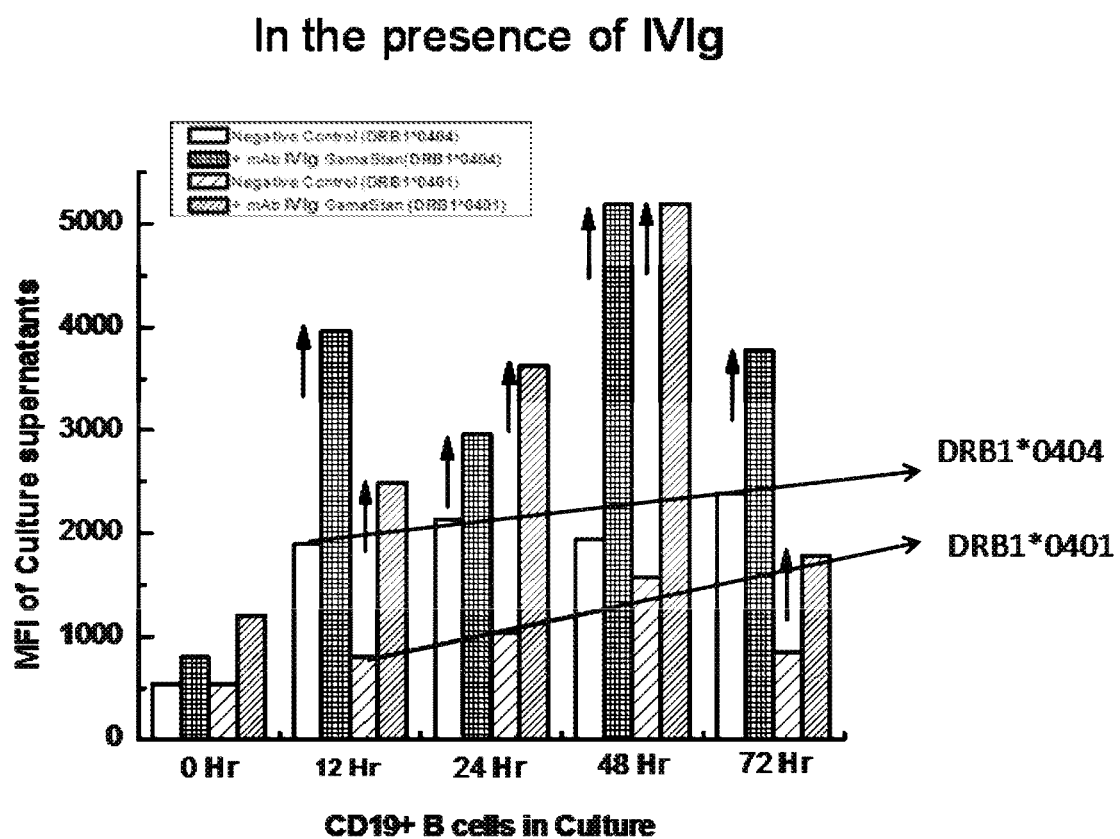

Figure 9D. IVIg-mimetic (TFL mAb PTER-007) is highly efficient in suppressing the secretion of anti-DRB1*04:04 and anti-DRB1*04:02 antibodies by the B cells of JH.
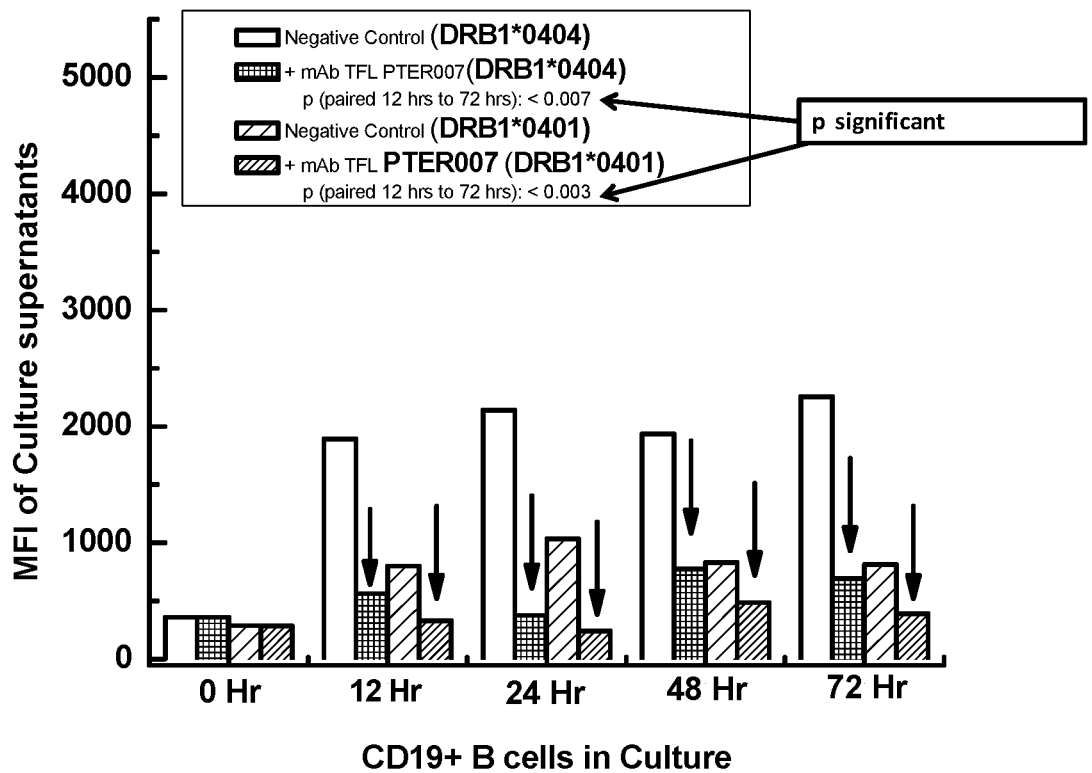

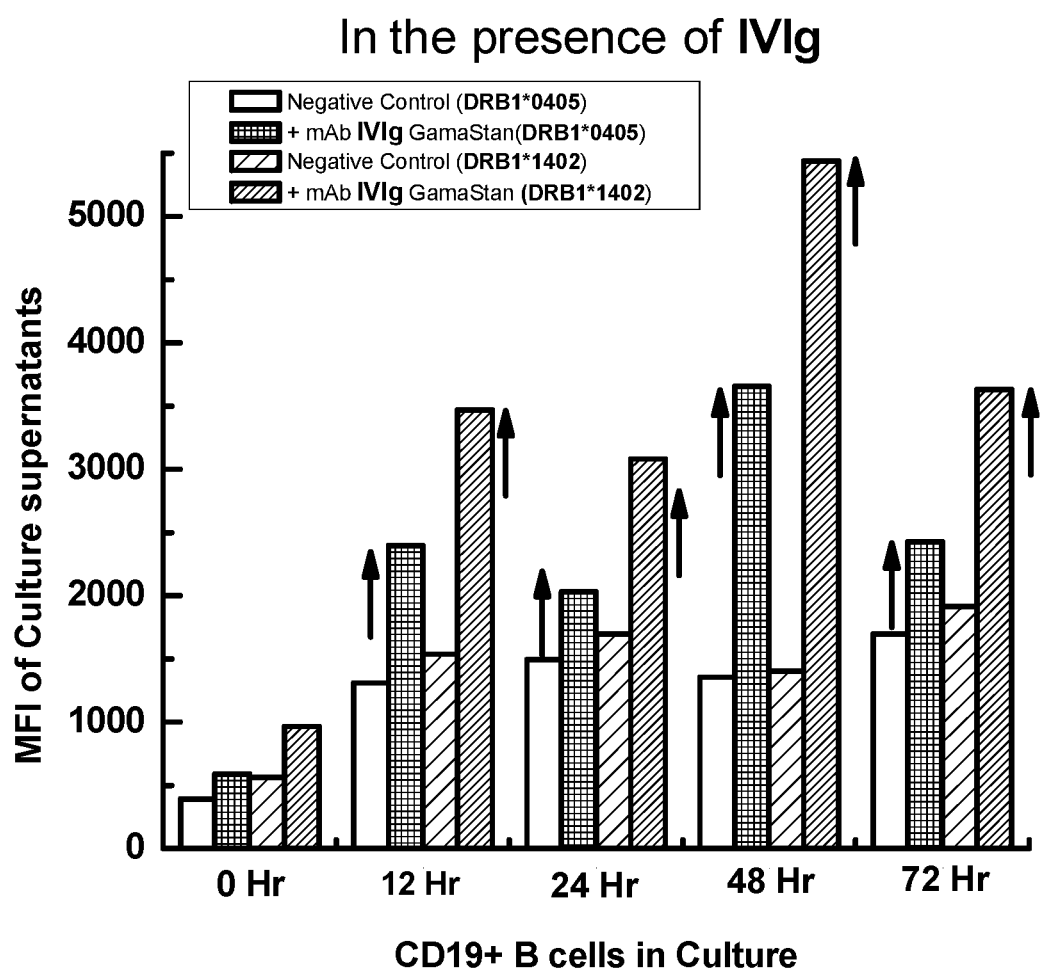
Figure 9E. IVIg increases the secretion of anti-DRB1*04:05 and anti-DRB1*14:02 antibodies by the B cells of JH.

Figure 9F. The IVIg-mimetic (TFL mAb PTER-007) is efficient in suppressing the secretion of anti-DRB1*04:05 and anti-DRB1*14:02 antibodies by the B cells of JH.
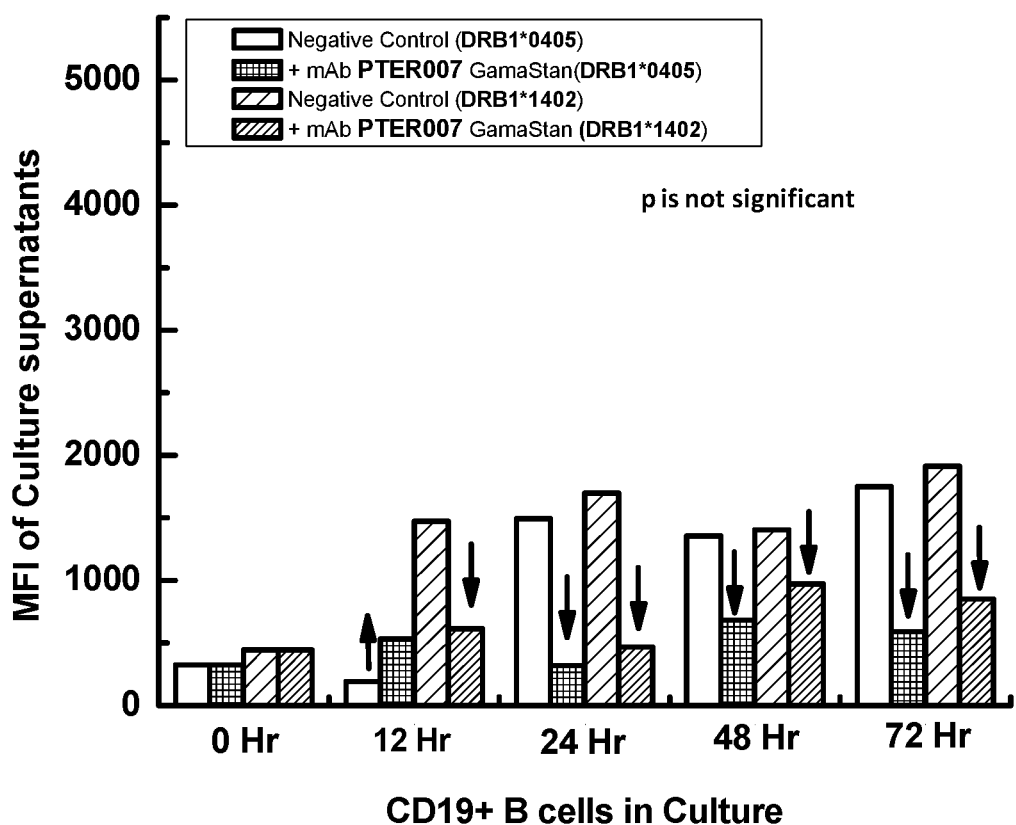

Figure 10. Sequence alignment of multiple HLA alleles.

SEQUENCE LISTING

```
<160> NUMBER OF SEQ ID NOS: 20

<210> SEQ ID NO 1
<211> LENGTH: 9
<212> TYPE: PRT
<213> ORGANISM: Artificial Sequence
<220> FEATURE:
<223> OTHER INFORMATION: Synthetic peptide

<400> SEQUENCE: 1

Pro Arg Ala Pro Trp Met Glu Gln Glu
1               5

<210> SEQ ID NO 2
<211> LENGTH: 8
<212> TYPE: PRT
<213> ORGANISM: Artificial Sequence
<220> FEATURE:
<223> OTHER INFORMATION: Synthetic peptide

<400> SEQUENCE: 2

Glu Tyr Trp Asp Arg Glu Thr Arg
1               5
```

```
<210> SEQ ID NO 3
<211> LENGTH: 7
<212> TYPE: PRT
<213> ORGANISM: Artificial Sequence
<220> FEATURE:
<223> OTHER INFORMATION: Synthetic peptide

<400> SEQUENCE: 3

Arg Ser Ala Arg Asp Thr Ala
1               5

<210> SEQ ID NO 4
<211> LENGTH: 8
<212> TYPE: PRT
<213> ORGANISM: Artificial Sequence
<220> FEATURE:
<223> OTHER INFORMATION: Synthetic peptide

<400> SEQUENCE: 4

Ala Gly Ser His Thr Leu Gln Trp
1               5

<210> SEQ ID NO 5
<211> LENGTH: 7
<212> TYPE: PRT
<213> ORGANISM: Artificial Sequence
<220> FEATURE:
<223> OTHER INFORMATION: Synthetic peptide

<400> SEQUENCE: 5

Arg Phe Leu Arg Gly Tyr Glu
1               5

<210> SEQ ID NO 6
<211> LENGTH: 9
<212> TYPE: PRT
<213> ORGANISM: Artificial Sequence
<220> FEATURE:
<223> OTHER INFORMATION: Synthetic peptide

<400> SEQUENCE: 6

Gln Phe Ala Tyr Asp Gly Lys Asp Tyr
1               5

<210> SEQ ID NO 7
<211> LENGTH: 7
<212> TYPE: PRT
<213> ORGANISM: Artificial Sequence
<220> FEATURE:
<223> OTHER INFORMATION: Synthetic peptide

<400> SEQUENCE: 7

Ala Tyr Asp Gly Lys Asp Tyr
1               5

<210> SEQ ID NO 8
<211> LENGTH: 10
<212> TYPE: PRT
<213> ORGANISM: Artificial Sequence
<220> FEATURE:
<223> OTHER INFORMATION: Synthetic peptide

<400> SEQUENCE: 8

Leu Asn Glu Asp Leu Arg Ser Trp Thr Ala
1               5                   10

<210> SEQ ID NO 9
```

```
<211> LENGTH: 6
<212> TYPE: PRT
<213> ORGANISM: Artificial Sequence
<220> FEATURE:
<223> OTHER INFORMATION: Synthetic peptide

<400> SEQUENCE: 9

Asp Thr Ala Ala Gln Ile
1               5

<210> SEQ ID NO 10
<211> LENGTH: 7
<212> TYPE: PRT
<213> ORGANISM: Artificial Sequence
<220> FEATURE:
<223> OTHER INFORMATION: Synthetic peptide

<400> SEQUENCE: 10

Asp Thr Ala Ala Gln Ile Ser
1               5

<210> SEQ ID NO 11
<211> LENGTH: 10
<212> TYPE: PRT
<213> ORGANISM: Artificial Sequence
<220> FEATURE:
<223> OTHER INFORMATION: Synthetic peptide

<400> SEQUENCE: 11

Ser Glu Gln Lys Ser Asn Asp Ala Ser Glu
1               5                   10

<210> SEQ ID NO 12
<211> LENGTH: 6
<212> TYPE: PRT
<213> ORGANISM: Artificial Sequence
<220> FEATURE:
<223> OTHER INFORMATION: Synthetic peptide

<400> SEQUENCE: 12

Arg Ala Tyr Leu Glu Asp
1               5

<210> SEQ ID NO 13
<211> LENGTH: 6
<212> TYPE: PRT
<213> ORGANISM: Artificial Sequence
<220> FEATURE:
<223> OTHER INFORMATION: Synthetic peptide

<400> SEQUENCE: 13

Thr Cys Val Glu Trp Leu
1               5

<210> SEQ ID NO 14
<211> LENGTH: 8
<212> TYPE: PRT
<213> ORGANISM: Artificial Sequence
<220> FEATURE:
<223> OTHER INFORMATION: Synthetic peptide

<400> SEQUENCE: 14

Glu Pro Pro Lys Thr His Val Thr
1               5

<210> SEQ ID NO 15
<211> LENGTH: 229
```

```
<212> TYPE: PRT
<213> ORGANISM: Artificial Sequence
<220> FEATURE:
<223> OTHER INFORMATION: Synthetic

<400> SEQUENCE: 15

Gly Asp Thr Arg Pro Arg Phe Leu Trp Gln Leu Lys Phe Glu Cys His
1               5                   10                  15

Phe Phe Asn Gly Thr Glu Arg Val Arg Leu Leu Glu Arg Cys Ile Tyr
            20                  25                  30

Asn Gln Glu Glu Ser Val Arg Phe Asp Ser Asp Val Gly Glu Tyr Arg
        35                  40                  45

Ala Val Thr Glu Leu Gly Arg Pro Asp Ala Glu Tyr Trp Asn Ser Gln
50                  55                  60

Lys Asp Leu Leu Glu Gln Arg Arg Ala Ala Val Asp Thr Tyr Cys Arg
65                  70                  75                  80

His Asn Tyr Gly Val Gly Glu Ser Phe Thr Val Gln Arg Arg Val Glu
                85                  90                  95

Pro Lys Val Thr Val Tyr Pro Ser Lys Thr Gln Pro Leu Gln His His
            100                 105                 110

Asn Leu Leu Val Cys Ser Val Ser Gly Phe Tyr Pro Gly Ser Ile Glu
        115                 120                 125

Val Arg Trp Phe Arg Asn Gly Gln Glu Glu Lys Ala Gly Val Val Ser
130                 135                 140

Thr Gly Leu Ile Gln Asn Gly Asp Trp Thr Phe Gln Thr Leu Val Met
145                 150                 155                 160

Leu Glu Thr Val Pro Arg Ser Gly Glu Val Tyr Thr Cys Gln Val Glu
                165                 170                 175

His Pro Ser Val Thr Ser Pro Leu Thr Val Glu Trp Arg Ala Arg Ser
            180                 185                 190

Glu Ser Ala Gln Ser Lys Met Leu Ser Gly Val Gly Gly Phe Val Leu
        195                 200                 205

Gly Leu Leu Phe Leu Gly Ala Gly Leu Phe Ile Tyr Phe Arg Asn Gln
210                 215                 220

Lys Gly His Ser Gly
225

<210> SEQ ID NO 16
<211> LENGTH: 229
<212> TYPE: PRT
<213> ORGANISM: Artificial Sequence
<220> FEATURE:
<223> OTHER INFORMATION: Synthetic

<400> SEQUENCE: 16

Gly Asp Thr Arg Pro Arg Phe Leu Trp Gln Leu Lys Phe Glu Cys His
1               5                   10                  15

Phe Phe Asn Gly Thr Glu Arg Val Arg Leu Leu Glu Arg Cys Ile Tyr
            20                  25                  30

Asn Gln Glu Glu Ser Val Arg Phe Asp Ser Asp Val Gly Glu Tyr Arg
        35                  40                  45

Ala Val Thr Glu Leu Gly Arg Pro Asp Ala Glu Tyr Trp Asn Ser Gln
50                  55                  60

Lys Asp Leu Leu Glu Gln Arg Arg Ala Ala Val Asp Thr Tyr Cys Arg
65                  70                  75                  80

His Asn Tyr Gly Ala Val Glu Ser Phe Thr Val Gln Arg Arg Val Glu
                85                  90                  95
```

Pro Lys Val Thr Val Tyr Pro Ser Lys Thr Gln Pro Leu Gln His His
            100                 105                 110

Asn Leu Leu Val Cys Ser Val Ser Gly Phe Tyr Pro Gly Ser Ile Glu
        115                 120                 125

Val Arg Trp Phe Arg Asn Gly Gln Glu Lys Ala Gly Val Val Ser
130                 135                 140

Thr Gly Leu Ile Gln Asn Gly Asp Trp Thr Phe Gln Thr Leu Val Met
145                 150                 155                 160

Leu Glu Thr Val Pro Arg Ser Gly Glu Val Tyr Thr Cys Gln Val Glu
                165                 170                 175

His Pro Ser Val Thr Ser Pro Leu Thr Val Glu Trp Arg Ala Arg Ser
            180                 185                 190

Glu Ser Ala Gln Ser Lys Met Leu Ser Gly Val Gly Gly Phe Val Leu
        195                 200                 205

Gly Leu Leu Phe Leu Gly Ala Gly Leu Phe Ile Tyr Phe Arg Asn Gln
    210                 215                 220

Lys Gly His Ser Gly
225

<210> SEQ ID NO 17
<211> LENGTH: 229
<212> TYPE: PRT
<213> ORGANISM: Artificial Sequence
<220> FEATURE:
<223> OTHER INFORMATION: Synthetic

<400> SEQUENCE: 17

Gly Asp Thr Arg Pro Arg Phe Leu Glu Gln Val Lys His Glu Cys His
1               5                   10                  15

Phe Phe Asn Gly Thr Glu Arg Val Arg Phe Leu Asp Arg Tyr Phe Tyr
            20                  25                  30

His Gln Glu Glu Tyr Val Arg Phe Asp Ser Asp Val Gly Glu Tyr Arg
        35                  40                  45

Ala Val Thr Glu Leu Gly Arg Pro Asp Ala Glu Tyr Trp Asn Ser Gln
    50                  55                  60

Lys Asp Leu Leu Glu Gln Lys Arg Ala Ala Val Asp Thr Tyr Cys Arg
65                  70                  75                  80

His Asn Tyr Gly Val Gly Glu Ser Phe Thr Val Gln Arg Arg Val Tyr
                85                  90                  95

Pro Glu Val Thr Val Tyr Pro Ala Lys Thr Gln Pro Leu Gln His His
            100                 105                 110

Asn Leu Leu Val Cys Ser Val Asn Gly Phe Tyr Pro Gly Ser Ile Glu
        115                 120                 125

Val Arg Trp Phe Arg Asn Gly Gln Glu Glu Lys Thr Gly Val Val Ser
    130                 135                 140

Thr Gly Leu Ile Gln Asn Gly Asp Trp Thr Phe Gln Thr Leu Val Met
145                 150                 155                 160

Leu Glu Thr Val Pro Arg Ser Gly Glu Val Tyr Thr Cys Gln Val Glu
                165                 170                 175

His Pro Ser Leu Thr Ser Pro Leu Thr Val Glu Trp Arg Ala Arg Ser
            180                 185                 190

Glu Ser Ala Gln Ser Lys Met Leu Ser Gly Val Gly Gly Phe Val Leu
        195                 200                 205

Gly Leu Leu Phe Leu Gly Ala Gly Leu Phe Ile Tyr Phe Arg Asn Gln
    210                 215                 220

Lys Gly His Ser Gly
225

<210> SEQ ID NO 18
<211> LENGTH: 229
<212> TYPE: PRT
<213> ORGANISM: Artificial Sequence
<220> FEATURE:
<223> OTHER INFORMATION: Synthetic

<400> SEQUENCE: 18

Gly Asp Thr Arg Pro Arg Phe Leu Glu Gln Val Lys His Glu Cys His
1               5                   10                  15

Phe Phe Asn Gly Thr Glu Arg Val Arg Phe Leu Asp Arg Tyr Phe Tyr
            20                  25                  30

His Gln Glu Glu Tyr Val Arg Phe Asp Ser Asp Val Gly Glu Tyr Arg
        35                  40                  45

Ala Val Thr Glu Leu Gly Arg Pro Asp Ala Glu Tyr Trp Asn Ser Gln
    50                  55                  60

Lys Asp Leu Leu Glu Gln Arg Arg Ala Ala Val Asp Thr Tyr Cys Arg
65                  70                  75                  80

His Asn Tyr Gly Val Val Glu Ser Phe Thr Val Gln Arg Arg Val Tyr
                85                  90                  95

Pro Glu Val Thr Val Tyr Pro Ala Lys Thr Gln Pro Leu Gln His His
            100                 105                 110

Asn Leu Leu Val Cys Ser Val Asn Gly Phe Tyr Pro Gly Ser Ile Glu
        115                 120                 125

Val Arg Trp Phe Arg Asn Gly Gln Glu Glu Lys Thr Gly Val Val Ser
    130                 135                 140

Thr Gly Leu Ile Gln Asn Gly Asp Trp Thr Phe Gln Thr Leu Val Met
145                 150                 155                 160

Leu Glu Thr Val Pro Arg Ser Gly Glu Val Tyr Thr Cys Gln Val Glu
                165                 170                 175

His Pro Ser Leu Thr Ser Pro Leu Thr Val Glu Trp Arg Ala Arg Ser
            180                 185                 190

Glu Ser Ala Gln Ser Lys Met Leu Ser Gly Val Gly Gly Phe Val Leu
        195                 200                 205

Gly Leu Leu Phe Leu Gly Ala Gly Leu Phe Ile Tyr Phe Arg Asn Gln
    210                 215                 220

Lys Gly His Ser Gly
225

<210> SEQ ID NO 19
<211> LENGTH: 229
<212> TYPE: PRT
<213> ORGANISM: Artificial Sequence
<220> FEATURE:
<223> OTHER INFORMATION: Synthetic

<400> SEQUENCE: 19

Gly Asp Thr Arg Pro Arg Phe Leu Glu Gln Val Lys His Glu Cys His
1               5                   10                  15

Phe Phe Asn Gly Thr Glu Arg Val Arg Phe Leu Asp Arg Tyr Phe Tyr
            20                  25                  30

His Gln Glu Glu Tyr Val Arg Phe Asp Ser Asp Val Gly Glu Tyr Arg
        35                  40                  45

Ala Val Thr Glu Leu Gly Arg Pro Ser Ala Glu Tyr Trp Asn Ser Gln

```
                50                  55                  60
Lys Asp Leu Leu Glu Gln Arg Arg Ala Val Asp Thr Tyr Cys Arg
 65                  70                  75                  80

His Asn Tyr Gly Val Gly Glu Ser Phe Thr Val Gln Arg Arg Val Tyr
                 85                  90                  95

Pro Glu Val Thr Val Tyr Pro Ala Lys Thr Gln Pro Leu Gln His His
                100                 105                 110

Asn Leu Leu Val Cys Ser Val Asn Gly Phe Tyr Pro Gly Ser Ile Glu
            115                 120                 125

Val Arg Trp Phe Arg Asn Gly Gln Glu Glu Lys Thr Gly Val Val Ser
        130                 135                 140

Thr Gly Leu Ile Gln Asn Gly Asp Trp Thr Phe Gln Thr Leu Val Met
145                 150                 155                 160

Leu Glu Thr Val Pro Arg Ser Gly Glu Val Tyr Thr Cys Gln Val Glu
                165                 170                 175

His Pro Ser Leu Thr Ser Pro Leu Thr Val Glu Trp Arg Ala Arg Ser
            180                 185                 190

Glu Ser Ala Gln Ser Lys Met Leu Ser Gly Val Gly Phe Val Leu
        195                 200                 205

Gly Leu Leu Phe Leu Gly Ala Gly Leu Phe Ile Tyr Phe Arg Asn Gln
    210                 215                 220

Lys Gly His Ser Gly
225

<210> SEQ ID NO 20
<211> LENGTH: 229
<212> TYPE: PRT
<213> ORGANISM: Artificial Sequence
<220> FEATURE:
<223> OTHER INFORMATION: Synthetic

<400> SEQUENCE: 20

Gly Asp Thr Arg Pro Arg Phe Leu Glu Tyr Ser Thr Ser Glu Cys His
  1               5                  10                  15

Phe Phe Asn Gly Thr Glu Arg Val Arg Phe Leu Glu Arg Tyr Phe His
                 20                  25                  30

Asn Gln Glu Glu Asn Val Arg Phe Asp Ser Asp Val Gly Glu Tyr Arg
             35                  40                  45

Ala Val Thr Glu Leu Gly Arg Pro Asp Ala Glu Tyr Trp Asn Ser Gln
         50                  55                  60

Lys Asp Leu Leu Glu Gln Arg Arg Ala Val Asp Thr Tyr Cys Arg
 65                  70                  75                  80

His Asn Tyr Gly Val Gly Glu Ser Phe Thr Val Gln Arg Arg Val His
                 85                  90                  95

Pro Lys Val Thr Val Tyr Pro Ser Lys Thr Gln Pro Leu Gln His His
                100                 105                 110

Asn Leu Leu Val Cys Ser Val Ser Gly Phe Tyr Pro Gly Ser Ile Glu
            115                 120                 125

Val Arg Trp Phe Arg Asn Gly Gln Glu Glu Lys Thr Gly Val Val Ser
        130                 135                 140

Thr Gly Leu Ile His Asn Gly Asp Trp Thr Phe Gln Thr Leu Val Met
145                 150                 155                 160

Leu Glu Thr Val Pro Arg Ser Gly Glu Val Tyr Thr Cys Gln Val Glu
                165                 170                 175

His Pro Ser Val Thr Ser Pro Leu Thr Val Glu Trp Arg Ala Arg Ser
```

```
                    180                 185                 190
Glu Ser Ala Gln Ser Lys Met Leu Ser Gly Val Gly Gly Phe Val Leu
            195                 200                 205

Gly Leu Leu Phe Leu Gly Ala Gly Leu Phe Ile Tyr Phe Arg Asn Gln
        210                 215                 220

Lys Gly His Ser Gly
225
```

ANTI-HLA CLASS-IB ANTIBODIES MIMIC IMMUNOREACTIVITY AND IMMUNOMODULATORY FUNCTIONS OF INTRAVENOUS IMMUNOGLOBULIN (IVIG) USEFUL AS THERAPEUTIC IVIG MIMETICS AND METHODS OF THEIR USE

1. CROSS REFERENCE TO RELATED APPLICATION

This application is the National Stage of International Application No. PCT/US/2013/021054, filed Jan. 10, 2013, which is a continuation-in-part of U.S. patent application Ser. No. 13/348,602 filed on Jan. 11, 2012, each of which is hereby incorporated by reference in its entirety.

0.1 SEQUENCE LISTING

This application incorporates by reference the computer readable sequence listing in the file "2020-06-19 118179.00003_ST25.txt," created Jun. 19, 2020, having 14.9 KB.

2. FIELD OF THE INVENTION

Provided herein are composition of antibodies against non-classical Human Leukocyte Antigens (HLA-Ib) that mimic immunoreactivity and immunomodulatory functions of IVIg and methods using the same as IVIg mimetics for the prevention, treatment, therapy and/or amelioration of inflammation induced diseases, and allograft rejection. In certain embodiments, provided herein are chimeric, humanized or recombinant or human anti-HLA-Ib IgG antibodies, produced from murine hybridoma clones that mimic IVIg (i) in immunoreactivity to both classical, HLA class Ia, and non-classical, HLA class Ib antigens and (ii) in immunomodulatory activities. In certain embodiments, the aforementioned anti-HLA-Ib IgG antibodies are immunoreactive to all HLA-Ib antigens, namely all the alleles of HLA-E, HLA-F and HLA-G, as wells as to several HLA-Ia antigens, namely several alleles for HLA-A, HLA-B and HLA-Cw. In particular embodiments, provided herein are compositions comprising such antibodies and methods of their use for treating or ameliorating inflammatory diseases and allograft rejection.

3. BACKGROUND OF THE INVENTION

Intravenous immune globulin (IVIg) is a blood product administered intravenously. It contains IgG (immunoglobulin G) pooled from the plasma (without any other proteins) from over 1,000 to 60,000 normal and healthy blood donors. IVIg contains a high percentage of native human monomeric IgG with very low IgA content. IVIg's effects last between 2 weeks to 3 months.

When administered intravenously, IVIg has been shown to ameliorate several disease conditions. Therefore, the United States Food and Drug Administration (FDA) has approved the use of IVIg for a number of diseases including (1) Kawasaki disease; (2) immune-mediated thrombocytopenia; (3) primary immunodeficiencies; (4) hematopoietic stem cell transplantation (for those older than 20 yrs); (5) chronic B-cell lymphocytic leukemia; and (6) pediatric HIV type 1 infection. In 2004, the FDA approved the Cedars-Sinai IVIg Protocol for kidney transplant recipients so that such recipients could accept a living donor kidney from any healthy donor, regardless of blood type (ABO incompatible) or tissue match.

In addition, inflammatory diseases that are also treated with IVIg include but not limited to the following:
1. Solid organ transplantation
2. Hematological Diseases
   a. Aplastic anemia
   b. Pure red cell aplasia
   c. Diamond-Blackfan anemia
   d. Autoimmune hemolytic anemia
   e. Hemolytic disease of the newborn
   f. Acquired factor I inhibitors
   g. Acquired von Willebrand disease
   h. Immune-mediated neutropenia
   i. Refractoriness to platelet transfusion
   j. Neonatal alloimmune/ne thrombocytopenia
   k. Post transfusion purpura
   l. Thrombotic thrombocytopenia purpura/hemolytic uremic syndrome
   m. Hemolytic transfusion reaction
   n. Hemophagocytic syndrome
   o. Thrombocytopenia
   p. Acute lymphoblastic leukemia
   q. Multiple myeloma
   r. Human T-cell lymphotrophic virus-1-myelopathy
3. Nephropathy
   a. Nephritic syndrome
   b. Membranous nephropathy
   c. Nephrotic syndrome
   d. Acute renal failure
4. Neuropathy
   a. Epilepsy
   b. Chronic inflammatory demyelinating polyneuropathy and Guillain-Barré syndrome
   c. Myasthenia gravis
   d. Lambert-Eaton myasthenic syndrome
   e. Multifocal motor neuropathy
   E Multiple sclerosis
   g. Wegener granulomatosis
   h. Amyotrophic lateral sclerosis
   i. Lower motor neuron syndrome
   j. Acute disseminated encephalomyelitis
   k. Paraneoplastic cerebellar degeneration
   l. Paraproteinemic neuropathy
   m. Polyneuropathy,
   n. Progressive lumbosacral plexopathy
5. Infection
   a. HIV infection
   b. Lyme radiculoneuritis
   c. Endotoxemia of Pregnancy
   d. Parvovirus infection
   e. Streptococcal toxic shock syndrome
6. Autoimmune Diseases
   a. Rheumatoid arthritis
   b. Systemic lupus erythematosus
   c. Systemic vasculitis
   d. Dermatomyositis, polymyositis
   e. Inclusion-body myositis
   f. Autoimmune blistering dermatosis
7. Cardiomyopathy
   a. Acute cardiomyopathy
8. Eye and Ear diseases
   a. Euthyroid ophthalmopathy
   b. Uveitis
   c. Recurrent otitis media
9. Lung diseases a. Asthma
b. Cystic fibrosis
10. Other disease conditions
a. Recurrent pregnancy loss
b. Behçet syndrome
c. Chronic fatigue syndrome
d. Congenital heart block
e. Diabetes mellitus
f. Acute idiopathic dysautonomia
g. Opsoclonus-myoclonus
h. Rasmussen syndrome
i. Reiter syndrome
j. Vogt-Koyanagi-Harada syndrome trauma
k. burns IVIg is used as a therapeutic immunomodulatory agent. For instance, IVIg is administered at a high dose (generally 1-2 grams IVIg per kg body weight) to decrease the severity of the immune response in patients with autoimmune diseases. Previous studies have shown that IgG antibodies in Wig have immunosuppressive capabilities. It remains unclear from these studies, however, how these IgG antibodies act as immunomodulatory agents in the context of IVIg and whether these immunomodulatory effects are due to all IgGs or specific IgGs within IVIg. To date, the major component of IVIg that may be responsible for its immunomodulatory function has not been identified. Preparations of IVIg require labor-intensive and cost-intensive processes. See, e.g., access-medical<dot>com</>alpha-trax<> Download</>IGIV-ALPHA<dot>ppt. It is well known that commercial preparations of IVIg vary in composition. See Table 1. A preparation of IVIg typically comprises pooled IgG from over a thousand blood donors. Reports in 2009 estimate that the utilization of IVIg (approx. $60/gm) regularly exceeds $10,000 per treatment course.

TABLE 1

Summary of Characteristics of Different Commercial Preparations of IVIg

| Characteristics | Alpha | Baxter | Bayer | Centeon | Novartis |
| --- | --- | --- | --- | --- | --- |
| Donor Pool (min) | 10,000 | 8,000 | 2,000 | 1,000 | 16,000 |
| IgG (%) | >99 | >90 | >98 | >99 | >96 |
| IgG | All | Low IgG$_4$ | All | Low IgG$_4$ | All |
| IgA (mg/ml) | 22 | <3.7 | 270 | 25 | 720 |

The lack of uniformity in commercial preparations of IVIg is a major concern. In addition, it can lead to varying side effects among the different commercial preparations. Common adverse side effects include chills, headache, fever, nausea/vomiting, back pain, hypotension, joint pain and allergic responses. Serious adverse side effects include anaphylactic shock, renal insufficiency, Steven-Johnson syndrome, aseptic meningitis, thromboembolic events, thrombosis, cytopenia, hemolysis, stroke, seizure, loss of consciousness, acute respiratory distress syndrome, pulmonary edema, acute bronchospasm, transfusion associated lung injury, aseptic meningitis, delayed hemolytic reaction, acute myocardial infarction and even acute renal failure. Twenty-nine cases of thrombotic complications associated with the use of IVIg have been reported and include acute myocardial infarction, cerebral infarction, pulmonary embolism, deep venous thrombosis, hepatic veno-occlusive disease, and spinal cord ischemia. Specific adverse side effects were attributed to differences in osmolality, pH, and sugar and sodium content of IVIg products. Due to the varying side effects in the different IVIg commercial preparations, the FDA has allowed only certain IVIg preparations for the treatment of particular diseases. See Table 2.

TABLE 2

Summary of FDA Approved Uses of Different Commercial Preparations of IVIg.

| | Commercial IVIg Prep Approved by FDA for Treatment | | | | |
| --- | --- | --- | --- | --- | --- |
| Diseases | Alpha | Baxter | Bayer | Centeon | Novartis |
| Primary Immune Deficiencies (PID) | Yes | Yes | Yes | Yes | Yes |
| Idiopathic Thrombocytopenic Purpura (ITP) | Yes | Yes | Yes | No | Yes |
| Chronic Lymphocytic Leukemia (CLL) | No | Yes | No | No | No |
| Kawasaki Disease | Yes | Yes | No | No | No |
| Bone Marrow Transplantation (BMT) | No | No | Yes | No | No |
| Pediatric HIV Infection | No | No | Yes | No | No |

The demand for therapeutic IVIg has steadily increased each year since 1992, which has resulted in product shortages and increased market prices. See, for example, Lemieux et al., 2005, *Mol. Immunol.* 42: 839-848. However, there are intrinsic limitations with respect to conventional production of therapeutic IVIgs: the quantities of human plasma that can be collected from donors are limited. Thus, there is a need for a cost-effective, evidence-based immunoreactive and immunomodulatory IVIg substitute or IVIg mimetic. Development of such IVIg substitutes or mimetics would stabilize and even reduce the use of donor-plasma derived IVIg, thereby securing such IVIg supplies for the most restricted and life threatening immunodeficiency diseases.

4. SUMMARY OF THE INVENTION

Provided herein are methods for better understanding the mechanisms of the therapeutic IVIgs based on their major immunoreactivity in correlation with immunomodulatory functions. Such understanding allows development of prospective IVIg mimetics for use in inflammatory diseases and human cancer. More precisely, provided herein are methods for producing IVIg substitutes or IVIg mimetics that comprise uniform and well defined compositions without immunointerfering substances, thereby retaining the therapeutic and/or prophylactic effects of IVIg while minimizing IVIg related side effects. In particular, provided herein are compositions of IVIg-mimetics, namely, "anti-HLA-Ib antibodies." The term refers to antibodies having immunoreactivity to non-classical class Ib antigens, for example, to one or more alleles from each of HLA-E, HLA-F and HLA-G. It will also be understood that the anti-HLA-Ib antibodies refer to the IVIg mimetics described herein.

Provided herein are compositions of anti-HLA Ib antibodies and methods for using the same as IVIg mimetics for the prevention, treatment, therapy and/or amelioration of inflammation induced diseases and allograft rejection, including but not limited to hematological, autoimmune, eye, ear and lung inflammatory diseases, nephropathy, cardiomyopathy, infection, solid organ transplant and several other inflammatory disease conditions including malignant tumorigenesis.

While not intending to be bound by any particular theory of operation, the invention is based, at least in part, on the identification of a characteristic, potent and hitherto unknown or unreported immunoreactivity of IVIg, from different commercial sources (see FIGS. 1 to 3). The human polyclonal IgG antibodies with immunoreactivity to HLA-E, HLA-F and HLA-G are a substantial component of the IVIg (FIGS. 1A-1D) used for treatment of patients of various maladies, listed earlier. When IVIg from different sources were tested at different dilutions for reactivity with HLA class Ia (e.g., HLA-A, HLA-B and HLA-Cw) and class Ib molecules (e.g., HLA-E, HLA-F and HLA-G), they showed dose dependent affinity for all the three HLA-Ia and all the three HLA-Ib antigens, with preference to HLA-E (except for one of the commercial IVIg, namely, Sandoglobulin). The binding of antibodies to a conserved region of a few HLA-Ia alleles in pooled normal immunoglobulin has been reported (Kaveri et al., 1996 *J. Clin Invest.* 97:865-869). However, the wide-ranging and detailed immunoreactivity profile (e.g., that of IVIg to both HLA-Ia and HLA-Ib alleles as shown in the present application) has not been recognized or used to characterize immunoreactivity of IVIg. Most importantly, existing studies are limited by the number of commercially available HLA class Ia molecules coated on microbeads for Luminex Flowcytometric assay (around 100 different HLA Ia proteins), when many more HLA proteins and/or alleles were reported. As shown in Table 3 below, there are 1264 HLA-A proteins, 1786 HLA-B proteins and 938 HLA-Cw proteins known. For example, more than 95% of the HLA-Ia molecules coated on the commercial microbeads are recognized by IgG in human IVIg. It is possible that the actual numbers of HLA-Ia molecules recognized by IVIg are much more or even closer to the numbers reported in Table 3. Assuming that not all the known HLA proteins are only variations of the known HLA types, wide-ranging and detailed immunoreactivity profiles can be established to characterize immunoreactive molecules.

TABLE 3

Numbers of HLA Alleles.
Human Leukocyte Antigen (HLA) alleles (genotype) and protein (phenotype)

|  | Classical HLA-Ia | | | Non-classical HLA-Ib | | |
| --- | --- | --- | --- | --- | --- | --- |
|  | A | B | Cw | E | F | G |
| Alleles | 2,012 | 2,605 | 1,551 | 11 | 22 | 50 |
| Proteins | 1,448 | 1,988 | 1,119 | 3 | 4 | 16 |

Based on information published at EBML-EBI website at www<dot>ebi<dot>ac<dot>uk</>imgt</>hla</>stats<dot>html Further, while not intending to be bound by any particular theory of operation, certain aspects provided herein are based on the identification of immunoreactivity of a commercially available purified human IgG (used as standard for test purposes) to HLA Class Ib antigens, namely, HLA-E, HLA-F and HLA-G (see FIG. 1C) as well as with the HLA-Ia molecules. Loss of HLA-Ia reactivities after adsorbing out anti-HLA-Ib antibodies (FIG. 3C) strongly supports the hypothesis that the anti-HLA-Ia reactivity of IVIg is associated with the anti-HLA-class Ib immunoreactivity of IVIg.

In particular, it was observed that IVIg reacted to free and β2-microglobulin-associated heavy chains of several polypeptides or proteins of HLA class Ia. The anti-HLA-Ib monoclonal antibodies (PTER006 and PTER007) were also immunoreactive to free and β2-microglobulin-associated heavy chains of HLA class Ia antigens (FIG. 4). Importantly, the anti-HLA-Ib antibodies, befitting the characteristics of an IVIg mimetic, also showed wide-ranging and detailed immunoreactivities (80 to 97%), parallel with those of IVIg. It is also interesting to note that more than 95% of the HLA-Ia molecules coated on the microbeads are recognized by several anti-HLA-Ib antibodies strikingly similar to Wig. As shown in FIG. 4, the wide-ranging and detailed HLA-Ia immunoreavity of anti-HLA-Ib antibodies suggests that they function as IVIg mimetics.

Further provided herein, in certain aspects, are pharmaceutical compositions of chimeric, humanized or human anti-HLA-Ib antibodies that can provide cost effective substitutes for IVIg, used as IVIg mimetics. In certain embodiments, the pharmaceutical compositions are uniform in composition, without immunointerfering antibodies (e.g., anti-albumin antibodies) or immune complexes (HLA-Ia or HLA-Ib antigens or any other antigen-bound antibodies) and can minimize the side effects often associated with the varying commercial preparations of IVIg. Certain pharmaceutical compositions provided herein comprise antibodies in a pharmaceutically acceptable carrier, wherein said antibodies are chimeric, humanized (the chimeric and humanized mAbs were generated after immunizing HLA-E$^R$ and/or HLA-E$^G$ into mice) or human anti-HLA-Ib antibodies immunoreactive to HLA-E, HLA-F and HLA-G. In exemplary embodiments described herein, a series of anti-HLA-Ib monoclonal antibodies were obtained after immunizing with HLA-E$^R$ (e.g., PTER006 and PTER007); and another series of anti-HLA-Ib monoclonal antibodies were obtained after immunizing with HLA-E$^G$ (e.g., PTEG016, PTEG017 and PTEG032). One or more of these exemplary monoclonal antibodies are used for humanization.

The aforementioned pharmaceutical compositions, namely the anti-HLA-Ib antibodies and when intended for therapeutic use, are administered into patients in the same manner as IVIg is administered. The protocol of therapeutic administration is referred to as passive therapy or passive immunotherapy.

In another aspect, active specific immunotherapy is used to administer compositions of the present invention. For example, a typical approach of therapeutic administration involves induction of polyclonal anti-HLA-Ib antibodies in patients, for example in cancer patients wherein the intention is to neutralize the soluble HLA-Ib that may bind to the receptors on CD8+ cytotoxic T cells (CTLs) or Natural killer T cells (NKT), to restore CTL/NKT killing of tumor cells. The pharmaceutical composition may include whole or part of the heavy chains of HLA-Ib molecules with or without an adjuvant and/or carrier and/or liposomes to induce antibody production in the patients.

In another aspect, provided herein is a strategy to induce polyclonal anti-HLA-Ib antibodies, using a whole cell or cell lysate vaccine/preparation created using patients' own tumor cells (autologous cells) or other patients tumor cells (allogeneic). In some embodiments, the vaccine/preparation is grown in cytokines (e.g., IFNγ, GM-CSF, IL-2, IL-6, IL-15, or IL-17) to induce over-expression of HLA-Ib molecules on the cell surface. When the whole cell or lysate vaccine/preparation is administered with or without adjuvant or carriers or stimulants, it can induce or elicit polyclonal anti-HLA-Ib antibodies with HLA-Ia reactivity and immunomodulatory functions similar to IVIg.

This pattern of reactivity of IVIg to HLA non-classical Class Ib and classical Class Ia antigens strongly suggests that IVIg comprise either (1) aggregates of IgGs with immunoreactivity to different HLA class Ia and Ib alleles or (2) an HLA-Ib IgG that may react with three well known classical HLA-Ia molecules (HLA-A, HLA-B and HLA-Cw), possibly due to the shared peptide sequences or epitopes (e.g., SEQ ID NOs: 7 and 8 in Table 4) between classical and non-classical HLA molecules.

7, 8 and 9) (Ravindranath et al., 2012, *J. Immunotox. doiI*:10.3109/1547691X.2011.645582).

In another aspect, provided herein are peptides in HLA class Ia and class Ib molecules that are recognized by anti-HLA-Ib antibodies. For example, the peptides comprise

TABLE 4

Peptide sequences or epitopes shared between HLA-E and HLA class Ia epitopes: monospecific versus polyspecific epitopes.

| SEQ ID No: | HLA-E peptide sequences [number of amino acids] | | Classical class Ia | | | Non-Classical class Ib | | Specificity |
|---|---|---|---|---|---|---|---|---|
| | | | A | B | Cw | F | G | |
| 1 | $^{47}$PRAPWMEQE$^{55}$ | [9] | 1 | 0 | 0 | 0 | 0 | A*3306 |
| 2 | $^{59}$EYWDRETR$^{65}$ | [8] | 5 | 0 | 0 | 0 | 0 | A restricted |
| 3 | $^{65}$RSARDTA$^{71}$ | [6] | 0 | 0 | 0 | 0 | 0 | E-restricted |
| 4 | $^{90}$AGSHTLQW$^{97}$ | [8] | 1 | 10 | 48 | 0 | 0 | Polyspecific |
| 5 | $^{108}$RFLRGYE$^{123}$ | [7] | 24 | 0 | 0 | 0 | 0 | A restricted |
| 6 | $^{115}$QFAYDGKDY$^{123}$ | [9] | 1 | 104 | 75 | 0 | 0 | Polyspecific |
| 7 | $^{117}$AYDGKDY$^{123}$ | [7] | 491 | 831 | 271 | 21 | 30 | Polyspecific |
| 8 | $^{126}$LNEDLRSWTA$^{135}$ | [10] | 239 | 219 | 261 | 21 | 30 | Polyspecific |
| 9 | $^{137}$DTAAQI$^{142}$ | [6] | 0 | 824 | 248 | 0 | 30 | Polyspecific |
| 10 | $^{137}$DTAAQIS$^{143}$ | [7] | 0 | 52 | 4 | 0 | 30 | Polyspecific |
| 11 | $^{143}$SEQKSNDASE$^{152}$ | [10] | 0 | 0 | 0 | 0 | 0 | E-restricted |
| 12 | $^{157}$RAYLED$^{162}$ | [6] | 0 | 1 | 0 | 0 | 0 | B*8201 |
| 13 | $^{163}$TCVEWL$^{168}$ | [6] | 282 | 206 | 200 | 0 | 30 | Polyspecific |
| 14 | $^{182}$EPPKTHVT$^{190}$ | [8] | 0 | 0 | 19 | 0 | 0 | C restricted |

The hypothesis that an HLA-Ib IgG may react with three well-known classical HLA-Ia molecules (HLA-A, HLA-B and HLA-Cw) was supported by HLA-Ia reactivity of commercial anti-HLA-E monoclonal antibodies (MEM-E/02, MEM-E/06 & 3D12) and simultaneous inhibition of HLA-E and HLA-Ia reactivities by synthetic shared peptide sequences (SEQ ID NOs: 7,8 and 9) (Ravindranath et al., 2010, *Mol. Immunol.* 47: 1121-1131; Ravindranath et al., 2010, *Mol. Immunol.* 47. 1663-1664; Ravindranath et al., 2011, *Mol. Immunol.* 48:423-428; Ravindranath et al., 2010, *J. Immunol.* 185: 1935-1948). Such shared epitopes or polyspecific peptide sequences (as listed in Table 4) that may be responsible for the IVIg reactivity with both HLA class Ia molecules (e.g., HLA-A, HLA-B and HLA-Cw) and HLA-Ib molecules (e.g., HLA-E, HLA-F and HLA-G). The contention was also supported by inhibition of HLA-Ia reactivity of anti-HLA-E monoclonal antibody with recombinant HLA-E or purified HLA-E from sera of allograft recipients (Ravindranath et al. 2011 Internatl. Immunol. (doi:10.1093/intimm/dxr094). In addition, the second contention was also supported by HLA-Ia reactivity of polyclonal anti-HLA-E sera antibodies generated after immunizing cancer patients with autologous tumor cells, expressing HLA-Ib antigens, grown in medium containing IFN-γ and simultaneous inhibition of anti-HLA-E and HLA-Ia reactivities by synthetic shared peptide sequences (SEQ ID NOs:

individual amino acid sequences (e.g., SEQ ID Nos 7 and 8 in Table 4) shared by HLA-Ib (HLA-E, HLA-F and HLA-G) and HLA-Ia (HLA-A, HLA-B, HLA-Cw) molecules. In some embodiments, the IVIg mimetics (anti-HLA-Ib antibodies) recognize more than one peptide sequence that are shared by HLA-Ib (e.g., HLA-E, HLA-F and HLA-G) and HLA-Ia (e.g., HLA-A, HLA-B, HLA-Cw) molecules. In these embodiments, each of the two amino acid sequences has different amino acid sequences. In some embodiments, the two or more segments of amino acid sequences are recognized continuously or discontinuously by the Fragment Antigen Binding (Fab) portion of the antibodies. In some embodiments, a linker sequence is present to connect the two or more segments of amino acid sequences of the peptide.

In another aspect, peptides provided herein (e.g., those in Table 4) are used to block or reduce immunoreactivity of the anti-HLA-Ib antibodies (used as IVIg mimetics) against antigens including HLA-E, HLA-F, or HLA-G.

In some embodiments, compositions of anti-HLA Ib IgG antibodies provided herein are chimeric, humanized or human anti-HLA-Ib IgG antibodies that mimic IVIg in the following aspects: (i) mimics immunoreactivity to both classical, HLA class Ia, and non-classical, HLA class Ib antigens and (ii) mimics immunomodulatory activities. At the same time, the anti-HLA Ib IgG antibodies do not contain any anti-albumin IgG reactivity as was observed with IVIg. For example, FIG. 1B shows (1) IVIg has anti-albumin IgG reactivity, (2) the anti-albumin IgG may interfere with anti-HLA IgG reactivities of IVIg (see at dilution below 1/32).

Importantly, IVIg mimetics such as anti-HLA Ib antibodies as disclosed herein are monoclonal antibodies while conventional and commercial sources IVIg are polyclonal antibodies pooled from 1,000 to 10,000 individuals (see Table 1, Row 1). While not intending to be bound by any particular theory of operation, the unique composition of anti-HLA Ib IgG antibodies (used as IVIg mimetics) are monoclonally derived or humanized IVIg mimetics with HLA-immunoreactivity and immunomodulatory activity characteristic of polyclonal IVIg and at the same time free from interference of other antibodies (e.g., anti-albumin antibodies).

While not intending to be bound by any particular theory of operation, certain aspects provided herein are based, at least in part, on the identification of a potent immunoreactive anti-HLA-Ib monoclonal antibodies (PTER006 and PTER007) that reacted to three well known HLA-Ib molecules (e.g., HLA-E, HLA-F and HLA-G), in addition to HLA-Ia molecules (several HLA-A* molecules, in addition to 50 of HLA-B* and 16 of HLA-Cw* molecules) (see FIG. 4 & Table 4).

In some embodiments, the compositions provided herein are IVIg mimetics, including but not limited to purified antibodies, purified monoclonal antibodies, chimeric murine-human monoclonal antibodies, purified and recombinant human monoclonal antibodies, immunoreactive against non-classical anti-HLA-Ib antigens (HLA-E, HLA-F and HLA-G) as well as classical HLA-Ia antigens (HLA-A, HLA-B and HLA-Cw). In particular, it has been observed that IVIg reacted to free and intact HLA (β2-microglobulin-associated heavy chains of several alleles of HLA-A* in addition to HLA-B* and HLA-Cw*). However different therapeutic preparations of IVIg differed in their reactivity to free and intact HLA (see Table 5A, 5B and 5C). HLA-Ia alleles on regular beads may occur both as intact HLA with β2microglobulin (β2m) as well as heavy chains without (β2m. The manufacturer of HLA beads (One Lambda, Inc) has recently generated beads with reduced amounts of (β2m-free HLA, called IBEADS™ (HLA Class 1 antigen beads). Differences in the reactivity of IVIg preparations to regular beads and IBEADS™ may indicate whether IVIg binds more to intact HLA or to HLA heavy chain. All mAbs were also tested on IBEADS™.

In one aspect, provided herein are compositions that have immunoreactivity to HLA class Ib antigens: HLA-E, HLA-F and HLA-G. In some embodiments, compositions provided herein have greater immunoreactivity to HLA-E than to HLA-F (see FIG. 4, mAb PTER006, mAb PTEG032, mAb PTER007, mAb PTEG016 and mAb PTEG017). In some embodiments, compositions provided herein have much greater immunoreactivity to HLA-E than to HLA-G (e.g., mAb PTER006, mAb PTEG032, mAb PTER007, mAb PTEG016 and mAb PTEG017). In some embodiments, compositions provided herein have much greater immunoreactivity to HLA-F than to HLA-G (e.g., mAb PTER006, mAb PTEG032 and mAb PTER007). In some embodiments, compositions provided herein have much greater immunoreactivity to HLA-G than to HLA-F (e.g., mAb PTEG016 and mAb PTEG017). In some embodiments, compositions provided herein have much greater immunoreactivity to HLA-Ib than to classical anti-HLA-Ia antigens (e.g., HLA-A, HLA-B and HLA-Cw). It will be understood that antibodies (IVIg mimetics) provided herein can be prepared by any methods known to one of skill in the art.

In some embodiments, the anti-HLA-Ib antibodies are purified monoclonal antibodies, recombinantly produced antibodies, Fab fragments, F(ab') fragments, or epitope-binding fragments, generated by immunizing HLA-$E^R$ and/or HLA-$E^G$ by immunizing the antigens in mice, rats, rabbits or other animals. In particular embodiments, the anti-HLA-Ib antibodies are purified monoclonal antibodies. In particular embodiments, the anti-HLA-Ib antibodies are a mixture of two or more monoclonal antibodies generated by immunizing HLA-$E^R$ and/or HLA-$E^G$. In other embodiments, the anti-HLA class-Ib antibodies are F(ab) fragments.

In exemplary embodiments, said anti-HLA-Ib antibodies (generated by immunizing HLA-$E^R$ and/or HLA-$E^G$) are also immunoreactive to heavy chains of HLA-E, HLA-F, HLA-G and to many alleles of HLA-A, HLA-B and HLA-Cw, in a manner strikingly similar to IVIg. In some embodiments, said heavy chains are free heavy chains, not associated with β2-microglobulin. In some embodiments, said heavy chains are associated with β2-microglobulin. In specific embodiments, said anti-HLA-Ib antibodies are also more immunoreactive to heavy chains of HLA-F, like some of the commercial preparations of Wig and to several alleles of HLA-A, HLA-B and HLA-Cw.

Further, while not intending to be bound by any particular theory of operation, the anti-HLA-Ib IgG antibodies or the IVIg mimetics described herein are capable of clearing and/or neutralizing soluble HLA-E, HLA-F and HLA-G heavy chains from the circulation or the blood (plasma or serum), synovial fluid, seminal fluid or in any other body fluid. According to previous literature documents, HLA-A, HLA-B, HLA-Cw, HLA-E, HLA-F and HLA-G are shed periodically into circulation as heavy chains in "normal" individuals and in patients with inflammation and cancer. The anti-HLA-Ib antibodies or Wig mimetics provided herein might be able to complex with soluble HLA (both HLA-Ia and Ib) to remove them from circulation. It has been suggested that soluble HLA-Ib molecules such as HLA-E can be cytotoxic to both CD4+ and CD8+ T-lymphocytes. The cytotoxic capabilities of such HLA molecules warrant their clearance from circulation and tissue microenvironments and the IVIg mimetics or anti-HLA-Ib antibodies are the most appropriate agents for such clearance.

In exemplary embodiments, the anti-HLA-Ib antibodies are immunoreactive to 21 (mAb PTEG017), 22 (mAb PTEG016), 26 (mAb PTER007), 29 (mAb PTEG032) and 31 (mAb PTER006) HLA-A* alleles, similar to IVIG which showed immunoreactivity to 20 to 31 HLA-A* alleles. Similarly, anti-HLA-Ib mAbs reacted to 44 (mAb PTER007, mAb PTEG016), 48 (mAb PTEG032) and 50 (mAb PTER006) HLA-B* alleles, respectively, and to all 16 HLA-Cw* alleles, identical to commercial IVIg preparations. In this regard they differ from anti-HLA-E mAbs which recognized fewer HLA-Ia alleles.

In some embodiments, immunoreactivity/immunomodulatory activity profiles of IVIg are established. Also provided herein are methods for modulating stimulated T-lymphocytes and T-lymphoblasts growth and activities (cell growth, proliferation and blastogenesis and cell death) using IVIg-mimetics compositions provided herein. In another aspect, provided herein are methods and systems for screening immunoreactive IVIg-mimetics by establishing immunoreactivity/immunomodulatory profiles, using activity profiles of IVIg as a standard. In some embodiments, compositions identified by the screening methods and systems are used as anti-HLA Ib antibodies for preventing, managing, treating and/or ameliorating a graft rejection, the method comprising administering to a mammal a therapeutically effective amount of any one of the compositions provided herein. In yet other embodiments, compositions identified by the screening methods and systems are used as anti-HLA Ib antibodies for managing, treating and/or ameliorating an inflammatory disease or condition.

Further, while not intending to be bound by any particular theory of operation, certain aspects provided herein are based, at least in part, on the identification of T-cell suppressive immunomodulatory activity of human IVIg. This activity has been identified to be similar to the T-cell suppressive activity of the different IVIg-mimetics or HLA class Ib reactive monoclonal antibodies, examples, PTER006 and PTER007 generated by immunizing mice with recombinant HLA-$E^R$ (FIGS. 5 and 6).

Provided herein, in certain aspects, are chimeric, humanized or human recombinant anti-HLA-Ib antibodies capable of T-cell suppressive immunomodulatory activity of human IVIg. The chimeric and humanized or purified recombinant mAbs were produced from hybridoma (clones) generated after immunizing HLA-$E^R$ and/or HLA-$E^G$ into mice.

In some embodiments, the composition of anti-HLA Ib antibodies (or IVIg-mimetic) is capable of suppressing naïve and/or activated CD4+ T-cells in a recipient of the pharmaceutical composition (e.g., FIG. 5) in a manner similar or identical to that of IVIg.

In some embodiments, the composition of anti-HLA Ib antibodies (or IVIg-mimetic) is capable of suppressing the proliferation and/or blastogenesis of naïve and/or activated CD4+ T-cells in a recipient of the pharmaceutical composition (e.g., FIG. 6) in a manner similar or identical to that of IVIg.

In some embodiments, the composition of anti-HLA Ib antibodies (or IVIg-mimetic) is capable of suppressing naïve and/or activated CD4+ T-cells in a recipient of the pharmaceutical composition (e.g., FIG. 5) in a manner similar or identical to that of IVIg.

In some embodiments, the composition of anti-HLA Ib antibodies (or IVIg-mimetic) is capable of suppressing the proliferation and/or blastogenesis of naïve and/or activated CD4+ T-cells in a recipient of the pharmaceutical composition (e.g., FIG. 6) in a manner similar or identical to that of IVIg.

In some embodiments, the composition of anti-HLA Ib antibodies (or IVIg-mimetic) is capable of suppressing naïve and/or activated CD8+ T-cells in a recipient of the pharmaceutical composition (e.g., FIG. 5), in a manner similar or identical to that of IVIg.

In some embodiments, the composition of anti-HLA Ib antibodies (or IVIg-mimetic) is capable of suppressing the proliferation and/or blastogenesis of naïve and/or activated CD8+ T-cells in a recipient of the pharmaceutical composition (e.g., FIG. 6) in a manner similar or identical to that of IVIg.

In certain embodiments, the composition of anti-HLA Ib antibodies (or IVIg-mimetic) is capable of inducing cell death of naïve CD4+ T-cells (reduction in number of events as seen in FIG. 5(A6) and and/or activated CD4+ T-cells (FIG. 6, A8) in a recipient of the pharmaceutical composition, in a manner similar or identical to that of IVIg (FIG. 5, A3, A4).

In certain embodiments, the composition of anti-HLA Ib antibodies (or IVIg-mimetic) is capable of inducing cell death of activated CD8+ T-cells (reduction in number of events as seen in FIG. 5, A8, A9) and and/or activated CD4+ T-cells (as shown in FIG. 6, A9) in a recipient of the pharmaceutical composition, in a manner similar or identical to that of IVIg.

In some embodiments, the pharmaceutical composition of anti-HLA Ib antibodies (or IVIg-mimetic) is capable of suppressing even at early stage of sequence of events leading to formation of T-cell dependent HLA antibodies in a recipient (FIGS. 7 and 8). In certain embodiments, the T-cell dependent HLA antibodies are anti-HLA Ia antibodies. In certain embodiments, the recipient is a transplant recipient. In some embodiments, the pharmaceutical composition of anti-HLA-Ib antibodies (or IVIg-mimetic) is capable of suppressing B lymphocytes secreting HLA Class-II antibodies from an alloimmunized female. In certain embodiments, level of suppression is similar to or better than IVIg, which is normally considered as a treatment protocol to reduce HLA antibodies in patients waiting for transplant or in patients (e.g., sensitized patients) after transplantation (FIGS. 8 through 10). In some embodiments, the sensitized patients include patients that are waiting for donor kidney, under dialysis and have high titers of HLA antibodies.

In some embodiments, the pharmaceutical composition of anti-HLA Ib antibodies (or IVIg-mimetic) is suitable for intramuscular administration, intradermal administration, intraperitoneal administration, intravenous administration, subcutaneous administration, or any combination thereof. In some embodiments, the pharmaceutical composition is suitable for subcutaneous administration. In some embodiments, the composition is suitable for intravenous administration. In some embodiments, the composition is suitable for intramuscular administration.

In some embodiments, at least 50% of the antibodies of the composition are anti-HLA-Ib antibodies according to the description provided herein. In some embodiments, at least 60% of the antibodies of the composition are anti-HLA-Ib antibodies according to the description provided herein. In some embodiments, at least 70% of the antibodies of the composition are anti-HLA-Ib antibodies according to the description provided herein. In some embodiments, at least 80% of the antibodies of the composition are anti-HLA-Ib antibodies according to the description provided herein. In some embodiments, at least 85% of the antibodies of the composition are anti-HLA-Ib antibodies. In some embodiments, at least 90% of the antibodies of the composition are anti-HLA-Ib antibodies. In some embodiments, at least 95% of the antibodies of the composition are anti-HLA-Ib antibodies. In some embodiments, at least 99% of the antibodies of the composition are anti-HLA-Ib antibodies.

In some embodiments, a composition or pharmaceutical composition of anti-HLA Ib antibodies (or IVIg-mimetic) provided herein can be used to prevent formation of T-cell dependent HLA antibodies in a recipient. In certain embodiments, the T-cell dependent HLA antibodies are anti-HLA Ia antibodies. In certain embodiments, the recipient is a transplant recipient.

In another aspect, provided herein is a method of preventing, managing, treating and/or ameliorating a graft rejection, the method comprising administering to a mammal a therapeutically effective amount of any one of the compositions provided herein.

In yet another aspect, provided herein is a method of managing, treating and/or ameliorating an inflammatory disease or condition. In some embodiments, provided herein is a method of managing, treating and/or ameliorating transfusion-induced acute lung injury (TRALI).

5. BRIEF DESCRIPTION OF THE DRAWINGS

Those of skill in the art will understand that the drawings, described below, are for illustrative purposes only. The drawings are not intended to limit the scope of the present teachings in any way.

The values represented in the Drawings and Tables refer to normalized trimmed mean, which is termed MFI for simplicity. Interpretations of the data are based on the normalized trimmed mean (called MFI in this application). In all the drawings on the immunoreactivity of Wig or Wig mimetics to HLA-class Ia or class Ib molecules refer to values (designated as MFI in x-axis) obtained with a multiplex Luminex®-based immunoassay, which is described in details in the Example section.

FIGS. 1A-1F depict IgG antibodies in commercial IVIg preparations reacting to HLA-E, HLA-F and HLA-G heavy chains: A) Wig Reactivity to all non-classical HLA-Ib molecules inclusive of HLA-E, HLA-F & HLA-G heavy chains (IVIg: GamaSTAN™ S/D, Talecris Biotherapeutics, Inc. Research Triangle Park, N.C., USA); B) Wig Reactivity to all non-classical HLA-Ib molecules inclusive of HLA-E, HLA-F and HLA-G heavy chains (IVIg: Sandoglobulin); C) IVIg Reactivity to all non-classical HLA-Ib molecules inclusive of HLA-E, HLA-F & HLA-G heavy chains (IVIg: Octagam); D) IVIg Reactivity to all non-classical HLA-Ib molecules inclusive of HLA-E, HLA-F & HLA-G heavy chains (IVIg: IVIGlob® EX, VHB Life Sciences Ltd. India); E) IVIg contains reactivity against negative control or beads coated with albumin (One Lambda, coated either with human or bovine albumin), indicating that Wig has anti-albumin antibodies and the interference of anti-albumin IgG in Wig with MFI obtained with anti-Human HLA Ia or Ib reactivities is obvious at dilutions ½ to ⅟₁₆ or ⅟₃₂; it is necessary to correct the interference of anti-albumin IgG in Wig with MFI obtained with anti-Human HLA Ia or Ib reactivities. There are evidences in literature that the anti-albumin antibody may interfere not only with immunoreactivity but also with immunomodulatory functions until it is diluted, and F) Purified Human IgG commercially available (for diagnostic but not for clinical purpose) (Southern Biotech, cat. No: 0150-01, Birmingham, Ala.) reveals reactivity to HLA-E, HLA-F and HLA-G at varying degrees.

FIGS. 2A-2D demonstrate that HLA-Ia reactivity of IVIg from two different commercial sources is due to HLA-Ia reactivity of anti-HLA-Ib antibodies: A) IVIg Reactivity to non-classical HLA-Ib molecules: HLA-E, -F and -G heavy chains, and classical HLA-Ia molecules HLA-A, HLA-B and HLA-Cw epitopes (IVIg: GamaSTAN™ S/D, Talecris Biotherapeutics, Inc., USA, experiment done in triplicates); B) IVIg Reactivity to all non-classical HLA-Ib molecules: HLA-E, -F and -G heavy chains, and all classical HLA-Ia molecules: HLA-A, HLA-B and HLA-Cw epitopes (IVIg: Sandoglobulin); C) IVIg Reactivity to all non-classical HLA-Ib molecules: HLA-E, -F and -G heavy chains, and all classical HLA-Ia molecules: HLA-A, HLA-B and HLA-Cw epitopes Octagam); and D) IVIg reactivity to all classical HLA-Ia molecules HLA-A, HLA-B and HLA-Cw epitopes (IVIGlob® EX, VHB Life Sciences Ltd. India, experiments done in duplicates). In FIGS. 2B-2D, ■ MFI: >10,000; ▨ MFI: 5000-9,999; ▦ MFI: 2000-4999; ▤ MFI: 1000-1999; □ MFI: 500-1999; ▥ MFI<500.

FIGS. 3A-3C show that both HLA-E and HLA-Ia reactivity of IVIg is lost after adsorbing IVIg to Affi-Gel conjugated with HLA-E: A) Loss of HLA-E reactivity of WIG after adsorption with a non-classical HLA-Ib (HLA-E)-conjugated Affi Gel 10; B) Loss of HLA-Ia reactivity of IVIg after adsorption with a non-classical HLA-Ib (HLA-E)-conjugated Affi Gel 10; and C) Percentage Loss of HLA-E antibody reactivity of IVIg after adsorption with a non-classical HLA-Ib (HLA-E)-conjugated Affi-Gel 10. The figures illustrate that removal of anti-HLA-Ib reactivity by absorption of IVIg to HLA-Ib coated agarose also removes all the HLA-Ia reactivity, which suggests that the HLA-Ia reactivity of IVIg is indeed due to the anti-HLA-Ib antibodies. The illustration used HLA-E as the model.

FIG. 4 shows that HLA-Ia reactivity (in comparison to WIG) by anti-HLA-Ib murine monoclonal antibodies. A) Reactivity data to HLA-Ib (HLA-E, HLA-F and HLA-G) for PTER006 are in upper row and PTER007 in lower row. These monoclonal antibodies are IgG purified from the respective culture supernatants using Protein-G columns. The purified IgG is diluted ⅟₁₀ and tested against Luminex beads coated with HLA class Ia alleles as listed. Non-reactive alleles are in white box and reactive alleles are in the colored boxes; B Reactivity data to HLA-Ib (HLA-E, HLA-F and HLA-G) are shown First Row: PTER006, Second row: PTEG032; Third row: mAb PTER007; Fourth row: PTEG016; Last Row: PTEG017). The culture supernatants of the monoclonal antibodies are further IgG purified using Protein-G columns. Both culture supernatants and the purified IgG were diluted ⅟₁₀ and tested against Luminex beads coated with HLA class Ia alleles as listed. All the anti-HLA-Ib monoclonal antibodies show reactivity with HLA-Ia (HLA-A, HLA-B and HLA-Cw) alleles. The values (levels of reactivity) are expressed as Mean Fluorescent Intensity (MFI). The MFI values of each Monoclonal antibody (Right column) are presented against HLA-Ia and Ib alleles (Left column). MFI values higher than 10,000 are marked with asterisks. The shaded HLA-Ia alleles indicate similarities in the HLA-Ia reactivity of the monoclonal antibodies. All shaded alleles refer that all the anti-HLA-Ib monoclonal antibodies recognize these alleles. Asterisks (*) above alleles refer that these alleles show very high MFI (>10,000). Note that all of the mAbs are raised by immunizing mice (BALB/c) with recombinant heavy chains of HLA-E$^R$ or HLA-E$^G$. These monoclonal antibodies are IgG purified from the respective culture supernatants using Protein-G columns. The purified IgG is diluted ⅟₁₀ and tested against Luminex beads coated with HLA class Ia epitopes as listed.

FIGS. 5A-5I show that T-lymphocyte modulatory activity of IVIG and anti-HLA-Ib monoclonal antibodies (PTER007 and PTER006), which are reactive to both HLA-classes Ia and Ib similar to IVIg. Note that all of the anti-HLA-Ib antibodies (including Ab PTER006 and PTER007) and other categories are raised by immunizing mice (BALB/c) with recombinant heavy chains of HLA-E$^R$ or HLA-E$^G$: A) Events occurring 70 hrs after PHA-L stimulation of T-Lymphocytes (CD3+/CD4+); B) Changes that occur in T-lymphocyte populations 70 hrs after PHA-L stimulation; C) Human IVIg induces cell death, arrests proliferation and blastogenesis of PHA-L stimulated T lymphocytes (CD3+/CD4+); D) IVIg dosimetrically (at different dilutions) inhibits PHA-stimulated CD4+ T-lymphocytes and T lymphoblasts; E) IVIg dosimetrically (at different dilutions) inhibits PHA-stimulated CD8+ T-lymphocytes and T lymphoblasts; F) Anti-HLA-Ib monoclonal antibody (PTER007 at ⅟₁₀ dilution) arrest proliferation and blastogenesis of PHA-L stimulated CD4+ T-lymphocytes; G) Anti-HLA-Ib monoclonal antibody PTER007 at ⅟₁₀₀ dilution arrest proliferation and blastogenesis of PHA-L stimulated CD4+ T-lymphocytes; H) Anti-HLA-Ib monoclonal antibody PTER007 at ⅟₁₀ and ⅟₁₀₀ dilutions arrest proliferation and blastogenesis of PHA-L stimulated CD8+ T-lymphocytes; I) Anti-HLA-Ib monoclonal antibody, mAb PTER006 arrests blastogenesis of PHA-L stimulated CD4+ and CD8+ T-lymphocytes at 1/10 dilution. At 1/100 dilution of mAb PTER006, the failure of proliferation of CD4+ T cells were significant at p2<0.05 decline in Blastogenesis of CD8+ T cells were significant at p2<0.05; J) Monoclonal antibodies PTER037 (non-reactive to HLA-F and HLA-G), PTER006 and PTER007 (at two different dilutions) inhibit PHA-stimulated CD4+T-lymphocytes and T lymphoblasts (Activated); K) Monoclonal antibodies PTER037 (reactive to HLA-E but not to HLA-F and HLA-G), PTER006 and PTER007 (at two different dilutions) inhibit PHA-stimulated CD8+ T-lymphocytes and T lymphoblasts (Activated); L) Illustrated Summary of the influence of anti-HLA-Ib monoclonal antibodies, PTER007 at two different dilutions) inhibits PHA-stimulated CD8+ T-lymphocytes and T lymphoblasts (Activated).

FIGS. 6A-6I show that IVIg and anti-HLA-Ib monoclonal antibodies (PTER007 and PTER006) share similarities in activities by T-lymphocyte proliferation Assay. Proliferation was assessed by carboxyfluorescein diacetate succinimidyl ester (CFSE) Stain Technology. A) An Approximated Profile of the CFSE fluorescence intensity of proliferating T cells after 70 hours of exposure to PHA closely follows the predicted sequential halving due to cell division (M1, M2, M3 and M4); B) IVIg inhibits PHA-L induced proliferation CD3+CFSE+ T-Lymphocytes at 72 hrs; C) Percentage inhibition of T-cell proliferation by IVIg (at different dilutions) 72 hrs after PHA-stimulation; D) Comparison of anti-HLA-Ib monoclonal antibodies (PTER007) and IVIg reactivity against CD4+ T cells. Specific Inhibition of PHA-L induced Proliferation CD4+CFSE+ T-Lymphocytes by anti-HLA-Ib monoclonal antibodies, PTER007 at dilution 1/10 after 72 hrs of incubation with the antibodies. Cell population [I] includes memory T cells; cell population [II] includes Naïve T cells; and cell population [III] includes Activated T cells, which proliferates upon PHA exposure. Compare Left side numbers of group [III] to appreciate differences after addition of PHA and PHA+mAb; E) Effects of anti-HLA-Ib monoclonal antibodies, PTER007 on CD8+ T cells: Specific Inhibition of PHA-L induced Proliferation CD8+CFSE+ T-lymphocytes by anti-HLA-Ib mAb PTER007 at dilution 1/10 after 72 hrs of incubation with the antibodies. Cell population [I] includes memory T cells; cell population [II] includes Naïve T cells; and cell population [III] includes Activated T cells, which proliferates upon PHA exposure. Compare Left side numbers of group [III] to appreciate differences after addition of PHA and PHA+mAb; F) Effects of anti-HLA-Ib monoclonal antibodies, PTER006 on CD4+ T cells. Specific Inhibition of PHA-L induced Proliferation CD4+CFSE+ T-lymphocytes by anti-HLA-Ib mAb PTER006 at dilution 1/10 after 72 hrs of incubation with the antibodies. Cell population [I] includes memory T cells; cell population [II] includes Naïve T cells; and cell population [III] includes Activated T cells, which proliferates upon PHA exposure. Compare Left side numbers of group [III] to appreciate differences after addition of PHA and PHA+mAb; G) Effects of anti-HLA-Ib monoclonal antibodies, PTER006 on CD8+ T cells. Specific Inhibition of PHA-L induced Proliferation CD8+CFSE+ T-lymphocytes by anti-HLA-Ib mAb PTER006 at dilution 1/10 after 72 hrs of incubation with the antibodies. Cell population [I] includes memory T cells; cell population [II] includes Naïve T cells; and cell population [III] includes Activated T cells, which proliferates upon PHA exposure. Compare Left side numbers of group [III] to appreciate differences after addition of PHA and PHA+mAb; H) Arrest of PHA-induced Proliferation newly divided CD4+ lymphoblasts and cell death of parent CD4+ lymphoblasts by anti-HLA-Ib monoclonal antibodies (PTER007, Left and PTER006, right) at different dilutions. Mean values were calculated from population III from FIGS. 6D and 6F. Left values represent newly divided lymphoblast and right values represent parent lymphoblasts; I) Arrest of PHA-induced Proliferation newly divided CD8+ lymphoblasts and cell death of parent CD8+ lymphoblasts by anti-HLA-Ib monoclonal antibodies (PTER007, Left and PTER006, right) at different dilutions. Mean values were calculated from population III from FIGS. 6E and 6G. Left values represent newly divided lymphoblast and right values represent parent lymphoblasts.

FIG. 7 depicts the immunomodulatory role of IVIg: One of the major immunosuppressive functions of IVIg dose dependent inhibition of PHA-L stimulated proliferation and blastogenesis of CD4+ T cells. Consequent to suppression of antigen presenting T cells, B cells are prevented from producing any new antibodies, such as donor specific antibodies produced after organ transplantation (see Djoumerska et al., 2005, *Scandinavian Journal of Immunology* 61: 357-363).

FIG. 8A-8C illustrate the exemplary experimental setup and alloreactivity of the B-lymphocytes from an alloimmunized human subject: A) Flow chart showing sample purification and treatment processes; B) schematic diagram of alloimmunication and HLA types of the human subject and her husband; and C) sample alloreactivity.

FIGS. 9A-9F illustrate additional exemplary experimental data of the B-lymphocytes from an alloimmunized subject: A) IVIg tends to reduce the secretion of anti-DRB1*0101 and anti-DRB1*0102 antibodies by the B cells of JH; B) In contrast to IVIg, mAb PTER007 (the IVIg mimetic) suppresses significantly the secretion of anti-DRB1*0101 ($p<0.007$) and anti-DRB1*0102 ($p<0.003$) antibodies by the B cells of JH; C) Wig increases the secretion of anti-DRB1*0404 and anti-DRB1*0402 antibodies by the B cells of JH; D) In contrast to IVIg, the IVIg-mimetic (mAb PTER-007) is highly efficient in suppressing the secretion of anti-DRB1*0404 and anti-DRB1*0402 antibodies by the B cells of JH; E) IVIg increases the secretion of anti-DRB1*0405 and anti-DRB1*1402 antibodies by the B cells of JH; and F) In contrast to IVIg, the IVIg-mimetic (mAb PTER-007) is efficient in suppressing the secretion of anti-DRB1*0405 and anti-DRB1*1402 antibodies by the B cells of JH.

FIG. 10 depicts a sequence alignment of six HLA alleles: DRB1*0101 (SEQ ID NO:15), DRB1*0102 (SEQ ID NO:16), DRB1*0401 (SEQ ID NO:17); DRB1*0404 (SEQ ID NO:18). DRB1*0405 (SEQ ID NO:19); and DRB1*1402 (SEQ ID NO:20).

6. DETAILED DESCRIPTION OF THE INVENTION

6.1 Definitions

The term "antigen" with respect to HLAs, refers to an HLA heavy chain associated with a β2-microglobulin to form a heterodimer or HLA heavy chain associated with a β2-microglobulin and a foreign peptide (e.g. viral) or an autologous peptide (e.g., a leader peptide of another antigen) or an HLA heavy chain or portion of an HLA heavy chain that is free (i.e., not bound to another HLA or β2-microglobulin) or an HLA heavy chain that is bound to another HLA heavy chain to form a homodimer (e.g. HLA-G), HLA antigens include those expressed or located on a cell surface or those occurring in soluble form in circulation or body fluids. The HLA-antigens are proteins (polypeptides), products of transcription and translation of genes. Numerous HLA alleles are known to date, as shown in Table 3.

One of two or more forms of a gene or a genetic locus (generally a group of genes) are referred to or designated by the term "allele" as used herein. It is known that sometimes different alleles can result in different observable phenotypic traits, such as different proteins. However, many variations at the genetic level result in little or no observable variation. The table above illustrates alleles at genetic level but phenotypic expression of the genes, namely the proteins are considerably less.

HLA polypeptides are made up of a long chain (the heavy chain) of amino acids (primary structure) and they are folded to appear in certain specific conformation (secondary structure) on the cell surface. These structures include three basic loops called α1, α2 and α3 helices (singular: Helix). When on the cell surface, the HLA secondary structure is strictly maintained due to its attachment on the cell membrane and also due its association with β2-microglobulin. The amino acid sequences when they occur in folded and coiled conditions, they are considered as "self" molecules and rarely an antibody can be elicited against these self antigens. However, when the β2-microglobulin in the intact HLA falls off from the cell surface, they expose some amino acid sequences that are new to the immune system of the host. These amino acid sequences are called as "cryptic" amino acid sequences. More cryptic amino acid sequences are exposed when the heavy chains of HLA molecules fall off from the cell surface into the tissue microenvironment or when it enters into blood or lymphatic circulation. It has been shown that heavy chains of many antigens, including HLA-A, HLA-B, HLA-Cw, HLA-E, HLA-F, and HLA-G are found in circulation, in "normal" individuals as well as in patients with inflammation and cancer. When the heavy chains of HLA enter into circulation, they may expose several amino acid sequences in the α1, α2 and α3 helices, hitherto cryptic on the cell surface. Exposure of such cryptic amino acid sequences may elicit antibody production against the amino acid sequences. Previous literature also documents those soluble HLA molecules in commercially purified IVIg suggesting that they may be bound to IgG antibodies.

The amino acid sequences (5 to 15 amino acids) to which an antibody will bind or against which an antibody will be produced or even a site to which the T-lymphocytes receptor binds or responds, are called "epitope" of the antigen. The epitope can be continuous or discontinuous peptide sequences or a sequence of amino acids (ranging from 5 amino acids to 15 amino acids) on an antigen molecule or polypeptide (e.g., an HLA-E, HLA-F or HLA-G a chain polypeptide). In general, the surface portion of a sequence of amino acids on an antigen capable of eliciting an immune response and of combining with the antibody produced. The term "epitopes" as used herein refers to the peptide sequences in an HLA heavy chain polypeptide recognized by the Fab portion of the antibody, and having immunogenic activity in an animal, preferably a mammal, and most preferably in a human. An epitope having immunogenic activity is a fragment of a polypeptide that elicits an antibody response in an animal or in a human. See Table 4 for epitope sequences shared between HLA-Ib molecules (e.g., HLA-E, HLA-F and HLA-G) and HLA-Ia molecules (e.g., HLA-A, HLA-B and HLA-Cw).

The term "antibodies that are immunoreactive" to a particular human leukocyte antigen (HLA) refer to antibodies that specifically bind to a particular HLA. For example, "antibodies immunoreactive to HLA-E" refers to antibodies, including both modified antibodies and unmodified antibodies that specifically bind to an HLA-E heavy chain polypeptide. Further, "antibodies immunoreactive to HLA-Ib," "anti-HLA-Ib antibodies," or "antibodies immunoreactive to HLA-E, HLA-F and HLA-G" refers to antibodies, including both modified antibodies and unmodified antibodies that specifically bind to an HLA-E heavy chain polypeptide, an HLA-F heavy chain polypeptide, and an HLA-G heavy chain polypeptide. An antibody or a fragment thereof is immunoreactive to a particular HLA or HLAs when it binds to the particular HLA or HLAs determined using experimental immunoassays known to those skilled in the art. Immunoassays combine the principles of immunology and biochemistry enabling tests, which include but are not limited to RIAs (radioimmunoassays), enzyme immunoassays like ELISAs (enzyme-linked immunosorbent assays), LIAs (Luminescent immunoassays) and FIAs (fluorescent immunoassays). Antibodies used in the aforementioned assays, for instance primary or secondary antibodies, can be labeled with radioisotopes (e.g., 125I), fluorescent dyes (e.g., PC or FITC) or enzymes (e.g., peroxidase or alkaline phosphatase), which catalyze fluorogenic or luminogenic reactions. See e.g., Eleftherios et al., 1996, Immunoassay, Academic Press; Law et al., 2005, Immunoassay: A Practical Guide, Taylor & Francis; Wild et al., 2005, The Immunoassay Handbook, Third Edition, Elsevier; Paul et al., 1989, Fundamental Immunology, Second Edition, Raven Press, for a discussion regarding antibody specificity.

In general, an antibody immunoreactive to HLA-E can bind to any of the epitopes (See Table 4) available for binding in HLA-E heavy chain polypeptide. Antibodies immunoreactive to a particular HLA-Ib heavy chain polypeptide (e.g., HLA-E, HLA-F and HLA-G heavy chain polypeptides) can specifically bind to polypeptides comprising the amino acid sequence of that particular HLA-Ib molecule and to other HLA epitopes. If the other HLA epitopes share sufficient amino acid sequence and physical conformation with the same polypeptide found in a corresponding HLA-Ia (HLA-A, HLA-B, HLA-Cw) and HLA-Ib molecules (HLA-E, HLA-F, HLA-G), they are referred to shared peptide sequences or shared epitopes. When an antibody is immunoreactive to HLA-E-specific epitope present of the heavy chain polypeptide at different positions, e.g., $^{65}$RSARDTA$^{71}$ (SEQ ID NO: 3) and $^{143}$SEQKSNDASE$^{152}$ (SEQ ID NO: 11), and that are not shared by any of the other HLA-Ib or HLA-Ia molecules, such an antibody can be considered as HLA-E monospecific antibody. (See Ravindranath et al., 2010, *J. Immunol.* 185:1935-1948 and Ravindranath et al., 2011, *Mol. Immunol.* 48: 423-430). However, the "IVIg-mimetics" described herein are antibodies that recognize shared epitopes or shared amino acid sequence of all the three HLA-Ib molecules and all the three HLA-Ia molecules.

Antibodies provided herein include any form of antibody known to those skilled in the art. Antibodies provided herein include both modified antibodies: i.e., antibodies that comprise any isotype of IgG (e.g., IgG1, IgG2a, IgG2b, IgG3) constant domain, or FcRn-binding fragment thereof, (e.g., the Fc-domain or hinge-Fc domain) and unmodified antibodies. Antibodies provided herein include, but are not limited to, synthetic antibodies, monoclonal antibodies, polyclonal antibodies (in the sense they are a mixture of monoclonal antibodies), recombinantly produced antibodies, human antibodies, humanized antibodies, chimeric antibodies, intrabodies, single-chain Fvs (scFv) (e.g., including monospecific, bispecific, etc.), Fab fragments, F(ab') fragments, disulfide-linked Fvs (sdFv), anti-idiotypic (anti-Id) antibodies, and epitope-binding fragments of any of the above. In particular, antibodies include immunoglobulin molecules and immunologically active portions of immunoglobulin molecules.

Antibodies provided herein can be of any subclass of IgG (e.g., IgG1, IgG2 (IgG2a and IgG2b), IgG3, IgG4).

The term "constant domain" refers to the portion of an immunoglobulin molecule having a more conserved amino acid sequence relative to the other portion of the immunoglobulin, the variable domain, which contains the antigen binding site. The constant domain contains the CH1, CH2 and CH3 domains of the heavy chain and the CHL domain of the light chain.

The terms "IgG Fc region," "Fc region," "Fc domain," "Fc fragment" and other analogous terms as used herein refer the portion of an IgG molecule that correlates to a crystallizable fragment obtained by papain digestion of an IgG molecule. The Fc region consists of the C-terminal half of the two heavy chains of an IgG molecule that are linked by disulfide bonds. It has no antigen binding activity and the binding sites for complement and Fc receptors, including the FcRn receptor (see below).

As used herein, the term "IVIg mimetics" refers to the anti-HLA-Ib antibodies provided herein, monoclonal, a mixture of monoclonals, recombinant or humanized or chimeric, conjugated or free, with their "Fab" portion of the antibody immunoreactive to the HLA-Ib alleles (HLA-E, HLA-F and HLA-G) and also with the HLA-Ia alleles (HLA-A, HLA-B and HLA-Cw), strikingly similar to that of IVIg from different commercial sources. The term "IVIg mimetics", as used herein, also refers to the anti-HLA-Ib antibodies with potential to react to several HLA-Ia alleles (HLA-A, HLA-B and HLA-Cw) and perform several immunomodulatory functions (e.g., suppression of naïve and activated CD4+ T-lymphocytes or enhance CD8+ T lymphocytes) strikingly similar to IVIg. In other words, the term "IVIg-mimetics" as used herein refers to anti-HLA-Ib antibodies that function as "immunomimetic" of IVIg. "IVIg-mimetics," as used herein, refer mainly to the similarities in immunoreactivities and immunomodulatory activities between the anti-HLA-IB antibodies and commercial IVIg preparations. The term need not include any other property of IVIg—activity, toxicity, side effect or otherwise.

The term "immunomodulatory agent" and variations thereof including, but not limited to, immunomodulatory agents, as used herein refer to an agent that modulates one or more of the components (e.g., immune cells, or subcellular factors, genes regulating immune components, cytokines, chemokines or such molecules) of a host's immune system. In certain embodiments, an immunomodulatory agent is an immunosuppressive agent. In certain other embodiments, an immunomodulatory agent is an immunostimulatory agent. In certain embodiments, an immunomodulatory agent is agent that may bind to immunosuppressive or immunotoxic agents. For example, HLA-E present on tumor cells or shed form tumor cells (soluble HLA-E) is known to bind to CD94/NKG2A receptors on CD8+ cytotoxic T– lymphocytes (CTL) and Natural Killer T cells (NKT) and prevent their anti-tumor, cytotoxic or killer function. Antibody binding to HLA-E, can bind to the cell surface or soluble HLA-E, and neutralize the effect and thus immunopotentiate CTL and NKT functions.

An "isolated" or "purified" antibody is substantially free of cellular material or other contaminating proteins or other antibodies. The language "substantially free of cellular material" includes preparations of an antibody in which the antibody is separated from cellular components of the cells from which it is isolated or recombinantly produced. When the antibody is recombinantly produced, it can also be substantially free of culture medium. When the antibody is produced by chemical synthesis, it can also be substantially free of chemical precursors or other chemicals, i.e., it is separated from chemical precursors or other chemicals which are involved in the synthesis of the protein. In a specific embodiment, antibodies provided herein are isolated or purified.

As used herein, the term "modified antibody" encompasses any antibody described herein that comprises one or more "modifications" to the amino acid residues at given positions of the antibody constant domain or FcRn-binding fragment thereof wherein the antibody has an increased in vivo half-life as compared to known antibodies and/or as compared to the same antibody that does not comprise one or more modifications in the IgG constant domain, or FcRn-binding fragment thereof. As used herein, a "modified antibody" may or may not be a high potency, high affinity and/or high avidity modified antibody. In certain embodiments, the modified antibody is a high potency antibody. In certain embodiments, the modified antibody is a high potency, high affinity modified antibody.

The term "effective amount" as used herein refers to the dose or amount required for treatment (e.g., an antibody provided herein) which is sufficient to reduce and/or ameliorate the severity and/or duration of any one of the disease or conditions described herein. In some embodiments, the effective amount of an antibody of the pharmaceutical composition provided herein is between about 0.025 mg/kg and about 60 mg/kg body weight of a human subject. In some embodiments, the effective amount of an antibody of the pharmaceutical composition provided herein is about 0.025 mg/kg or less, about 0.05 mg/kg or less, about 0.10 mg/kg or less, about 0.20 mg/kg or less, about 0.40 mg/kg or less, about 0.80 mg/kg or less, about 1.0 mg/kg or less, about 1.5 mg/kg or less, about 3 mg/kg or less, about 5 mg/kg or less, about 10 mg/kg or less, about 15 mg/kg or less, about 20 mg/kg or less, about 25 mg/kg or less, about 30 mg/kg or less, about 35 mg/kg or less, about 40 mg/kg or less, about 45 mg/kg or less, about 50 mg/kg or about 60 mg/kg or less.

The term "excipients" as used herein refers to inert substances which are commonly used as a diluent, vehicle, preservatives, binders, or stabilizing agent for drugs and includes, but not limited to, proteins (e.g., serum albumin, etc.), amino acids (e.g., aspartic acid, glutamic acid, lysine, arginine, glycine, histidine, etc.), fatty acids and phospholipids (e.g., alkyl sulfonates, caprylate, etc.), surfactants (e.g., SDS, polysorbate, nonionic surfactant, etc.), saccharides (e.g., sucrose, maltose, trehalose, etc.) and polyols (e.g., mannitol, sorbitol, etc.). Also see Remington et al., 1990, Remington's Pharmaceutical Sciences, Mack Publishing Co, which is hereby incorporated in its entirety.

As used herein, "administer" or "administration" refers to the act of injecting or otherwise physically delivering a substance as it exists outside the body (e.g., a pharmaceutical composition described herein such as an IVIg-mimetic) into a patient, such as by, but not limited to, pulmonary (e.g., inhalation), mucosal (e.g., intranasal), intradermal, intravenous, intramuscular delivery and/or any other method of physical delivery described herein or known in the art. When a disease, or symptoms thereof, is being treated, administration of the substance typically occurs after the onset of the disease or symptoms thereof. When a disease, or symptoms thereof, is being prevented, administration of the substance typically occurs before the onset of the disease or symptoms thereof. Administering the anti-HLA-Ib antibodies passively in patients for the purpose of neutralize the HLA-Ib antigens or for immuno-modulation is herein referred to as passive immunotherapy, such that their immune interference with anti-tumor activities of immune cells can be prevented, is herein referred to as passive immunotherapy.

As used herein, administering purified, humanized murine or human monoclonal anti-HLA-Ib antibodies (as described herein) to cancer patients, preferably at early stages of cancer (stage I and/or stage II) is referred to as "passive immunotherapy," a therapeutic procedure or protocol often used in FDA approved clinical trials on cancer patients. The objective of the anti-HLA-Ib passive immunotherapy is to neutralize cell surface or soluble HLA-Ib antigens (HLA-E, HLA-F and HLA-G) in circulation or in tumor microenvironment, which may otherwise bind to CD94/NKGa2 receptors and prevent CD8+ cytotoxic T cells (CTL) or NKT cells from attacking and killing tumor cells. In the passive immunotherapy, the anti-HLA-Ib antibodies bind to HLA-Ib antigens and restore cytotoxic functions of CTLs and NKT cells.

As used herein, administering purified or cellular HLA-Ib molecules, with the purpose of generating anti-HLA-Ib antibodies or IVIg-mimetics, is also herein referred to as "active immunotherapy," a therapeutic procedure or protocol often used in FDA approved clinical trials on cancer patients. The objective is to induce anti-HLA-Ib antibodies production in patients to neutralize and bind to HLA-Ib antigens and restore cytotoxic functions of CTLs and NKT cells.

As used herein, the terms "manage," "managing," and "management" refer to the beneficial effects that a subject derives from a therapy (e.g., a prophylactic or therapeutic agent), which does not result in a cure of the disease or condition described herein.

The term "pharmaceutically acceptable" as used herein means being approved by a regulatory agency of the Federal or a state government, or listed in the U.S. Pharmacopia, European Pharmacopia or other generally recognized pharmacopia for use in animals, and more particularly in humans.

As used herein, the terms "prevent," "preventing," and "prevention" refer to the total or partial inhibition of any of the diseases or conditions by the anti-HLA-Ib antibodies or IVIg mimetic administered at the specific dosage, described herein.

The terms "stability" and "stable" as used herein in the context of a liquid formulation comprising an antibody provided herein refer to the resistance of the antibody in the formulation to thermal and chemical unfolding, aggregation, degradation or fragmentation under given manufacture, preparation, transportation and storage conditions. The "stable" formulations of the antibodies and pharmaceutical compositions provided herein retain biological activity equal to or more than 80%, 85%, 90%, 95%, 98%, 99%, or 99.5% under given manufacture, preparation, transportation and storage conditions. The stability of the antibody can be assessed by either by assessing the affinity or avidity of the antibody or by assessing the degrees of aggregation, degradation or fragmentation using techniques known to those skilled in the art, including but not limited to or reduced Capillary Gel Electrophoresis (rCGE), Sodium Dodecyl Sulfate Polyacrylamide Gel Electrophoresis (SDS-PAGE), Western Blotting of the PAGE-gels and HPSEC. The overall stability of a formulation comprising an antibody that immunospecifically binds to an HLA-Ib antigen can be assessed by various immunological assays including, for example, Enzyme Linked Immunosorbant assay (ELISA) or Flow cytometric assays or dual-laser flow cytometry (Luminex® xMAP® multiplex technology), or LABScreen® Single Antigen assay and radioimmunoassay using the entire or part of the polypeptide of HLA-Ib or HLA-Ia molecules.

As used herein, the terms "subject" and "patient" are used interchangeably. In some embodiments, the subject is a human and in others it is an animal.

The term "substantially free of surfactant" as used herein refers to a formulation of a pharmaceutical composition, said formulation containing less than 0.0005%, less than 0.0003%, or less than 0.0001% of surfactants and/or less than 0.0005%, less than 0.0003%, or less than 0.0001% of surfactants.

The term "substantially free of salt" as used herein refers to a formulation of a pharmaceutical composition, said formulation containing less than 0.0005%, less than 0.0003%, or less than 0.0001% of inorganic salts.

The term "surfactant" as used herein refers to organic substances having amphipathic structures; namely, they are composed of groups of opposing solubility tendencies, typically an oil-soluble hydrocarbon chain and a water-soluble ionic group. Surfactants can be classified, depending on the charge of the surface-active moiety, into anionic, cationic, and nonionic surfactants. Surfactants are often used as wetting, emulsifying, solubilizing, and dispersing agents for various pharmaceutical compositions and preparations of biological materials.

As used herein, the term "therapeutic agent" refers to Wig-mimetic with or without any other agent that can be used in the treatment, management or amelioration of one of the human diseases or conditions described herein.

As used herein, the term "therapy" refers to any protocol, method and/or agent that can be used in the prevention, management, treatment and/or amelioration of one of the diseases or conditions described herein.

In certain embodiments provided herein, the term "therapeutically effective" with respect to the pharmaceutical composition, refers to the ability of the composition to reduce the severity, the duration and/or the symptoms of a particular disease or condition.

As used herein, the terms "treat," "treatment" and "treating" refer to the reduction or amelioration of the progression, severity, and/or duration of one of the conditions described herein.

6.2 Antibodies and Pharmaceutical Compositions

The anti-HLA-Ib antibodies provided herein are monoclonal, recombinant, chimeric, humanized or human antibodies that are immunoreactive IVIg mimetics to the heavy chain polypeptides of HLA-E, HLA-F and HLA-G as well as with HLA-Ia molecules in a manner identical or similar to that IVIg. In some embodiments, Wig mimetics include compositions comprising the antibodies and a pharmaceutically acceptable carrier. In some embodiments, the compositions of IVIg mimetics include but are not limited to purified antibodies, purified monoclonal antibodies, purified human antibodies (e.g., human IgG), purified human monoclonal antibodies, or a combination thereof.

The anti-HLA-Ib antibodies provided herein are compositions and methods using the same for the prevention, treatment, therapy and/or amelioration of inflammation induced diseases and allograft rejection, including but not limited to hematological, autoimmune, eye, ear and lung inflammatory diseases, nephropathy, cardiomyopathy, infection, solid organ transplant and several other disease conditions. In some embodiments, the compositions of the anti-HLA-Ib antibodies provided herein are IVIg mimetics, including but not limited to purified antibodies, purified monoclonal antibodies, purified human antibodies (e.g., human IgG), purified human monoclonal antibodies, or a combination thereof. In some embodiments, the compositions provided herein are chimeric, humanized or human antibodies that are immunoreactive against non-classical anti-HLA-Ib antigens, e.g., HLA-E, HLA-F and HLA-G in addition to classical anti-HLA-Ia antigens (e.g., HLA-A, HLA-B & HLA-Cw).

In one aspect, provided herein are compositions of the anti-HLA-Ib antibodies that have immunoreactivity to HLA class Ib antigens: HLA-E, HLA-F and HLA-G. In some embodiments, compositions of the anti-HLA-Ib antibodies provided herein have greater immunoreactivity to HLA-E than to HLA-F (mAb PTER006, mAb PTEG032; mAb PTER007; mAb PTEG016; mAb PTEG017). In some embodiments, compositions of the anti-HLA-Ib antibodies provided herein have much greater immunoreactivity to HLA-E than to HLA-G (mAb PTER006, mAb PTEG032; mAb PTER007; mAb PTEG016; mAb PTEG017). In some embodiments, compositions provided herein have much greater immunoreactivity to HLA-E than to classical of the anti-HLA-Ib antibodies provided herein have greater immunoreactivity to HLA-F than to HLA-E. In some embodiments, compositions provided herein have much greater immunoreactivity to HLA-F than to HLA-G (mAb PTER006, mAb PTEG032; mAb PTER007). In some embodiments, compositions provided herein have much greater immunoreactivity to HLA-E and HLA-F than to HLA-G (mAb PTER006, mAb PTEG032; mAb PTER007). In some embodiments, compositions provided herein have much greater immunoreactivity to HLA-G than to HLA-F (mAb PTER016, mAb PTER017). In some embodiments, compositions of the anti-HLA-Ib antibodies provided herein have much greater immunoreactivity to HLA-F than to classical anti-HLA-Ia antigens (e.g., HLA-A, HLA-B & HLA-Cw). It will be understood that the antibodies (or "IVIg mimetics") provided herein can be prepared by any methods known to one of skill in the art.

Exemplary anti-HLA-Ib antibodies include those developed and characterized in the Example Section. In some embodiments, anti-HLA-Ib antibodies are raised against one or more alleles of HLA-E; for example, HLA-E$^R$ or HLA-E$^G$.

For example, monoclonal antibodies were raised by immunizing mice (BALB/c) with recombinant heavy chains of HLA-E$^R$ or HLA-E$^G$. Five exemplary monoclonal antibodies are listed in FIG. 4, which were subsequently labeled as mAb PTER006, mAb PTEG032, mAb PTER007, mAb PTEG016 and mAb PTEG017, in the order of their affinity for HLA-class Ia reactivity, respectively. These antibodies specifically reacted to all molecules of HLA-class Ib (HLA-E, HLA-F and HLA-G), in a manner strikingly similar to HLA-Ib immunoreactivity of IVIg documented in FIGS. 1A-1D. Remarkably, similar to IVIg (as shown in FIG. 2A-2D), these monoclonal antibodies were immunoreactive to free and β2-microglobulin-associated heavy chains of several HLA-Ia antigens (HLA-A, HLA-B, or HLA-Cw) (FIG. 4). FIG. 4 details the number of HLA-class Ia epitopes recognized by IVIg in Luminex Bead assay.

In some embodiments, anti-HLA-Ib antibodies can be identified in commercially available human purified antibodies that are identified as being reactive against epitopes shared by HLA-Ia and HLA-Ib molecules. For example, commercially available purified Human IgG from Southern Biotech (Catalog Number: 0150-01, Birmingham, Ala.) reacted with HLA-E, HLA-F and HLA-G. In some embodiments, HLA-F reactivity was higher than that of HLA-E and HLA-G (FIG. 1C). The commercial antibody also reacted with HLA-Ia alleles.

In another aspect, peptides listed in Table 4 and in Table 1 are used to block or reduce immunoreactivity of the anti-HLA-Ib antibodies against antigens such as HLA-E, HLA-F, and HLA-G as well as against HLA-Ia antigens including HLA-A, HLA-B and HLA-Cw. In some embodiments, the peptide comprises one or more segments of amino acid sequences that are shared by HLA-Ib antigens and HLA-Ia antigens. In some embodiments, each of the two or more segments of amino acid sequences has different amino acid sequences. In some embodiments, the two or more segments of amino acid sequences are linked contiguously or discontiguously; or continuously or discontinuously. See; Ravindranath et al., 2010, *Mol. Immunol.* 47: 1121-1131 and Ravindranath, et al., 2011, *Mol. Immunol.* 48:423-430.

In another aspect, the anti-HLA-Ib antibodies (e.g., used as IVIg mimetics) are found in normal, non-alloimmunized, healthy males; anti-HLA-Ia reactivity of anti-HLA-E IgG antibodies in the sera of these healthy individuals has also been observed (Ravindranath et al., 2010, *J. Immunol.* 185: 1935-1948). IVIg's immunoreactivity to HLA-Ia, which can be attributed to the anti-HLA-Ib activity of IVIg, is identified to be strong and potent. These findings indicate that the anti-HLA-Ia reactivity of IVIg is associated with the anti-HLA-class Ib immunoreactivity of IVIg. The IVIg mimetic is also immunoreactive to HLA-Ia molecules, which is documented to be due to HLA-Ib antibodies.

In another aspect, anti-HLA-Ib antibodies found in renal and liver allograft recipients showed immunoreactivity to HLA-Ia molecules very similar to IVIg. Sera of (73% of renal and 53% of liver) allograft recipients with high level of anti-HLA-Ib antibodies showed allo-HLA-Ia reactivity which is attributed to the anti-HLA-Ib Abs recognizing the epitope sequences shared between HLA-Ib and HLA-Ia. The sera of (50% renal and 52% liver) allograft recipients with low level of anti-HLA-Ib antibodies had no reactivity to any HLA-Ia alleles, thereby supporting the contention that the allo-HLA-Ia reactivity could be due to anti-HLA-Ib antibodies. However, the IgG isolated from the same sera with protein-G columns, showed the presence of the anti-HLA-Ib IgG antibodies and concomitantly HLA-Ia reactivity, suggesting serum proteins or soluble HLA-E in the serum can interfere with the binding of anti-HLA-Ib antibodies to allo-HLA-Ia alleles. In support, both the recombinant HLA-Ib and the IgG-free serum containing soluble HLA-Ib inhibited HLA-Ia reactivity of anti-HLA-Ib murine monoclonal IgG significantly. The data suggest that the HLA-Ia-reactivity of the anti-HLA-Ib Ab confirm similarity to IVIg and accounts for the non-donor-specific allo-anti-HLA-Ia antibodies (see Ravindranath et al., 2011, *Int. Immunol.* (doi. 10.1093/intimm/DXR094).

Also provided herein are methods for modulating stimulated T-lymphocytes and T-lymphoblasts growth and activities (cell growth, proliferation and blastogenesis and cell death) using compositions provided herein.

In another aspect, provided herein are methods and systems for screening immunoreactive samples by establishing immunoreactivity/immunomodulatory profiles. In some embodiments, immunoreactivity/immunomodulatory activity profiles of IVIg are established and used as standards. In some embodiments, compositions identified by the screening methods and systems are used as anti-HLA-Ib antibodies (exhibiting reactivity and modulatory activities as IVIg mimetics) for preventing, managing, treating and/or ameliorating a graft rejection, the method comprising administering to a mammal a therapeutically effective amount of any one of the compositions provided herein. In yet other embodiments, compositions identified by the screening methods and systems are used as anti-HLA-Ib antibodies (exhibiting reactivity and modulatory activities as IVIg mimetics) for managing, treating and/or ameliorating an inflammatory disease or condition. In some embodiments, the compositions identified are commercially available but used for a different therapeutic purpose.

In some embodiments, provided herein is a method of managing, treating and/or ameliorating transfusion-induced acute lung injury (TRALI). In TRALI, the presence of antibodies to intact HLA is of some concern, since in high titers they can be expected to produce TRALI. And indeed, five instances of TRALI following administration of IVIG have been reported, with one death. See, for example, Rizk A, Gorson K C, Kenney L, et al., Transfusion-related acute lung injury after the infusion of IVIG. *Transfusion* 2001; 41:264-268; Dooren M C, Ouwehand W H, Verhoeven A J, et al., Adult respiratory distress syndrome after experimental intravenous gamma-globulin concentrate and monocyte-reactive IgG antibodies. *Lancet* 1998; 352:1601-1602; Berger-Achituv S, Ellis M H, Curtis B R, et al., Transfusion-related acute lung injury following intravenous anti-D administration in an adolescent. *Am. J. Hematol.* 2008; 83:676-678; Voulgari P V, Paschou S, Svarna E, et al., Images in rheumatology. Transfusion-related acute lung injury during intravenous immunoglobulin treatment. *J. Rheumatol.* 2010; 37:190-191; and Gupta V, Gupta P, Yadav TP Transfusion related acute lung injury with intravenous immunoglobulin. *Indian Pediatr.* 2011; 48:807-808; each of which is hereby incorporated herein in its entirety. These studies suggest that further use of IVIg should be preceded by titer tests of HLA antibodies because there is a distinct possibility that the active agent in IVIg is actually the HLA antibody itself. In that case, a careful balancing of the danger of TRALI must be carefully considered, and the effective action of the HLA antibody needs to be monitored when using IVIg. It is likely that TRALI will be produced by antibodies to intact HLA antigens. Therefore, IVIg can be replaced by the monoclonal anti-HLA-E antibodies (such as the IVIg-mimetic described above) since they react against denatured antigens, so unlikely to cause TRALI, and may also have the antibody-reducing effect reported for IVIG. Of course, IVIg-mimetic will have the added advantage of being a uniform agent with more predictable effect.

In some embodiments, immunoreactivity/immunomodulatory activity profiles of IVIg are established and used as standards. For example, immunoreactivity of IVIg against non-classical HLA class Ib antigens including HLA-E, HLA-F and HLA-G can be compared to the IVIg-mimetic or the monoclonal antibody representing the IVIg-mimetic (mAb PTER006, mAb PTEG032, mAb PTER007, mAb PTEG016 and mAb PTEG017). Also, immunoreactivity of IVIg and IVIg mimetics against classical HLA-Ia molecules can be compared. In some embodiments, a profile immunoreactivity against can be established based on reactivity measurements against classical HLA-Ia molecules and non-classical HLA-Ib molecules. In some embodiments, commercial preparations of IVIg are used. In some embodiments, non-selective immuno-reactivity of the IVIg is measured and used to calibrate the selective anti-HLA activity accordingly, using for example ubiquitous proteins such as albumin as background controls. Further, purified and commercially available Human IgG (from Southern Biotech, Birmingham, Ala.) was tested for its immunoreactivity with heavy chains of HLA Class Ib antigens, namely, HLA-E, HLA-F and HLA-G. See FIG. 1F and Examples 1. The level of reactivity of anti-HLA-Ib antibodies (as IVIg mimetics, raised using HLA-$E^R$) can be determined using methods known in the art to establish reactivity profiles. For example, mAb PTER006, mAb PTEG032, mAb PTER007, mAb PTEG016 and mAb PTEG017 showed immunoreactivities to heavy chains of HLA Class Ib antigens (e.g., HLA-E, HLA-F and HLA-G) at levels similar to those determined for commercial IVIg preparations. See FIG. 4. Further, immunoreactivity to free and β2-microglobulin-associated heavy chains of HLA-Ia (e.g., FIGS. 1A-1D and FIGS. 2A-2D) can also be used to establish reactivity profiles for IVIg and IVIg-mimetics such as anti-HLA-Ib antibodies or anti-HLA-Ib antibodies. Further, changes in immunoreactivity can also be used to establish reactivity profiles for IVIg and IVIG-mimetics (e.g., anti-HLA-Ib antibodies). For example, both anti-HLA-Ia and anti-HLA-Ib immunoreactivity of IVIg was lost after adsorbing IVIg to gel conjugated only to HLA-E. The results indicate that the immunoreactivity to HLA-Ia is due to anti-HLA-Ib, particularly anti-HLA-E immunoreactivity in IVIg (FIG. 3A-3C). In particular, it has been observed that IVIg reacted to free and β2-microglobulin-associated heavy chains of several epitopes of HLA-A, HLA-B and HLA-Cw. The feature is also characteristic of monoclonal antibodies (IVIg-mimetics) developed after immunizing mice with recombinant HLA-E heavy chain of either HLA-$E^R$ or HLA-$E^G$, two well known alleles of HLA-E.

Immunomodulatory activities of exemplary IVIg are shown in FIGS. 5A-5E and FIGS. 6A-6C. Immunomodulatory activities of the exemplary anti-HLA-Ib antibodies (IVIg-mimetics) provided herein, e.g., mAb PTER006 and mAb PTER007, are shown in FIGS. 5F-5L and FIG. 6D-6I. The two types of immunomodulatory activities were shown to be similar.

In another aspect, provided herein are methods and systems for preparing IVIg-mimetics (e.g., anti-HLA-Ib antibodies); for example, immunoreactive antibodies that are immunoreactive to HLA-E, HLA-F, HLA-G and also to HLA-Ia molecules (HLA-A, HLA-B, HLA-Cw). It will be understood that antibodies provided herein can be prepared by any methods known to one of skill in the art. In some embodiments, the chimeric and humanized anti-HLA-Ib antibodies are generated by immunizing mice, rabbit or other animals with selected HLA-$E^R$ molecule.

In certain aspects, further provided herein are pharmaceutical compositions that can substitute for IVIg. In certain embodiments, the pharmaceutical compositions are uniform in composition. In some embodiments, the pharmaceutical compositions can minimize the side effects often associated with the varying commercial preparations of IVIg. In some embodiments, pharmaceutical compositions provided herein comprise in a pharmaceutically acceptable carrier, chimeric, humanized or human anti-HLA-Ib antibodies that are immunoreactive to HLA-E, HLA-F, HLA-G, and also to HLA-Ia molecules (HLA-A, HLA-B, HLA-Cw). In some embodiments, the chimeric and humanized anti-HLA-Ib antibodies (the IVIg-mimetics) are generated by immunizing mice, rabbits or other animals with selected HLA alleles such as HLA-$E^R$ or HLA-$E^G$. In some embodiments, the anti-HLA-Ib antibodies (IVIg-mimetics) are purified antibodies immunoreactive to the heavy chain polypeptide of HLA-E, HLA-F, HLA-G, and also to HLA-Ia molecules (HLA-A, HLA-B, HLA-Cw) but not immunoreactive to heavy chain polypeptides associated with β2-microglobulin. In some embodiments, the anti-HLA-Ib antibodies (IVIg-mimetics) are purified antibodies immunoreactive to the heavy chain polypeptide of HLA-E, HLA-F, HLA-G, and also to HLA-Ia molecules (HLA-A, HLA-B, HLA-Cw) and to the HLA heavy chain polypeptides associated with β2-microglobulin.

In some embodiments, the anti-HLA-Ib antibodies are purified monoclonal antibodies, purified polyclonal antibodies, recombinantly produced antibodies, Fab fragments, F(ab') fragments, or epitope-binding fragments. The antibodies can be generated, for example, by immunizing mice, rabbits or other animals with selected HLA-Ib alleles such as HLA-E$^R$ and HLA-E$^G$. In particular embodiments, the anti-HLA-Ib antibodies (IVIg-mimetics) are purified monoclonal antibodies. In particular embodiments, the anti-HLA-Ib antibodies (IVIg-mimetics) are a mixture of two or more monoclonal antibodies. In other embodiments, the anti-HLA class-Ib antibodies (IVIg-mimetics) are Fab fragments. In some embodiments, the anti-HLA-Ib antibodies are IgG antibodies. In particular embodiments, the anti-HLA-Ib antibodies (IVIg-mimetics) are IgG1 antibodies.

In some embodiments, the pharmaceutical composition is suitable for intramuscular administration, intradermal administration, intraperitoneal administration, intravenous administration, subcutaneous administration, or any combination thereof. In some embodiments, the pharmaceutical composition is suitable for subcutaneous administration. In some embodiments, the composition is suitable for intravenous administration. In some embodiments, the composition is suitable for intramuscular administration.

In some embodiments, the anti-HLA-Ib antibodies (e.g., generated by immunizing HLA-E$^R$ or HLA-E$^G$) are immunoreactive to the heavy chains of HLA-E, HLA-F, and HLA-G and to other HLA-Ia alleles (HLA-A, HLA-B and HLA-Cw). The reactivity will be or can be strikingly similar to that of IVIg.

In some embodiments, the anti-HLA-Ib antibodies provided herein are more immunoreactive to the heavy chains of HLA-F than to the heavy chains of HLA-E or HLA-G. This can be similar to the reactivity profile of some commercial preparations of IVIg (see FIG. 1). In some embodiments, the anti-HLA-Ib antibodies (IVIg-mimetics) are capable of clearing and/or neutralizing soluble HLA-E, HLA-F and HLA-G present in the circulation or blood (plasma or serum), synovial fluid, seminal fluid or in any other body fluid. In some embodiments, the anti-HLA-Ib antibodies (IVIg-mimetics) are also capable of clearing and/or neutralizing soluble HLA-A, HLA-B and HLA-Cw from the circulation or the body fluid. It is known that HLA-E, HLA-F and HLA-G are shed into circulation as heavy chains.

In some embodiments, the anti-HLA-Ib antibodies provided herein have immunoreactivities that are strikingly similar to those of IVIg. In some embodiments, the anti-HLA-Ib antibodies (IVIg-mimetics) are immunoreactive to a plurality of HLA-A* molecules (e.g., 21 to 31), which is similar to the reactivity profile of IVIg. See Example 4 and Tables 4 and 5. In some embodiments, anti-HLA-Ib antibodies (IVIg-mimetics) are immunoreactive to a plurality of HLA-B* molecules (e.g., 43 to 50) and to most of the HLA-Cw* epitopes (e.g., 16), which is identical to the reactivity profile of commercial IVIg preparations. See Example 4 and Tables 4 and 5. In some embodiments, anti-HLA-Ib antibodies differ from anti-HLA-E monoclonal antibodies (commercial or produced herein), because the latter recognize fewer HLA-A molecules (see FIG. 4). In some embodiments, the anti-HLA-Ib antibodies (IVIg-mimetics) are immunoreactive to HLA-Ia heavy chains and to HLA-Ib heavy chains similar to a commercial preparation of IVIg. In certain embodiments, the anti-HLA-Ib antibodies are immunoreactive to at least 80% of the same HLA-Ia antigens as Wig.

In some embodiments, concentration of the anti-HLA-Ib antibodies can vary. In some embodiment, at least 50% of the antibodies of the composition are anti-HLA-Ib antibodies according to the description provided herein. In some embodiments, at least 60% of the antibodies of the composition are anti-HLA-Ib antibodies (IVIg-mimetics) according to the description provided herein. In some embodiments, at least 70% of the antibodies of the composition are anti-HLA-Ib antibodies (IVIg-mimetics) according to the description provided herein. In some embodiments, at least 80% of the antibodies of the composition are anti-HLA-Ib antibodies (IVIg-mimetics) according to the description provided herein. In some embodiments, at least 85% of the antibodies of the composition are anti-HLA-Ib antibodies (IVIg-mimetics). In some embodiments, at least 90% of the antibodies of the composition are anti-HLA-Ib antibodies (IVIg-mimetics). In some embodiments, at least 95% of the antibodies of the composition are anti-HLA-Ib antibodies (IVIg-mimetics). In some embodiments, at least 99% of the antibodies of the composition are anti-HLA-Ib antibodies (IVIg-mimetics).

In some embodiments, the immunoreactivity of the anti-HLA-Ib antibodies (IVIg-mimetics) as well as their immunoreactivity to HLA-Ia can be blocked by peptide sequences or epitopes of HLA-Ib shared with HLA-Ia alleles. For example, polypeptides comprising the amino acid sequence QFAYDGKDY (SEQ ID NO: 6) per se or in combination with DTAAQI (SEQ ID NO: 9) can effectively block anti-HLA-Ib monoclonal antibodies. In some embodiments, the immunoreactivity of the anti HLA-Ib antibodies can be blocked by polypeptides comprising the amino acid sequence AYDGKDY (SEQ ID NO: 7) per se or in combination with LNEDLRSWTA (SEQ ID NO: 8). As provided herein below, amino acid sequences forming the polypeptides can be continuous or discontinuous sequences.

In some embodiments, a composition of the anti-HLA-Ib antibodies (IVIg-mimetics) provided herein can be used to suppress proliferation and/or blastogenesis of naïve and/or activated CD4+ T-cells in a recipient of the composition in a manner similar or identical to that of IVIg. See, for example, FIGS. 5 and 6.

In some embodiments, a composition of the anti-HLA-Ib antibodies (IVIg-mimetics) provided can be used to suppress proliferation and/or blastogenesis of naïve and/or activated CD8+ T-cells in a recipient of the pharmaceutical composition, in a manner similar or identical to that of IVIg. See, for example, FIGS. 5 and 6.

In some embodiments, a pharmaceutical composition of the anti-HLA-Ib antibodies (IVIg-mimetics) provided herein can be used to suppress proliferation and/or blastogenesis of naïve and/or activated CD4+ T-cells in a recipient of the pharmaceutical composition, in a manner similar or identical to that of IVIg. See, for example, FIGS. 5 and 6.

In some embodiments, a pharmaceutical composition of the anti-HLA-Ib antibodies (IVIg-mimetics) provided herein can be used to suppress proliferation and/or blastogenesis of naïve and/or activated CD8+ T-cells in a recipient of the pharmaceutical composition, in a manner similar or identical to that of IVIg. See, for example, FIGS. 5 and 6.

In some embodiments, a composition or pharmaceutical composition of the anti-HLA-Ib antibodies (IVIg-mimetics)

provided herein can be used to prevent formation of T-cell dependent HLA antibodies in a recipient. In certain embodiments, the T-cell dependent HLA antibodies are anti-HLA-Ia antibodies. In certain embodiments, the recipient is a transplant recipient.

In some embodiments, a composition or pharmaceutical composition the anti-HLA-Ib antibodies (IVIg-mimetics) provided herein is immunoreactive to one or more HLA-A* proteins, in addition to one or more HLA-B* proteins and to one or more HLA-Cw* proteins, which is similar to the reactivity profile of IVIg. The composition or pharmaceutical composition of the anti-HLA-Ib antibodies (IVIg-mimetics) provided herein differs from anti-HLA-E antibodies, because the latter recognize very few HLA-A alleles. In certain embodiments, a composition or pharmaceutical composition provided herein is immunoreactive to at least 70% to 99% of the same HLA-Ia antigens as IVIg.

In some embodiments, the composition or pharmaceutical composition of the anti-HLA-Ib antibodies (IVIg-mimetics) is therapeutically effective for the treatment of one or more inflammatory diseases or symptoms thereof treatable by commercial preparations of IVIg. In specific embodiments, the composition or pharmaceutical composition is therapeutically effective for the treatment of a graft rejection.

In certain embodiments, the anti-HLA-Ib antibodies (IVIg-mimetics) have immunomodulatory activity comparable to commercial preparations of IVIg. In certain embodiments, the anti-HLA-Ib antibodies modulate T-cell growth, expansion and/or proliferation comparable to a commercial preparation of IVIg.

In another aspect, provided herein is a method of preventing, managing, treating and/or ameliorating a graft rejection, the method comprising administering anti-HLA-Ib antibodies (IVIg-mimetics) to a mammal a therapeutically effective amount of any one of the compositions provided herein.

In some embodiments, compositions provided herein are used in methods of prevention, management, treatment and amelioration of graft rejection.

In some embodiments, the method is for the prevention, management, treatment and/or amelioration of a tissue graft rejection. In some embodiments, the method is for the prevention, management, treatment and/or amelioration of an organ graft rejection. In particular embodiments, the organ graft is a heart, kidney or liver graft. In other embodiments, the method is for the prevention, management, treatment and/or amelioration of a cell graft rejection. In particular embodiments, the cell graft is a bone-marrow transplantation or a blood transfusion.

In yet another aspect provided herein is a method of managing, treating and/or ameliorating an inflammatory disease or condition selected from the group consisting of: Kawasaki disease, immune-mediated thrombocytopenia, primary immunodeficiencies, hematopoietic stem cell transplantation, chronic B-cell lymphocytic leukemia, pediatric HIV type 1 infection, hematological disease, nephropathy, neuropathy, a bacterial infection, a viral infection, an autoimmune disease that is not vasculitis, cardiomyopathy, an eye or ear inflammatory disease, a lung inflammatory disease, recurring pregnancy loss, Behçet syndrome, chronic fatigue syndrome, congenital heart block, diabetes mellitus, acute idiopathic dysautonomia, opsoclonus-myoclonus, Rasmussen syndrome, Reiter syndrome, or Vogt-Koyanagi-Harada syndrome, the method comprising administering to a human a therapeutically effective amount of any of the pharmaceutical compositions provided herein.

The pharmaceutical compositions anti-HLA-Ib antibodies (IVIg-mimetics) can be made by any technique apparent to one of skill in the art, including the techniques described herein. Each element of the pharmaceutical composition is discussed in further detail below.

6.3 Antibodies Having Reactivity to HLA-E, HLA-F and HLA-G

Provided herein are chimeric, humanized or human IgG antibodies that are immunoreactive to the heavy chain polypeptides of HLA-E, HLA-F and HLA-G (for example, anti-HLA-Ib antibodies used as IVIg-mimetics). In certain embodiments, the chimeric, humanized or human IgG antibodies are immunoreactive to the heavy chain polypeptides of HLA-E, HLA-F and HLA-G.

To date, Major Histocompatibility Class I (MHC-I) molecules include highly polymorphic classical HLA class-Ia and less polymorphic non-classical HLA-Ib (Table 3).

HLA-Ia molecules are co-dominantly expressed on the cell membrane as a pair of epitopes for each of the three HLA-Ia molecules. HLA-Ia molecules can bind and present peptide antigens produced intracellularly, including viral and tumor specific proteins, to CD8+ effector T-cells (e.g., cytotoxic T-cells, "CTLs"). In response to foreign antigens presented by HLA-Ia bearing cells, CD8+ effector T-cells can destroy the cells presenting the foreign antigen.

Each HLA-I molecule, when expressed on a cell surface, may consist of a heavy chain (HC) (of about 346 amino acids) that is free, an HC linked to an HC of the same allele or an HC non-covalently linked to $\beta$2-microglobulin ("$\beta$2m") (99 amino acids). HC consists of three extracellular domains (a1, a2 & a3), a transmembrane domain and a C-terminal cytoplasmic domain. However, HLA-I molecules can also be expressed without $\beta$2m on the cell surface on activated T-lymphocytes (see Schnabel et al., 1990, *J. Exp. Med.* 171: 1431-1432, Lee et al., 2010 *Eur J Immunol.* 40:2308-18), CD14+ blood monocytes, activated dendritic cells (see Raine et al., 2006, *Rheumatology* 45: 1338-1344) of healthy individuals and in cells and tissues of patients with inflammatory diseases (see Raine et al., 2006, *Rheumatology* 45: 1338-1344; Tsai et al., 2002, *Rheumatology* 29: 966-972). On the cell surface, HC and $\beta$2m can dissociate, leaving membrane bound HC only (Machold, et al., 1996, *J. Exp. Med.* 184: 2251-2259; Carreno et al., 1994, *Eur. J. Immunol.* 24: 1285-1292; Parker et al., 1992, *J. Immunol.* 149: 1896-1904). On the cell surface, the HC of MHC class I can occur in different conformations (Marozzi et al. 1996, *Immunogenetics*, 43: 289-295). The HC of HLA-I molecules are released from the cell surface into surrounding media and circulation (Demaria et al., 1994, *J. Biol. Chem.* 269:6689-6694). In circulation, in blood and in other body fluids, HLA I molecules occur as soluble fraction (heavy chains free or associated with $\beta$2m) of different molecular weights (47, 42, 35 kDa). Soluble HLA-I can trigger cell death of CD8+ cytotoxic T-lymphocytes and natural killer cells impair natural killer cell functions. See Demaria et al., 1993, *Int J Clin Lab Res.* 23:61-9; Puppo et al., 2000, *Int Immunol.* 12:195-203; Puppo et al., 2002, *Scientific World Journal.* 2:421-3; Contini et al., 2000, *Hum Immunol.* 61:1347-51; Contini et al., 2003, *Eur J Immunol.* 33:125-34; Spaggiari et al., 2002, *Blood* 99:1706-14; Spaggiari et al., 2002, *Blood* 100:4098-107).

The antibodies described herein are immunoreactive to HLA-E, HLA-F and HLA-G. See, Example 4 and FIG. 4. An antibody is immunoreactive to a particular HLA or HLAs when it binds to the particular HLA or HLAs as determined using experimental immunoassays known to those skilled in the art including, but not limited to, RIAs (radioimmunoassays), enzyme immunoassays like ELISAs (enzyme-linked immunosorbent assays), LIAs (luminescent immunoassays) and FIAs (fluorescent immunoassays), in which the antibodies, either used as primary or secondary antibodies, can be labeled with radioisotopes (e.g., 125I), fluorescent dyes (e.g., PC or FITC) or enzymes (e.g., peroxidase or alkaline phosphatase) that catalyze fluorogenic or luminogenic reactions.

IgG antibodies, particularly humanized antibodies, having reactivity to HLA-E, HLA-F and HLA-G can be produced by any methods known in the art for the synthesis of antibodies, in particular, by chemical synthesis or by recombinant expression techniques. These methods employ, unless otherwise indicated, conventional techniques in molecular biology, microbiology, genetic analysis, recombinant DNA, organic chemistry, biochemistry, PCR, oligonucleotide synthesis and modification, nucleic acid hybridization, and related fields within the skill of the art. These techniques are described in the references cited herein and are fully explained in the literature. See, e.g., Maniatis et al., 1982, Molecular Cloning: A Laboratory Manual, Cold Spring Harbor Laboratory Press; Sambrook et al., 1989, Molecular Cloning: A Laboratory Manual, Second Edition, Cold Spring Harbor Laboratory Press; Ausubel et al., 1987 and annual updates, Current Protocols in Molecular Biology, John Wiley & Sons; Gait ed., 1984, Oligonucleotide Synthesis: A Practical Approach, IRL Press; Eckstein ed., 1991, Oligonucleotides and Analogues: A Practical Approach, IRL Press; Birren et al., 1999, Genome Analysis: A Laboratory Manual, Cold Spring Harbor Laboratory Press.

Chimeric antibodies described herein can be produced by any technique known to those of skill in the art. See, e.g., Morrison, 1985, Science 229: 1202; Oi et al., 1986, BioTechniques 4: 214; Gillies et al., 1989, J. Immunol. Methods 125: 191-202; and U.S. Pat. Nos. 5,807,715; 4,816,567; 4,816,397; and 6,331,415, which are incorporated herein by reference in their entirety. Human antibodies described herein can be produced by any method known in the art, including but not limited to methods described in PCT Publication Nos. WO 98/24893, WO 96/34096, and WO 96/33735; and U.S. Pat. Nos. 5,413,923; 5,625,126; 5,633, 425; 5,569,825; 5,661,016; 5,545,806; 5,814,318; and 5,939,598, which are incorporated by reference herein in their entireties.

Humanized antibodies described herein can be produced using any technique known in the art, including but not limited to, CDR-grafting (European Patent No. EP 239,400; International Publication No. WO 91/09967; and U.S. Pat. Nos. 5,225,539, 5,530,101, and 5,585,089), veneering or resurfacing (European Patent Nos. EP 592,106 and EP 519,596; Padlan, 1991, Molecular Immunology 28(4/5): 489-498; Studnicka et al., 1994, Protein Engineering 7(6): 805-814; and Roguska et al., 1994, PNAS 91: 969-973), chain shuffling (U.S. Pat. No. 5,565,332), and techniques disclosed in, e.g., U.S. Pat. Nos. 6,407,213; 5,766,886; WO 9317105; Tan et al., 2002, J. Immunol. 169: 1119 25; Caldas et al., 2000, Protein Eng. 13(5): 353-60; Morea et al., 2000, Methods 20(3): 267 79; Baca et al., 1997, J. Biol. Chem. 272(16): 10678-84; Roguska et al., 1996, Protein Eng. 9(10): 895 904; Couto et al., 1995, Cancer Res. 55 (23 Supp): 5973s-5977s; Couto et al., 1995, Cancer Res. 55(8): 1717-22; Sandhu, 1994, Gene 150(2): 409-10; and Pedersen et al., 1994, J. Mol. Biol. 235(3): 959-73. See also U.S. Patent Pub. No. US 2005/0042664 A1 (Feb. 24, 2005), which are incorporated by reference herein in its entirety.

In some embodiments, the antibodies having reactivity to HLA-E, HLA-F and HLA-G are purified antibodies. Purified antibodies are substantially free of cellular material or other contaminating proteins from the cell or tissue source from which the protein is derived, or substantially free of chemical precursors or other chemicals when chemically synthesized. Methods of purifying antibodies are well known to those skilled in the art.

Antibodies having reactivity to HLA-E, HLA-F and HLA-G provided herein include, but are not limited to, synthetic antibodies, monoclonal antibodies, polyclonal antibodies recombinantly produced antibodies, multi-specific antibodies, single-chain Fvs (scFvs), Fab fragments, F(ab') fragments, disulfide-linked Fvs (sdFv), anti-idiotypic (anti-Id) antibodies, and epitope-binding fragments of any of the above. In particular embodiments, the antibodies having reactivity to HLA-E, HLA-F and HLA-G comprise immunoglobulin molecules and immunologically active portions of immunoglobulin molecules. In particular embodiments, the antibodies having reactivity to HLA-E, HLA-F and HLA-G comprise monoclonal antibodies. In particular embodiments, the antibodies having reactivity to HLA-E, HLA-F and HLA-G comprise purified monoclonal antibodies. In particular embodiments, the antibodies having reactivity to HLA-E, HLA-F and HLA-G comprise polyclonal antibodies. In particular embodiments, the antibodies having reactivity to HLA-E, HLA-F and HLA-G comprise purified polyclonal antibodies. In other embodiments, the antibodies having reactivity to HLA-E, HLA-F and HLA-G comprise Fab fragments.

Antibodies having reactivity to HLA-E, HLA-F and HLA-G described herein can be of any subclass of IgG (e.g., IgG1, IgG2 (e.g., IgG2a and IgG2b), IgG3, IgG4) of immunoglobulin molecule. In some embodiments, the antibodies having reactivity to HLA-E, HLA-F and HLA-G are IgG antibodies. In particular embodiments, the antibodies comprise IgG1 antibodies.

Antibodies having reactivity to HLA-E, HLA-F and HLA-G include both modified antibodies (i.e., antibodies that comprise a modified IgG (e.g., IgG1) constant domain, or FcRn-binding fragment thereof (e.g., the Fc-domain or hinge-Fc domain)) and unmodified antibodies (i.e., antibodies that do not comprise a modified IgG (e.g., IgG1) constant domain, or FcRn-binding fragment thereof (e.g., the Fc-domain or hinge-Fc domain)), that bind to HLA-E, HLA-F and HLA-G polyp eptides (e.g., heavy chain polypeptides). Techniques of making modified antibodies are well known to those skilled in the art. In some embodiments, the antibodies having reactivity to HLA-E, HLA-F and HLA-G are modified antibodies. In some embodiments, the antibodies having reactivity to HLA-E, HLA-F and HLA-G comprise modified IgG constant domain or FcRn-binding fragments.

In some embodiments, antibodies having reactivity to HLA-E, HLA-F and HLA-G are modified to increase the in vivo serum half life. In some embodiments, antibodies having reactivity to HLA-E, HLA-F and HLA-G comprise modified IgG constant domain or FcRn-binding fragments that increase the in vivo serum half-lives of the antibodies. In some embodiments, antibodies having reactivity to HLA-E, HLA-F and HLA-G are attached to inert polymer molecules to prolong the in vivo serum circulation of the antibodies. In particular embodiments, the inert polymer molecules are high molecular weight polyethyleneglycols (PEGs). PEGs can be attached to the antibodies with or without a multifunctional linker either through site-specific conjugation of the PEG to the N- or C-terminus of the antibodies or via epsilon-amino groups present on lysine residues. In another embodiment, antibodies having reactivity to HLA-E, HLA-F and HLA-G are conjugated to albumin. The techniques are well-known in the art. See, e.g., International Publication Nos. WO 93/15199, WO 93/15200, and WO 01/77137; and European Patent No. EP 413,622, all of which are incorporated herein by reference.

In some embodiments, antibodies provided herein are immunoreactive to the heavy chain polypeptide of HLA-E and to the heavy chain polypeptide of HLA-F or HLA-G. In some embodiments, antibodies provided herewith are immunoreactive to the heavy chain polypeptide of HLA-E and to the heavy chain polypeptide of HLA-F, HLA-G and β2-microglobulin.

In certain embodiments, antibodies provided herein are immunoreactive to HLA-E, HLA-F and HLA-G, either in native or denatured confirmation. In some embodiments, antibodies provided herein are immunoreactive to HLA-E, HLA-F and HLA-G in native form (i.e., a heavy chain polypeptide of HLA-E, HLA-F, or HLA-G in native confirmation). In other embodiments, antibodies provided herein are immunoreactive to HLA-E, HLA-F and HLA-G, in denatured form (i.e., a denatured heavy chain polypeptide of HLA-E and a denatured heavy chain polypeptide of HLA-F and HLA-G). In some embodiments, combinatory exposure to native or denatured peptides from HLA-E, HLA-F, or HLA-G can be used to determine immunoreactivity.

In some embodiments, antibodies provided herein are also immunoreactive to one or more HLA-Ia antigens. The HLA-Ia loci are highly polymorphic and, therefore, there exists many alleles, including those listed in Table 3. Antibodies immunoreactive to HLA-Ib can bind to a shared peptide (or epitope) sequences in a polypeptide encoded by a particular allele of HLA-A, HLA-B or HLA-C as determined by any method known to those skilled in the art, including, but not limited to, RIAs (radioimmunoassays), enzyme immunoassays like ELISAs (enzyme-linked immunosorbent assays), LIAs (luminescent immunoassays) and FIAs (fluorescent immunoassays), in which the antibodies, either used as primary or secondary antibodies, are labeled with radioisotopes (e.g., 125I), fluorescent dyes (e.g., PC or FITC) or enzymes (e.g., peroxidase or alkaline phosphatase) that catalyze fluorogenic or luminogenic reactions. An HLA-Ia antigen comprises an HLA heavy chain or portion of an HLA heavy chain associated with a β2-microglobulin to form a heterodimer or an HLA heavy chain or portion of an HLA heavy chain that is free (i.e., not bound to another HLA or β2-microglobulin). HLA antigens include those expressed or located on a cell surface or those occurring in soluble form in circulation or body fluids.

When an anti-HLA-Ib antibody binds an HLA-E, HLA-F, HLA-G, or HLA-Ia expressed on the surface of a cell, it can (1) suppress the immune activities of the cell; (2) cause death of the cell either by apoptosis or necrosis; (3) induce cytotoxicity to the cell; or (4) activate or stimulate the target cell to proliferate, in a manner similar or identical to that of IVIg. For example, an anti-HLA-Ib (used as IVIg-mimetics) described herein may suppress proliferation of PHA-L activated CD4+ T-lymphocytes, activate naïve CD8+ T-cells and induce cytotoxicity in CD8+ lymphoblasts.

When an antibody described herein (e.g., an anti-HLA-Ib antibody) binds a soluble HLA-E, HLA-F, HLA-G, or HLA-Ia antigen, it can block or prevent the activities of the soluble HLA antigen. For example, the antibody provided herein may prevent the soluble HLA antigen from binding to a receptor on a lymphocyte to suppress the ability of the lymphocyte to kill foreign, or pathogenic cells. Such blocking or inhibition of the soluble HLA antigen is referred to as "neutralization." Furthermore, an anti-HLA-Ib antibody described herein that binds to a soluble HLA antigen in circulation or a body fluid may clear the soluble HLA antigen from the circulation or body fluid before the soluble HLA causes any drastic effect on an immune system. Without being bound to any particular theory of operation, it is believed that the therapeutic efficacy of an antibody provided herein is dependent on the ability of the antibody to bind to a particular HLA-Ib or HLA-Ia.

When an antibody described herein (e.g., an anti-HLA-Ib antibody) binds a soluble HLA-E, HLA-F, HLA-G, or HLA-Ia antigen, it can block or prevent the activities of the soluble HLA antigen. For example, the antibody provided herein may prevent the soluble HLA-E from binding to the receptor (CD94/NKG2A) on a CD8+ lymphocytes (CTL/NKT cells), such that the anti-tumor cytotoxic capabilities of the tumor infiltrating CD8+ cytotoxic T lymphocytes can be suppressed. Such suppression to anti-tumor function of CD8+ T cells will help tumor to progress and spread. (Braud et al., 1998. Nature 391795-799, 1997, *Eur. J. Immunol.* 27:1164-1169; Derre et al., 2006, *J. Immunol.* 177: 3100-3107; Coupel et al., 2007, *Blood* 109:2806-2814; Berezhnoi et al., 2009, *Vopr. Onkol.* 55:224-229; Riederer et al., 2010, *PLoS One.* 5:e15339; Gooden et al., 2011, *Proc. Natl. Acad. Sci. USA* 108:10656-10661; Pietra et al., 2011). The IVIg-mimetic has the propensity to prevent binding of soluble HLA-Ib to receptors on T cells and NK cells.

In certain embodiments, the antibodies provided herein are also immunoreactive to HLA-A, HLA-B or HLA-Cw. In certain embodiments, the antibodies provided herein are also immunoreactive to several HLA-A. In certain embodiments, the antibodies provided herein are also immunoreactive to several HLA-B. In certain embodiments, the antibodies provided herein are also immunoreactive to several HLA-Cw. In certain embodiments, the antibodies provided herein are also immunoreactive to at least one HLA-A and more than one HLA-B and HLA-Cw. In certain embodiments, the antibodies provided herein are also immunoreactive to more than one of HLA-A, HLA-B and HLA-Cw.

6.4 Pharmaceutical Compositions

In certain embodiments, provided herein are pharmaceutical compositions comprising anti-HLA-Ib antibodies (e.g., used as IVIg mimetic) in a pharmaceutically acceptable carrier. In some embodiments, the pharmaceutical compositions comprise anti-HLA-Ib antibodies (e.g., used as IVIg mimetic), wherein at least 70% of the antibodies are anti-HLA-Ib antibodies. In certain embodiments, at least 75% of the antibodies are anti-HLA-Ib antibodies (e.g., used as IVIg mimetic) that have reactivity to HLA-E, HLA-F and HLA-G. In certain embodiments, at least 80% of the antibodies are anti-HLA-Ib antibodies (e.g., used as Wig mimetic). In certain embodiments, at least 85% of the antibodies are anti-HLA-Ib antibodies having reactivity to HLA-E, HLA-F and HLA-G (e.g., anti-HLA-Ib antibodies). In certain embodiments, at least 90% of the antibodies are anti-HLA-Ib antibodies having reactivity to HLA-E, HLA-F and HLA-G (e.g., used as IVIg mimetic). In certain embodiments, at least 95% of the antibodies are anti-HLA-Ib antibodies having reactivity to HLA-E, HLA-F and HLA-G (e.g., used as IVIg mimetic). In certain embodiments, at least 99% of the antibodies are anti-HLA-Ib antibodies having reactivity to HLA-E, HLA-F and HLA-G (e.g., used as Wig mimetic). In other embodiments, at least 99.5% of the antibodies are anti-HLA-Ib antibodies having reactivity to HLA-E, HLA-F and HLA-G (e.g., used as IVIg mimetic).

In some embodiments, the pharmaceutical compositions (e.g., anti-HLA-Ib antibodies) provided herein, the immunoreactivity of the antibodies having reactivity to HLA-E, HLA-F and HLA-G can be blocked by one or more particular peptides comprising an amino acid sequence listed in Table 4 or combinations thereof.

As shown in Table 4, certain amino acid sequences are shared among non-classical HLA-Ib epitopes (such as HLA-E, HLA-F and HLA-G) in addition to some or all three classical HLA-Ia alleles. Thus, while not being bound to any particular theory of operation, it is believed that in some embodiments, the immunoreactivity of the antibodies having reactivity to HLA-E, HLA-F and HLA-G (IVIg mimetic) can be blocked by polypeptides having these amino acid sequences. In some embodiments of the pharmaceutical compositions provided herein, the immunoreactivity of the antibodies having reactivity to HLA-E, HLA-F and HLA-G can be blocked by polypeptides comprising the amino acid sequence AYDGKDY (SEQ ID NO: 7). In some embodiments, the immunoreactivity of the antibodies having reactivity to HLA-E, HLA-F and HLA-G (IVIg mimetic) can be blocked by polypeptides comprising the amino acid sequence LNEDLRSWTA (SEQ ID NO: 8). In some embodiments, the immunoreactivity of the antibodies having reactivity to HLA-E, HLA-F and HLA-G (Wig mimetic) can be blocked by polyp eptides comprising the amino acid sequence DTAAQI (SEQ ID NO: 9). In some embodiments, the immunoreactivity of antibodies having reactivity to HLA-E, HLA-F and HLA-G (IVIg mimetic) can be blocked by polypeptides comprising the amino acid sequence DTAAQIS (SEQ ID NO: 10). In some embodiments, the immunoreactivity of the antibodies having reactivity to HLA-E, HLA-F and HLA-G (e.g., anti-HLA-Ib antibodies) can be blocked by polypeptides comprising the amino acid sequence TCVEWL (SEQ ID NO: 13).

In some embodiments, the immunoreactivity of the antibodies having reactivity to HLA-E, HLA-F and HLA-G (e.g., anti-HLA-Ib antibodies) can be blocked by at least two different polypeptides each comprising an amino acid sequence from one of the sequences of SEQ ID NO: 1 through SEQ ID NO: 5 in any combination. In some embodiments, the sequences on different polypeptides can be the same.

In some embodiments, the sequences on different polypeptides can be different. For example, when two different polypeptides are used, one can comprise the amino acid sequence of SEQ ID NO: 6 and the other can comprise the amino acid sequence of SEQ ID NO: 10.

In some embodiments, the immunoreactivity of the antibodies having reactivity to HLA-E, HLA-F and HLA-G (e.g., anti-HLA-Ib antibodies) can be blocked by a polypeptide comprising the amino acid sequences from more than one of the sequences of SEQ ID NO: 7 through SEQ ID NO: 10 in any combination. In some embodiments, when multiple sequences are encoded in the same polypeptide, adjacent sequences can be continuous or discontinuous. For example, the polypeptide can comprise AYDGKDY (SEQ ID NO:7) and DTAAQI (SEQ ID NO: 9) joined together by a linker sequence. See, e.g., Ravindranath et al., 2010, *Mol. Immunol.* 47: 1121-1131.

In some embodiments, the immunoreactivity of the antibodies having reactivity to HLA-E, HLA-F and HLA-G (e.g., anti-HLA-Ib antibodies) can be blocked by polypeptides comprising amino acid sequences that are polyspecific to classical class Ia sequences or non-classical class Ia sequences, or both. For example, in an exemplary embodiment, each polypeptide comprises the amino acid sequences QFAYDGKDY (SEQ ID NO: 6), LNEDLRSWTA (SEQ ID NO: 8) and DTAAQI (SEQ ID NO: 9).

Without being bound to any particular theory of operation, it is believed that the pharmaceutical compositions described herein (e.g., anti-HLA-Ib antibodies) can suppress proliferation and/or blastogenesis of naïve and/or activated T-cells in a recipient of the pharmaceutical composition. See, e.g., FIGS. 5 and 6. Further, without being bound to any particular theory of operation, it is believed that the pharmaceutical compositions described herein can induce cell death of naïve and/or activated T-cells in a recipient of the pharmaceutical composition. See, e.g., FIGS. 5 and 6.

In some embodiments provided herein, the pharmaceutical composition (e.g., anti-HLA-Ib antibodies) is capable of suppressing proliferation and/or blastogenesis of naïve and/or activated T-cells in a recipient. See, e.g., FIGS. 6A-6I. Techniques to determine suppression of T-cell proliferation and blastogenesis are well known to those skilled in the art, including, for example, flow cytometry analysis. In certain embodiments, the pharmaceutical composition (e.g., anti-HLA-Ib antibodies) is capable of suppressing proliferation of naïve CD3+/CD4+ T-cells in a recipient. In certain embodiments, the pharmaceutical composition (e.g., anti-HLA-Ib antibodies) is capable of suppressing proliferation of activated CD3+/CD4+ T-cells in a recipient. In certain embodiments, the pharmaceutical composition (e.g., anti-HLA-Ib antibodies) is capable of suppressing blastogenesis of naïve CD3+/CD4+ T-cells in a recipient. See, e.g., FIGS. 5 and 6. In certain embodiments, the pharmaceutical composition (e.g., anti-HLA-Ib antibodies) is capable of suppressing blastogenesis of activated CD3+/CD4+ T-cells in a recipient. See, e.g., FIGS. 5 and 6.

In certain embodiments, the pharmaceutical composition (e.g., anti-HLA-Ib antibodies) is capable of suppressing proliferation of naïve CD3+/CD8+ T-cells in a recipient. In certain embodiments, the pharmaceutical composition is capable of suppressing proliferation of activated CD3+/CD8+ T-cells in a recipient. See, e.g., FIGS. 5 and 6. In certain embodiments, the pharmaceutical composition (e.g., anti-HLA-Ib antibodies) is capable of suppressing blastogenesis of naïve CD3+/CD8+ T-cells in a recipient. In certain embodiments, the pharmaceutical composition (e.g., anti-HLA-Ib antibodies) is capable of suppressing blastogenesis of activated CD3+/CD8+ T-cells in a recipient. See, e.g., FIGS. 5 and 6.

In some embodiments provided herein, the pharmaceutical composition (e.g., anti-HLA-Ib antibodies) is capable of inducing cell death of naïve and/or activated T-cells in a recipient. In certain embodiments, the pharmaceutical composition (e.g., anti-HLA-Ib antibodies) is capable of inducing cell death of naïve CD3+/CD4+ T-cells. See, e.g., FIGS. 5 and 6. In certain embodiments, the pharmaceutical composition (e.g., anti-HLA-Ib antibodies) is capable of inducing cell death of activated CD3+/CD4+ T-cells. See, e.g., FIGS. 5 and 6. In certain embodiments, the pharmaceutical composition is capable of inducing cell death of naïve CD3+/CD8+ T-cells. See, e.g., FIGS. 5 and 6. In certain embodiments, the pharmaceutical composition (e.g., anti-HLA-Ib antibodies) is capable of inducing cell death of activated CD3+/CD8+ T-cells. See, e.g., FIGS. 5 and 6.

In certain embodiments, the pharmaceutical composition (e.g., anti-HLA-Ib antibodies) is capable of inducing apoptosis of naïve and/or activated CD3+/CD4+ T-cells in a recipient. See, e.g., FIGS. 5 and 6. In certain embodiments, the pharmaceutical composition (e.g., anti-HLA-Ib antibodies) is capable of inducing apoptosis of naïve and/or activated CD3+/CD8+ T-cells in a recipient. See, e.g., FIGS. 5 and 6. In certain embodiments, the pharmaceutical composition (e.g., anti-HLA-Ib antibodies) is capable of inducing necrosis of naïve and/or activated CD3+/CD4+ T-cells in a recipient. See, e.g., FIGS. 5 and 6. In certain embodiments, the pharmaceutical composition (e.g., anti-HLA-Ib antibodies or IVIg mimetic) is capable of inducing necrosis of naïve and/or activated CD3+/CD8+ T-cells in a recipient. See, e.g., FIGS. 5 and 6.

Without being bound to any particular theory of operation, it is believed that the pharmaceutical compositions (e.g., anti-HLA-Ib antibodies) described herein can suppress formation of T-cell dependent antibodies that have reactivity to HLA-E, HLA-F and HLA-G in a recipient. In certain embodiments, the pharmaceutical composition (e.g., anti-HLA-Ib antibodies) is capable of suppressing formation of T-cell dependent anti-HLA-A, HLA-B and HLA-Cw antibodies.

Without being bound to any particular theory of operation, it is believed that the pharmaceutical compositions (e.g., anti-HLA-Ib antibodies) described herein can block or neutralize the pro-inflammatory or adverse effects caused by a soluble HLA-E or HLA-F or HLA-G or HLA-Ia antigen by interfering with the ability of the soluble HLA antigen to bind to a lymphocyte bound receptor in a body fluid or circulation. In certain embodiments, the antibodies having reactivity to HLA-E, HLA-F and HLA-G (e.g., anti-HLA-Ib antibodies) are capable of blocking or neutralizing the pro-inflammatory or adverse effects caused by a soluble HLA antigen by interfering with the ability of the soluble HLA to bind to a lymphocyte bound receptor in a body fluid or circulation.

Without being bound to any particular theory of operation, it is believed that the pharmaceutical compositions (e.g., anti-HLA-Ib antibodies) described herein can bind to and clear any soluble HLA class I heavy chains from circulation. In some embodiments, the pharmaceutical composition (e.g., anti-HLA-Ib antibodies) is capable of clearing intact HLA class-Ia and Ib bound to β2-microglobulin from circulation.

In some embodiments of the pharmaceutical compositions (e.g., anti-HLA-Ib antibodies) provided herein, the antibodies having reactivity to HLA-E, HLA-F and HLA-G have immunoreactivity to HLA-Ia antigens similar to that of a commercial preparation of IVIg. In these embodiments, the pharmaceutical compositions are used as IVIg mimetics. Antibodies having reactivity to HLA-E, HLA-F and HLA-G that are also immunoreactive to HLA-Ia antigens similar to IVIg bind to a percentage of the same HLA-Ia antigens as IVIg as determined by any method known to those skilled in the art. A comparison of the binding of HLA-Ia antigens by IVIg and the pharmaceutical compositions (e.g., anti-HLA-Ib antibodies or IVIg mimetic) provided herein can be performed using any technique known to those skilled in the art, including, but not limited to, enzyme-linked immunosorbent assays (ELISAs). Commercial sources of IVIg are available, for example, from Baxter, Bayer, Centeon and Novartis. In some embodiments of the pharmaceutical composition provided herein (e.g., anti-HLA-Ib antibodies), the antibodies having reactivity to HLA-E, HLA-F and HLA-G are immunoreactive to at least 40%, at least 50%, or at least 60% of the same HLA-Ia antigens as a commercial preparation of IVIg. See, e.g., FIG. 4. In certain embodiments, the antibodies having reactivity to HLA-E, HLA-F and HLA-G are immunoreactive to at least 70% of the same HLA-Ia antigens as a commercial preparation of IVIg. See, e.g., FIG. 4. In certain embodiments, the antibodies having reactivity to HLA-E, HLA-F and HLA-G are immunoreactive to at least 75% of the same HLA-Ia antigens as a commercial preparation of IVIg. In certain embodiments, the antibodies having reactivity to HLA-E, HLA-F and HLA-G are immunoreactive to at least 80% of the same HLA-Ia antigens as a commercial preparation of IVIg. In certain embodiments, the antibodies having reactivity to HLA-E, HLA-F and HLA-G are immunoreactive to at least 85% of the same HLA-Ia antigens as a commercial preparation of IVIg. In certain embodiments, the antibodies having reactivity to HLA-E, HLA-F and HLA-G are immunoreactive to at least 90% of the same HLA-Ia antigens as a commercial preparation of IVIg. In certain embodiments, the antibodies having reactivity to HLA-E, HLA-F and HLA-G are immunoreactive to at least 95% of the same HLA-Ia antigens as a commercial preparation of IVIg. In certain embodiments, the antibodies having reactivity to HLA-E, HLA-F and HLA-G are immunoreactive to at least 99% of the same HLA-Ia antigens as a commercial preparation of IVIg.

In some embodiments of the pharmaceutical composition (e.g., anti-HLA-Ib antibodies), antibodies having reactivity to HLA-E, HLA-F and HLA-G have immunomodulatory activity comparable to a commercial preparation of IVIg; see, for example, FIGS. 1-6 and Table 4. Commercial preparations of IVIg are thought to provide immunomodulatory effects within a recipient. These immunomodulatory activities of IVIg are thought to include, but are not limited to, modulation of T-cell, B-cell and dendritic cell growth, expansion or proliferation, down-regulation of expression of MHC class II molecules, inhibition of expression of CD80/CD86 molecules, suppression of dendritic cell-mediated activation and proliferation of allo-reactive T-cells, induction of apoptosis of T-cells, suppression of the expansion of auto-reactive B-cells, inhibition of complement activation, and enhancement of clearance of endogenous pathogenic auto-antibodies (see also FIGS. 6 & 7).

Without being bound to any particular theory of operation, it is believed that a pharmaceutical composition comprising antibodies that have reactivity to HLA-E, HLA-F and HLA-G has at least one or more of the same immunomodulatory activities as compared to a commercial preparation of IVIg. The immunomodulatory activities described above can be measured by any technique known to those skilled in the art. In some embodiments, the antibodies having reactivity to HLA-E, HLA-F and HLA-G modulate T-cell growth, expansion and/or proliferation comparable to a commercial preparation of IVIg. In some embodiments, the antibodies having reactivity to HLA-E, HLA-F and HLA-G modulate B-cell growth, expansion and/or proliferation similar to a commercial preparation of IVIg. In some embodiments, the antibodies having reactivity to HLA-E, HLA-F and HLA-G modulate dendritic cell growth, expansion and/or proliferation comparable to a commercial preparation of IVIg. In some embodiments, the antibodies having reactivity to HLA-E, HLA-F and HLA-G modulate down-regulation of expression of MHC class II molecules comparable to a commercial preparation of IVIg. In some embodiments, the antibodies having reactivity to HLA-E, HLA-F and HLA-G modulate inhibition of expression of CD80/CD86 molecules comparable to a commercial preparation of IVIg. In some embodiments, the antibodies having reactivity to HLA-E, HLA-F and HLA-G modulate suppression of dendritic cell-mediated activation and/or proliferation of allo-reactive T-cells comparable to a commercial preparation of IVIg. In some embodiments, the antibodies having reactivity to HLA-E, HLA-F and HLA-G modulate suppression of the expansion of auto-reactive B-cells comparable to a commercial preparation of IVIg. In some embodiments, the antibodies having reactivity to HLA-E, HLA-F and HLA-G modulate suppression of the inhibition of complement activation comparable to a commercial preparation of IVIg. In some embodiments, the antibodies having reactivity to HLA-E, HLA-F and HLA-G modulate the enhancement of clearance of toxic or cytotoxic soluble HLA antigen or HLA antigens, comparable to a commercial preparation of IVIg.

In some embodiments, the pharmaceutical composition provided herein (e.g., anti-HLA-Ib antibodies), is therapeutically effective for the treatment of one or more inflammatory diseases or conditions treatable by a commercial preparation of IVIg. Without being bound to any particular theory of operation, it is believed that a pharmaceutical composition (e.g., anti-HLA-Ib antibodies), comprising antibodies having reactivity to HLA-E, HLA-F and HLA-G can mimic the immunomodulatory effects of whole IVIg. Thus, it is believed that in some embodiments, the pharmaceutical compositions provided herein (e.g., anti-HLA-Ib antibodies) based on the in vitro observations on T cells (see figures), are therapeutically effective for the treatment of one or more inflammatory diseases or conditions treatable by IVIg. The pharmaceutical composition provided herein (e.g., anti-HLA-Ib antibodies) based on the in vitro observations on T cells (see figures), is therapeutically effective for the treatment of inflammatory diseases or conditions reduces the severity, the duration and/or the number of symptoms associated with that disease or condition. Inflammatory diseases and conditions treatable by commercial preparations of IVIg include, but are not limited to: Kawasaki disease, immune-mediated thrombocytopenia, primary immunodeficiencies, hematopoietic stem cell transplantation, chronic B-cell lymphocytic leukemia, pediatric HIV type 1 infection, aplastic anemia, pure red cell aplasia, Diamond-Blackfan anemia, autoimmune hemolytic anemia, hemolytic disease of the newborn, acquired factor I inhibitors, acquired von Willebrand disease, immune-mediated neutropenia, refractoriness to platelet transfusion, neonatal alloimmune thrombocytopenia, posttransfusion purpura, thrombotic thrombocytopenic purpura/hemolytic uremic syndrome, hemolytic transfusion reaction, hemophagocytic syndrome thrombocytopenia, acute lymphoblastic leukemia, multiple myeloma, human T-cell lymphotrophic virus-1-myelopathy, nephritic syndrome, membranous nephropathy, nephrotic syndrome, acute renal failure, epilepsy, chronic inflammatory demyelinating polyneuropathy, Guillain-Barre syndrome, myasthenia gravis, Lambert-Eaton myasthenic syndrome, multifocal motor neuropathy, multiple sclerosis, Wegener granulomatosis, amyotrophic lateral sclerosis, lower motor neuron syndrome, acute disseminated encephalomyelitis, paraneoplastic cerebellar degeneration, paraproteinemic neuropathy, polyneuropathy, progressive lumbosacral plexopathy, lyme radiculoneuritis, endotoxemia of pregnancy, parvovirus infection, streptococcal toxic shock syndrome, rheumatoid arthritis, systemic lupus erythematosus, dermatomyositis, polymyositis, inclusion-body myositis, autoimmune blistering dermatosis, cardiomyopathy, acute cardiomyopathy, euthyroid ophthalmopathy, uveitis, recurrent otitis media, asthma, cystic fibrosis, Behçet syndrome, chronic fatigue syndrome, congenital heart block, diabetes mellitus, acute idiopathic dysautonomia, opsoclonus-myoclonus, Rasmussen syndrome, Reiter syndrome, Vogt-Koyanagi-Harada syndrome, trauma and burns. In some embodiments, the pharmaceutical composition is therapeutically effective for the treatment of one or more of the aforementioned inflammatory diseases or conditions treatable by a commercial preparation of IVIg.

Without being bound to any particular theory of operation, it is believed that the pharmaceutical compositions (e.g., anti-HLA-Ib antibodies) described herein can also be used as "passive immunotherapeutic agents" for human cancers such as melanoma, breast, prostate, colon and ovarian cancers, such that they can bind to and clear any soluble HLA class I heavy chains (e.g. HLA-E) in circulation or tumor microenvironment, which may otherwise bind to CD94/NKGa2 receptors and prevent CD8+ cytotoxic T cells (CTL) or NKT cells from attacking and killing tumor cells. In the passive immunotherapy of human cancer, the anti-HLA-Ib antibodies bind to HLA-E and restore Cytotoxic functions of CTLs and NKT cells.

5.4.1 Pharmaceutically Acceptable Carriers

The pharmaceutical compositions provided herein also comprise a pharmaceutically acceptable carrier. The carrier can be a diluent, excipient, or vehicle with which the pharmaceutical composition is administered. Such pharmaceutical carriers can be sterile liquids, such as water and oils, including those of petroleum, animal, vegetable or synthetic origin, such as peanut oil, soybean oil, mineral oil, sesame oil and the like. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in E. W. Martin, 1990, *Remington's Pharmaceutical Sciences*, Mack Publishing Co.

5.4.2 Formulations

In some embodiments, the pharmaceutical composition is provided in a form suitable for administration to a human subject. In some embodiments, the pharmaceutical composition will contain a prophylactically or therapeutically effective amount of the anti-HLA-E antibody together with a suitable amount of carrier so as to provide the form for proper administration to the patient. The formulation should suit the mode of administration.

In some embodiments, the pharmaceutical composition is provided in a form suitable for intravenous administration. Typically, compositions suitable for intravenous administration are solutions in sterile isotonic aqueous buffer. Where necessary, the composition may also include a solubilizing agent and a local anesthetic such as lignocaine to ease pain at the site of the injection. Such compositions, however, may be administered by a route other than intravenous administration.

In particular embodiments, the pharmaceutical composition is suitable for subcutaneous administration. In particular embodiments, the pharmaceutical composition is suitable for intramuscular administration.

Components of the pharmaceutical composition can be supplied either separately or mixed together in unit dosage form, for example, as a dry lyophilized powder or water free concentrate. Where the composition is to be administered by infusion, it can be dispensed with an infusion bottle containing sterile pharmaceutical grade water or saline. Where the composition is administered by injection, an ample of sterile water for injection or saline can be provided so that the ingredients may be mixed prior to administration.

In some embodiments, the pharmaceutical composition is supplied as a dry sterilized lyophilized powder that is capable of being reconstituted to the appropriate concentration for administration to a subject. In some embodiments, antibodies having reactivity to HLA-E, HLA-F and HLA-G are supplied as a water free concentrate. In some embodiments, the antibody is supplied as a dry sterile lyophilized powder at a unit dosage of at least 0.5 mg, at least 1 mg, at least 2 mg, at least 3 mg, at least 5 mg, at least 10 mg, at least 15 mg, at least 25 mg, at least 30 mg, at least 35 mg, at least 45 mg, at least 50 mg, at least 60 mg, or at least 75 mg.

In another embodiment, the pharmaceutical composition is supplied in liquid form. In some embodiments, the pharmaceutical composition is provided in liquid form and is substantially free of surfactants and/or inorganic salts. In some embodiments, the antibody is supplied as in liquid form at a unit dosage of at least 0.1 mg/ml, at least 0.5 mg/ml, at least 1 mg/ml, at least 2.5 mg/ml, at least 3 mg/ml, at least 5 mg/ml, at least 8 mg/ml, at least 10 mg/ml, at least 15 mg/ml, at least 25 mg/ml, at least 30 mg/ml, or at least 60 mg/ml.

In some embodiments, the pharmaceutical composition is formulated as a salt form. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

5.5 Methods for Treatment of Diseases

In another aspect provided herein are methods of preventing, managing, treating and/or ameliorating various diseases, the method comprising administering to a human subject a therapeutically effective amount of any one of the pharmaceutical compositions provided herein.

Studies described herein show that antibodies having reactivity to HLA-E, HLA-F and HLA-G (e.g., anti-HLA-Ib antibodies) recapitulate the immunosuppressive or immunomodulatory effects of whole IVIg. Therefore, the antibodies having reactivity to HLA-E, HLA-F and HLA-G in commercial preparations of IVIg may be responsible for the immunomodulatory activity of IVIg. Thus, while not intending to be bound by any particular theory of operation, it is believe that pharmaceutical compositions comprising antibodies that have reactivity to HLA-E, HLA-F and HLA-G (e.g., anti-HLA-Ib antibodies) can be used as immunomodulatory agents in preventing, managing, treating and/or ameliorating various diseases and conditions treatable by IVIg.

A therapeutically effective amount of the pharmaceutical composition (e.g., anti-HLA-Ib antibodies) is an amount that is required to reduce the severity, the duration and/or the symptoms of a particular disease or condition, in par with IVIg or even better. The amount of a pharmaceutical composition (e.g., anti-HLA-Ib antibodies) that will be therapeutically effective in the prevention, management, treatment and/or amelioration of a particular disease can be determined by standard clinical techniques. The precise amount of the pharmaceutical composition (e.g., anti-HLA-Ib antibodies) to be administered with depend, in part, on the route of administration, the seriousness of the particular disease or condition, and should be decided according to the judgment of the practitioner and each human patient's circumstances. Effective amounts may be extrapolated from dose-response curves derived from preclinical protocols either in vitro using T-cells from patients or using in vivo animal (e.g., Wistar or Lewis rat or different strains of mice used for different diseases, or Cynomolgous monkey) test systems.

In some embodiments, the effective amount of an antibody of the pharmaceutical composition provided herein is between about 0.025 mg/kg and about 1000 mg/kg body weight of a human subject. In certain embodiments, the pharmaceutical composition is administered to a human subject at an amount of about 1000 mg/kg body weight or less, about 950 mg/kg body weight or less, about 900 mg/kg body weight or less, about 850 mg/kg body weight or less, about 800 mg/kg body weight or less, about 750 mg/kg body weight or less, about 700 mg/kg body weight or less, about 650 mg/kg body weight or less, about 600 mg/kg body weight or less, about 550 mg/kg body weight or less, about 500 mg/kg body weight or less, about 450 mg/kg body weight or less, about 400 mg/kg body weight or less, about 350 mg/kg body weight or less, about 300 mg/kg body weight or less, about 250 mg/kg body weight or less, about 200 mg/kg body weight or less, about 150 mg/kg body weight or less, about 100 mg/kg body weight or less, about 95 mg/kg body weight or less, about 90 mg/kg body weight or less, about 85 mg/kg body weight or less, about 80 mg/kg body weight or less, about 75 mg/kg body weight or less, about 70 mg/kg body weight or less, or about 65 mg/kg body weight or less.

In some embodiments, the effective amount of an antibody of the pharmaceutical composition provided herein is between about 0.025 mg/kg and about 60 mg/kg body weight of a human subject. In some embodiments, the effective amount of an antibody of the pharmaceutical composition provided herein is about 0.025 mg/kg or less, about 0.05 mg/kg or less, about 0.10 mg/kg or less, about 0.20 mg/kg or less, about 0.40 mg/kg or less, about 0.80 mg/kg or less, about 1.0 mg/kg or less, about 1.5 mg/kg or less, about 3 mg/kg or less, about 5 mg/kg or less, about 10 mg/kg or less, about 15 mg/kg or less, about 20 mg/kg or less, about 25 mg/kg or less, about 30 mg/kg or less, about 35 mg/kg or less, about 40 mg/kg or less, about 45 mg/kg or less, about 50 mg/kg or about 60 mg/kg or less.

In some embodiments, the method further comprises co-administrating to the human subject one or more immunosuppressive agents with the pharmaceutical composition. Examples of immunosuppressive agents that can be co-administered with the pharmaceutical composition include, but are not limited to corticosteroids, vitamin D3, azathioprine, prednisone, cylcosporin, cyclophosphamide, OKT3, FK506, mycophenolic acid or the morpholinethylester thereof, 15-deoxyspergualin, rapamycin, mizoribine, misoprostol, anti-interleukin-1 receptor antibodies, an anti-lymphocyte globulin, Velcade, Bortesomib, inhibitors of plasma cells and antibody production, NFκB, MERK, Akt, Jun pathway inhibitors, and phytonutrients or plant chemical nutrients, such as carotenoids (alpha-carotene, beta-carotene, lycopene, lutein, zeaxanthin, and cryptoxanthin), capsaisin, coumarins, flavanoids, flavonolignans, xilibinin or mixture of silymarin (silibinin A and B, isosibilinin A and B, silicristin, silidianin), ellagic acid, isoflavones, isothiocyanates, lignans, polyphenols (e.g., epicatechins-EC, epicatechin gallate-ECG, epigallocatechin-EGC, epigallocatechin gallate, EGCG, oxidized quinonoids, curcuminoids, curcumin), saponins and phytosterols.

The pharmaceutical composition of the method can be administered using any method known to those skilled in the art. For example, the pharmaceutical composition can be administered intramuscularly, intradermally, intraperitoneally, intravenously, subcutaneously administration, or any combination thereof. In some embodiments, the pharmaceutical composition is administered subcutaneously. In some embodiments, the composition is administered intravenously. In some embodiments, the composition is administered intramuscularly.

5.5.1 Allograft Rejection

In one aspect provided herein, is a method of preventing, managing, treating and/or ameliorating an allograft rejection, the method comprising administering to a human subject a therapeutically effective amount of any one of the pharmaceutical compositions provided herein.

Rejection of donated grafts (e.g., organs, tissue, or cells), also known as allograft, by a transplant recipient can be caused by anti-HLA-Ia antibodies directed against the HLA-Ia antigens of the donor in the sera of the recipient. Such antibodies produced against donor HLA-Ia antigens are called Donor Specific Antibodies (DSA). IVIg has been used as an immunomodulatory agent in the prevention, management and treatment of allograft rejections. See, e.g., Glotz et al., 2004, *Transpl Int* 17: 1-8. As shown in the studies described herein, antibodies having reactivity to HLA-E, HLA-F and HLA-G (e.g., anti-HLA-Ib antibodies or IVIg mimetics) can recapitulate immunomodulatory effects of whole IVIg. Primarily suppression of activated CD4+ T cells which are involved in donor antigen presentation to recipients B cells are suppressed by both IVIg and anti-HLA-Ib antibodies. Thus, without being bound to any particular theory of operation, it is believed that pharmaceutical compositions comprising the immunomodulatory component of IVIg and antibodies having reactivity to HLA-E, HLA-F and HLA-G (e.g., anti-HLA-Ib antibodies or IVIg mimetics) are also useful in the prevention, management, treatment and amelioration of allograft rejections.

In some embodiments, the allograft is an organ. In some embodiments, the allograft is a heart, kidney or lung. In particular embodiments, the allograft is a heart. In particular embodiments, the allograft is a kidney. In other embodiments, the allograft is a lung. In other embodiments, the allograft is a liver. In other embodiments, the allograft is a pancreas. In some embodiments, the allograft is a tissue or cultured and cytokine-exposed cells from donor tissues such as tumor tissues. In other embodiments, the graft is a plurality of cells. In some embodiments, the allograft is a plurality of bone marrow cells. In some embodiments the allograft is a plurality of blood cells.

In some embodiments, the pharmaceutical composition (e.g., anti-HLA-Ib antibodies or IVIg mimetics) is administered to the human subject prior to transplantation. In some embodiments, the pharmaceutical composition (e.g., anti-HLA-Ib antibodies or IVIg mimetics) is administered to the human subject at a therapeutically effective amount of 0.1 to about 1000 mg/kg body weight. In some embodiments, the pharmaceutical composition (e.g., anti-HLA-Ib antibodies or IVIg mimetics) is administered to the human subject at a therapeutically effective amount of 1 to about 500 mg/kg body weight.

In some embodiments, the pharmaceutical composition (e.g. anti-HLA-Ib antibodies or IVIg mimetics) is administered to the human subject along with other known therapeutic monoclonal antibodies, such as Eculizumab (Locke et al., 2009, *Am. J. Transplant.* 9:231-235), Bortezomib (Everly et al. 2008, *Transplantation*, 86: 1754-1761), Campath (or Alemtuzumab) (Pham et al., 2009, *Drug Des. Dev. Ther.* 3: 41-49), Epratuzumab (Tamer, 2009, Z. Rhematol. 68: 380-389), Retuximab (Alausa et al., 2005, *Clin. Transplant.* 19:137-140), Belimumab (Vincenti, 2003, *Minerva Urol. Nefrol.* 55:57-66; Zarkhin et al., *Transplantation*, 88: 1229-1230; 2010, *Transplant. Rev.* 24:67-78). Cohen, 2006, *J. Rheumatol. Suppl.* 77:12-17).

5.5.2 Active Immunotherapy in Cancer Treatment

As provided herein, in passive immunotherapy, cell surface or soluble HLA-Ib antigens (HLA-E, HLA-F and HLA-G) in circulation or in tumor microenvironment are neutralized. These antigens may otherwise bind to CD94/NKGa2 receptors and prevent CD8+ cytotoxic T cells (CTL) or natural killer T cells (NKT) from attacking and killing tumor cells. In the passive immunotherapy, the anti-HLA-Ib antibodies bind to HLA-Ib antigens and restore cytotoxic functions of CTLs and NKT cells. In active immunotherapy, purified or cellular HLA-Ib molecules are administered to patients to induce anti-HLA-Ib antibodies production in patients to neutralize and bind to HLA-Ib antigen and restore cytotoxic functions of CTLs and NKT cells.

In some embodiments, production of anti-HLA-Ib antibodies in a cancer patient is induced by administering to the patient an effective amount of a composition comprising: a recombinant polypeptide comprising one or more epitopes from each of HLA-E, HLA-F and HLA-G polypeptides; a whole cell or lysate preparation of the patient's own tumor cells; or a whole cell or lysate preparation of tumor cells from one or more other patients with the same cancer type.

In some embodiments, the recombinant polypeptide comprises a recombinant HLA-E$^R$ heavy chain, a recombinant HLA-E$^G$ heavy chain or a mixture thereof.

In some embodiments, the whole cell or lysate preparation of the patient's own tumor cells or the whole cell or lysate preparation of tumor cells from one or more other patients with the same cancer type have been exposed to one or more cytokines such as IFNγ, GM-CSF, IL-2, IL-6, IL-15, IL-17 and a combination thereof, to induce over expression of the HLA-Ib antigens on the tumor cells.

In some embodiments, a pharmaceutically acceptable carrier, an adjuvant, a stimulant, an excipient, a diluent, or a vehicle is added to the recombinant polypeptide or whole cell or lysate preparation. The anti-HLA-Ib antibodies thus generated are capable of blocking or neutralizing pro-inflammatory or tumor-related adverse effects of soluble or circulating HLA-E or HLA-F or HLA-G polypeptide heavy chain.

Administration in active immunotherapy protocols refers to (1) administration of purified HLA-Ib molecules with or without adjuvants or cytokines or carriers for the purpose of inducing production of Anti-HLA Ib antibodies in the patients directly or (2) administration of cellular lysates or whole cells derived from the cancer patients (autologous or allogenic) exposed to cytokines such as IFN-γ, GM-CSF, IL-2, IL-6, IL-15, or IL-17 to enhance the over expression of HLA-Ib molecules on the cells. Protocols for inducing production of anti-HLA-E antibodies with immunoreactivity to HLA-Ia proteins are known (see, for example, Ravindranath et al., 2012, "Augmentation of anti-HLA-E antibodies with concomitant HLA-Ia reactivity in IFN-γ-treated autologous melanoma cell vaccine recipients," *J. Immunotoxicol. in Press, DOI:*10.3109/1547691X.2011.645582 and International Patent Application No. PCT/US11/68178, filed Dec. 30, 2011 and entitled "Anti-HLA-E Antibodies, Therapeutic Immunomodulartory Antibodies to Human HLA-E Heavy Chain, Useful as IVIg Mimetics and Methods of Their Use"). In that study, six melanoma patients were vaccine recipients, whose cell lines showed positivity for anti-HLA-E mAb MEM-E/02 (1/1000) post treatment.

Similar protocols can be used to induce production of anti-HLA-Ib antibodies with immunoreactivity to HLA-Ib and/or HLA-Ia proteins. More detailed experimental setup and conditions can be found in, e.g., Selvan et al., 2000, *Br. J. Cancer.* 82: 691-701; Selvan et al., 2008, *Int. J. Cancer* 122: 1374-1383; and Selvan et al., 2010, *Melanoma Res.* 20:280-292.

For example, tumor biopsy samples can be collected and processed in RPMI-1640 medium with iron-supplemented calf serum (7.5%, v/v) and fetal bovine serum (7.5%, v/v) (both Gemini Bio-Products, Calabasas, Calif.); the tumor cell lines (TC) were established as previously described. Melanoma cell lines were characterized by determining the expression of a panel of antigens including S-100, HMB45/gp100-cl, Melan-A/MART-1, MAGE-1, Tyrosinase, Mel-5 (TRP-1 and TRP-2), HLA-Class Ia, Claim Ib, Class II, and HLA-E. Once tumor cell lines are established and expanded to $150 \times 10^6$ cells, they can be treated with cytokines such as IFNγ, GM-CSF, IL-2, IL-6, IL-15, or IL-17 for 3 days with 1000 U/ml of ACTIMMUNE (InterMune, Brisbane, Calif.). The treated cells can be then harvested, irradiated (at 100 Gray) to arrest 100% growth, and cryopreserved until pulsing with autologous dendritic cells (DC). Before incubating with the DC overnight, irradiated tumor cells can have an average cell number of $7.9 \times 10^7$ ($\pm 1.7 \times 10^7$ (SD)) with a 77% viability. DC can be generated by Ficol-Paque density gradient centrifugation from the white blood cells recovered after leukopheresis from each patient, and placed into T-225 flasks for monocyte enrichment using the adherence technique.

For final preparation of the vaccine, irradiated tumor cells obtained from each patient can be incubated (overnight at 37° C.) with autologous DC at a ratio of 1:1 and cryopreserved into aliquots. Just prior to each vaccination, aliquots of DC loaded with tumor cells can be thawed at 37° C., washed twice with AIM-V medium (Gibco, Carlsbad, Calif.) and mixed with granulocyte-macrophage-colony stimulating factor (GM-CSF, 500 µg/ml) in saline. An average TC-DC dose of $1.6 \times 10^7$ ($\pm 0.8 \times 10^7$) cells with about 77% viability can be administered to patients. TC-pulsed with DC can be administered subcutaneously, weekly for 3 weeks, then monthly for 5 months. Sera can be collected at interval times, such as at Weeks 0 (before immunization), and 4 and 24 (after immunization). The sera can be aliquoted and frozen at −20° C., and a fraction thereof can be analyzed in the laboratory. Data can be obtained for 1:10 dilutions of the sample sera.

Immunoassays of the serum aliquots using single antigen beads can be carried out as described in International Patent Application No. PCT/US11/68178, filed Dec. 30, 2011 and entitled "Anti-HLA-E Antibodies, Therapeutic Immunomodulartory Antibodies to Human HLA-E Heavy Chain, Useful as IVIg Mimetics and Methods of Their Use.

An increase in anti-HLA-Ib antibody level and HLA-Ia reactivity can be expected after Week 4 and/or Week 28 post-immunization, as in the case with anti-HLA-E antibodies.

The polyclonal human anti-HLA-Ib antibodies, thus generated, can perform several functions in addition to the immunoreactive and immunomodulatory functions, characteristic of the commercial IVIgs. They can also bind to soluble HLA-Ib molecules in circulation, body fluids or tumor microenvironment, as well as tumor cell surface HLA-Ib molecules in patients, which would otherwise paralyze the tumor killing activity of CTLs and NKT cells.

5.5.3 Methods of Treatment of Other Diseases

In another aspect provided herein, is a method of managing, treating and/or ameliorating a disease or condition selected from the aforementioned diseases or conditions listed in Section 2. In some embodiments, is a method of managing, treating and/or ameliorating a disease or condition selected from the group consisting of: Kawasaki disease, immune-mediated thrombocytopenia, a primary immunodeficiency, hematopoietic stem cell transplantation, chronic B-cell lymphocytic leukemia, pediatric HIV type 1 infection, a hematological disease, nephropathy, neuropathy, a bacterial infection, a viral infection, an autoimmune disease that is not vasculitis, cardiomyopathy, an eye or ear disease, a lung disease, recurring pregnancy loss, Behçet syndrome, chronic fatigue syndrome, congenital heart block, diabetes mellitus, acute idiopathic dysautonomia, opsoclonus-myoclonus, Rasmussen syndrome, Reiter syndrome, or Vogt-Koyanagi-Harada syndrome, the method comprising administering to a human subject a therapeutically effective amount of any one of the pharmaceutical compositions provided herein.

IVIg has been shown to be a useful immunomodulatory agent in the prevention, management, treatment and amelioration of the disease conditions listed in Section 2. Thus, compositions comprising the immunomodulatory component of IVIg, antibodies having reactivity to HLA-E, HLA-F and HLA-G (e.g., anti-HLA-Ib antibodies or IVIg mimetics), are thought to be useful in the prevention, management, treatment and amelioration of such conditions.

In one embodiment of the method, the disease or condition is Kawasaki disease. In another embodiment, the disease or condition is immune-mediated thrombocytopenia. In another embodiment, the disease or condition is a primary immunodeficiency. In another embodiment, the disease or condition is hematopoietic stem cell transplantation. In another embodiment, the disease or condition is chronic B-cell lymphocytic leukemia. In another embodiment, the disease or condition is pediatric HIV type 1 infection.

In some embodiments, the disease or condition is a hematological disease. In certain embodiments, the hematological disease is aplastic anemia, pure red cell aplasia, Diamond-Blackfan anemia, autoimmune hemolytic anemia, hemolytic disease of the newborn, acquired factor I inhibitors, acquired von Willebrand disease, immune-mediated neutropenia, refractoriness to platelet transfusion, neonatal alloimmune thrombocytopenia, posttransfusion purpura, thrombotic thrombocytopenic purpura/hemolytic uremic syndrome, hemolytic transfusion reaction, hemophagocytic syndrome thrombocytopenia, acute lymphoblastic leukemia, multiple myeloma, or human T-cell lymphotrophic virus-1-myelopathy.

In some embodiments, the disease or condition is nephropathy. In some embodiments, the nephropathy is nephritic syndrome, membranous nephropathy, nephrotic syndrome, or acute renal failure. In some embodiments, the disease or condition is neuropathy. In some embodiments, the neuropathy is epilepsy, chronic inflammatory demyelinating polyneuropathy and Guillain-BarreSyndrome, myasthenia gravis, Lambert-Eaton myasthenic syndrome, multifocal motor neuropathy, multiple sclerosis, Wegener granulomatosis, Amyotrophic lateral sclerosis, lower motor neuron syndrome, acute disseminated encephalomyelitis, paraneoplastic cerebellar degeneration, paraproteinemic neuropathy, polyneuropathy, or progressive lumbosacral plexopathy.

In some embodiments, the disease or condition is an infection. In certain embodiments, the infection is an HIV infection, lyme radiculoneuritis, endotoxemia of pregnancy, a parovirus infection or streptococcal toxic shock syndrome.

In some embodiments, the disease or condition is an autoimmune disease that is not vasculitis. In certain embodiments, the autoimmune disease is rheumatoid arthritis, systemic lupus erythematosus, dermatomyositis, polymyositis, inclusion-body myositis, or autoimmune blistering dermatosis.

In some embodiments, the disease or condition is cardiomyopathy. In particular embodiments, the cardiomyopathy is acute cardiomyopathy.

In some embodiments, the disease or condition an eye or ear disease. In particular embodiments, the eye or ear disease is euthyroid ophthalmopathy, uveitis, or recurrent otitis media.

In some embodiments, the disease may be inflammatory dental disease like gingivitis or periodontitis.

In some embodiments, the condition is a lung disease. In specific embodiments, the lung disease is asthma or cystic fibrosis.

Having described the invention in detail, it will be apparent that modifications, variations, and equivalent embodiments are possible without departing the scope of the invention defined in the appended claims. Furthermore, it should be appreciated that all examples in the present disclosure are provided as non-limiting examples.

7. EXAMPLES

The following non-limiting examples are provided to further illustrate embodiments of the present invention (e.g., anti-HLA-Ib antibodies that function as IVIg mimetics). It should be appreciated by those of skill in the art that the techniques disclosed in the examples that follow represent approaches discovered by the inventors to function well in the practice of the invention, and thus can be considered to constitute examples of modes for its practice. However, those of skill in the art should, in light of the present disclosure, appreciate that many changes can be made in the specific embodiments that are disclosed and still obtain a like or similar result without departing from the spirit and scope of the invention.

Example 1 provides evidence showing that IgG antibodies constituting commercial IVIg preparation have remarkable capability and very high or potent affinity for heavy chains of HLA-E, HLA-F and HLA-G. Example 2 shows IVIg from different commercial sources also have immunoreactivity to HLA-Ia. Example 3 provides evidence showing that the immunoreactivity of IVIg to HLA-E and HLA-Ia is lost after adsorbing IVIg to Affi-Gel conjugated with HLA-E. Example 4 compares immunoreactivities of exemplary HLA-Ib antibodies with those of IVIg. Examples 5 and 6 show comparison analysis of T-lymphocyte modulatory activity of WIG and anti-HLA-Ib mAbs.

Example 1: Determination of IgG Antibodies in IVIg with Potential Reactivity to Non-Classical HLA-Ib Molecules: HLA-E, HLA-F and HLA-G This example demonstrates that IgG immunoreactive to HLA-E, HLA-F and HLA-G is present in commercially available preparations of IVIgs. IVIg was obtained from four different commercial sources: (1) GamaSTAN™ S/D from Talecris, USA; (2) Sandoglobulin from Novartis in Basel, Switzerland (3) Octagam from Octapharma in Lachen, Switzerland; and (4) IVIGlob® EX from VHB Life Sciences Ltd., India. IVIg was serially diluted with PBS (pH 7.2), for example, starting from a ½ dilution and ending in a $\frac{1}{4096}$ dilution for GamaSTAN™; from ½ to $\frac{1}{1024}$ for Sandoglobulin; from ½ to 2048 for Octagam; and from ½ to 4096 for IVIGlob® EX.

Multiplex Luminex-based immunoassays were used to detect the presence of antibodies (Abs) that react to HLA-E, HLA-F and HLA-G antibodies in IVIg, and in anti-HLA-Ib antibodies (as IVIg mimetics). Using dual-laser flow cytometric principles of Luminex® xMAP® multiplex technology, the single Ag (allele) assays were carried out for data acquisition and quantitative estimation of the level of antibodies reactive to HLA-E, HLA-F, or HLA-G. The Luminex® assays utilized microbeads on which HLA-E heavy chains, HLA-F heavy chains or HLA-G heavy chains had been covalently bonded (xMap® assays). Three kinds of beads were used: (1) negative control (also known as background control) beads coated with human or bovine albumin; (2) positive control beads coated with human Immunoglobulin (Ig), most commonly IgG; and (3) experimental beads coated with HLA-E, HLA-F or HLA-G heavy chain. The recombinant heavy chains of HLA-E, HLA-F, or HLA-G were attached to 5.6µ polystyrene microspheres by a process of simple chemical coupling and the microspheres were internally dyed at One Lambda with red and infrared fluorophores, using different intensities of two dyes (xMAP® microsphere number #005). Recombinant folded heavy chains (e.g., at a concentration of 10 mg/ml in MES buffer) of HLA-E, HLA-F, or HLA-G were purchased from the core facility at the Immune Monitoring Lab., Fred Hutchinson Cancer Research Center, University of Washington, Seattle, Wash. For example, the recombinant HLA-E heavy chain, by a process of simple chemical coupling, was attached to 5.6 micron polystyrene microspheres, which were internally dyed with red and infrared fluorophores, using different intensities of two dyes (xMAP microsphere number #005). Data generated with Luminex® Multiplex Flow Cytometry (LABScan® 100) was analyzed using computer software as previously reported (see Ravindranath et al., 2010, Mol. Immunol. 47: 1121-1131; Ravindranath et al., 2010, Mol. Immunol. 47. 1663-1664; and Ravindranath et al., 2011, Mol. Immunol. 48:423-428).

Similarly, the immunoreactivity of IVIg or anti-HLA-E antibodies to HLA-class Ia (HLA-A, HLA-B and HLA-Cw) was acquired by the LABScreent single antigen (SA) assay, which consisted of 100 color-coded microspheres (single antigen beads, SAB) coated with HLA class I antigens to identify antibody specificities. Additional information on the array of HLA antigens representing various alleles on the beads can be found at the website of One Lambda Inc. (Canoga Park, Calif.) under the section of Antibody detection products/Lab-Screen® Single Antigen Product sheet (as HLA-Ia combi-LS1A04-Lot 003 Worksheet Rev-1;

www<dot>onelambda<dot>com). The single recombinant HLA-Ia antigens in LS1A04-Lot 003 contain 31 HLA-A, 50 HLA-B and 16 HLA-C molecules. Data generated with Luminex Multi-plex Flow Cytometry (LABScan® 100) were analyzed using computer software. The fluorescent intensities of each antibody bound to more than 100 beads were recorded by Luminex Multi-plex Flow Cytometry (LABScan® 100). The values were expressed as Trimmed MFI also refers to the average of the fluorescent intensity obtained with at least 100 beads.

The fluorescent intensities of each antibody bound to 90 to 100 beads were recorded via Luminex Multi-plex Flow Cytometry (LABScan® 100). To express the fluorescence intensity of anti-HLA-E antibodies or IVIg bound to the beads, an average value of antibody bound to 90-100 microbeads was calculated and the following values were obtained as described in Luminex® IS™ Software Manual for Version 2.3 (Luminex Corporation, TX):

a. % CV (the measure of relative dispersion within the distribution (100×SD/mean).
b. Peak: The value that is equal to the largest number of data points within the distribution.
c. SD: The measure of dispersion within the distribution [Std. Dev=((NΣxi2−Σxi)2/N(N−1))½], wherein N is the number of data points in the distributionTrimmed count: The number of data points in the trimmed distribution (Nt).
d. The trimmed distribution represents the events was collected for an individual allele (e.g., HLA-E or HLA-B8201) in a single analysis, with the lowest and highest 5% of the data points removed to help to eliminate outliers. The data points represented fluorescence intensities of the antibody bound to the number of single antigen beads for an allele. In most experiments, over 100 microbeads were used. The measurements showed slight assay-to-assay variation when about 2 or 3 μl of single antigen beads were added for each analysis.
e. Trimmed mean: The sum of the data points in the trimmed distribution was divided by the number of data points (Σxi/Nt). The sample specific fluorescent value (Trimmed MFI) for each set of beads was taken into consideration.
f. Trimmed % CV, Trimmed Peak, and Trimmed SD. were also calculated. The entire datasheet for each analysis was stored with their respective ID and data analyses.

Different kinds of Sample # Number (S # N) of beads (for each HLA molecules a particular numbered beads were used). Additional information concerning HLA-Ia molecules can be found under the section of Antibody detection products/Lab-Screen® Single Antigen Product sheet, as HLA-Ia combi-LS1A04-Lot 003 Worksheet Rev-, at the website of One Lambda Inc. (Canoga Park, Calif., at www<dot>onelambda<dot>com) are obtained. The Number 1 bead always referred to the negative control; Number 2 referred to the positive control. The other (experimental) or HLA-coated beads and their numbers refer to different HLA alleles of different HLA-Ia or Ib classes (HLA-Ia: HLA-A, HLA-B, and HLA-Cw; HLA-Ib: HLA-E, HLA-F and HLA-G). The Trimmed mean fluorescence values for the Single Antigen Bead reactions were obtained from the output (.csv is converted to .xls) file generated by the flow analyzer, and were adjusted for blank and background signal using the formula below. In essence, the following four different kinds of values were obtained. They were referred to as Normalized Trimmed mean calculated as follows:

(i) Trimmed MFI for Wig IgG Abs or anti-HLA-Ib antibodies obtained with HLA coated beads (differ in the bead numbers) (experimental);
(ii) Trimmed MFI for the negative control beads (bead #1) used for IVIg IgG Ab and anti-HLA-Ib antibodies (control #1);
(iii) Trimmed MFI for HLA coated beads (PE-conjugated 2nd antibody only) (control #2); and,
(iv) Trimmed MFI for the negative control beads (with PE-Conjugated 2nd antibody only) (control #3).

Normalized trimmed MFI is calculated as follows: (S # N value of (i)–S # N value of (ii))–(S # N value (iii)–S # N value of (iii). The values represented in the tables refer to normalized trimmed mean. Interpretations of the data are based on the normalized trimmed mean. The HLA-Ia microbeads have in-built control beads: Positive control beads were coated with human IgG (or murine IgG, when murine MAb was used in this study) and the negative control beads were coated with serum albumin (HSA/BSA). For HLA-E, HLA-F and HLA-G control beads (both positive and negative controls) were added separately. For each analysis, at least 90 to 100 beads were counted. Mean and standard deviation of MFI for each allele was recorded. All the data are stored and archived; basic statistical analyses were then carried out with Excel software. Basically, the reporter fluorophores intensity was then measured in a specialized flow cytometer together with the microbead identifiers, and the fluorescence measurement was classified by bead identifier. Florescence intensity from a sample of 90 or more beads was collected. The Trimmed Mean is obtained by trimming a percent off the high and low ends of a distribution and finding the mean of the remaining distribution.

FIGS. 1A through 1D illustrate the presence of IgG immunoreactive (to HLA-E, HLA-F, or HLA-G in IVIg. The levels of the antibody were high as evidenced at different dilutions. The values were expressed as mean fluorescent intensity (MFI). The MFI values significantly increased from ¼ to ¹⁄₁₆ dilution for IVIg from GamaSTAN™ S/D against HLA-E, HLA-F, and HLA-G (FIG. 1A). The same trend was not observed for the positive control. Such increases signify the aggregation of IgG immunoreactive to HLA-E, HLA-F, and HLA-G at high concentration and also indicate the high titer of anti-HLA-E, anti-HLA-F, and anti-HLA-G IgG antibodies in the Wig preparations. Similar trend was not observed for the other IVIg preparations (FIGS. 1B-1D). In particular, the MFI values for anti-HLA-E, anti-HLA-F, and anti-HLA-G IgG antibodies showed similar minor variations for Sandoglobulin. However, a similar trend was observed for the positive control as well. See FIG. 1B.

The MFI values for anti-HLA-E, anti-HLA-F, and anti-HLA-G IgG antibodies showed minor and inconsistent variations for Octagam, even though the data for anti-HLA-E, anti-HLA-F antibodies appeared to be more similar to each other than those of anti-HLA-G antibodies. See FIG. 1C. In FIG. 1D, the MFI values for anti-HLA-E, anti-HLA-F, and anti-HLA-G IgG antibodies showed similar trends from dilution ratio of ¹⁄₆₄ and beyond. Interestingly, the MFI values for the positive control sample remained largely unchanged over a large range of dilutions.

When tested at different dilutions for reactivity with HLA class Ib antigens (HLA-E, HLA-F and HLA-G), all samples showed dose dependent affinity for all the three HLA-Ib antigens, with preference of HLA-E except Sandoglobulin, which showed higher affinity for HLA-F and HLA-G, as shown in FIG. 1B. GamaSTAN™ at higher dilutions shifted its affinity from HLA-E to HLA-F; see FIG. 1A. Strikingly, as observed in FIG. 1A, the immunoreactivity tested against HLA-E, HLA-F and HLA-G, increased with increase in dilutions ¼ to ¹/₁₆, but declined steadily from dilution ¹/₃₂ onwards, possibly due to interference of anti-albumin antibodies since negative control beads were higher (see below). This pattern of reactivity of IVIg to HLA Class Ib antigens strongly suggests that IVIg may comprise either aggregates of IgGs with immunoreactivity to different HLA class Ib epitopes or an HLA-E IgG that may also react with HLA-F and HLA-G, possibly due to shared peptide epitopes (Table 3). These findings indicate that an IgG with immunoreactivity to HLA-E, HLA-F and HLA-G is a significant feature and a substantial component of the IVIg used for treatment of patients of various maladies, listed earlier.

The effects of the background control (in which albumin sample bound to the beads) were also analyzed (FIG. 1E). The background control examines the effects of non-specific binding to the Wig preparations. FIG. 1E shows consistent decrease in MFI values as the samples are further diluted, suggesting that the albumin samples do not aggregated. Here, non-selective immuno-reactivity is determined by measuring anti-albumin IgG reactivity with HLA-Ia or HLA-Ib epitopes coated beads, as illustrated in FIG. 1E. FIG. 1E shows (1) IVIg has anti-albumin IgG reactivity, (2) anti-albumin IgG may interfere with anti-HLA IgG reactivities of IVIg at dilution ratio at or above ¹/₃₂, and (3) anti-HLA IgG values obtained at or above a dilution ratio of ¹/₆₄ (and corrected against negative background) are reliable and also reproducible.

Commercially available human IgG samples (not meant for therapeutic use and prepared in a manner different from that of Wig) (e.g., sample No: 0150-01 from Southern Biotech in Birmingham, Ala.) also exhibited reactivity against HLA-E, HLA-F, and HLA-G (FIG. 1F). The purified human IgG did indeed react with HLA-E, HLA-F and HLA-G. HLA-F reactivity was higher than that of HLA-E and HLA-G (FIG. 1F). The MFI levels for human IgG samples appear to be lower than the other commercial IVIg preparations.

Example 2: Determination of the Presence of Potential Anti-HLA-Ia-Reactivity of IVIg Obtained from Different Commercial Sources This example demonstrates that commercial sources of IVIg are immunoreactive to HLA-Ia. To detect the presence of antibodies (Abs) that are immunoreactive to HLA-Ia epitopes in Wig, a multiplex Luminex®-based immunoassay was used. Samples from the same four commercial sources in Example 1 were examined: (1) GamaSTAN™ S/D from Talecris, USA; (2) Sandoglobulin from Novartis in Basel, Switzerland; (3) Octagam from Octapharma in Lachen, Switzerland; and (4) IVIGlob™ EX from VHB Life Sciences Ltd., India. IVIg was serially diluted with PBS (pH 7.2), for example, starting from a ½ dilution and ending in a ¹/₅₁₂ dilution for GamaSTAN™; from ½ to ¹/₁₀₂₄ for Sandoglobulin; from ½ to 2048 for Octagam; and from ½ to 4096 for IVIGlob™ EX.

FIGS. 2A through 2D demonstrate the presence of Abs immunoreactive to HLA-Ia in four commercial sources of IVIg. It should be noted that according to the recent estimate (e.g. Table 3) there are 1729 HLA-A alleles with 1,264 proteins, 2329 HLA-B alleles with 1,786 proteins, 1291 HLA-Cw alleles with 938 proteins, whereas our assay system from One Lambda Inc. contains the following number of beads containing different HLA-Ia proteins (HLA-A 31, HLA-B 50 and HLA-Cw 16). IVIg may react to 90 to 95% of the test beads to suggest that they may have many more anti-HLA-Ia antibodies or HLA-Ia reactivity than we observed. This will be known only when we have beads for other HLA-Ia alleles or proteins.

FIG. 2A represents an immunoreactivity profile of GamaSTAN™, Sandoglobulin, Octagam, and IVIGlob™ EX, respectively. In FIGS. 2A and 2D, the immunoreactivities of the respective IVIg preparations to HLA-Ia epitopes are compared to those to HLA-E. In FIGS. 2B and 2C, the immunoreactivities of the respective IVIg preparations to HLA-Ia epitopes are compared to those to HLA-E, HLA-F and HLA-G.

Example 3: Loss of Both HLA-E and HLA-Ia Reactivity of IVIg after Adsorption of IVIg to Affi-Gel Conjugated with HLA-E This example demonstrates that HLA-Ia reactivity of IVIg is due to the presence of HLA-Ib antibodies in IVIg. To prove this concept, one of the HLA-Ib molecules (HLA-E heavy chain) (6 mg) was dialyzed overnight at 4° C. against sodium bicarbonate buffer (pH 8.5) to remove Urea and DTT. For conjugating HLA-E to Affi-Gel 10, Affi-Gel 10 was washed with distilled water and sodium bicarbonate buffer for 20 minutes. After removing supernatant, HLA-E (6 mg) in 1 ml of buffer was mixed with 500 µl of the Affi-Gel 10 suspension (3380 suspension. The mixture was kept on an inverting rotator for overnight in a refrigerator. The tube was taken out and centrifuged at 600 g for 5 minutes. The supernatant was recovered and the gel was washed three times in distilled water and twice with carbonate buffer (Elution Buffer). After removing the supernatant completely, 100 µl of IVIg (¹/₁₂₈ dilution) was added to the gel and mixed well. The HLA-E coupled Affi-Gel-10 and IVIg (¹/₁₂₈ dilution) mixture was placed on an inverter for 1 hour. In the meantime, 100 µl of ¹/₁₂₈ diluted IVIg was further serially diluted (¹/₁₂₈, ¹/₂₅₆, ¹/₅₁₂ and ¹/₁₀₂₄ dilutions, to a total volume of 50 µl). IVIg adsorbed to HLA-E gel (or control Affi-Gel 10 without HLA-E) was recovered and designated Eluate # 1a and # 1b. Eluate #1 was also serially diluted as ¹/₁₂₈, ¹/₂₅₆, ¹/₅₁₂ and ¹/₁₀₂₄ dilutions. The entire sets were tested against HLA-E beads and HLA-Ia beads.

IVIg used for this specific experiment came from the same batch as the original, but had been stored in aliquots in the refrigerator for six months. Consequently, the IVIg used in the experiment had reduced potency in binding to HLA but it did bind ¼$^{th}$ of the original. The MFI of anti-HLA-E reactivity was >18,000 but the aliquot was 4,500.

As shown in FIGS. 3A-C, both IVIg immunoreactivity to HLA-E and HLA-Ia are lost after adsorbing IVIg to HLA-E conjugated Affi-Gel. The data provides evidence that IVIg immunoreactivity to HLA-Ia is due to the presence of HLA-E antibodies in IVIg.

Example 4: Generating Anti-HLA-Ib Antibodies

Several anti-HLA-Ib antibodies were used here as examples, including mAb PTER006, mAb PTEG032, mAb PTER007, mAb PTER016 and mAb PTER017 and other categories. These two anti-HLA-Ib monoclonal antibodies (mAbs) were generated after immunizing BALB/c mice with recombinant heavy chains of two alleles of HLA-E: HLA-E$^R$ and HLA-E$^G$. The two alleles differ at position 107 of the HLA-E heavy chain: HLA-E$^R$ has a glycine (G) and HLA-E$^G$ has an Arginine®. Clone Nos 1-100 were subject to analysis. For example, the two antibodies disclosed in Table 5, mAb PTER006 and mAb PTER007, were both generated with recombinant heavy chains of HLA-E$^R$ and thus accordingly named to include "ER" in their annotations. In particular, mAb PTER006 is from clone No. 6 and mAb PTER007 is from clone No. 7. Also, antibodies generated with HLA-ER heavy chain are named to include "ER" in their annotations. For example, in Table 5, antibodies generated with HLA-E$^G$ heavy chain include but are not limited to mAb PTEG016, mAb PTEG017, and mAb PTEG032.

These monoclonal antibodies were IgG purified from the respective culture supernatants using Protein-G columns. The culture supernatant (or purified IgG or concentrated IgG) was diluted 1/10 and tested against Luminex beads coated with HLA class Ia epitopes as listed. Non-reactive epitopes are in white box and reactive epitopes are in the colored boxes (FIG. 4). The tainted (bluish) HLA-Ia epitopes signify common epitopes reacted by both the monoclonal antibodies. The immunoreactivity to HLA-E accompanied immunoreactivity to HLA-Ia, as evidenced by the reactivity and affinity profiles of the anti-HLA-E monoclonal antibodies generated with two different antigen sources (HLA-E$^R$ and HLA-E$^G$).

As seen in FIG. 4, there are differences in recognition of some of the HLA-Ia epitopes among the five anti-HLA-Ib monoclonal antibodies. It appeared that mAb PTER006 antibodies have slightly higher immunoreactivities against more HLA-Ia epitopes than mAb PTEG017 does. However, as noted in Table 3, there are 1729 HLA-A alleles with 1,264 proteins, 2329 HLA-B alleles with 1,786 proteins, 1291 HLA-Cw alleles with 938 proteins, whereas the assay system from One Lambda Inc. contains the following number of beads containing different HLA-Ia proteins (HLA-A 31, HLA-B 50 and HLA-Cw 16). The IVIg-mimetics (exemplified by mAb PTER006, mAb PTEG032, mAb PTER007, mAb PTER016 and mAb PTER017) can react to 80 to 97% of the test beads (see FIG. 4) to suggest that they may have more HLA-Ia reactivity than that observed. This can be proved or clarified only when we have beads for more HLA-Ia proteins.

Polyclonal anti-HLA-Ib antibodies immunoreactive to HLA-Ia antigens similar to IVIg can also be generated by (1) administering purified HLA-Ib molecules with or without adjuvants or cytokines or carriers for the purpose of inducing production of Anti-HLA Ib antibodies in the patients directly, or (2) administering cellular lysates or whole cells derived from the cancer patients (autologous or allogenic) exposed to cytokines such as IFN-γ, GM-CSF, IL-2, IL-6, IL-15, or IL-17 to enhance the over expression of HLA-Ib molecules on the cells. These two protocols induce HLA-Ib antibodies with immunoreactivity to HLA-Ia proteins (see, for example, Ravindranath et al., 2012, "Augmentation of anti-HLA-E antibodies with concomitant HLA-Ia reactivity in IFN-g-treated autologous melanoma cell vaccine recipients," *J. Immunotoxicol. In Press, DOI*:10.3109/1547691X.2011.645582).

Example 5: Exemplary Anti-HLA-Ib Monoclonal Antibodies (mAb PTER006, mAb PTEG032, mAb PTER007, mAb PTEG016 and mAb PTEG017) are Reactive with HLA-Class Ia Epitopes This example demonstrates that monoclonal antibodies (mAb PTER006, mAb PTER007, mAb PTEG032, mAb PTEG016 and mAb PTEG017) were not only immunoreactive to HLA-E, HLA-F and HLA-G, but also immunoreactive to HLA-class Ia epitopes (FIG. 4).

A multiplex Luminex®-based immunoassay was used to determine the HLA-Ia immunoreactivity of HLA-Ib monoclonal antibodies. The anti-HLA-Ib mAbs were diluted 1/100, 1/200 and 1/400 with PBS (pH 7.2). Using dual-laser flow cytometric principles of Luminex® xMAP® multiplex technology, the single Ag (allele) assays were carried out for data acquisition and quantitative (Mean Florescent Intensity or MFI) estimation of the level of HLA-Abs. The Luminex® assays utilize microbeads on which individual HLA Ags (HLA-E and HLA-Ia antigens) have been covalently bonded (xMap® assays). XMap® microbeads contain two reporter fluorophores that are proportionally varied to identify them as one of 100 possible bead identifiers. The LABScreen® (One Lambda, Canoga Park, Calif.) consists of a panel of color-coded microspheres (SAB, coated with single Ag HLA epitopes) to identify antibody specificities. The array of HLA antigens representing various alleles on the beads are listed at the One Lambda website under antibody detection products/LABScreen® Single Ag Product sheet/HLA-Ia combi-LS1A04-Lot 003 Worksheet Rev-1. The SAB products in LS1A04 include 31 HLA-A, 50 HLA-B and 16 HLA-C epitopes. It should be noted that not all existing HLA-Ia epitopes are represented in the beads analyzed.

The HLA-Ia microbeads have in-built control beads: Positive control beads were coated with human IgG for human Abs (or murine IgG, when murine MAbs were used) and the negative control beads were coated with serum albumin (HSA/BSA). For HLA-Ib antigens, control beads (both positive and negative controls) were added separately. For each analysis, at least 100 beads were counted. Mean and standard deviation of MFI for each allele was recorded. All the data are stored and archived at the Paull. Terasaki Foundation Laboratory, basic statistical analyses were then carried out with Excel software.

FIG. 4 summarizes the immunoreactivity of mAb PTER006, mAb PTEG032, mAb PTER007, mAb PTEG016 and mAb PTEG017 monoclonal antibodies against HLA-Ia antigens: HLA-A, HLA-B and HLA-Cw, as well as against HLA-Ib antigens, HLA-E, HLA-F and HLA-G. Non-reactive epitopes are in white box and reactive epitopes are in the colored boxes. The tainted (bluish) HLA-Ia epitopes signify common epitopes reacted by both the monoclonal antibodies. It is evident that immunoreactivity to HLA-E accompanies immunoreactivities to HLA-Ia as evidenced from the affinity of two different sources of anti-HLA-E monoclonal antibodies. As seen in FIG. 4, there are differences in recognition of some of the HLA-Ia epitopes between the two antibodies. It appeared that mAb PTER006 antibodies have higher reactivities against more HLA-Ia epitopes than mAb PTER007 does.

Table 5 details the number of HLA-class Ia and Ib epitopes recognized by IVIg in Luminex Bead assay. It is important to note that mAb PTER006 and mAb PTER007, in contrast to other anti-HLA-E monoclonal antibodies recognized more epitopes of HLA-A, HLA-B and HLA-Cw loci. mAb PTER007 reacted to 26 epitopes of HLA-A* (Table 5), and mAb PTER006 reacted to 31 epitopes of HLA-A*(Table 5), strikingly similar to the HLA-A* reactivity of IVIg. Furthermore, mAb PTER006 recognized 49 of HLA-B* epitopes and all the 16 of Cw* epitopes recognized by IVIg and mAb PTER007 recognized 44 of HLA-B* epitopes and all the 16 of Cw* epitopes recognized by IVIg (Table 5).

The reactivity to HLA-A* by different kinds of antibodies generated against HLA-E epitopes are very much restricted, as illustrated in Table 5. Again, all of the mAbs (including mAb PTER006, mAb PTER007 and other categories) were raised by immunizing mice BALB/c with recombinant heavy chains of HLA-E$^R$ or HLA-E$^G$.

It was observed that IVIg reacted to free and β2-microglobulin-associated heavy chains of several epitopes of HLA-A* in addition to HLA-B* and HLA-Cw*. While anti-HLA-E monoclonal antibodies reacted with one or few HLA-A epitopes and a plurality of HLA-B* and HLA-Cw* epitopes (Tables 5 and 6), mAbs (mAb PTER006 and mAb PTER007) reacting to all HLA-Ib molecules (HLA-E, HLA-F and HLA-G) reacted to more HLA-A* epitopes (FIG. 4, Table 5), in addition to 49 of HLA-B* and 16 of HLA-Cw epitopes (FIG. 4, Table 5), as observed with IVIg.

TABLE 5

HLA-reactivity of commercial IVIgs is compared with exemplary anti-HLA-Ib mAbs obtained at the Terasaki Foundation Laboratory (Los Angeles, CA).

| IVIg versus exemplary anti-HLA-Ib antibodies | Reactivity of different HLA Class 1 antigens | | | | | |
|---|---|---|---|---|---|---|
| | Classical HLA-Ia alleles | | | Non-classical HLA-Ib | | |
| | A | B | Cw | E | F | G |
| Commercial IVIgs | | | | | | |
| IVIg (GamaSTAN™, USA) | 31 | 50 | 16 | Positive | Positive | Positive |
| IVIg (Octogram, Mexico) | 30 | 47 | 16 | Positive | Positive | Positive |
| IVIg (GlobEx, India) | 20 | 39 | 16 | Positive | Positive | Positive |
| IVIg (Sandoglobulin, Euro) | 30 | 47 | 16 | Positive | Positive | Positive |
| Anti-HLA-lb antibodies | | | | | | |
| Anti-HLA-Ib antibodies as IVIg mimetics | | | | | | |
| mAb PTER006 | 31 | 50 | 16 | Positive | Positive | Positive |
| mAb PTEG032 | 29 | 48 | 16 | Positive | Positive | Positive |
| mAb PTER007 | 26 | 44 | 16 | Positive | Positive | Positive |
| mAb PTEG016 | 22 | 44 | 16 | Positive | Positive | Positive |
| mAb PTEG017 | 21 | 43 | 16 | Positive | Positive | Positive |

These monoclonal antibodies were immunoreactive to free and β2-microglobulin-associated heavy chains of several HLA-Ia antigens (HLA-A epitopes, HLA-B epitopes and HLA-Cw epitopes) (Table 5 and FIG. 4).

Moreover, the HLA-E peptide sequences commonly shared by all HLA-Ib epitopes were used to block the binding of anti-HLA-E antibodies to HLA-E also blocked the binding of the anti-HLA-class Ib antibodies to HLA-Ia epitopes. Anti-HLA-E, anti-HLA-F and anti-HLA-G antibodies are also found in normal, non-alloimmunized, healthy males and HLA-Ia reactivity of anti-HLA-E IgG antibodies in the sera of these healthy individuals are also observed. IVIg's immunoreactivity to HLA-Ia, which is attributed to anti-HLA-Ib activity of IVIg, is identified to be stronger and more potent than anti-HLA-E antibodyper se. These findings indicate that the anti-HLA-Ia reactivity of IVIg is associated with the anti-HLA-Ib immunoreactivity of IVIg.

Example 6: Comparison of Anti-HLA-Ib IgG (IVIg Mimetics) and IVIg in Inducing Cell Death, Arrest and Suppress Proliferation and Suppression of Blastogenesis of PHA-L Stimulated T-Lymphocytes (CD3+/CD4+)

A lectin Phytohemagglutinin (PHA-L) can stimulate human T-lymphocytes and induce blastogenesis; see, FIGS. 5A and 5B. PHA-L stimulated T-lymphocytes were used to test the IVIg and the claimed antibodies (IVIg mimetics) provided herein to induce cell death, proliferation arrest and suppression of blastogenesis. This example demonstrates that IVIg can induce cell death, proliferation arrest and suppression of blastogenesis of PHA-L stimulated T-lymphocytes (CD3+/CD4+). See, FIGS. 5C and 5D. Determining cell culture reactivity and the effects of IVIg induced suppression of PHA-stimulated T-lymphocytes and lymphoblasts, isolating T-cell populations were performed based on methods known in the art.

FIG. 5D shows that serially diluted IVIg preparations dosimetrically inhibited PHA-stimulated CD4+ T-lymphocytes and T-lymphoblasts. Triple samples at each dilution level were used in the reactivity experiments. FIG. 5E shows that serially diluted IVIg preparations dosimetrically inhibited PHA-stimulated CD8+ T-lymphocytes and T-lymphoblasts, even though the correlation between inhibitory activities and dilution levels is not strong.

This example also demonstrates that anti-HLA-Ib antibodies (for example, mAb PTER007 at ⅒ and ¹⁄₁₀₀ dilution levels) induced cell death, proliferation arrest and suppression of blastogenesis of PHA-L stimulated T-lymphocytes (CD4+ and CD8+). See FIGS. 5F through 5H.

Anti-HLA-Ib antibodies mAb PTER006 at ⅒ and ¹⁄₁₀₀ dilution levels, also induced cell death, proliferation arrest and suppression of blastogenesis of PHA-L stimulated T-lymphocytes (CD4+ and CD8+). See, FIG. 5I.

The activities of these anti-HLA-Ib antibodies were compared to those of another monoclonal antibody, mAb PTER-037 (which is reactive to HLA-E but not to HLA-F and HLA-G), as shown in FIGS. 5J-5L.

Example 7: Comparison of Inhibition of PHA-Induced T Cell Proliferation by Anti-HLA-Ib IgG (IVIg Mimetics) and IVIg, Using Carboxyfluorescein Diacetate Succinimidyl Ester (CFSE) Staining Technology Example 6 compares the inhibition of PHA-induced T-cell proliferation by anti-HLA-Ib antibodies (used as IVIg mimetics) and commercial IVIgs. In this assay system, carboxufluorescein diacetate succinimidyl ester (CFSE) staining technology is used.

Whole blood (20 ml) was drawn from a healthy donor into Acid Citrate Dextrose (ACD) tubes. Fifteen ml of is the blood sample was pipetted into 25 ml of PBS (without Calcium or Magnesium) in a 50-ml conical centrifuge tube and underlayed with Ficoll-Hyp ague (10 ml) at RT. After centrifugation (20 min at 800 g (2000 rpm in H-1000 rotor), 20° C.), the plasma-platelet-containing supernatant was aspirated from above the interface band. The interface band, which that includes the lymphocytes, was then aspirated with <5 ml of fluid and transferred to a new centrifuge tube (50 ml), combining the bands from 2 to 3 Ficoll-Hypaque gradients. PBS was added to the separated bands to a volume of 50 ml and centrifuged (10 min at 600 g (1500 rpm in H-1000 rotor), 20° C.). The supernatants were aspirated and the pellets in the tubes were combined and resuspended in PBS (10 ml) at RT. PBS was added to a volume of 50 ml and centrifuged (15 min 300 g (750 rpm in H-1000 rotor), 20° C.). The resulting lymphocyte pellet was resuspended in PBS (1 ml) at RT and the viable cells were counted. The cells were distributed equally among three Fisher tubes with PBS and centrifuged (1 mm at 1000 g). The supernatant was discarded and the pellet was resuspended and mixed well with 0.8 ml of Lympho-Kwik® T. The mixture was incubated (20 min at 37° C. or RT) in a water bath or heat block with occasional mix by inverting capped tube. PBS (0.2 ml) was then layered over cell preparation and centrifuged (2 min. at 2000 g). The pellet was resuspended in PBS and centrifuged (1 min. at 1000 g). Washing was repeated once and each pellet was resuspended in 0.8 ml of the following Lympho-Kwik® T Prep. The entire mixing, incubation, centrifugation and resuspension of pellet was repeated. In the final step, the pellet was resuspended in AIM-V medium+1% HEPES at a final concentration of $5 \times 10^7$ cells/ml. An aliquot was tested for purity of T-cells using CD3 monoclonal antibody in flow cytometry.

The cells were labeled with carboxyfluorescein succinimidyl ester (CFSE). CSFE is a fluorescent cell staining dye that is cell permeable and retained for long periods within cells. Within cells, CSFE covalently couples, via its succinimidyl group, to intracellular molecules. Due to this stable linkage, once in a cell, CFSE is not transferred to adjacent cells. The quantity of cells labeled was $10^5$ to $10^6$ cells/ml. Ten percent of heparinized donor plasma was added. Two µl of 5 mM CFSE per milliliter cells (final 10 µM) was added in a tube containing greater than or equal to 6 times the volume of cells. The cells were incubated for 15 min. at RT or for 10 min. at 37° C. The staining was quenched by adding 5 volume ice-cold AIM-V medium (+1% HEPES buffer, with 10% heparinized plasma from donor) and the cells were incubated for 5 min. on ice. The cells were washed three times in the culture medium to ensure that CFSE bound to protein in the supernatant was removed, preventing any subsequent uptake into bystander cells.

The in vitro cell culture assays were set up in 96 well tissue culture plates. Purified PHA-L was added to specific wells at a concentration of 1.12 µg/ml. The final cell concentration was $2 \times 10^5$ cells/well. Negative and positive controls were run in triplicates. For PHA without Wig or anti-HLA-E mAb 1 control, 10 µl of CFSE labeled cells ($2 \times 10^5$ cells in 100 µl/well) were added to 90 µl of PHA-L in AIM-V and 100 µl of AIM-V. For PHA with Wig or anti-HLA-E mAb 1 experiments, 10 µl of CFSE labeled cells ($2 \times 10^5$ cells in 100 µl/well) were added to 90 µl of PHA-L in AIM-V and 100 µl AIM-V containing different dilutions of IVIg or anti-HLA-Ib mAbs.

FIG. 6A shows the CFSE fluorescence intensity of proliferating T-cells after 70 hours of exposure to PHA. The fluorescence intensity closely follows the predicted sequential halving due to cell division (M1, M2, M3 and M4). FIG. 6B shows the inhibition of PHA-L induced proliferation of CD3+CFSE+ T-lymphocytes by IVIg at 72 hrs. FIG. 6C shows the percentage of inhibition of T cell proliferation by IVIg at different dilutions, 72 hrs after PHA-L stimulation.

FIG. 6D shows the inhibition of PHA-L induced proliferation of CD4+CFSE+ T lymphocytes by anti-HLA-Ib mAb PTER007 at 72 hrs. FIG. 6E shows the inhibition of PHA-L induced proliferation of CD8+CFSE+ T lymphocytes by anti-HLA-Ib mAb PTER007 at 1/10 dilution level at 72 hrs.

FIG. 6F shows the inhibition of PHA-L induced proliferation CD4+CFSE+ T lymphocytes by anti-HLA-Ib mAb PTER006 at 1/10 dilution level at 72 hrs. FIG. 6G shows the inhibition of PHA-L induced proliferation CD8+CFSE+ T lymphocytes by anti-HLA-Ib mAb PTER006 at 1/10 dilution level at 72 hrs.

Figure 8A:
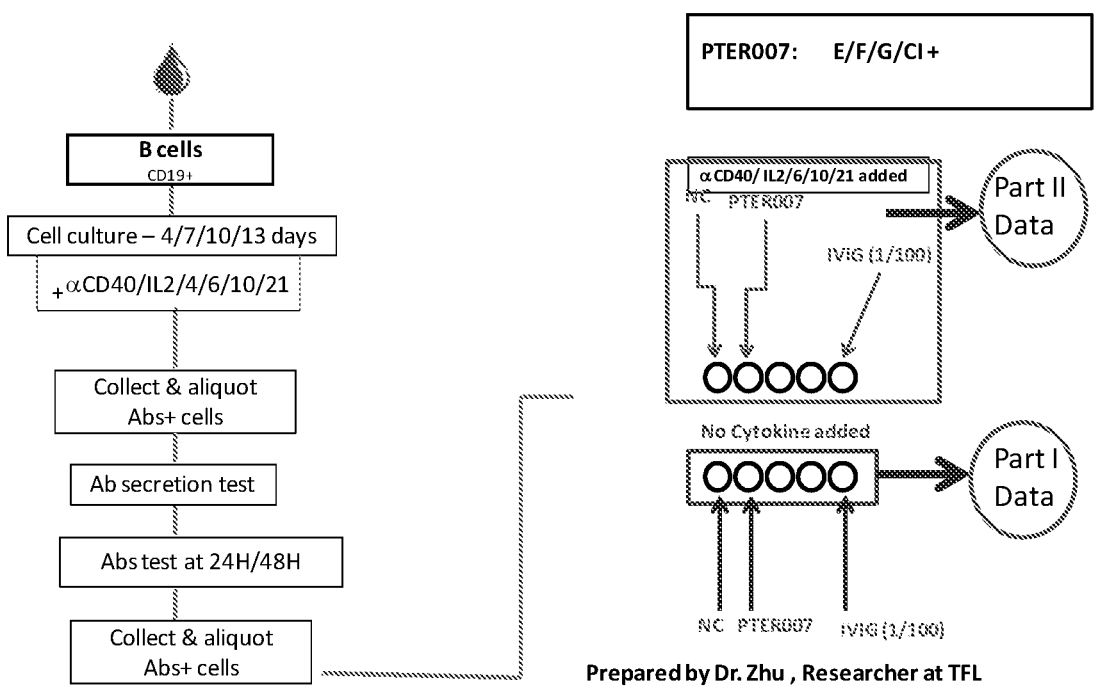

FIG. 6H shows the arrest of PHA-induced Proliferation newly divided CD4+ lymphoblasts and cell death of parent CD4+ lymphoblasts by anti-HLA-Ib antibodies (mAb PTER007, Left and mAb PTER006, right) at different dilutions. Mean values were calculated from population III from FIGS. 6D and 6F. Left values represent newly divided lymphoblast and right values represent parent lymphoblasts. FIG. 6I shows the arrest of PHA-induced Proliferation newly divided CD8+ lymphoblasts and cell death of parent CD8+ lymphoblasts by anti-HLA-Ib antibodies (mAb PTER007, Left and mAb PTER006, right) at different dilutions. Mean values were calculated from population III from FIGS. 6E and 6G. Left values represent newly divided lymphoblast and right values represent parent lymphoblasts.

Table 6A shows that mAb PTER007 antibodies are capable of lowering the population of CD4+ naive and activated T-lymphocytes. The T-lymphocytes were cultured with or without PHA-L for 70 hrs and the antibodies were tested after purification of hybridoma supernatants with Protein-G (not concentrated, but diluted at 1/10 and 1/100).

Table 6B shows that mAb PTER007 lowers naïve and activated CD8+ T lymphocyte populations at 1/10 but not at 1/100 dilution. The T-lymphocytes were cultured with or without PHA-L for 70 hrs and the antibodies were tested after purification of hybridoma supernatants with Protein-G (not concentrated, but diluted at 1/10 and 1/100).

Table 6C shows that mAb PTER006 lowers the population of Activated CD4+ T lymphocytes in manner similar to IVIg. The T lymphocytes were cultured with or without PHA-L for 70 hrs and the antibodies were tested after purification of hybridoma supernatants with Protein-G (not concentrated, but diluted at 1/10).

Table 6D shows that mAb PTER006 increases activated CD8+ T lymphocyte populations similar to Wig. The T lymphocytes were cultured with or without PHA-L for 70 hrs) and the antibodies were tested after purification of hybridoma supernatants with Protein-G (not concentrated, but diluted at 1/100).

TABLE 6A mAb PTER007 antibodies are capable of lowering the populations of CD4+ Naïve and Activated T lymphocytes.

| | 1 | 2 | 3 | Mean | Std. Dev | Paired Sample two tailed p | 4 | 5 | 6 | Mean | Std. Dev | Paired Sample two tailed p |
|---|---|---|---|---|---|---|---|---|---|---|---|---|
| | A No PHA/No mAB | | | | | | B with PHA/No mAB | | | | | A versus B |
| Group 1 | | | | | | | | | | | | |
| CD4 | 1122 | 1232 | 1174 | 1176 | 55 | | 1722 | 1516 | 1433 | 1557 | 149 | $p^2 = 0.014$ (increase) |
| Group 2 | | | | | | | | | | | | |
| CD4 | 3224 | 3100 | 2841 | 3055 | 195 | | 1048 | 1105 | 1144 | 1099 | 48 | $p^2 = 0.0001$ |

TABLE 6A-continued mAb PTER007 antibodies are capable of lowering the populations of CD4+ Naïve and Activated T lymphocytes.

| | 1 | 2 | 3 | Mean | Std. Dev | Paired Sample two tailed p | 4 | 5 | 6 | Mean | Std. Dev | Paired Sample two tailed p |
|---|---|---|---|---|---|---|---|---|---|---|---|---|
| Group 3 | | | | | | | | | | | | |
| CD4 | 246 | 242 | 275 | 254 | 18 | | 844 | 986 | 1077 | 969 | 117 | $p^2 = 0.0005$ (increase) |
| | | | C | | | | | | D | | | |
| | | No PHA/with mAB TFL-PTR007 [1/10] | | | | A versus C | | with PHA/with mAB TFL-PTR007 [1/10] | | | | B versus D |
| Group 1 | | | | | | | | | | | | |
| CD4 | 871 | 1511 | 933 | 1105 | 353 | 0.748 (NS) | 1233 | 1378 | 1595 | 1402 | 182 | 0.317 (NS) |
| Group 2 | | | | | | | | | | | | |
| CD4 | 1314 | 2444 | 1364 | 1707 | 638 | $p^2 = 0.025$ | 862 | 788 | 898 | 849 | 56 | $p^2 = 0.004$ |
| Group 3 | | | | | | | | | | | | |
| CD4 | 104 | 178 | 131 | 138 | 37 | $p^2 = 0.008$ | 120 | 180 | 267 | 189 | 74 | $p^2 = 0.001$ |
| | | | E | | | | | | F | | | |
| | | No PHA/with mAB TFL-PTR007 [1/100] | | | | A versus E | | with PHA/ with mAB TFL-PTR007 [1/100] | | | | B versus F |
| Group 1 | | | | | | | | | | | | |
| CD4 | 1030 | 1011 | 1072 | 1038 | 31 | $p^2 = 0.019$ | 1998 | 1743 | 1756 | 1832 | 144 | 0.082 (NS) |
| Group 2 | | | | | | | | | | | | |
| CD4 | 3610 | 3484 | 3508 | 3534 | 67 | $p^2 = 0.016$ (increase) | 944 | 984 | 1071 | 1000 | 65 | 0.101 (NS) |
| Group 3 | | | | | | | | | | | | |
| CD4 | 249 | 218 | 254 | 240 | 20 | 0.413 (NS) | 514 | 785 | 620 | 640 | 137 | $p^2 = 0.034$ |

TABLE 6B mAb PTER007 antibodies lower naive and activated CD8+ T lymphocyte populations at 1/10 but not at 1/100 dilution.

| | 1 | 2 | 3 | Mean | Std. Dev | Paired Sample two tailed p | 4 | 5 | 6 | Mean | Std. Dev | Paired Sample two tailed p |
|---|---|---|---|---|---|---|---|---|---|---|---|---|
| | | | A | | | | | | B | | | |
| | | No PHA/No mAB | | | | | | with PHA/No mAB | | | | A versus B |
| Group 1 | | | | | | | | | | | | |
| CD8 | 62 | 98 | 69 | 76 | 19 | | 58 | 57 | 51 | 55 | 4 | 0.135 |
| Group 2 | | | | | | | | | | | | |
| CD8 | 543 | 518 | 510 | 524 | 17 | | 435 | 483 | 550 | 489 | 58 | 0.380 |
| Group 3 | | | | | | | | | | | | |
| CD8 | 35 | 56 | 60 | 50 | 13 | | 228 | 282 | 249 | 253 | 27 | $p^2 = 0.0003$ |
| | | | C | | | | | | D | | | |
| | | No PHA/with mAB TFL-PTR007 [1/10] | | | | A versus C | | with PHA/with mAB TFL-PTR007 [1/10] | | | | B versus D |
| Group 1 | | | | | | | | | | | | |
| CD8 | 57 | 87 | 42 | 62 | 23 | 0.452 | 61 | 52 | 51 | 55 | 6 | 0.871 |
| Group 2 | | | | | | | | | | | | |
| CD8 | 207 | 312 | 227 | 249 | 56 | $p^2 = 0.001$ | 98 | 174 | 243 | 172 | 73 | $p^2 = 0.004$ |
| Group 3 | | | | | | | | | | | | |
| CD8 | 24 | 24 | 20 | 23 | 2 | $p^2 = 0.025$ | 21 | 44 | 97 | 54 | 39 | $p^2 = 0.002$ |
| | | | E | | | | | | F | | | |
| | | No PHA/with mAB TFL-PTR007 [1/100] | | | | A versus E | | with PHA/with mAB TFL-PTR007 [1/100] | | | | B versus F |
| Group 1 | | | | | | | | | | | | |
| CD8 | 74 | 57 | 58 | 63 | 10 | 0.340 | 48 | 74 | 71 | 64 | 14 | 0.349 |

TABLE 6B-continued mAb PTER007 antibodies lower naive and activated CD8+ T lymphocyte populations at 1/10 but not at 1/100 dilution.

| | 1 | 2 | 3 | Mean | Std. Dev | Paired Sample two tailed p | 4 | 5 | 6 | Mean | Std. Dev | Paired Sample two tailed p |
|---|---|---|---|---|---|---|---|---|---|---|---|---|
| Group 2 | | | | | | | | | | | | |
| CD8 | 467 | 540 | 476 | 494 | 40 | 0.306 | 324 | 400 | 371 | 365 | 38 | $p^2 = 0.036$ |
| Group 3 | | | | | | | | | | | | |
| CD8 | 41 | 38 | 34 | 38 | 4 | 0.189 | 187 | 258 | 212 | 219 | 36 | 0.262 |

TABLE 6C mAb PTER006 antibodies lower the population of Activated CD4+ T lymphocytes similar to IVIg.

| | 1 | 2 | 3 | Mean | Std. Dev | Paired Sample two tailed p | 4 | 5 | 6 | Mean | Std. Dev | Paired Sample two tailed p |
|---|---|---|---|---|---|---|---|---|---|---|---|---|
| | A No PHA/No mAB | | | | | | B with PHA/No mAB | | | | | A versus B |
| Group 1 | | | | | | | | | | | | |
| CD4 | 1122 | 1232 | 1174 | 1176 | 55 | | 1722 | 1516 | 1433 | 1557 | 149 | $p^2 = 0.014$ (increase) |
| Group 2 | | | | | | | | | | | | |
| CD4 | 3224 | 3100 | 2841 | 3055 | 195 | | 1048 | 1105 | 1144 | 1099 | 48 | $p^2 = 0.0001$ |
| Group 3 | | | | | | | | | | | | |
| CD4 | 246 | 242 | 275 | 254 | 18 | | 844 | 986 | 1077 | 969 | 117 | $p^2 = 0.0005$ (increase) |
| | C No PHA/with mAB TFL-PTR006 [1/10] | | | | | A versus C | D with PHA/with mAB TFL-PTR006 [1/10] | | | | | B versus D |
| Group 1 | | | | | | | | | | | | |
| CD4 | 1364 | 1387 | 1343 | 1365 | 22 | $p^2 = 0.005$ (increase) | 1501 | 1521 | 1464 | 1495 | 29 | 0.520 (NS) |
| Group 2 | | | | | | | | | | | | |
| CD4 | 2761 | 2758 | 2754 | 2758 | 4 | 0.058 (NS) | 1192 | 1249 | 1119 | 1187 | 65 | 0.134 (NS) |
| Group 3 | | | | | | | | | | | | |
| CD4 | 205 | 187 | 230 | 207 | 22 | $p^2 = 0.044$ | 612 | 605 | 290 | 502 | 184 | $p^2 = 0.021$ |

TABLE 6D mAb PTER006 antibodies increase activated CD8+ T lymphocyte populations similar to the commercial IVIgs.

| | 1 | 2 | 3 | Mean | Std. Dev | Paired Sample two tailed p | 4 | 5 | 6 | Mean | Std. Dev | Paired Sample two tailed p |
|---|---|---|---|---|---|---|---|---|---|---|---|---|
| | A No PHA/No mAB | | | | | | B with PHA/No mAB | | | | | A versus B |
| Group 1 | | | | | | | | | | | | |
| CD8 | 62 | 98 | 69 | 76 | 19 | | 58 | 57 | 51 | 55 | 4 | 0.135 |
| Group 2 | | | | | | | | | | | | |
| CD8 | 543 | 518 | 510 | 524 | 17 | | 435 | 483 | 550 | 489 | 58 | 0.380 |
| Group 3 | | | | | | | | | | | | |
| CD8 | 35 | 56 | 60 | 50 | 13 | | 228 | 282 | 249 | 253 | 27 | $p^2 = 0.0003$ |

TABLE 6D-continued mAb PTER006 antibodies increase activated CD8+ T lymphocyte populations similar to the commercial IVIgs.

| | 1 | 2 | 3 | Mean | Std. Dev | Paired Sample two tailed p | 4 | 5 | 6 | Mean | Std. Dev | Paired Sample two tailed p |
|---|---|---|---|---|---|---|---|---|---|---|---|---|
| | \multicolumn{6}{c}{E No PHA/with mAB TFL-PTR007 [1/100]   A versus E} | \multicolumn{6}{c}{F with PHA/with mAB TFL-PTR007 [1/100]   B versus F} |

Group 1

| CD8 | 65 | 43 | 60 | 56 | 12 | 0.189 | 59 | 65 | 54 | 59 | 6 | 0.358 |

Group 2

| CD8 | 616 | 733 | 700 | 683 | 60 | $p^2 = 0.012$ (increase) | 568 | 548 | 524 | 547 | 22 | 0.183 |

Group 3

| CD8 | 69 | 78 | 79 | 75 | 6 | $p^2 = 0.041$ (increase) | 350 | 319 | 290 | 320 | 30 | $p^2 = 0.046$ (increase) |

Example 8: Analysis of with iBeads

HLA-Ia alleles on regular beads may occur both as intact HLA with β2 microglobulin (β2m) as well as heavy chains without (β2m). Additional beads with reduced amounts of (β2m-free HLA, called IBEADS™, were generated (One Lambda, Inc.). Differences in the reactivity of IVIg preparations to regular beads and IBEADS™ are illustrated in Tables 7A, 7B and 7C.

If MFI of an HLA allele with IBEADS™ is higher (indicated in bold) than that of the regular bead it is indicates that the HLA-reactivity in question is towards intact HLA. Percentage of increase also refers to the same.

If MFI of an allele with IBEADS™ is lower than that of the regular bead it is indicative of the affinity of the antibody towards heavy chain of HLA. Percentage of decrease also refers to the same.

Table 7A illustrates the difference in MFI value and percentage of HLA-Ia reactivity of different therapeutic IVIg preparations between regular beads and IBEADS™ (reduced amount of heavy chain) coated with HLA-A (A).

Table 7B illustrates the difference in MFI value and percentage of HLA-Ia reactivity of different therapeutic IVIg preparations between regular beads and IBEADS™ (reduced amount of heavy chain) coated with HLA-B (B).

Table 7C illustrates the difference in MFI value and percentage of HLA-Ia reactivity of different therapeutic IVIg preparations between regular beads and IBEADS™ (reduced amount of heavy chain) coated with HLA-Cw (C).

TABLE 7A

Comparison of reactivity to HLA-A(A).

| | Sandaglobulin | | | Gamunex-C Lot NKLG1 | | | Gamunex-C Lot NKLK1 | | | Gamastan | | | Octagram | | |
|---|---|---|---|---|---|---|---|---|---|---|---|---|---|---|---|
| Antigen | Regular (# 7) (1:4) | iBead (# 6) (1:4) | Difference % | Regular (# 7) (1:8) | iBead (# 6) (1:8) | Difference % | Regular (# 7) (1:8) | iBead (# 6) (1:8) | Difference % | Regular (# 7) (1:8) | iBead (# 6) (1:8) | Difference % | Regular (# 7) (1:8) | iBead (# 6) (1:8) | Difference % |
| Albumin-NC | 1196 | 667 | −44 | 10753 | 7147 | −34 | 10268 | 7799 | −24 | 3793 | 5034 | 33 | 2340 | 1673 | −29 |
| A*0101(A1) | 0 | 551 | 100 | 368 | 3589 | 875 | 0 | 1355 | 100 | 0 | 809 | 100 | 260 | 262 | 1 |
| A*0201(A2) | 8 | 772 | 9550 | 0 | 4976 | 100 | 0 | 1989 | 100 | 659 | 2215 | 236 | 0 | 1002 | 100 |
| A*0203(A2) | 0 | 354 | 100 | 0 | 2975 | 100 | 233 | 648 | 178 | 24 | 328 | 1258 | 0 | 0 | 0 |
| A*0206(A2) | 125 | 799 | 539 | 445 | 4409 | 891 | 913 | 2303 | 152 | 471 | 3061 | 550 | 780 | 1330 | 71 |
| A*0301(A3) | 2 | 199 | 9850 | 0 | 2839 | 100 | 410 | −211 | −151 | 236 | 0 | −100 | 515 | 0 | −100 |
| A*1101(A11) | 187 | 439 | 135 | 2535 | 3763 | 48 | 1942 | 1301 | −33 | 1073 | 1226 | 14 | 1556 | 351 | −77 |
| A*1102(A11) | 115 | 475 | 313 | 824 | 2861 | 247 | 529 | 858 | 62 | 1089 | 1859 | 71 | 829 | 46 | −94 |
| A*2301(A23) | 373 | 667 | 79 | 1775 | 3567 | 101 | 1125 | 1338 | 19 | 1877 | 1178 | −37 | 1417 | 576 | −59 |
| A*2402(A24) | 567 | 725 | 28 | 3171 | 4513 | 42 | 2352 | 2090 | −11 | 2312 | 2218 | −4 | 3071 | 663 | −78 |
| A*2403(A24) | 366 | 593 | 62 | 2701 | 3977 | 47 | 2049 | 1668 | −19 | 2297 | 1462 | −36 | 2868 | 443 | −85 |
| A*2501(A25) | 143 | 581 | 306 | 506 | 2975 | 488 | 488 | 408 | −16 | 1436 | 1905 | 33 | 790 | 58 | −93 |
| A*2601(A26) | 188 | 638 | 239 | 1732 | 4418 | 155 | 1116 | 1560 | 40 | 1004 | 1565 | 56 | 1169 | 402 | −66 |
| A*2901(A29) | 275 | 916 | 233 | 1243 | 4562 | 267 | 634 | 1418 | 124 | 897 | 3265 | 264 | 1046 | 1172 | 12 |
| A*2902(A29) | 200 | 932 | 366 | 1751 | 6014 | 243 | 820 | 2892 | 253 | 991 | 4433 | 348 | 1578 | 2268 | 44 |
| A*3001(A30) | 222 | 540 | 143 | 2107 | 4466 | 112 | 1230 | 1339 | 9 | 924 | 624 | −32 | 928 | 510 | −45 |
| A*3002(A30) | 174 | 526 | 202 | 896 | 3705 | 314 | 562 | 1412 | 151 | 1050 | 929 | −11 | 533 | 369 | −31 |
| A*3101(A31) | 0 | 295 | 100 | 166 | 3411 | 1955 | 0 | 0 | 0 | 121 | 351 | 189 | 366 | 0 | −100 |
| A*3201(A32) | 255 | 769 | 202 | 875 | 3764 | 330 | 424 | 915 | 116 | 856 | 1821 | 113 | 738 | 518 | −30 |
| A*3301(A33) | 185 | 684 | 270 | 1694 | 4462 | 163 | 925 | 1315 | 42 | 1119 | 1877 | 68 | 1494 | 1358 | −9 |
| A*3303 (A33) | 0 | 439 | 100 | 476 | 3329 | 599 | 179 | 517 | 189 | 322 | 725 | 125 | 542 | 152 | −72 |
| A*3401(A34) | 640 | 1150 | 80 | 3543 | 5215 | 47 | 2149 | 3415 | 59 | 3042 | 4323 | 42 | 2879 | 2059 | −28 |
| A*3402(A34) | 0 | 177 | 100 | 0 | 2053 | 100 | 0 | 0 | 0 | 684 | 1206 | 76 | 0 | 0 | 0 |
| A*3601(A36) | 51 | 636 | 1147 | 916 | 3949 | 331 | 704 | 1551 | 120 | 564 | 1379 | 145 | 778 | 572 | −26 |
| A*4301(A43) | 397 | 949 | 139 | 1961 | 5601 | 186 | 1170 | 2719 | 132 | 1913 | 4182 | 119 | 1898 | 1693 | −11 |

TABLE 7A-continued

Comparison of reactivity to HLA-A(A).

| | Sandaglobulin | | | Gamunex-C | | | | | | Gamastan | | | Octagram | | |
|---|---|---|---|---|---|---|---|---|---|---|---|---|---|---|---|
| | | | | Lot NKLG1 | | | Lot NKLK1 | | | | | | | | |
| Antigen | Regular (# 7) (1:4) | iBead (# 6) (1:4) | Difference % | Regular (# 7) (1:8) | iBead (# 6) (1:8) | Difference % | Regular (# 7) (1:8) | iBead (# 6) (1:8) | Difference % | Regular (# 7) (1:8) | iBead (# 6) (1:8) | Difference % | Regular (# 7) (1:8) | iBead (# 6) (1:8) | Difference % |
| A*6601(A66) | 93 | 783 | 742 | 648 | 5328 | 722 | 875 | 2331 | 166 | 1408 | 2613 | 86 | 1695 | 1019 | -40 |
| A*6602(A66) | 364 | 768 | 111 | 1101 | 5194 | 372 | 838 | 1863 | 122 | 2362 | 4316 | 83 | 3650 | 684 | -81 |
| A*6801(A68) | 0 | 307 | 100 | 0 | 3148 | 100 | 0 | 662 | 0 | 192 | 634 | 230 | 0 | 0 | 0 |
| A*6802(A68) | 455 | 596 | 31 | 1421 | 4662 | 228 | 1332 | 1948 | 46 | 2060 | 2084 | 1 | 1748 | 489 | -72 |
| A*6901(A69) | 470 | 788 | 68 | 2813 | 6243 | 122 | 2777 | 2885 | 4 | 1877 | 2410 | 28 | 1724 | 814 | -53 |
| A*7401(A74) | 0 | 316 | 100 | 666 | 3904 | 486 | 224 | 515 | 130 | 80 | 431 | 437 | 201 | 82 | -59 |
| A*8001(A80) | 401 | 564 | 41 | 3194 | 3969 | 24 | 1679 | 1188 | -29 | 2705 | 2847 | 5 | 2289 | 845 | -63 |

TABLE 7B

Comparison of reactivity to HLA-B(B).

| | Sandaglobulin | | | Gamunex-C | | | | | | Gamastan | | | Octagram | | |
|---|---|---|---|---|---|---|---|---|---|---|---|---|---|---|---|
| | | | | Lot NKLG1 | | | Lot NKLK1 | | | | | | | | |
| Antigen | Regular (# 7) (1:4) | iBead (# 6) (1:4) | Difference % | Regular (# 7) (1:8) | iBead (# 6) (1:8) | Difference % | Regular (# 7) (1:8) | iBead (# 6) (1:8) | Difference % | Regular (# 7) (1:8) | iBead (# 6) (1:8) | Difference % | Regular (# 7) (1:8) | iBead (# 6) (1:8) | Difference % |
| Albumin NC | 1196 | 667 | -44 | 10753 | 7147 | -34 | 10268 | 7799 | -24 | 3793 | 5034 | 33 | 2340 | 1673 | -29 |
| B*0702(B7) | 309 | 436 | 41 | 1539 | 2134 | 39 | 837 | 0 | -100 | 2223 | 2010 | -10 | 714 | 0 | -100 |
| B*0801(B8) | 233 | 274 | 18 | 2186 | 1511 | -31 | 1755 | 0 | -100 | 884 | 324 | -63 | 2119 | 114 | -95 |
| B*1301(B13) | 524 | 504 | -4 | 5168 | 3565 | -31 | 3522 | 1031 | -71 | 2244 | 1836 | -18 | 3679 | 52 | -99 |
| B*1302(B13) | 476 | 502 | 5 | 3103 | 1709 | -45 | 2532 | 0 | -100 | 2222 | 1199 | -46 | 1943 | 0 | -100 |
| B*1401(B64) | 621 | 206 | -67 | 3133 | 2100 | -33 | 2276 | 410 | -82 | 1749 | 269 | -85 | 2397 | 102 | -96 |
| B*1402(B65) | 239 | 152 | -36 | 2249 | 929 | -59 | 1441 | 0 | -100 | 670 | 0 | -100 | 1458 | 0 | -100 |
| B*1501(B62) | 0 | 148 | 100 | 0 | 749 | 100 | 15 | 53 | 253 | 106 | 394 | 270 | 100 | 0 | -100 |
| B*1502(B75) | 157 | 245 | 56 | 1525 | 2008 | 32 | 1536 | 91 | -94 | 526 | 709 | 35 | 861 | 0 | -100 |
| B*1503(B72) | 0 | 0 | 0 | 2375 | 507 | -79 | 2296 | 0 | -100 | 689 | 0 | -100 | 1057 | 0 | -100 |
| B*1510(B71) | 240 | 271 | 13 | 1434 | 1452 | 1 | 1622 | 347 | -79 | 857 | 492 | -43 | 1293 | 0 | -100 |
| B*1511(B75) | 637 | 552 | -13 | 4058 | 3380 | -17 | 3825 | 1860 | -51 | 2822 | 2380 | -16 | 3640 | 1087 | -70 |
| B*1512(B76) | 382 | 1141 | 199 | 816 | 2811 | 244 | 942 | 1418 | 51 | 2655 | 5973 | 125 | 1129 | 1385 | 23 |
| B*1513(B77) | 550 | 445 | -19 | 4274 | 2353 | -45 | 3211 | 841 | -74 | 1238 | 904 | -27 | 2257 | 256 | -89 |
| B*1516(B63) | 799 | 756 | -5 | 3755 | 2400 | -36 | 3133 | 1212 | -61 | 3536 | 3285 | -7 | 3132 | 880 | -72 |
| B*1801(B18) | 0 | 114 | 100 | 538 | 1142 | 112 | 567 | 0 | -100 | 0 | 0 | 0 | 246 | 0 | -100 |
| B*2705(B27) | 141 | 377 | 167 | 388 | 1657 | 327 | 160 | 0 | -100 | 1366 | 1085 | -21 | 154 | 0 | -100 |
| B*2708(B27) | 13 | 302 | 2223 | 0 | 1344 | 100 | 0 | 0 | 0 | 1067 | 1407 | 32 | 54 | 0 | -100 |
| B*3501(B35) | 243 | 352 | 45 | 1672 | 1614 | -3 | 1478 | 577 | -61 | 680 | 653 | -4 | 964 | 0 | -100 |
| B*3701(B37) | 1099 | 740 | -33 | 6133 | 3639 | -41 | 4788 | 612 | -87 | 3236 | 392 | -88 | 9974 | 0 | -100 |
| B*3801(B38) | 254 | 248 | -2 | 1356 | 1375 | 1 | 1259 | 0 | -100 | 619 | 0 | 100 | 1002 | 0 | -100 |
| B*3901(B39) | 0 | 0 | 0 | 0 | 242 | 100 | 0 | 0 | 0 | 0 | 0 | 0 | 0 | 0 | 0 |
| B*4001(B60) | 237 | 409 | 73 | 1677 | 2474 | 48 | 1240 | 93 | -93 | 1723 | 2286 | 33 | 987 | 4 | -100 |
| B*4002(B61) | 134 | 242 | 81 | 569 | 1679 | 195 | 0 | 0 | 0 | 1564 | 1188 | -24 | 271 | 0 | -100 |
| B*4006(B61) | 765 | 359 | -53 | 5394 | 2144 | -60 | 4341 | 421 | -90 | 3470 | 2373 | -32 | 4972 | 167 | -97 |
| B*4101(B41) | 32 | 182 | 469 | 716 | 1486 | 108 | 605 | 0 | -100 | 1067 | 870 | -19 | 393 | 0 | -100 |
| B*4201(B42) | 0 | 86 | 100 | 455 | 1088 | 139 | 13 | 0 | -100 | 598 | 286 | -52 | 364 | 0 | -100 |
| B*4402(B44) | 683 | 461 | -33 | 6465 | 1869 | -71 | 5313 | 786 | -85 | 4301 | 3376 | -22 | 3997 | 702 | -82 |
| B*4403(B44) | 284 | 413 | 45 | 1110 | 2395 | 116 | 1213 | 836 | -31 | 3391 | 2904 | -14 | 1146 | 698 | -39 |
| B*4501(B45) | 272 | 612 | 125 | 1106 | 2110 | 91 | 562 | 399 | -29 | 3667 | 5397 | 47 | 956 | 308 | -68 |
| B*4601(B46) | 537 | 473 | -12 | 3014 | 3537 | 17 | 2450 | 851 | -65 | 1834 | 1460 | -20 | 2438 | 526 | -78 |
| B*4701(B47) | 355 | 655 | 85 | 2554 | 2799 | 10 | 2031 | 1235 | -39 | 1771 | 3211 | 81 | 2200 | 955 | -57 |
| B*4801(B48) | 297 | 341 | 15 | 3280 | 3131 | -5 | 1984 | 757 | -62 | 2252 | 1694 | -25 | 1863 | 104 | -94 |
| B*4901(B49) | 356 | 630 | 77 | 1586 | 1419 | -11 | 1881 | 158 | -92 | 1640 | 446 | -73 | 1340 | 0 | -100 |
| B*5001(B50) | 72 | 198 | 175 | 789 | 968 | 23 | 814 | 0 | -100 | 627 | 176 | -72 | 505 | 0 | -100 |
| B*5101(B51) | 669 | 687 | 3 | 3370 | 2343 | -30 | 2798 | 1101 | -61 | 1662 | 1336 | -20 | 1896 | 339 | -82 |
| B*5102(B51) | 688 | 604 | -12 | 2599 | 1898 | -27 | 2699 | 694 | -74 | 1677 | 476 | -72 | 1671 | 0 | -100 |
| B*5201(B52) | 707 | 869 | 23 | 3207 | 2125 | -34 | 2745 | 1224 | -55 | 1788 | 1341 | -25 | 1962 | 280 | -86 |
| B*5301(B53) | 692 | 536 | -23 | 3265 | 2368 | -27 | 4078 | 678 | -83 | 2040 | 478 | -77 | 2561 | 0 | -100 |
| B*5401(B54) | 299 | 168 | -44 | 2623 | 1463 | -44 | 1455 | 0 | -100 | 1633 | 476 | -71 | 2238 | 0 | -100 |
| B*5501(B55) | 222 | 44 | -80 | 3308 | 1072 | -68 | 1753 | 0 | -100 | 1558 | 686 | -56 | 1874 | 0 | -100 |
| B*5601(B56) | 507 | 183 | -64 | 2689 | 1269 | -53 | 2222 | 0 | -100 | 1995 | 0 | -100 | 1607 | 0 | -100 |
| B*5701(B57) | 419 | 560 | 34 | 1045 | 1987 | 90 | 942 | 286 | -70 | 1101 | 542 | -51 | 957 | 3 | -100 |
| B*5703(B57) | 897 | 382 | -57 | 2710 | 1620 | -40 | 2983 | 0 | -100 | 2148 | 0 | -100 | 2425 | 0 | -100 |
| B*5801(B58) | 726 | 455 | -37 | 4435 | 1829 | -59 | 3479 | 662 | -81 | 2758 | 106 | -96 | 3157 | 0 | -100 |
| B*5901(B59) | 502 | 446 | -11 | 3855 | 2216 | -43 | 3052 | 720 | -76 | 1798 | 1058 | -41 | 2444 | 470 | -81 |
| B*6701(B67) | 225 | 362 | 61 | 64 | 1113 | 1639 | -237 | -569 | 140 | 1108 | 603 | -46 | 841 | 0 | -100 |

TABLE 7B-continued

Comparison of reactivity to HLA-B(B).

| | Sandaglobulin | | | Gamunex-C Lot NKLG1 | | | Gamunex-C Lot NKLK1 | | | Gamastan | | | Octagram | | |
|---|---|---|---|---|---|---|---|---|---|---|---|---|---|---|---|
| Antigen | Regular (# 7) (1:4) | iBead (# 6) (1:4) | Difference % | Regular (# 7) (1:8) | iBead (# 6) (1:8) | Difference % | Regular (# 7) (1:8) | iBead (# 6) (1:8) | Difference % | Regular (# 7) (1:8) | iBead (# 6) (1:8) | Difference % | Regular (# 7) (1:8) | iBead (# 6) (1:8) | Difference % |
| B*7301(B73) | 243 | 572 | 135 | 1817 | 3226 | 78 | 1945 | 1022 | −47 | 1755 | 3145 | 79 | 1740 | 1118 | −36 |
| B*7801(B78) | 446 | 556 | 25 | 2491 | 1568 | −37 | 2410 | 260 | −89 | 1737 | 283 | −84 | 1786 | 0 | −100 |
| B*8101(681) | 364 | 550 | 51 | 2969 | 3082 | 4 | 1848 | 1096 | −41 | 2541 | 2799 | 10 | 1323 | 372 | −72 |
| B*8201(B82) | 639 | 360 | −44 | 6055 | 2731 | −55 | 4783 | −193 | −104 | 3857 | 4259 | 10 | 5026 | 510 | −90 |

TABLE 7C

Comparison of reactivity to HLA-Cw(C).

| | Sandaglobulin | | | Gamunex-C Lot NKLG1 | | | Gamunex-C Lot NKLK1 | | | Gamastan | | | Octagram | | |
|---|---|---|---|---|---|---|---|---|---|---|---|---|---|---|---|
| Antigen | Reg (# 7) (1:4) | IBead (# 6) (1:4) | Difference % | Reg (# 7) (1:8) | IBead (# 6) (1:8) | Difference % | Reg (# 7) (1:8) | IBead (# 6) (1:8) | Difference % | Reg (# 7) (1:8) | IBead (# 6) (1:8) | Difference % | Reg (# 7) (1:8) | IBead (# 6) (1:8) | Difference % |
| Albumin NC | 1196 | 667 | −44 | 10753 | 7147 | −34 | 10268 | 7799 | −24 | 3793 | 5034 | 33 | 2340 | 1673 | −29 |
| CW*0102(Cw1) | 998 | 511 | −49 | 5361 | 5231 | −2 | 4314 | 1058 | −75 | 4538 | 2828 | −38 | 7724 | 1778 | −77 |
| CW*0202(Cw2) | 1275 | 719 | −44 | 7890 | 5379 | −32 | 6814 | 2800 | −59 | 7183 | 8101 | 13 | 9379 | 1840 | −80 |
| CW*0302(Cw10) | 1024 | 522 | −49 | 4952 | 4874 | −2 | 4130 | 1769 | −57 | 4010 | 2378 | −41 | 5608 | 1170 | −79 |
| CW*0303(Cw9) | 703 | 500 | −29 | 4262 | 4286 | 1 | 3017 | 1665 | −45 | 2855 | 2607 | −9 | 3350 | 1220 | −64 |
| CW*0304(Cw10) | 844 | 520 | −38 | 5758 | 4141 | −28 | 4429 | 1816 | −59 | 3713 | 2748 | −26 | 5552 | 1435 | −74 |
| CW*0401(Cw4) | 1569 | 601 | −62 | 7529 | 3726 | −51 | 6484 | 1882 | −71 | 6287 | 5051 | −20 | 9884 | 2013 | −80 |
| CW*0501(Cw5) | 1230 | 710 | −42 | 7553 | 4013 | −47 | 5975 | 2020 | −66 | 6968 | 6352 | −9 | 8769 | 1513 | −83 |
| CW*0602(Cw6) | 1557 | 627 | −60 | 12049 | 4226 | −65 | 10614 | 2108 | −80 | 9171 | 8176 | −11 | 16706 | 586 | −96 |
| CW*0702(Cw7) | 1973 | 746 | −62 | 11789 | 5474 | −54 | 10541 | 2402 | −77 | 7620 | 3483 | −54 | 15321 | 1619 | −89 |
| CW*0801(Cw8) | 669 | 391 | −42 | 5375 | 3227 | −40 | 4539 | 467 | −90 | 2833 | 1937 | −32 | 4419 | 650 | −85 |
| CW*1203(Cw12) | 985 | 636 | −35 | 7102 | 4807 | −32 | 5608 | 1946 | −65 | 5804 | 2663 | −54 | 8662 | 1624 | −81 |
| CW*1402(Cw14) | 991 | 410 | −59 | 7238 | 3968 | −45 | 6160 | 1073 | −83 | 4272 | 1819 | −57 | 8432 | 976 | −88 |
| CW*1502(Cw15) | 778 | 458 | −41 | 4946 | 3586 | −27 | 3693 | 1198 | −68 | 6167 | 7673 | 24 | 4819 | 255 | −95 |
| CW*1601(Cw16) | 973 | 613 | −37 | 8463 | 4069 | −52 | 6851 | 1557 | −77 | 5376 | 2954 | −45 | 9259 | 1111 | −88 |
| CW*1701(Cw17) | 1487 | 1050 | −29 | 6561 | 6148 | −6 | 5638 | 3253 | −42 | 7856 | 9610 | 22 | 8983 | 2709 | −70 |
| CW*1802(Cw18) | 1549 | 570 | −63 | 8432 | 3579 | −58 | 7155 | 1481 | −79 | 7981 | 7814 | −2 | 10610 | 873 | −92 |

While anti-HLA-E monoclonal antibodies reacted with one or a few of HLA-A alleles and a plurality of HLA-B* and HLA-Cw* alleles (e.g., Tables 4 and 5), mAbs (mAb PTR006 & PTR007) reacting to all HLA-Ib molecules (HLA-E, HLA-F and HLA-G) reacted to more HLA-A* alleles (e.g., FIG. 4, Table 4), in addition to 49 of HLA-B* and 16 of HLA-Cw alleles (e.g., FIG. 4, Table 4), as observed with IVIg.

These monoclonal antibodies failed to bind to IBEADS™ (MFI lower than 500) (e.g., Tables 8A-8C). Therefore, it is inferred that IVIg-mimetics were immunoreactive to free rather than to intact (β2-microglobulin-associated heavy chains) HLA-Ia antigens (HLA-A alleles, HLA-B alleles and HLA-Cw alleles) as some lots of IVIg (see, e.g., Tables 7A-7C). Both the therapeutic preparations of IVIg as well as the anti-HLA-E mAbs including IVIg-mimetics reacted only with heavy chains of C alleles.

TABLE 8A

Comparison of reactivity to HLA-A(A).

| | | TFL Anti-HLA-E Mabs (culture supernatants0) | | | | | | | | |
|---|---|---|---|---|---|---|---|---|---|---|
| | | E+/A+/B+/Cs+ | | | | | | | | |
| Bead No | Antigen | PTR-048 | PTR-017 | PTR-018 | PTR-051 | PTG-006 | PTG-007 | PTG-008 | PTG-009 | PTG-039 | PTG-040 |
| 1 | NC | 2 | 3 | 2 | 3 | 6 | 4 | 8 | 4 | 9 | 15 |
| 3 | A*0101(A1) | 29 | 41 | 37 | 30 | 28 | 28 | 29 | 29 | 33 | 37 |
| 4 | A*0201(A2) | 27 | 32 | 28 | 31 | 31 | 30 | 29 | 29 | 36 | 44 |
| 5 | A*0203(A2) | 31 | 40 | 35 | 34 | 31 | 32 | 33 | 31 | 36 | 43 |
| 6 | A*0206(A2) | 28 | 42 | 36 | 29 | 27 | 30 | 30 | 29 | 34 | 42 |
| 7 | A*0301(A3) | 38 | 49 | 47 | 40 | 36 | 38 | 39 | 38 | 45 | 49 |

TABLE 8A-continued

Comparison of reactivity to HLA-A(A).

| 8 | A*1101(A11) | 70 | 191 | 160 | 70 | 51 | 46 | 50 | 51 | 54 | 58 |
| 9 | A*1102(A11) | 60 | 70 | 64 | 64 | 60 | 60 | 58 | 61 | 68 | 73 |
| 10 | A*2301(A23) | 36 | 43 | 39 | 38 | 36 | 35 | 37 | 35 | 42 | 46 |
| 11 | A*2402(A24) | 44 | 75 | 64 | 46 | 42 | 43 | 42 | 42 | 48 | 55 |
| 12 | A*2403(A24) | 55 | 77 | 71 | 56 | 53 | 52 | 53 | 53 | 58 | 65 |
| 13 | A*2501(A25) | 25 | 37 | 32 | 25 | 24 | 25 | 24 | 23 | 30 | 33 |
| 14 | A*2601(A26) | 60 | 78 | 71 | 59 | 57 | 56 | 57 | 57 | 65 | 71 |
| 15 | A*2901(A29) | 118 | 149 | 147 | 122 | 115 | 117 | 110 | 116 | 121 | 125 |
| 16 | A*2902(A29) | 22 | 38 | 33 | 23 | 23 | 22 | 23 | 21 | 27 | 33 |
| 17 | A*3001(A30) | 46 | 61 | 56 | 47 | 45 | 46 | 47 | 46 | 55 | 60 |
| 18 | A*3002(A30) | 71 | 91 | 87 | 74 | 69 | 68 | 69 | 70 | 79 | 79 |
| 19 | A*3101(A31) | 25 | 31 | 30 | 26 | 25 | 25 | 27 | 26 | 32 | 37 |
| 20 | A*3201(A32) | 100 | 127 | 116 | 106 | 102 | 101 | 97 | 97 | 107 | 113 |
| 21 | A*3301(A33) | 77 | 105 | 93 | 78 | 75 | 77 | 73 | 75 | 82 | 91 |
| 100 | A*3303 (A33) | 21 | 26 | 24 | 22 | 24 | 23 | 24 | 23 | 31 | 35 |
| 23 | A*3401(A34) | 36 | 82 | 68 | 30 | 27 | 27 | 28 | 28 | 31 | 36 |
| 24 | A*3402(A34) | 42 | 83 | 73 | 36 | 33 | 32 | 35 | 34 | 41 | 48 |
| 25 | A*3601(A36) | 35 | 51 | 46 | 33 | 33 | 31 | 34 | 33 | 39 | 40 |
| 26 | A*4301(A43) | 84 | 132 | 122 | 88 | 84 | 81 | 79 | 82 | 88 | 93 |
| 27 | A*6601(A66) | 44 | 69 | 60 | 45 | 42 | 40 | 42 | 42 | 48 | 55 |
| 28 | A*6602(A66) | 44 | 58 | 50 | 43 | 39 | 42 | 37 | 40 | 48 | 54 |
| 29 | A*6801(A68) | 34 | 46 | 43 | 29 | 29 | 29 | 31 | 30 | 35 | 41 |
| 30 | A*6802(A68) | 25 | 46 | 41 | 25 | 24 | 24 | 23 | 23 | 29 | 32 |
| 31 | A*6901(A69) | 39 | 60 | 53 | 37 | 33 | 33 | 34 | 34 | 39 | 46 |
| 32 | A*7401(A74) | 28 | 35 | 30 | 24 | 23 | 22 | 24 | 22 | 32 | 40 |
| 33 | A*8001(A80) | 27 | 38 | 36 | 29 | 27 | 26 | 28 | 27 | 32 | 38 |

TFL Anti-HLA-E Mabs (culture supernatants0

| | E+/A+/B+/Cs+ | | | | | E+/F+/G+/A+/B+/Cs+ | | | | |
|---|---|---|---|---|---|---|---|---|---|---|
| Bead No | PTG-041 | PTG-086 | PTG-010 | PTG-011 | PTG-012 | PTR-006 | PTR-007 | PTG-016 | PTG-017 | PTG-032 |
| 1 | 13 | 4 | 5 | 12 | 10 | 4 | 2 | 2 | 2 | 39 |
| 3 | 39 | 32 | 28 | 722 | 637 | 112 | 161 | 227 | 236 | 70 |
| 4 | 40 | 32 | 28 | 84 | 90 | 47 | 59 | 77 | 75 | 74 |
| 5 | 41 | 31 | 30 | 91 | 88 | 81 | 113 | 161 | 159 | 76 |
| 6 | 41 | 31 | 27 | 83 | 82 | 112 | 165 | 229 | 235 | 90 |
| 7 | 48 | 40 | 39 | 1899 | 1887 | 94 | 134 | 189 | 194 | 752 |
| 8 | 60 | 86 | 51 | 758 | 756 | 2115 | 2800 | 2086 | 2143 | 624 |
| 9 | 72 | 64 | 61 | 1300 | 1381 | 108 | 130 | 166 | 168 | 102 |
| 10 | 49 | 40 | 36 | 48 | 51 | 69 | 90 | 131 | 136 | 1267 |
| 11 | 56 | 47 | 43 | 57 | 57 | 301 | 424 | 528 | 524 | 2402 |
| 12 | 63 | 57 | 52 | 69 | 71 | 270 | 382 | 436 | 454 | 1792 |
| 13 | 35 | 26 | 25 | 35 | 36 | 96 | 142 | 203 | 206 | 72 |
| 14 | 72 | 60 | 55 | 72 | 72 | 189 | 261 | 368 | 361 | 109 |
| 15 | 125 | 121 | 112 | 129 | 130 | 414 | 535 | 653 | 663 | 309 |
| 16 | 32 | 23 | 22 | 34 | 35 | 137 | 204 | 291 | 302 | 186 |
| 17 | 61 | 49 | 46 | 1940 | 2007 | 170 | 246 | 308 | 323 | 302 |
| 18 | 83 | 77 | 70 | 546 | 597 | 273 | 376 | 435 | 430 | 312 |
| 19 | 36 | 27 | 26 | 1728 | 1773 | 59 | 80 | 125 | 122 | 338 |
| 20 | 111 | 103 | 102 | 862 | 789 | 282 | 369 | 496 | 487 | 285 |
| 21 | 83 | 81 | 76 | 92 | 91 | 254 | 357 | 451 | 471 | 370 |
| 100 | 34 | 23 | 24 | 80 | 73 | 38 | 46 | 66 | 65 | 53 |
| 23 | 37 | 34 | 28 | 41 | 40 | 499 | 689 | 815 | 816 | 399 |
| 24 | 45 | 39 | 33 | 49 | 50 | 491 | 740 | 739 | 777 | 230 |
| 25 | 40 | 33 | 32 | 44 | 44 | 131 | 190 | 260 | 255 | 95 |
| 26 | 95 | 91 | 83 | 740 | 751 | 574 | 819 | 820 | 826 | 258 |
| 27 | 55 | 45 | 44 | 54 | 57 | 232 | 345 | 439 | 459 | 108 |
| 28 | 51 | 45 | 43 | 56 | 57 | 153 | 240 | 306 | 314 | 102 |
| 29 | 41 | 32 | 29 | 43 | 41 | 125 | 180 | 241 | 244 | 487 |
| 30 | 31 | 24 | 22 | 35 | 35 | 145 | 216 | 311 | 309 | 222 |
| 31 | 45 | 37 | 34 | 49 | 51 | 206 | 296 | 368 | 363 | 226 |
| 32 | 40 | 25 | 23 | 40 | 40 | 93 | 141 | 196 | 202 | 90 |
| 33 | 37 | 29 | 28 | 2009 | 2112 | 85 | 119 | 199 | 203 | 402 |

TABLE 8B

Comparison of reactivity to HLA-B(B).

TFL Anti-HLA-E Mabs (culture supernatants0)

E+/A+/B+/Cs+

| Bead No | Antigen | PTR-048 | PTR-017 | PTR-018 | PTR-051 | PTG-006 | PTG-007 | PTG-008 | PTG-009 | PTG-039 | PTG-040 |
|---|---|---|---|---|---|---|---|---|---|---|---|
| 34 | B*0702(B7) | 59 | 74 | 69 | 61 | 59 | 61 | 58 | 59 | 67 | 70 |
| 35 | B*0801(B8) | 35 | 36 | 37 | 36 | 38 | 36 | 37 | 36 | 43 | 47 |
| 97 | B*1301(B13) | 26 | 31 | 29 | 28 | 29 | 29 | 30 | 29 | 36 | 44 |
| 36 | B*1302(B13) | 50 | 50 | 47 | 51 | 53 | 51 | 53 | 50 | 55 | 62 |
| 37 | B*1401(B64) | 39 | 42 | 40 | 41 | 41 | 40 | 42 | 40 | 452 | 444 |
| 38 | B*1402(B65) | 48 | 50 | 48 | 49 | 47 | 49 | 52 | 49 | 53 | 59 |
| 39 | B*1501(B62) | 34 | 38 | 33 | 37 | 34 | 34 | 36 | 36 | 39 | 46 |
| 40 | B*1502(B75) | 17 | 19 | 17 | 18 | 20 | 18 | 20 | 19 | 255 | 290 |
| 41 | B*1503(B72) | 63 | 65 | 65 | 70 | 65 | 66 | 64 | 66 | 1022 | 1114 |
| 42 | B*1510(B71) | 25 | 26 | 25 | 25 | 27 | 25 | 26 | 26 | 29 | 33 |
| 98 | B*1511(B75) | 19 | 20 | 19 | 19 | 21 | 19 | 23 | 21 | 3302 | 3360 |
| 43 | B*1512(B76) | 23 | 25 | 23 | 25 | 25 | 23 | 27 | 24 | 27 | 34 |
| 44 | B*1513(B77) | 38 | 39 | 38 | 40 | 38 | 40 | 40 | 38 | 299 | 274 |
| 45 | B*1516(B63) | 100 | 102 | 97 | 101 | 98 | 100 | 97 | 102 | 1270 | 1309 |
| 46 | B*1801(B18) | 42 | 44 | 42 | 45 | 43 | 44 | 46 | 42 | 612 | 609 |
| 47 | B*2705(B27) | 48 | 49 | 48 | 51 | 50 | 48 | 50 | 51 | 56 | 62 |
| 48 | B*2708(B27) | 38 | 37 | 35 | 38 | 37 | 36 | 39 | 37 | 43 | 48 |
| 49 | B*3501(B35) | 57 | 59 | 55 | 60 | 60 | 58 | 57 | 58 | 64 | 71 |
| 50 | B*3701(B37) | 40 | 44 | 43 | 43 | 43 | 40 | 42 | 42 | 47 | 54 |
| 51 | B*3801(B38) | 28 | 29 | 28 | 23 | 24 | 24 | 25 | 22 | 33 | 40 |
| 52 | B*3901(B39) | 21 | 22 | 21 | 21 | 21 | 21 | 23 | 22 | 28 | 31 |
| 53 | B*4001(B60) | 29 | 31 | 31 | 28 | 28 | 29 | 31 | 28 | 34 | 38 |
| 54 | B*4002(B61) | 32 | 32 | 30 | 32 | 33 | 31 | 33 | 30 | 38 | 44 |
| 99 | B*4006(B61) | 37 | 40 | 36 | 40 | 41 | 40 | 42 | 39 | 579 | 615 |
| 55 | B*4101(B41) | 86 | 92 | 89 | 89 | 89 | 87 | 86 | 88 | 98 | 100 |
| 56 | B*4201(B42) | 30 | 33 | 30 | 31 | 32 | 31 | 32 | 31 | 37 | 42 |
| 57 | B*4402(B44) | 32 | 33 | 31 | 34 | 32 | 32 | 33 | 32 | 38 | 41 |
| 58 | B*4403(B44) | 15 | 18 | 16 | 18 | 18 | 17 | 21 | 18 | 26 | 31 |
| 59 | B*4501(B45) | 17 | 17 | 16 | 17 | 18 | 18 | 20 | 17 | 26 | 32 |
| 60 | B*4601(B46) | 21 | 23 | 22 | 23 | 23 | 22 | 25 | 23 | 29 | 32 |
| 61 | B*4701(B47) | 36 | 39 | 37 | 39 | 38 | 38 | 39 | 37 | 782 | 840 |
| 62 | B*4801(B48) | 17 | 20 | 17 | 19 | 21 | 20 | 22 | 19 | 26 | 32 |
| 63 | B*4901(B49) | 70 | 71 | 67 | 72 | 71 | 71 | 70 | 70 | 81 | 86 |
| 64 | B*5001(B50) | 64 | 67 | 64 | 68 | 67 | 65 | 66 | 65 | 70 | 76 |
| 65 | B*5101(B51) | 45 | 49 | 47 | 48 | 45 | 46 | 45 | 46 | 53 | 55 |
| 66 | B*5102(B51) | 31 | 32 | 32 | 33 | 32 | 31 | 34 | 33 | 40 | 45 |
| 67 | B*5201(B52) | 33 | 35 | 32 | 33 | 34 | 33 | 34 | 34 | 39 | 46 |
| 68 | B*5301(B53) | 38 | 41 | 39 | 40 | 41 | 40 | 41 | 38 | 47 | 52 |
| 69 | B*5401(B54) | 38 | 41 | 40 | 42 | 41 | 39 | 40 | 39 | 48 | 53 |
| 70 | B*5501(B55) | 25 | 28 | 27 | 28 | 27 | 27 | 28 | 26 | 31 | 38 |
| 71 | B*5601(B56) | 49 | 52 | 50 | 52 | 50 | 49 | 52 | 51 | 58 | 63 |
| 72 | B*5701(B57) | 16 | 16 | 15 | 17 | 18 | 17 | 19 | 18 | 24 | 29 |
| 73 | B*5703(B57) | 21 | 24 | 21 | 23 | 25 | 23 | 25 | 24 | 455 | 473 |
| 74 | B*5801(B58) | 13 | 15 | 13 | 15 | 16 | 16 | 18 | 16 | 425 | 406 |
| 75 | B*5901(B59) | 24 | 26 | 23 | 24 | 25 | 25 | 26 | 25 | 32 | 41 |
| 76 | B*6701(B67) | 27 | 28 | 27 | 31 | 30 | 30 | 30 | 29 | 39 | 46 |
| 77 | B*7301(B73) | 34 | 36 | 34 | 37 | 34 | 35 | 34 | 36 | 43 | 47 |
| 78 | B*7801(B78) | 55 | 60 | 55 | 58 | 58 | 59 | 57 | 59 | 68 | 72 |
| 79 | B*8101(B81) | 37 | 37 | 36 | 39 | 38 | 39 | 39 | 39 | 48 | 50 |
| 80 | B*8201(B82) | 17 | 17 | 16 | 20 | 20 | 18 | 21 | 19 | 26 | 33 |

TFL Anti-HLA-E Mabs (culture supernatants0)

| | E+/A+/B+/Cs+ | | | | | E+/F+/G+/A+/B+/Cs+ | | | | |
|---|---|---|---|---|---|---|---|---|---|---|
| Bead No | PTG-041 | PTG-086 | PTG-010 | PTG-011 | PTG-012 | PTR-006 | PTR-007 | PTG-016 | PTG-017 | PTG-032 |
| 34 | 70 | 65 | 64 | 102 | 102 | 173 | 253 | 327 | 335 | 113 |
| 35 | 44 | 38 | 36 | 41 | 41 | 37 | 36 | 35 | 37 | 628 |
| 97 | 40 | 28 | 28 | 142 | 141 | 48 | 53 | 84 | 86 | 72 |
| 36 | 62 | 52 | 49 | 55 | 55 | 50 | 51 | 47 | 48 | 594 |
| 37 | 449 | 43 | 43 | 92 | 96 | 42 | 40 | 41 | 40 | 68 |
| 38 | 60 | 50 | 51 | 55 | 54 | 55 | 57 | 65 | 68 | 347 |
| 39 | 44 | 37 | 36 | 40 | 40 | 35 | 38 | 38 | 39 | 731 |
| 40 | 285 | 19 | 18 | 49 | 52 | 20 | 18 | 17 | 18 | 302 |
| 41 | 1100 | 65 | 67 | 68 | 73 | 69 | 70 | 71 | 75 | 99 |
| 42 | 32 | 26 | 25 | 68 | 66 | 27 | 26 | 30 | 29 | 529 |
| 98 | 3415 | 20 | 21 | 360 | 340 | 21 | 23 | 28 | 28 | 61 |
| 43 | 33 | 24 | 24 | 29 | 29 | 24 | 25 | 25 | 25 | 309 |
| 44 | 276 | 41 | 39 | 70 | 71 | 40 | 38 | 41 | 40 | 460 |
| 45 | 1330 | 106 | 100 | 103 | 108 | 99 | 101 | 103 | 104 | 142 |
| 46 | 614 | 47 | 43 | 848 | 809 | 47 | 46 | 47 | 49 | 86 |

TABLE 8B-continued

Comparison of reactivity to HLA-B(B).

| | | | | | | | | | | |
|---|---|---|---|---|---|---|---|---|---|---|
| 47 | 60 | 53 | 52 | 52 | 54 | 51 | 54 | 60 | 61 | 480 |
| 48 | 45 | 37 | 37 | 63 | 67 | 39 | 38 | 38 | 37 | 463 |
| 49 | 69 | 58 | 58 | 81 | 80 | 61 | 62 | 60 | 60 | 281 |
| 50 | 48 | 44 | 42 | 46 | 46 | 52 | 58 | 70 | 69 | 78 |
| 51 | 39 | 26 | 22 | 3240 | 2969 | 25 | 30 | 39 | 38 | 3761 |
| 52 | 31 | 22 | 21 | 28 | 26 | 22 | 22 | 23 | 22 | 488 |
| 53 | 36 | 28 | 27 | 32 | 34 | 34 | 37 | 38 | 40 | 431 |
| 54 | 46 | 32 | 32 | 76 | 78 | 33 | 35 | 38 | 38 | 595 |
| 99 | 621 | 40 | 40 | 45 | 46 | 41 | 41 | 48 | 47 | 352 |
| 55 | 102 | 90 | 89 | 145 | 141 | 94 | 93 | 93 | 99 | 801 |
| 56 | 41 | 32 | 31 | 85 | 76 | 36 | 36 | 44 | 46 | 64 |
| 57 | 40 | 33 | 30 | 37 | 38 | 33 | 33 | 31 | 30 | 624 |
| 58 | 29 | 18 | 18 | 34 | 35 | 19 | 19 | 22 | 22 | 62 |
| 59 | 31 | 16 | 17 | 39 | 38 | 19 | 20 | 24 | 24 | 58 |
| 60 | 31 | 24 | 22 | 57 | 52 | 28 | 29 | 39 | 39 | 50 |
| 61 | 847 | 42 | 39 | 189 | 178 | 40 | 39 | 44 | 44 | 645 |
| 62 | 32 | 19 | 20 | 81 | 75 | 22 | 20 | 25 | 25 | 478 |
| 63 | 86 | 74 | 73 | 132 | 131 | 74 | 71 | 75 | 76 | 826 |
| 64 | 77 | 68 | 66 | 250 | 237 | 68 | 66 | 65 | 65 | 95 |
| 65 | 56 | 47 | 47 | 189 | 178 | 47 | 47 | 47 | 46 | 73 |
| 66 | 46 | 33 | 30 | 39 | 39 | 33 | 33 | 35 | 35 | 72 |
| 67 | 45 | 36 | 34 | 40 | 40 | 35 | 36 | 39 | 41 | 69 |
| 68 | 49 | 42 | 40 | 115 | 119 | 42 | 40 | 43 | 46 | 76 |
| 69 | 54 | 43 | 40 | 46 | 45 | 45 | 49 | 60 | 60 | 76 |
| 70 | 37 | 27 | 28 | 31 | 32 | 30 | 31 | 35 | 37 | 59 |
| 71 | 61 | 54 | 53 | 55 | 56 | 52 | 53 | 53 | 54 | 77 |
| 72 | 29 | 17 | 17 | 25 | 23 | 19 | 16 | 17 | 16 | 49 |
| 73 | 475 | 25 | 23 | 43 | 43 | 24 | 21 | 21 | 22 | 57 |
| 74 | 440 | 16 | 16 | 33 | 34 | 16 | 13 | 15 | 15 | 50 |
| 75 | 40 | 25 | 25 | 46 | 46 | 30 | 33 | 42 | 43 | 59 |
| 76 | 43 | 30 | 30 | 35 | 37 | 29 | 30 | 31 | 32 | 65 |
| 77 | 48 | 38 | 37 | 39 | 40 | 34 | 38 | 35 | 34 | 438 |
| 78 | 73 | 59 | 59 | 62 | 63 | 59 | 61 | 64 | 65 | 95 |
| 79 | 49 | 39 | 37 | 44 | 46 | 41 | 41 | 45 | 46 | 69 |
| 80 | 31 | 20 | 19 | 26 | 25 | 19 | 19 | 17 | 20 | 722 |

TABLE 8C

Comparison of reactivity to HLA-Cw(C).
TFL Anti-HLA-E Mabs (culture supernatants0

| | | E+/A+/B+/Cs+ | | | | | | | | | |
|---|---|---|---|---|---|---|---|---|---|---|---|
| Bead No | Antigen | PTR-048 | PTR-017 | PTR-018 | PTR-051 | PTG-006 | PTG-007 | PTG-008 | PTG-009 | PTG-039 | PTG-040 |
| 81 | CW*0102(Cw1) | 70 | 74 | 71 | 75 | 74 | 73 | 70 | 76 | 77 | 79 |
| 82 | CW*0202(Cw2) | 26 | 27 | 26 | 28 | 27 | 27 | 29 | 27 | 36 | 42 |
| 83 | CW*0302(Cw10) | 18 | 21 | 20 | 20 | 22 | 20 | 23 | 20 | 30 | 38 |
| 84 | CW*0303(Cw9) | 41 | 43 | 42 | 45 | 44 | 41 | 42 | 43 | 49 | 56 |
| 85 | CW*0304(Cw10) | 19 | 22 | 20 | 21 | 22 | 20 | 23 | 20 | 29 | 34 |
| 86 | CW*0401(Cw4) | 29 | 29 | 27 | 30 | 31 | 30 | 32 | 30 | 39 | 45 |
| 87 | CW*0501(Cw5) | 15 | 15 | 14 | 16 | 17 | 16 | 18 | 16 | 25 | 35 |
| 88 | CW*0602(Cw6) | 16 | 18 | 16 | 18 | 18 | 17 | 21 | 17 | 25 | 33 |
| 89 | CW*0702(Cw7) | 22 | 22 | 21 | 22 | 23 | 23 | 24 | 22 | 30 | 38 |
| 90 | CW*0801(Cw8) | 15 | 18 | 16 | 17 | 18 | 18 | 20 | 17 | 27 | 33 |
| 91 | CW*1203(Cw12) | 34 | 37 | 34 | 36 | 37 | 37 | 35 | 35 | 45 | 49 |
| 92 | CW*1402(Cw14) | 18 | 19 | 18 | 20 | 20 | 20 | 21 | 20 | 29 | 36 |
| 93 | CW*1502(Cw15) | 20 | 21 | 19 | 21 | 22 | 20 | 22 | 20 | 27 | 35 |
| 94 | CW*1601(Cw16) | 41 | 44 | 42 | 41 | 43 | 43 | 42 | 43 | 49 | 56 |
| 95 | CW*1701(Cw17) | 27 | 28 | 27 | 29 | 29 | 29 | 30 | 28 | 36 | 45 |
| 96 | CW*1802(Cw18) | 34 | 38 | 36 | 37 | 38 | 38 | 37 | 38 | 47 | 53 |

| | E+/A+/B+/Cs+ | | | | | E+/F+/G+/A+/B+/Cs+ | | | | |
|---|---|---|---|---|---|---|---|---|---|---|
| Bead No | PTG-041 | PTG-086 | PTG-010 | PTG-011 | PTG-012 | PTR-006 | PTR-007 | PTG-016 | PTG-017 | PTG-032 |
| 81 | 80 | 75 | 70 | 73 | 73 | 73 | 74 | 74 | 75 | 680 |
| 82 | 39 | 29 | 27 | 395 | 406 | 30 | 30 | 36 | 37 | 1272 |
| 83 | 37 | 23 | 20 | 100 | 102 | 23 | 21 | 26 | 26 | 438 |
| 84 | 56 | 43 | 44 | 220 | 223 | 45 | 45 | 49 | 50 | 136 |
| 85 | 33 | 21 | 20 | 203 | 197 | 24 | 23 | 31 | 31 | 56 |
| 86 | 43 | 32 | 30 | 182 | 174 | 32 | 31 | 34 | 34 | 72 |
| 87 | 31 | 17 | 16 | 72 | 69 | 16 | 15 | 17 | 16 | 59 |
| 88 | 31 | 18 | 18 | 86 | 82 | 25 | 29 | 40 | 42 | 297 |

TABLE 8C-continued

Comparison of reactivity to HLA-Cw(C).
TFL Anti-HLA-E Mabs (culture supernatants0)

| 89 | 34 | 23 | 21 | 208 | 197 | 23 | 25 | 24 | 25 | 62 |
| 90 | 33 | 19 | 17 | 143 | 145 | 20 | 18 | 19 | 20 | 64 |
| 91 | 48 | 37 | 36 | 151 | 139 | 43 | 44 | 56 | 54 | 379 |
| 92 | 32 | 20 | 19 | 100 | 99 | 19 | 20 | 19 | 19 | 587 |
| 93 | 33 | 22 | 21 | 113 | 113 | 22 | 22 | 26 | 27 | 606 |
| 94 | 52 | 44 | 43 | 198 | 193 | 44 | 45 | 45 | 45 | 89 |
| 95 | 41 | 30 | 29 | 141 | 139 | 30 | 30 | 32 | 32 | 1159 |
| 96 | 53 | 41 | 35 | 742 | 780 | 41 | 43 | 48 | 50 | 1618 |

Example 9: Analysis of Alloimmunization in Human Subject

B lymphocytes were collection from the peripheral blood cells of an alloimmunized female subject (ID: JH), who was alloimmunized by her husband's HLA during pregnancy. CD19+ B cells were collected from the blood of the female subject following the purification and treatment procedures depicted in FIG. 8A. The female subject has sera reactive to her husband's alleles. The alloimmunization occurred during her first pregnancy, as evidence by the HLA typing of her, her husband and children (FIG. 8B).

Figure 8B:
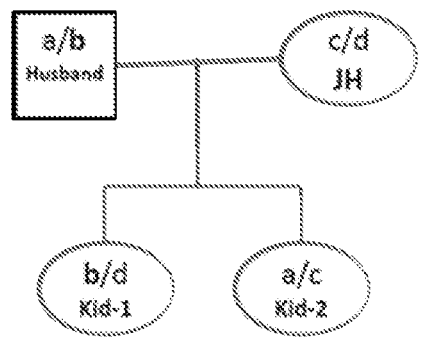

The diagrammatic chart of FIG. 8A depicts a sample strategy that promoted antibody production by the purified B cell population, by exposing them to selected cytokines. In particular, peripheral blood was collected from the female (JH) and the peripheral blood cells were separated by Ficol-Hypacque. The B lymphocytes were isolated from the peripheral blood cells using B cell marker CD19 coated magnetic beads. Once B cells were recovered and counted they were kept in specific culture medium for 4, 7, 10 and 13 days in the presence of anti-CD40 monoclonal antibody and cytokines IL-2, IL-4, IL-6, IL-10 and IL-21. The culture supernatants were monitored for antibody secretion. Antibodies were tested at 24 Hr and 49 Hr. Once presence of the specific antibodies was confirmed, the cells were collected from the wells, pooled and re-aliquoted into well containing culture medium without Cytokines.

Antibody production occurred in wells containing isolated B lymphocytes. In order to study the effect of IVIg or selected anti-HLA-E antibody, a proper control was established using wells containing cell contain only the tissue culture media without IVIg or selected monoclonal anti-HLA-E antibodies. Media only served as a negative control for the experiment.

Figure 8C:
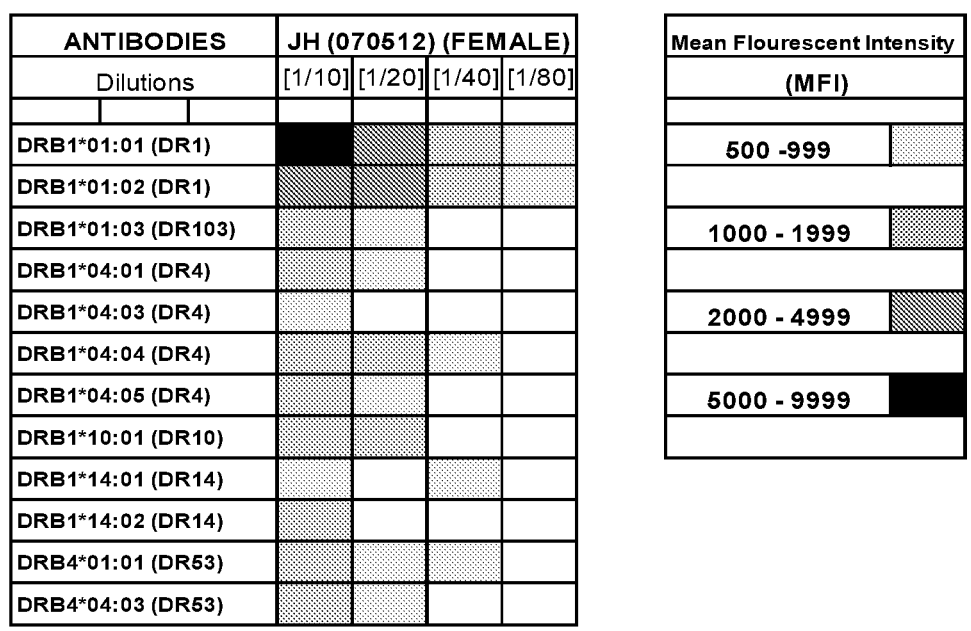

FIG. 8C shows that the antibodies found in the alloimmunized female after delivery are reactive to husband HLA Class II, DRB1*0101. The reactivity persisted for more than fifteen years after delivery of the child.

FIG. 9A shows that in the presence of IVIg, section of certain antibodies, e.g., DRB1*0101 (i.e., DRB1*01:01) and DRB1*0102 (i.e., DRB1*01:02), is reduced. In contrast, mAb PTER007 (the IVIg mimetic) suppresses significantly the secretion of anti-DRB1*0101 (p<0.007) and anti-DRB1*0102 (p<0.003) antibodies by the B cells of JH (FIG. 9B). In this study, the isolated, antibody secreting B cells were culture in wells containing medium without cytokines. These cells were exposed to none, IVIg (1/100) and mAb PTER007. The effects of IVIg and mAb are compared with control (PBS only).

FIGS. 9A-9F document that mAb PTER007 is more efficient than IVIg in arresting antibody production. The implications can be better realized with physicians administer IVIg for suppressing antibody production in Organ transplant recipients, in spite of several published reports that IVIg cannot suppress B cells proliferation or antibody production.

FIGS. 9A and 9B showed that both IVIg and the IVIg-mimetic (PTER007) inhibit antibodies reacting to husband HLA Class II, DRB1*0101. The DRB1*0101 allele differs from DRB1*0102 in two amino acids at positions 85 and 86. The antibodies cross-reacted with the other allele. The reactivities of both antibodies were reduced in the presence of IVIg or anti-HLA-E mAb PTER007.

As noted above, the culture supernatants of B lymphocytes obtained from alloimmunized female contained antibodies against husbands HLA class II (namely DRB1*0101). However, the antibodies cross-reacted with DRB1*0102 equally well, possibly due to the fact the two HLA alleles differ in the amino acid sequences at only two positions (85 and 86). In addition, the antibodies also reacted at low levels with HLA-DRB1*401, DRB1*0404, DRB1*0405 and DRB1*1402 (FIGS. 9C-9F). These alleles while differing in the amino acid sequence at different positions, also share peptide sequences with DRB1*0101. Cross reactivities between these alleles were reduced by the presence of mAb PTER007 (e.g., FIGS. 9D and 9F) while IVIg per se failed to reduce the cross-reactivities of DRB1*0101 antibodies (e.g., FIGS. 9C and 9E).

Figure 10:
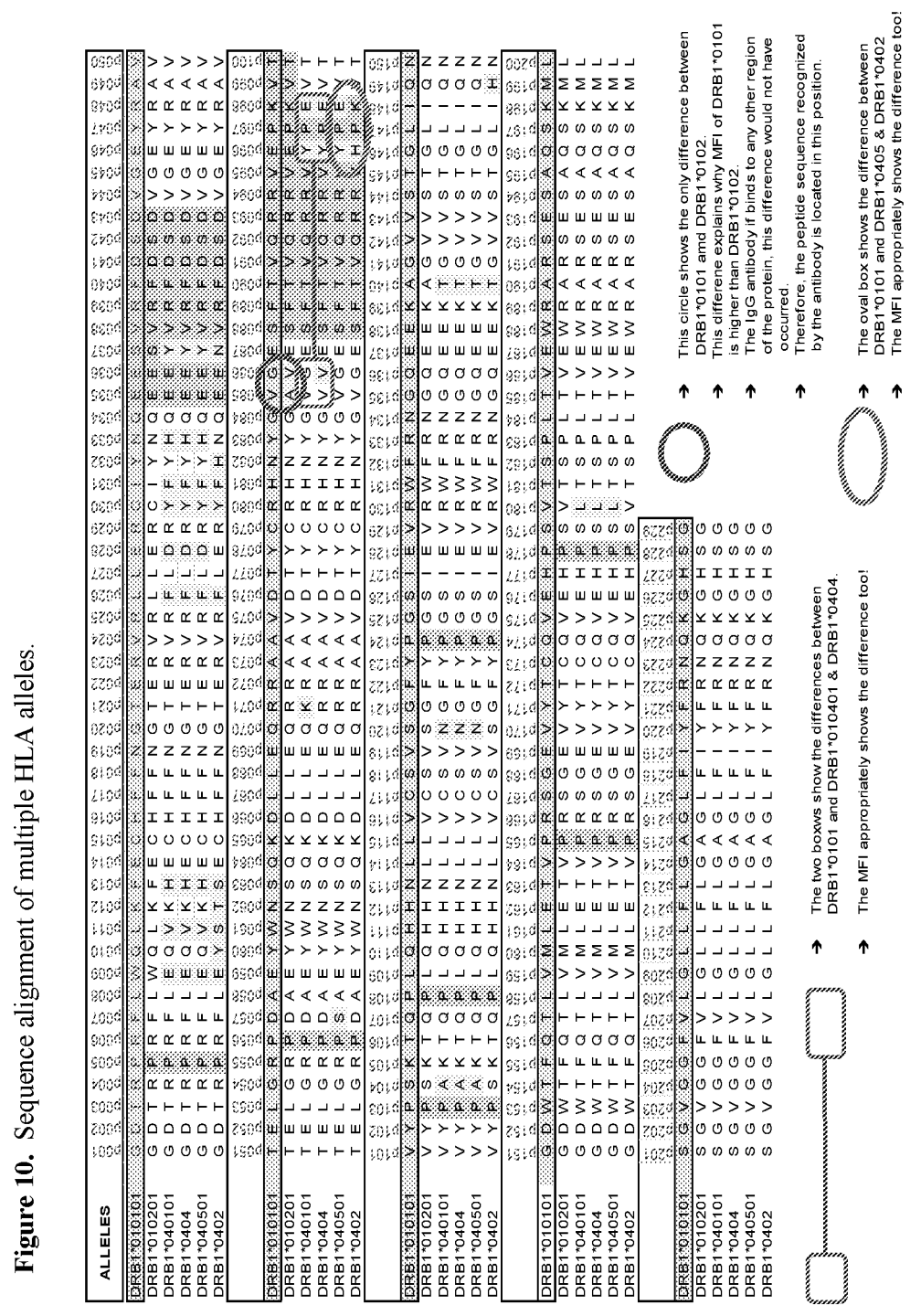

FIG. 10 depicts the sequence alignment of multiple HLA class II alleles. The differences in the efficacy of IVIg-mimetic to suppress antibody production by the B cells of JH seem to depend on the level of antibodies secreted by the B cells, which in turn depends on the epitope recognized by the monoclonal antibodies recognized by the B cells.

It appears that the monoclonal antibody cross reacts with different DRB haplotypes, but may primarily be reacting to DRB1*0101 as shown by the peptide analyses of different haplotypes recognized by the antibody (FIG. 10). The epitope is tentatively identified between position 85 and 98.

The various methods and techniques described above provide a number of ways to carry out the test of efficacy of IVIg-mimetics such as anti-HLA-Ib antibodies in comparison with IVIg (both immunoreactivity and immunomodulatory activities). Of course, it is to be understood that not necessarily all objectives or advantages described may be achieved in accordance with any particular embodiment described herein. Thus, for example, those skilled in the art will recognize that the methods may be performed in a manner that achieves or optimizes one advantage or group of advantages as taught herein without necessarily achieving other objectives or advantages as may be taught or suggested herein. A variety of advantageous and disadvantageous alternatives are mentioned herein. It is to be understood that some preferred embodiments specifically include one, another, or several advantageous features, while others specifically exclude one, another, or several disadvantageous features, while still others specifically mitigate a present disadvantageous feature by inclusion of one, another, or several advantageous features.

Furthermore, the skilled artisan will recognize the applicability of various features from different embodiments. Similarly, the various elements, features and steps discussed above, as well as other known equivalents for each such element, feature or step, can be mixed and matched by one of ordinary skill in this art to perform methods in accordance with principles described herein. Among the various elements, features, and steps some will be specifically included and others specifically excluded in diverse embodiments.

Although the invention has been disclosed in the context of certain embodiments and examples, it will be understood by those skilled in the art that the invention extends beyond the specifically disclosed embodiments to other alternative embodiments and/or uses and modifications and equivalents thereof.

In some embodiments, the terms "a" and "an" and "the" and similar referents used in the context of describing a particular embodiment of the invention (especially in the context of certain of the following claims) may be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context the use of any and all examples, or exemplary language (e.g., "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is herein deemed to contain the group as modified thus fulfilling the written description of all Markush groups used in the appended claims.

Preferred embodiments of this invention are described herein, including the best mode known to the inventors for carrying out the invention. Variations on those preferred embodiments will become apparent to those of ordinary skill in the art upon reading the foregoing description. It is contemplated that skilled artisans may employ such variations as appropriate, and the invention may be practiced otherwise than specifically described herein. Accordingly, many embodiments of this invention include all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents and printed publications throughout this specification. Each of the above cited references and printed publications are herein individually incorporated by reference in their entirety.

In closing, it is to be understood that the embodiments of the invention disclosed herein are illustrative of the principles of the present invention, namely anti-HLA-Ib or anti-HLA-EFG antibodies (used as IVIg mimetics). Other modifications that may be employed may be within the scope of the invention. Thus, by way of example, but not of limitation, alternative configurations of the present invention may be utilized in accordance with the teachings herein. Accordingly, the present invention is not limited to that precisely as shown and described.

The invention claimed is:

1. An antibody comprising the heavy chain and light chain complementarity determining regions of the antibody that is produced by the hybridoma that is deposited at American Type Culture Collection Patent Deposit Number PTA-126075 or 126076.

2. The antibody of claim 1 that is produced by the hybridoma that is deposited at American Type Culture Collection Patent Deposit Number PTA-126075.

3. The antibody of claim 1 that is produced by the hybridoma that is deposited at American Type Culture Collection Patent Deposit Number PTA-126076.

4. The antibody of claim 1 that is capable of binding to at least one allele of each of HLA-A, HLA-B, HLA-C, HLA-E, HLA-F, and HLA-G.

5. A pharmaceutical composition comprising the antibody of claim 1 and one or more pharmaceutically acceptable carriers.

6. The composition of claim 5, wherein the composition is suitable for subcutaneous, intravenous, or intramuscular administrations.

* * * * *